United States Patent
Lee et al.

(10) Patent No.: US 11,758,802 B2
(45) Date of Patent: Sep. 12, 2023

(54) COMPOSITION AND ORGANIC LIGHT-EMITTING DEVICE INCLUDING THE SAME

(71) Applicant: Samsung Electronics Co., Ltd., Suwon-si (KR)

(72) Inventors: Banglin Lee, Suwon-si (KR); Soyeon Kim, Seoul (KR); Jiyoun Lee, Anyang-si (KR); Jongwon Choi, Yongin-si (KR); Dmitry Kravchuk, Hwaseong-si (KR); Sangdong Kim, Seongnam-si (KR); Sukekazu Aratani, Hwaseong-si (KR); Yongsuk Cho, Hwaseong-si (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 0 days.

(21) Appl. No.: 16/669,770

(22) Filed: Oct. 31, 2019

(65) Prior Publication Data

US 2020/0313095 A1      Oct. 1, 2020

(30) Foreign Application Priority Data

Mar. 29, 2019   (KR) .......... 10-2019-0037214
Oct. 30, 2019   (KR) .......... 10-2019-0136949

(51) Int. Cl.
*H10K 85/30*   (2023.01)
*C07D 403/14*   (2006.01)
(Continued)

(52) U.S. Cl.
CPC ......... *H10K 85/342* (2023.02); *C07D 403/14* (2013.01); *C07D 487/04* (2013.01);
(Continued)

(58) Field of Classification Search
CPC ...... C09K 2211/185; C09K 2211/1029; C09K 11/06; C09K 2211/1018;
(Continued)

(56) References Cited

U.S. PATENT DOCUMENTS 6,465,115 B2   10/2002   Shi et al.
6,596,415 B2    7/2003   Shi et al.
(Continued)

FOREIGN PATENT DOCUMENTS

EP    3637489 A1    4/2020
JP    2000003782 A  6/1998

OTHER PUBLICATIONS

M. A. Baldo, et al., Nature, Highly efficient phosphorescent emission fromorganic electroluminescent devices, v395, pp. 151-154 (1998).
(Continued)

*Primary Examiner* — Dylan C Kershner
*Assistant Examiner* — Elizabeth M. Dahlburg
(74) *Attorney, Agent, or Firm* — CANTOR COLBURN LLP

(57) ABSTRACT

A composition including a first compound represented by Formula 1 and a second compound represented by Formula 2 and an organic light-emitting device including the composition:
(Continued)

US 11,758,802 B2

Page 2

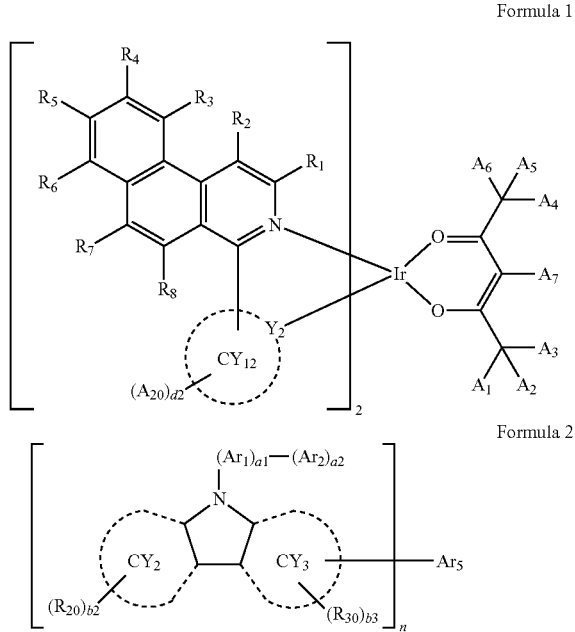

Formula 1

Formula 2

Formulae 1 and 2 may each be understood by referring to the descriptions thereof provided herein.

17 Claims, 1 Drawing Sheet

(51) Int. Cl.
  C07D 487/04 (2006.01)
  C07F 15/00 (2006.01)
  C09K 11/06 (2006.01)
  H10K 85/60 (2023.01)
  H10K 50/11 (2023.01)
  H10K 101/10 (2023.01)
(52) U.S. Cl.
  CPC .......... C07F 15/0033 (2013.01); C09K 11/06 (2013.01); H10K 85/6572 (2023.02); C09K 2211/1018 (2013.01); C09K 2211/1029 (2013.01); C09K 2211/185 (2013.01); H10K 50/11 (2023.02); H10K 2101/10 (2023.02)
(58) Field of Classification Search
  CPC .... C09K 2211/1033; C09K 2211/1037; C09K 2211/1044; C09K 2211/1048; C09K 2211/1059; C07F 15/0033; H01L 51/0085; H01L 51/0067; H01L 51/0071; H01L 51/0072; H01L 51/0073; H01L 51/5012; H01L 51/5016; C07D 401/14; C07D 403/04; C07D 403/10; C07D 403/14; C07D 405/14; C07D 487/04; C07D 491/048; C07D 491/147; C07D 491/153; C07D 495/04; C07D 519/00; H10K 85/342; H10K 50/11; H10K 50/12; H10K 2101/10
  See application file for complete search history.

(56) References Cited

U.S. PATENT DOCUMENTS

| | | | |
|---|---|---|---|
| 9,554,442 B2 | 1/2017 | Kamatani et al. | |
| 9,960,370 B2 | 5/2018 | Kishino et al. | |
| 10,038,152 B2 | 7/2018 | Kosuge et al. | |
| 2001/0019782 A1 | 9/2001 | Igarashi et al. | |
| 2010/0219407 A1* | 9/2010 | Kamatani | H01L 51/006 257/40 |
| 2012/0235123 A1* | 9/2012 | Lee | C07F 7/0814 257/40 |
| 2015/0295188 A1* | 10/2015 | Kosuge | C07F 15/0033 345/173 |
| 2015/0303386 A1 | 10/2015 | Kishino et al. | |
| 2015/0364703 A1 | 12/2015 | Miyashita et al. | |
| 2016/0285007 A1* | 9/2016 | Swager | H01L 51/0061 |
| 2017/0092882 A1 | 3/2017 | Kamatani et al. | |
| 2018/0130956 A1 | 5/2018 | Boudreault et al. | |
| 2020/0099000 A1* | 3/2020 | Zhang | C07F 15/0033 |
| 2020/0111977 A1* | 4/2020 | Choi | C07F 15/0033 |
| 2020/0308203 A1* | 10/2020 | Kim | H01L 51/0085 |

OTHER PUBLICATIONS

M. A. Baldo, et al., Very high-efficiency green organic light-emitting devices based on electrophosphorescence, Appl Phys. Lett. 75, 1-4 (1999).

Qin Wang, et al., Effects of charged self-assembled quantum dots on two-dimensional quantum transport, Appl. Phys. Lett. 76, 1704 (2000), 4 pp.

Raymond C. Kwong, et al., High operational stability of electrophosphorescent devices, Appl. Phys. Lett. 81, 162 (2002), 4 pp.

Sergey Lamansky, et al., Highly Phosphorescent Bis-Cyclometalated Iridium Complexes: Synthesis, Photophysical Characterization, and Use in Organic Light Emitting Diodes, J. Am Chem Soc. 2001, 123, 4304-4312.

Sergey Lamansky, et al., Synthesis and Characterization of Phosphorescent Cyclometalated Iridium Complexes, Inorg. Chem. 2001, 40, 1704-1711.

Extended European search report issued by the European Patent Office dated Jul. 22, 2020 in the examination of the European Patent Application No. 20165590.9, which corresponds to the U.S. Application above.

* cited by examiner

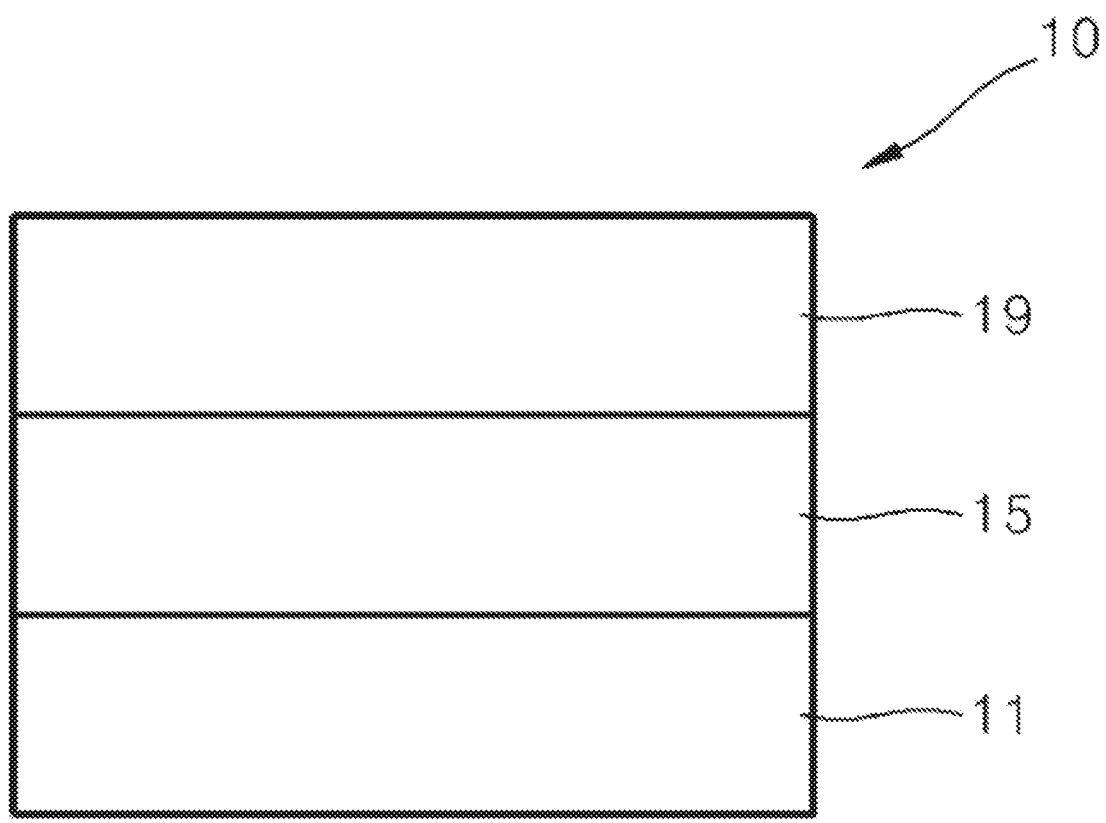

COMPOSITION AND ORGANIC LIGHT-EMITTING DEVICE INCLUDING THE SAME

CROSS-REFERENCE TO RELATED APPLICATION

This application claims priority to and the benefit of Korean Patent Applications Nos. 10-2019-0037214, filed on Mar. 29, 2019, and 10-2019-0136949, filed on Oct. 30, 2019, in the Korean Intellectual Property Office, and all the benefits accruing therefrom under 35 U.S.C. § 119, the content of which is incorporated herein in its entirety by reference.

BACKGROUND

1. Field

The present disclosure relates to a composition and an organic light-emitting device including the same.

2. Description of the Related Art

Organic light-emitting devices (OLEDs) are self-emission devices which produce full-color images. In addition, OLEDs have wide viewing angles and exhibit excellent driving voltage and response speed characteristics.

OLEDs include an anode, a cathode, and an organic layer between the anode and the cathode and including an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transit from an excited state to a ground state to thereby generate light.

SUMMARY

Provided are a novel composition, and an organic light-emitting device including the same.

Additional aspects will be set forth in part in the description which follows and, in part, will be apparent from the description, or may be learned by practice of the presented embodiments.

According to an aspect of an embodiment, a composition may include a first compound and a second compound, wherein the first compound may include a compound represented by Formula 1, and the second compound may include a compound represented by Formula 2:

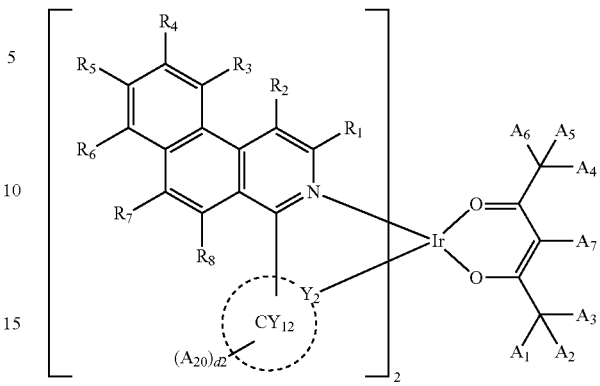

Formula 1

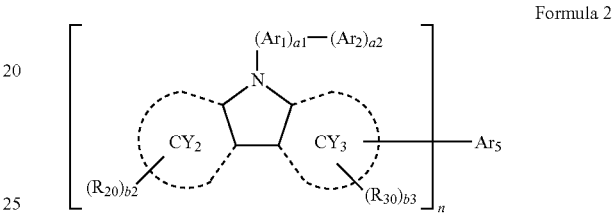

Formula 2 wherein, $Y_2$ in Formula 1 may be C, ring $CY_2$ in Formula 1 may be a $C_5$-$C_{60}$ carbocyclic group or a $C_1$-$C_{60}$ heterocyclic group, $Ar_1$ in Formula 2 may be a $C_5$-$C_{60}$ carbocyclic group unsubstituted or substituted with at least one $R_{61}$ or a $C_1$-$C_{60}$ heterocyclic group unsubstituted or substituted with at least one $R_{61}$, $Ar_2$ in Formula 2 may be a π electron-depleted nitrogen-containing $C_1$-$C_{60}$ cyclic group unsubstituted or substituted with at least one $R_{62}$, $Ar_5$ in Formula 2 may not be present or be a single bond, a $C_5$-$C_{60}$ carbocyclic group unsubstituted or substituted with at least one $R_{65}$ or a $C_1$-$C_{60}$ heterocyclic group unsubstituted or substituted with at least one $R_{65}$, n in Formula 2 may be 1, 2, or 3, and when n is 1, $Ar_5$ may not be present, a1 and a2 in Formula 2 may each independently be an integer from 0 to 5, and the sum of a1 and a2 may be 1 or greater, ring $CY_2$ and ring $CY_3$ in Formula 2 may each independently be a $C_5$-$C_{60}$ carbocyclic group or a $C_1$-$C_{60}$ heterocyclic group, and ring $CY_2$ and ring $CY_3$ may optionally be linked to each other via or a $C_5$-$C_{60}$ carbocyclic group unsubstituted or substituted with at least one $R_{66}$ or a $C_1$-$C_{60}$ heterocyclic group unsubstituted or substituted with at least one $R_{66}$, $R_1$ to $R_8$, $A_{20}$, $A_1$ to $A_7$, $R_{20}$, $R_{30}$, $R_{61}$, $R_{62}$, $R_{65}$, and $R_{66}$ in Formulae 1 and 2 may each independently be hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$Ge(Q_3)(Q_4)(Q_5)$, —$B(Q_6)(Q_7)$, —$P(=O)(Q_8)(Q_9)$, or —$P(Q_8)(Q_9)$, b2 and b3 in Formula 2 may each independently be an integer from 0 to 20, when b2 is 2 or more, two or more $R_{20}$(s) may be identical to or different from each other, and when b3 is 2 or more, two or more $R_{30}$(s) may be identical to or different from each other, d2 may be an integer from 0 to 10, and when d2 is 2 or more, two or more $A_{20}$(s) may be identical to or different from each other, at least one of $R_1$ to $R_8$, $A_{20}$, or any combination thereof may comprise at least one fluoro group (—F), two or more of $R_1$ to $R_8$ and $A_{20}$ in Formula 1 may optionally be linked to form a $C_5$-$C_{60}$ carbocyclic group which is unsubstituted or substituted with at least one $R_{1a}$ or a $C_1$-$C_{60}$ heterocyclic group which is unsubstituted or substituted with at least one $R_{1a}$, two or more of $A_1$ to $A_7$ in Formula 1 may optionally be linked to form a $C_5$-$C_{60}$ carbocyclic group which is unsubstituted or substituted with at least one $R_{1a}$ or a $C_1$-$C_{60}$ heterocyclic group which is unsubstituted or substituted with at least one $R_{10}$, two or more of ring $CY_2$, ring $CY_3$, $R_{20}$, and $R_{30}$ in Formula 2 in Formula 1 may optionally be linked to form a $C_5$-$C_{60}$ carbocyclic group which is unsubstituted or substituted with at least one $R_{1a}$ or a $C_1$-$C_{60}$ heterocyclic group which is unsubstituted or substituted with at least one $R_{1a}$, $R_{1a}$ may be understood by referring to the description of $A_7$ provided herein, and a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, $C_1$-$C_{60}$ alkoxy group, or any combination thereof;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$Ge(Q_{13})(Q_{14})(Q_{15})$, —$B(Q_{16})(Q_{17})$, —$P(=O)(Q_{18})(Q_{19})$, —$P(Q_{18})(Q_{19})$, or any combination thereof;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$Ge(Q_{23})(Q_{24})(Q_{25})$, —$B(Q_{26})(Q_{27})$, —$P(=O)(Q_{28})(Q_{29})$, —$P(Q_{28})(Q_{29})$, or any combination thereof;

—$N(Q_{31})(Q_{32})$, —$Si(Q_{33})(Q_{34})(Q_{35})$, —$Ge(Q_{33})(Q_{34})(Q_{35})$, —$B(Q_{36})(Q_{37})$, —$P(=O)(Q_{38})(Q_{39})$, or —$P(Q_{38})(Q_{39})$; or any combination thereof, wherein $Q_1$ to $Q_9$, $Q_{11}$ to $Q_{19}$, $Q_{21}$ to $Q_{29}$, and $Q_{31}$ to $Q_{39}$ may each independently be hydrogen; deuterium; —F; —Cl; —Br; —I; a hydroxyl group; a cyano group; a nitro group; an amidino group; a hydrazine group; a hydrazone group; a carboxylic acid group or a salt thereof; a sulfonic acid group or a salt thereof; a phosphoric acid group or a salt thereof; a $C_1$-$C_{60}$ alkyl group, unsubstituted or substituted with deuterium, a $C_1$-$C_{60}$ alkyl group, a $C_6$-$C_{60}$ aryl group, or any combination thereof; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_2$-$C_{10}$ heterocycloalkyl group; a $C_3$-$C_{10}$ cycloalkenyl group; a $C_2$-$C_{10}$ heterocycloalkenyl group; a $C_6$-$C_{60}$ aryl group, unsubstituted or substituted with deuterium, a $C_1$-$C_{60}$ alkyl group, a $C_6$-$C_{60}$ aryl group, or any combination thereof; a $C_6$-$C_{60}$ aryloxy group; a $C_6$-$C_{60}$ arylthio group; a $C_1$-$C_{60}$ heteroaryl group; a monovalent non-aromatic condensed polycyclic group; or a monovalent non-aromatic condensed heteropolycyclic group.

According to an aspect of another embodiment, an organic light-emitting device may include: a first electrode; a second electrode; and an organic layer disposed between the first electrode and the second electrode and including an emission layer, wherein the organic layer includes the composition the first compound and the second compound described above.

The composition may be included in the emission layer of the organic layer, and the first compound included in the emission layer may serve as a dopant.

BRIEF DESCRIPTION OF THE DRAWINGS

These and/or other aspects will become apparent and more readily appreciated from the following description of the embodiments, taken in conjunction with the accompanying drawings in which:

The FIGURE is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween In contrast, when an element is referred to as being "directly on" another element, there are no intervening elements present It will be understood that, although the terms "first," "second," "third" etc. may be used herein to describe various elements, components, regions, layers and/or sections, these elements, components, regions, layers and/or sections should not be limited by these terms These terms are only used to distinguish one element, component, region, layer or section from another element, component, region, layer or section Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." As used herein, the term "and/or" includes any and all combinations of one or more of the associated listed items It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the FIGURES It will be understood that relative terms are intended to encompass different orientations of the device in addition to the orientation depicted in the FIGURES For example, if the device in one of the FIGURES is turned over, elements described as being on the "lower" side of other elements would then be oriented on "upper" sides of the other elements The exemplary term "lower," can therefore, encompasses both an orientation of "lower" and "upper," depending on the particular orientation of the FIGURE Similarly, if the device in one of the FIGURES is turned over, elements described as "below" or "beneath" other elements would then be oriented "above" the other elements The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments As such, variations from the shapes of the illustrations as a result, for example, of manufacturing techniques and/or tolerances, are to be expected Thus, embodiments described herein should not be construed as limited to the particular shapes of regions as illustrated herein but are to include deviations in shapes that result, for example, from manufacturing For example, a region illustrated or described as flat may, typically, have rough and/or nonlinear features Moreover, sharp angles that are illustrated may be rounded Thus, the regions illustrated in the figures are schematic in nature and their shapes are not intended to illustrate the precise shape of a region and are not intended to limit the scope of the present claims.

A composition may include a first compound and a second compound, wherein the first compound may include a compound represented by Formula 1, and the second compound may include a compound represented by Formula 2:

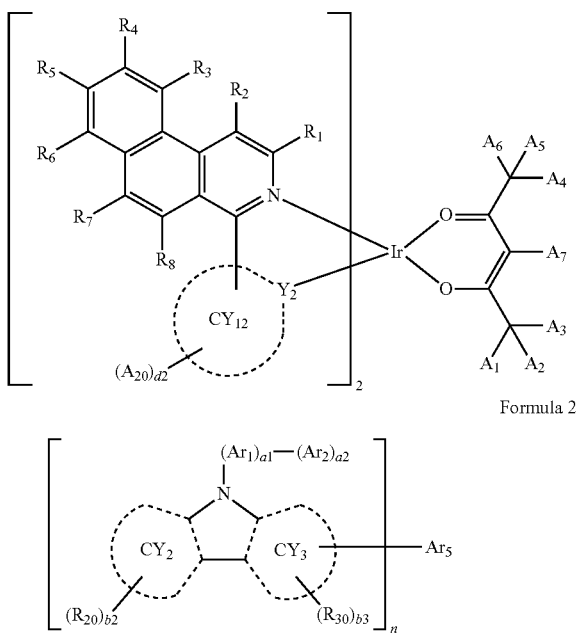

Formula 1

Formula 2

The first compound may include one compound represented by Formula 1 only or at least two different compounds represented by Formula 1.

The second compound may include one compound represented by Formula 2 only or at least two different compounds represented by Formula 2.

Description of Formula 1

$Y_2$ in Formula 1 may be C.

A ring $CY_{12}$ in Formula 1 may be a $C_5$-$C_{60}$ carbocyclic group or a $C_1$-$C_{60}$ heterocyclic group.

For example, the ring $CY_{12}$ in Formula 1 may be i) a third ring, ii) a fourth ring, iii) a condensed cyclic group in which two or more third rings are condensed with each other, iv) a condensed cyclic group in which two or more fourth rings are condensed with each other, or v) a condensed cyclic group in which at least one third ring is condensed with at least one fourth ring, the third ring is a cyclopentane group, a cyclopentadiene group, a furan group, a thiophene group, a pyrrole group, a silole group, an indene group, a benzofuran group, a benzothiophene group, an indole group, a benzosilole group, an oxazole group, an isoxazole group, an oxadiazole group, an isoxadiazole group, an oxatriazole group, an isoxatriazole group, a thiazole group, an isothiazole group, a thiadiazole group, an isothiadiazole group, a thiatriazole group, an isothiatriazole group, a pyrazole group, an imidazole group, a triazole group, a tetrazole group, an azasilole group, a diazasilole group, or a triazasilole group, and the fourth ring may be an adamantane group, a norbornene group, a bicyclo[1.1.1]pentane group, a bicyclo[2.1.1]hexane group, a bicyclo[2.2.1]heptane group (a norbornane group), a bicyclo[2.2.2]octane group, a cyclohexane group, a cyclohexene group, a benzene group, a pyridine group, a pyrimidine group, a pyrazine group, a pyridazine group, or a triazine group.

In one or more embodiments, the ring $CY_{12}$ in Formula 1 may be a cyclopentane group, a cyclohexane group, a cyclohexene group, a benzene group, a naphthalene group, an anthracene group, a phenanthrene group, a triphenylene group, a pyrene group, a chrysene group, a 1,2,3,4-tetrahydronaphthalene group, a thiophene group, a furan group, a pyrrole group, a cyclopentadiene group, a silole group, a borole group, a phosphole group, a selenophene group, a germole group, a benzothiophene group, a benzofuran group, an indole group, an indene group, a benzosilole group, a benzoborole group, a benzophosphole group, a benzoselenophene group, a benzogermole group, a dibenzothiophene group, a dibenzofuran group, a carbazole group, a fluorene group, a dibenzosilole group, a dibenzoborole group, a dibenzophosphole group, a dibenzoselenophene group, a dibenzogermole group, a dibenzothiophene 5-oxide group, 9H-fluorene-9-one group, a dibenzothiophene 5,5-dioxide group, an azabenzothiophene group, an azabenzofuran group, an azaindole group, an azaindene group, an azabenzosilole group, an azabenzoborole group, an azabenzophosphole group, an azabenzoselenophene group, an azabenzogermole group, an azadibenzothiophene group, an azadibenzofuran group, an azacarbazole group, an azafluorene group, an azadibenzosilole group, an azadibenzoborole group, an azadibenzophosphole group, an azadibenzoselenophene group, an azadibenzogermole group, an azadibenzothiophene 5-oxide group, an aza-9H-fluorene-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, a 5,6,7,8-tetrahydroquinoline group, an adamantane group, a norbornane group, or a norbornene group.

In one or more embodiments, the ring $CY_{12}$ may be a benzene group, a naphthalene group, a 1, 2, 3, 4-tetrahydronaphthalene group, a thiophene group, a furan group, a pyrrole group, a cyclopentadiene group, a silole group, a benzothiophene group, a benzofuran group, an indole group, an indene group, a benzosilole group, a dibenzothiophene group, a dibenzofuran group, a carbazole group, a fluorene group, or a dibenzosilole group.

In Formula 1, $R_1$ to $R_8$, $A_{20}$ and $A_1$ to $A_7$ may each independently be hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$Ge(Q_3)(Q_4)(Q_5)$, —$B(Q_6)(Q_7)$, —P(=O)(Q$_8$)(Q$_9$), or —P(Q$_8$)(Q$_9$). Q$_1$ to Q$_9$ may respectively be understood by referring to the descriptions of Q$_1$ to Q$_9$ provided herein.

In embodiments, A$_{20}$ in Formula 1 may include neither a fluoro group (—F) nor a cyano group. For example, A$_{20}$ may be a group that includes neither a fluoro group (—F) nor a cyano group.

In embodiments, in Formula 1, R$_1$ to R$_8$, A$_{20}$ and A$_1$ to A$_7$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —SF$_5$, a C$_1$-C$_{20}$ alkyl group, or a C$_1$-C$_{20}$ alkoxy group;

a C$_1$-C$_{20}$ alkyl group or a C$_1$-C$_{20}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a deuterium-containing C$_1$-C$_{20}$ alkyl group, a fluorinated C$_1$-C$_{20}$ alkyl group, a cyclopentyl group, a cyclohexyl group, a cycloheptyl group, a cyclooctyl group, an adamantyl group, a norbomenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group (a norbornanyl group), a bicyclo[2.2.2]octyl group, a (C$_1$-C$_{20}$ alkyl)cyclopentyl group, a (C$_1$-C$_{20}$ alkyl)cyclohexyl group, a (C$_1$-C$_{20}$ alkyl)cycloheptyl group, a (C$_1$-C$_{20}$ alkyl)cyclooctyl group, a (C$_1$-C$_{20}$ alkyl)adamantyl group, a (C$_1$-C$_{20}$ alkyl)norbomenyl group, a (C$_1$-C$_{20}$ alkyl)cyclopentenyl group, a (C$_1$-C$_{20}$ alkyl)cyclohexenyl group, a (C$_1$-C$_{20}$ alkyl)cycloheptenyl group, a (C$_1$-C$_{20}$ alkyl)bicyclo[1.1.1]pentyl group, a (C$_1$-C$_{20}$ alkyl)bicyclo[2.1.1]hexyl group, a (C$_1$-C$_{20}$ alkyl)bicyclo[2.2.1]heptyl group, a (C$_1$-C$_{20}$ alkyl)bicyclo[2.2.2]octyl group, a silolanyl group, a phenyl group, a (C$_1$-C$_{20}$ alkyl)phenyl group, a biphenyl group, a terphenyl group, a naphthyl group, a 1,2,3,4-tetrahydronaphthyl group, a pyridinyl group, a pyrimidinyl group, or any combination thereof;

a cyclopentyl group, a cyclohexyl group, a cycloheptyl group, a cyclooctyl group, an adamantyl group, a norbornenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a silolanyl group, a phenyl group, a (C$_1$-C$_{20}$ alkyl)phenyl group, a biphenyl group, a terphenyl group, a naphthyl group, a 1,2,3,4-tetrahydronaphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, or an azadibenzothiophenyl group, each unsubstituted or substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a deuterium-containing C$_1$-C$_{20}$ alkyl group, a fluorinated C$_1$-C$_{20}$ alkyl group, a C$_1$-C$_{20}$ alkoxy group, a cyclopentyl group, a cyclohexyl group, a cycloheptyl group, a cyclooctyl group, an adamantyl group, a norbomenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group, a bicyclo[2.2.2]octyl group, a (C$_1$-C$_{20}$ alkyl)cyclopentyl group, a (C$_1$-C$_{20}$ alkyl)cyclohexyl group, a (C$_1$-C$_{20}$ alkyl)cycloheptyl group, a (C$_1$-C$_{20}$ alkyl)cyclooctyl group, a (C$_1$-C$_{20}$ alkyl)adamantyl group, a (C$_1$-C$_{20}$ alkyl)norbomenyl group, a (C$_1$-C$_{20}$ alkyl)cyclopentenyl group, a (C$_1$-C$_{20}$ alkyl)cyclohexenyl group, a (C$_1$-C$_{20}$ alkyl)cycloheptenyl group, a (C$_1$-C$_{20}$ alkyl)bicyclo[1.1.1]pentyl group, a (C$_1$-C$_{20}$ alkyl)bicyclo[2.1.1]hexyl group, a (C$_1$-C$_{20}$ alkyl)bicyclo[2.2.1]heptyl group, a (C$_1$-C$_{20}$ alkyl)bicyclo[2.2.2]octyl group, a silolanyl group, a phenyl group, a (C$_1$-C$_{20}$ alkyl)phenyl group, a biphenyl group, a terphenyl group, a naphthyl group, a 1,2,3,4-tetrahydronaphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, or any combination thereof; or —N(Q$_1$)(Q$_2$), —Si(Q$_3$)(Q$_4$)(Q$_5$), —Ge(Q$_3$)(Q$_4$)(Q$_5$), —B(Q$_6$)(Q$_7$), —P(=O)(Q)(Q), or —P(Q$_5$)(Q$_6$), Q$_1$ to Q$_9$ may each independently be:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H or —CD$_2$CDH$_2$; or an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, a $C_1$-$C_{20}$ alkyl group, a phenyl group, or any combination thereof. Herein, $A_{20}$ in Formula 1 may include neither a fluoro group (—F) nor a cyano group.

In one or more embodiments, $R_1$ to $R_8$, $A_{20}$ and $A_1$ to $A_7$ in Formula 1 may each independently be hydrogen, deuterium, —F, a substituted or unsubstituted $C_1$-$C_{20}$ alkyl group, a substituted or unsubstituted $C_3$-$C_{10}$ cycloalkyl group, a substituted or unsubstituted $C_2$-$C_{10}$ heterocycloalkyl group, a substituted or unsubstituted phenyl group, —Si$(Q_3)(Q_4)(Q_5)$, or —Ge$(Q_3)(Q_4)(Q_5)$. Herein, $A_{20}$ may include neither a fluoro group nor a cyano group.

In one or more embodiments, $R_1$ to $R_8$ and $A_1$ to $A_7$ in Formula 1 may each independently be:

hydrogen, deuterium, or —F;

a $C_1$-$C_{20}$ alkyl group, a $C_3$-$C_{10}$ cycloalkyl group, a $C_2$-$C_{10}$ heterocycloalkyl group, or a phenyl group, each unsubstituted or substituted with deuterium, —F, $C_1$-$C_{20}$ alkyl group, a $C_3$-$C_{10}$ cycloalkyl group, a $C_2$-$C_{10}$ heterocycloalkyl group, a phenyl group, or any combination thereof; or —Si$(Q_3)(Q_4)(Q_5)$, or —Ge$(Q_3)(Q_4)(Q_5)$.

In one or more embodiments, $A_{20}$ in Formula 1 may be:

hydrogen or deuterium;

a $C_1$-$C_{20}$ alkyl group, a $C_3$-$C_{10}$ cycloalkyl group, a $C_2$-$C_{10}$ heterocycloalkyl group, or a phenyl group, each unsubstituted or substituted with deuterium, a $C_1$-$C_{20}$ alkyl group, a $C_3$-$C_{10}$ cycloalkyl group, a $C_2$-$C_{10}$ heterocycloalkyl group, a phenyl group, or any combination thereof; or —Si$(Q_3)(Q_4)(Q_5)$, or —Ge$(Q_3)(Q_4)(Q_5)$.

The designation d2 in Formula 1 indicates the number of $A_{20}$(s), and may be an integer from 0 to 10. When d2 is 2 or more, two or more $A_{20}$(s) may be identical to or different from each other. For example, d2 may be an integer from 0 to 6.

In an exemplary embodiment, at least one of $R_1$ to $R_8$, $A_{20}$ or any combination thereof in Formula 1 may include at least one fluoro group (—F).

In an exemplary embodiment, at least one of $R_1$ to $R_8$ (for example, at least one of $R_2$ to $R_8$, or at least one of $R_3$ to $R_8$) of Formula 1 may include at least one fluoro group (—F).

In an exemplary embodiment, at least one of $R_1$ to $R_8$ (for example, at least one of $R_2$ to $R_8$, or at least one of $R_3$ to $R_8$) of Formula 1 may be a group including at least one fluoro group (—F).

In one or more embodiments, at least one of $R_1$ to $R_8$ in Formula 1 may each independently be:

a fluoro group (—F); or a fluorinated $C_1$-$C_{20}$ alkyl group, a fluorinated $C_3$-$C_{10}$ cycloalkyl group, a fluorinated $C_2$-$C_{10}$ heterocycloalkyl group, or a fluorinated phenyl group, each unsubstituted or substituted with deuterium, a $C_1$-$C_{20}$ alkyl group, a $C_3$-$C_{10}$ cycloalkyl group, a $C_2$-$C_{10}$ heterocycloalkyl group, a phenyl group, or any combination thereof.

In one or more embodiments, at least one of $A_1$ to $A_5$ in Formula 1 may each independently be a substituted or unsubstituted $C_2$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

In one or more embodiments, at least one of $A_1$ to $A_6$ in Formula 1 may each independently be a substituted or unsubstituted $C_2$-$C_{60}$ alkyl group, a substituted or unsubstituted $C_3$-$C_{10}$ cycloalkyl group, or a substituted or unsubstituted $C_2$-$C_{10}$ heterocycloalkyl group.

In one or more embodiments, at least one of $A_1$ to $A_3$ and at least one of $A_4$ to $A_6$ in Formula 1 may each independently be a substituted or unsubstituted $C_2$-$C_{60}$ alkyl group, a substituted or unsubstituted $C_3$-$C_{10}$ cycloalkyl group, or a substituted or unsubstituted $C_2$-$C_{10}$ heterocycloalkyl group.

In one or more embodiments, at least one of $A_1$ to $A_6$ in Formula 1 may each independently be a $C_2$-$C_{60}$ alkyl group, a $C_3$-$C_{10}$ cycloalkyl group, or a $C_2$-$C_{10}$ heterocycloalkyl group, each unsubstituted or substituted with deuterium, —F, a $C_1$-$C_{20}$ alkyl group, a $C_3$-$C_{10}$ cycloalkyl group, a $C_2$-$C_{10}$ heterocycloalkyl group, or any combination thereof.

In one or more embodiments, $A_1$ to $A_6$ in Formula 1 may each independently be a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

In one or more embodiments, $A_1$ to $A_6$ in Formula 1 may each independently be a substituted or unsubstituted $C_1$-$C_{60}$ alkyl group, a substituted or unsubstituted $C_3$-$C_{10}$ cycloalkyl group, or a substituted or unsubstituted $C_2$-$C_{10}$ heterocycloalkyl group.

In one or more embodiments, $A_1$ to $A_5$ in Formula 1 may each independently be a $C_1$-$C_{60}$ alkyl group, a $C_3$-$C_{10}$ cycloalkyl group, or a $C_2$-$C_{10}$ heterocycloalkyl group, each unsubstituted or substituted with deuterium, —F, a $C_1$-$C_{20}$ alkyl group, a $C_3$-$C_{10}$ cycloalkyl group, a $C_2$-$C_{10}$ heterocycloalkyl group, or any combination thereof.

In one or more embodiments, $A_7$ in Formula 1 may be hydrogen or deuterium.

In one or more embodiments, $A_7$ in Formula 1 may not be hydrogen.

In one or more embodiments, $A_7$ in Formula 1 may be a substituted or unsubstituted $C_1$-$C_{60}$ alkyl group, a substituted or unsubstituted $C_3$-$C_{10}$ cycloalkyl group, or a substituted or unsubstituted $C_2$-$C_{10}$ heterocycloalkyl group.

In one or more embodiments, $A_7$ in Formula 1 may be a $C_1$-$C_{60}$ alkyl group, a $C_3$-$C_{10}$ cycloalkyl group, or a $C_2$-$C_{10}$ heterocycloalkyl group, each unsubstituted or substituted with deuterium, —F, a $C_1$-$C_{20}$ alkyl group, a $C_3$-$C_{10}$ cycloalkyl group, a $C_2$-$C_{10}$ heterocycloalkyl group, or any combination thereof.

For example, $R_1$ to $R_8$, $A_{20}$ and $A_1$ to $A_7$ in Formula 1 may each independently be hydrogen, deuterium, —F, —$CH_3$, —$CD_3$, —$CD_2H$, —$CDH_2$, —$CF_3$, —$CF_2H$, —$CFH_2$, a group represented by one of Formulae 9-1 to 9-39, a group represented by one of Formulae 9-1 to 9-39 in which at least one hydrogen is substituted with deuterium, a group represented by one of Formulae 9-1 to 9-39 in which at least one hydrogen is substituted with —F, a group represented by one of Formulae 9-201 to 9-233, a group represented by one of Formulae 9-201 to 9-233 in which at least one hydrogen is substituted with deuterium, a group represented by one of Formulae 9-201 to 9-233 in which at least one hydrogen is substituted with —F, a group represented by one of Formulae 10-1 to 10-126, a group represented by one of Formulae 10-1 to 10-126 in which at least one hydrogen is substituted with deuterium, a group represented by one of Formulae 10-1 to 10-126 in which at least one hydrogen is substituted with —F, a group represented by one of Formulae 10-201 to 10-343, a group represented by one of Formulae 10-201 to 10-343 in which at least one hydrogen is substituted with deuterium, a group represented by one of Formulae 10-201 to 10-343 in which at least one hydrogen is substituted with —F, —$Si(Q_3)(Q_4)(Q_5)$, or —$Ge(Q_3)(Q_4)(Q_5)$ (herein $Q_3$ to $Q_5$ are the same as described in the present specification), and at least one of $R_1$ to $R_8$ (for example, at least one of $R_2$ to $R_8$, or at least one of $R_3$ to $R_6$) may be —F, —$CF_3$, —$CF_2H$, —$CFH_2$, a group represented by one of Formulae 9-1 to 9-39 in which at least one hydrogen is substituted with —F, a group represented by one of Formulae 9-201 to 9-233 in which at least one hydrogen is substituted with —F, a group represented by one of Formulae 10-1 to 10-126 in which at least one hydrogen is substituted with —F, or a group represented by one of Formulae 10-201 to 10-343 in which at least one hydrogen is substituted with —F.

In one or more embodiments, $A_{20}$ in Formula 1 may be hydrogen, deuterium, —$CH_3$, —$CD_3$, —$CD_2H$, —$CDH_2$, a group represented by one of Formulae 9-1 to 9-39, a group represented by one of Formulae 9-1 to 9-39 in which at least one hydrogen is substituted with deuterium, a group represented by one of Formulae 9-201 to 9-233, a group represented by one of Formulae 9-201 to 9-233 in which at least one hydrogen is substituted with deuterium, a group represented by one of Formulae 10-1 to 10-126, a group represented by one of Formulae 10-1 to 10-126 in which at least one hydrogen is substituted with deuterium, a group represented by one of Formulae 10-201 to 10-343, a group represented by one of Formulae 10-201 to 10-343 in which at least one hydrogen is substituted with deuterium, —Si($Q_3$)($Q_4$)($Q_5$), or —Ge($Q_3$)($Q_4$)($Q_5$) (herein $Q_3$ to $Q_5$ are the same as described in the present specification).

In one or more embodiments, at least one of $A_1$ to $A_6$ in Formula 1 may each independently be a group represented by one of Formulae 9-1 to 9-39, a group represented by one of Formulae 9-1 to 9-39 in which at least one hydrogen is substituted with deuterium, a group represented by one of Formulae 9-1 to 9-39 in which at least one hydrogen is substituted with —F, a group represented by one of Formulae 9-201 to 9-233, a group represented by one of Formulae 9-201 to 9-233 in which at least one hydrogen is substituted with deuterium, a group represented by one of Formulae 9-201 to 9-233 in which at least one hydrogen is substituted with —F, a group represented by one of Formulae 10-1 to 10-126, a group represented by one of Formulae 10-1 to 10-126 in which at least one hydrogen is substituted with deuterium, a group represented by one of Formulae 10-1 to 10-126 in which at least one hydrogen is substituted with —F, a group represented by one of Formulae 10-201 to 10-343, a group represented by one of Formulae 10-201 to 10-343 in which at least one hydrogen is substituted with deuterium, or a group represented by one of Formulae 10-201 to 10-343 in which at least one hydrogen is substituted with —F.

In one or more embodiments, $A_1$ to $A_5$ in Formula 1 may each independently be —$CH_3$, —$CD_3$, —$CD_2H$, —$CDH_2$, —$CF_3$, —$CF_2H$, —$CFH_2$, a group represented by one of Formulae 9-1 to 9-39, a group represented by one of Formulae 9-1 to 9-39 in which at least one hydrogen is substituted with deuterium, a group represented by one of Formulae 9-1 to 9-39 in which at least one hydrogen is substituted with —F, a group represented by one of Formulae 9-201 to 9-233, a group represented by one of Formulae 9-201 to 9-233 in which at least one hydrogen is substituted with deuterium, a group represented by one of Formulae 9-201 to 9-233 in which at least one hydrogen is substituted with —F, a group represented by one of Formulae 10-1 to 10-126, a group represented by one of Formulae 10-1 to 10-126 in which at least one hydrogen is substituted with deuterium, a group represented by one of Formulae 10-1 to 10-126 in which at least one hydrogen is substituted with —F, a group represented by one of Formulae 10-201 to 10-343, a group represented by one of Formulae 10-201 to 10-343 in which at least one hydrogen is substituted with deuterium, or a group represented by one of Formulae 10-201 to 10-343 in which at least one hydrogen is substituted with —F:

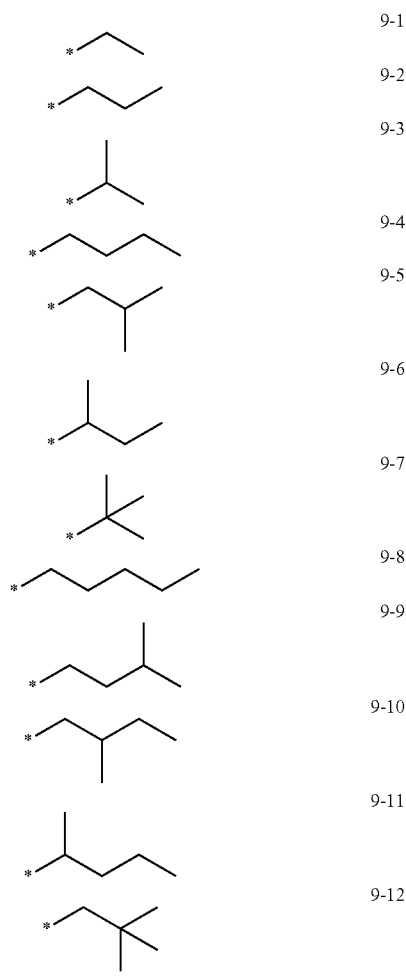

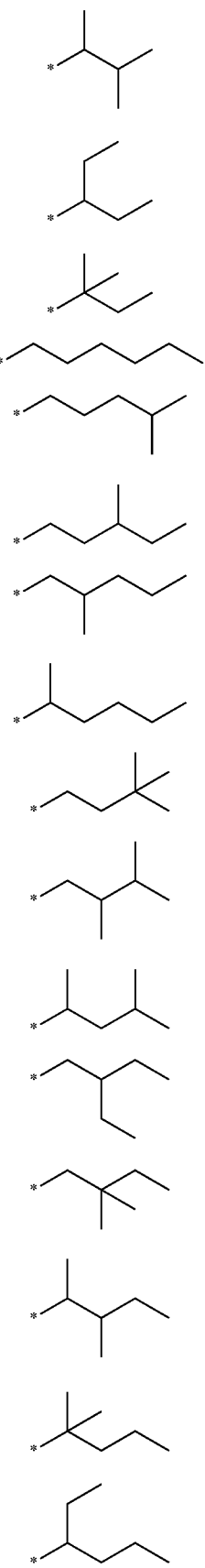
9-13
9-14
9-15
9-16
9-17
9-18
9-19
9-20
9-21
9-22
9-23
9-24
9-25
9-26
9-27
9-28
9-29 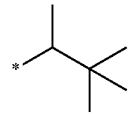
9-30 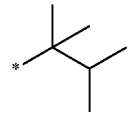
9-31 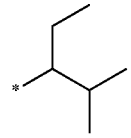
9-32 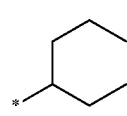
9-33 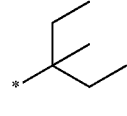
9-34 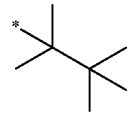
9-35 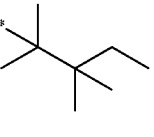
9-36 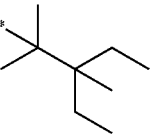
9-37 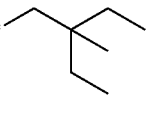
9-38 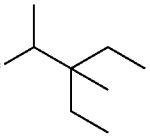
9-39 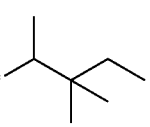
9-201 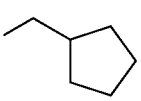

| | |
|---|---|
| 9-202 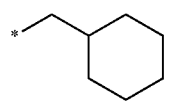 | 9-213 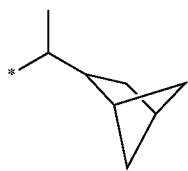 |
| 9-203  | 9-214 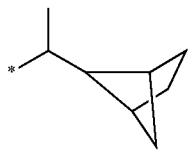 |
| 9-204 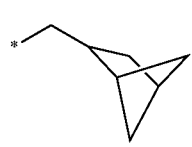 | 9-215 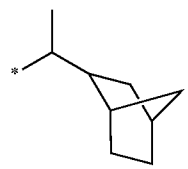 |
| 9-205 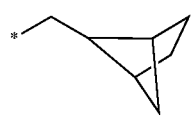 | 9-216 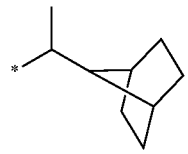 |
| 9-206 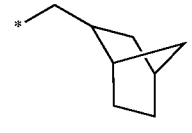 | 9-217 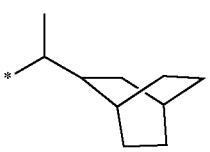 |
| 9-207 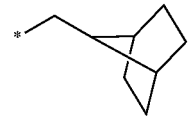 | 9-218 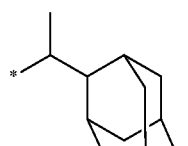 |
| 9-208 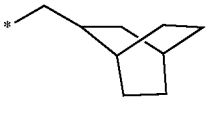 | 9-219 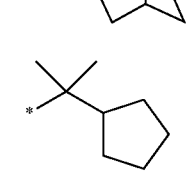 |
| 9-209 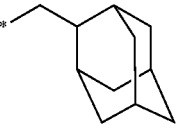 | 9-220 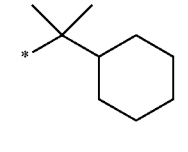 |
| 9-210 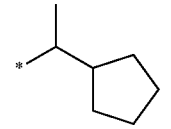 | 9-221  |
| 9-211 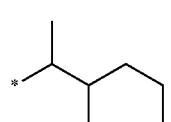 | 9-222 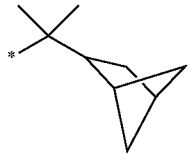 |
| 9-212 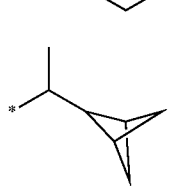 | |

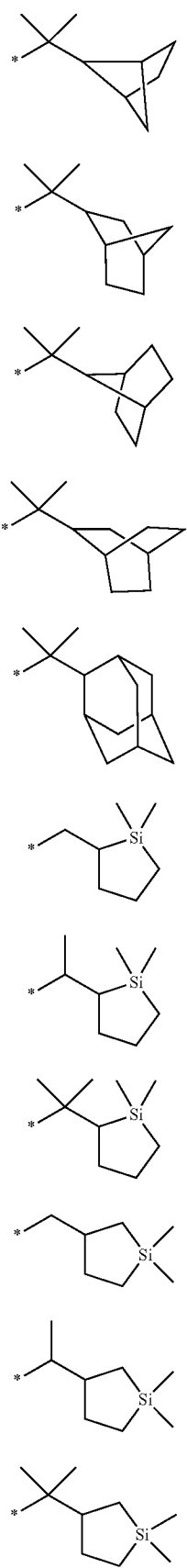
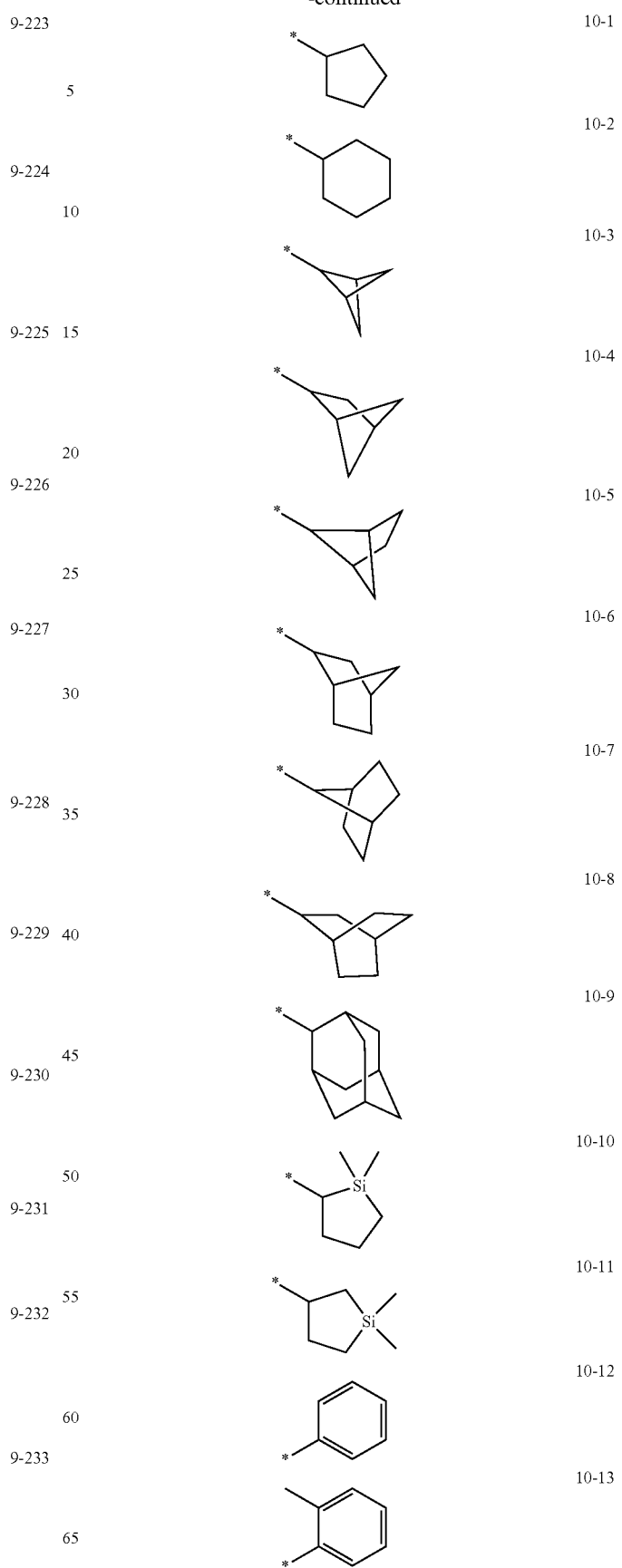

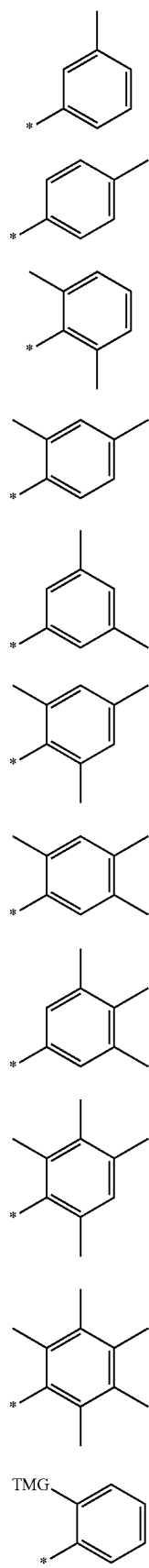
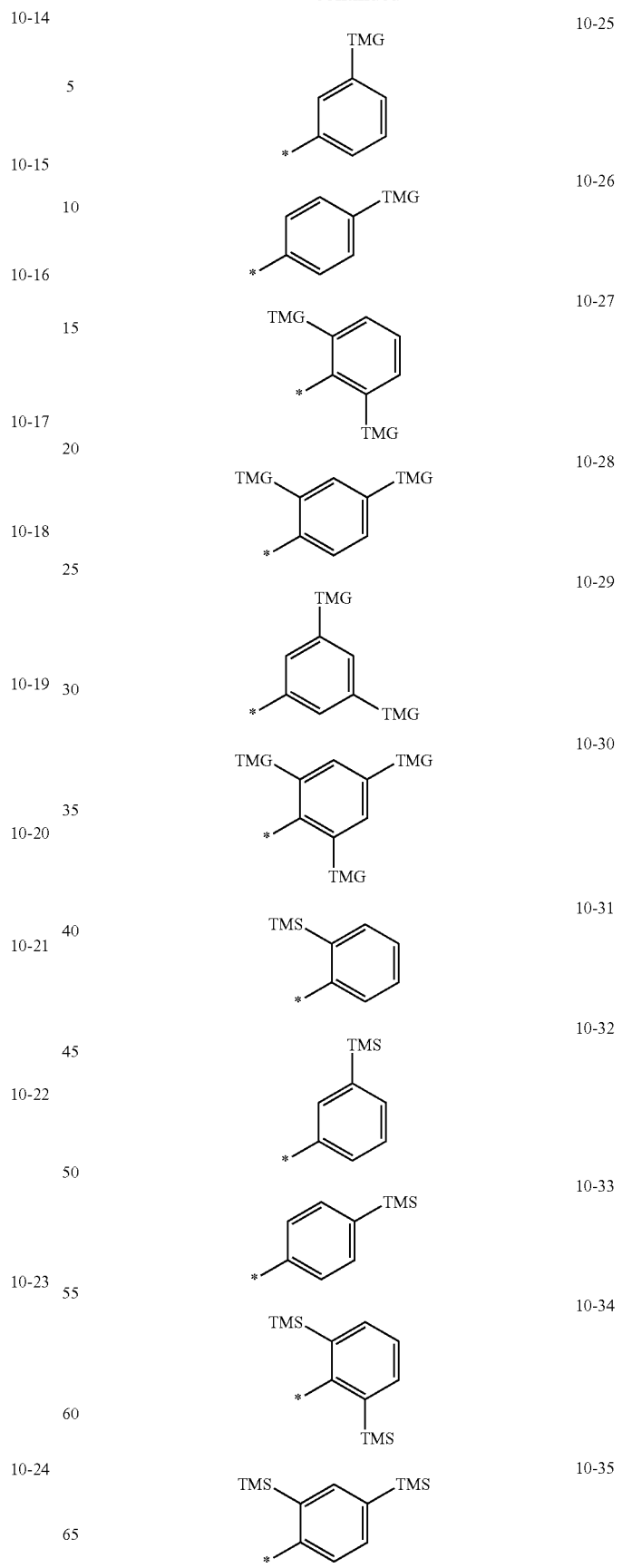

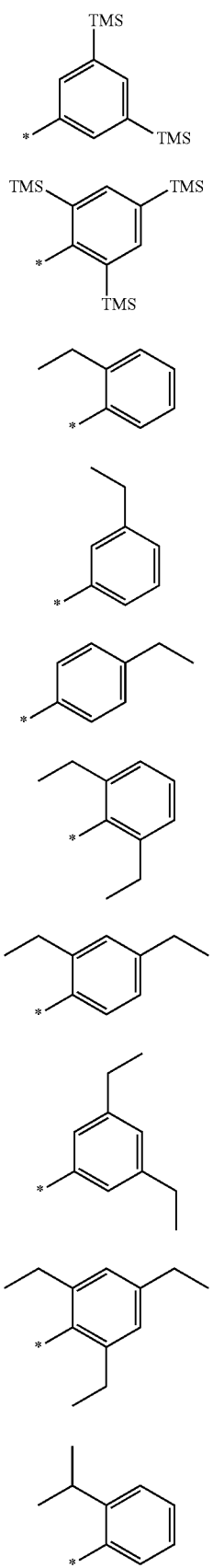
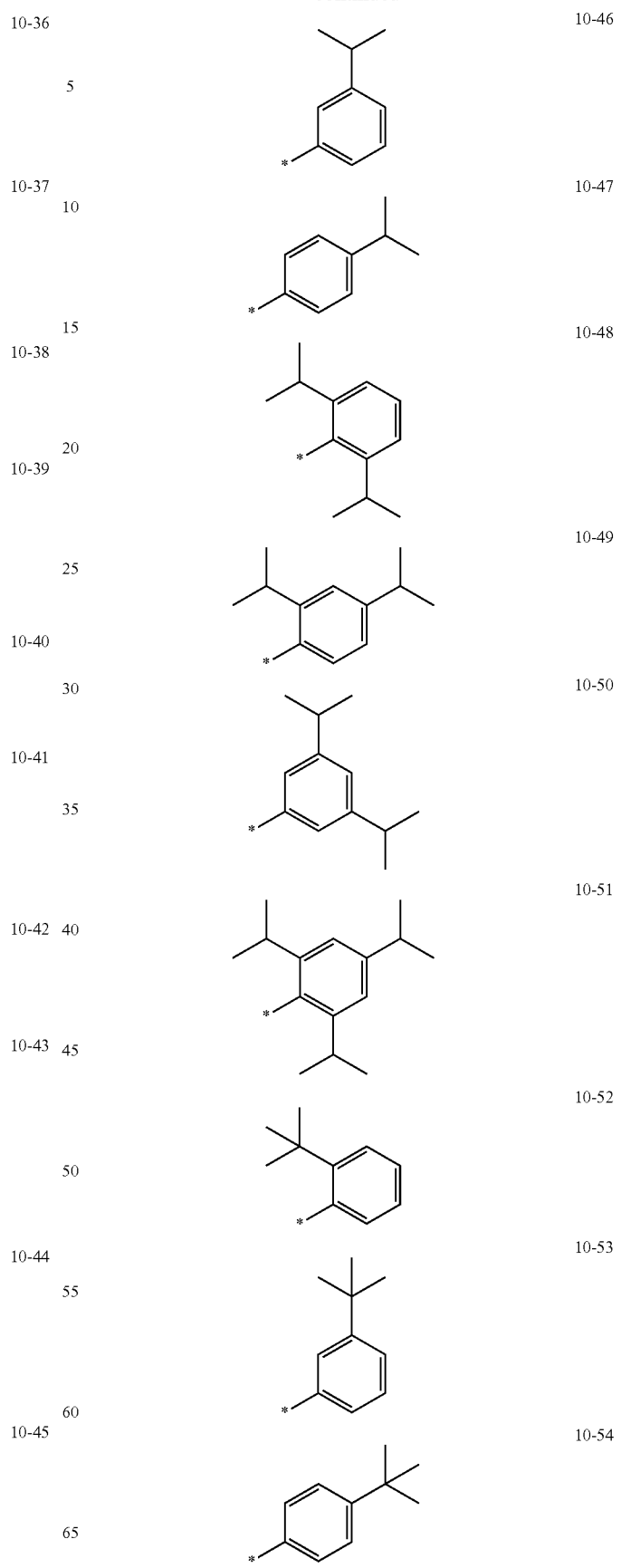

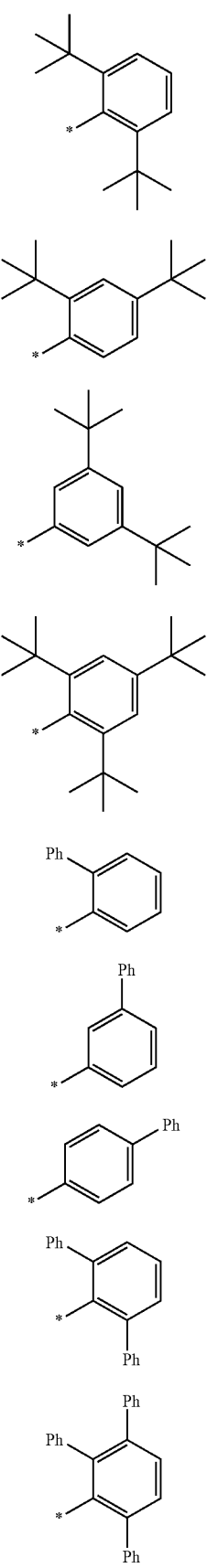
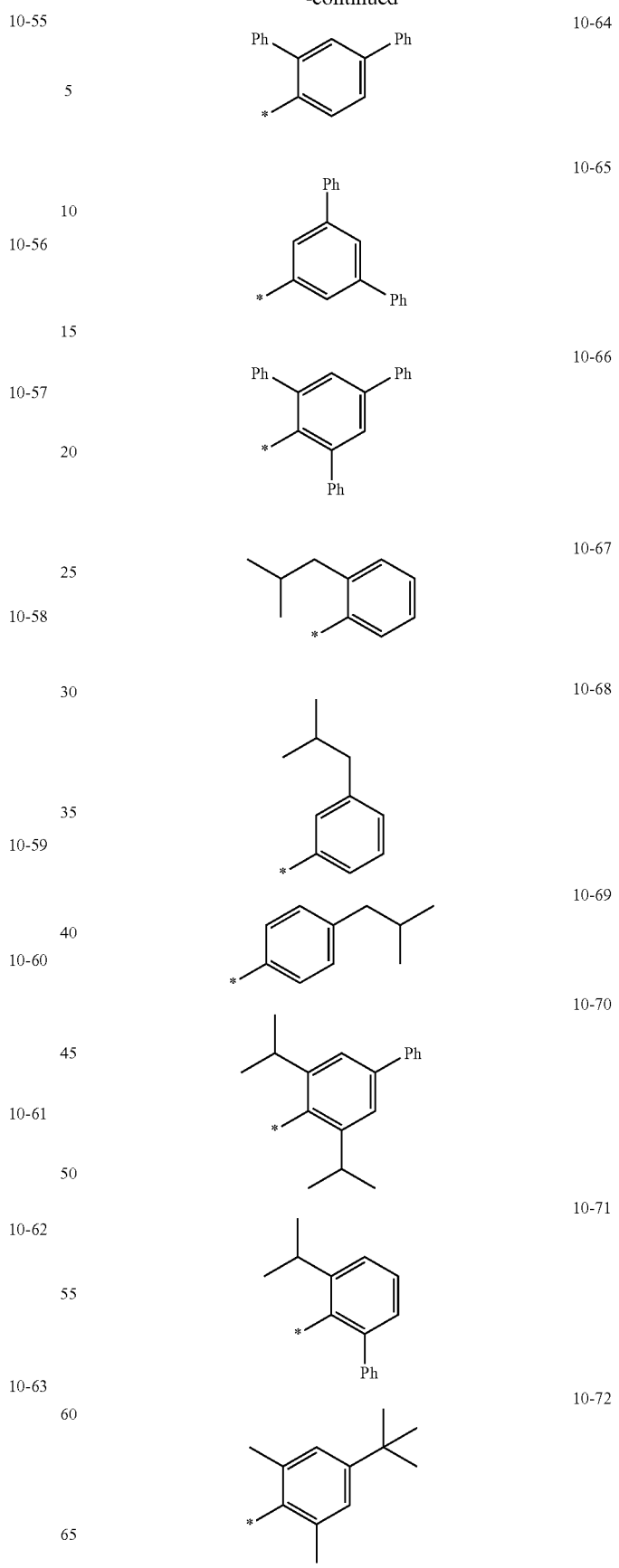

10-73 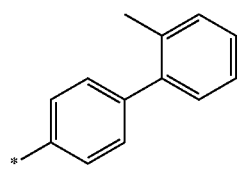
10-74 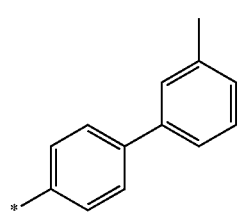
10-75 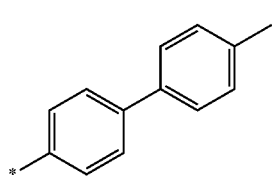
10-76 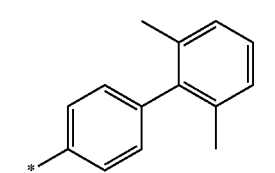
10-77 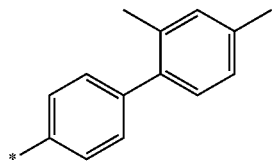
10-78 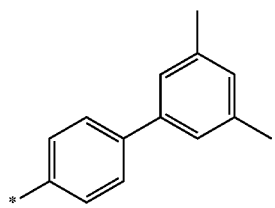
10-79 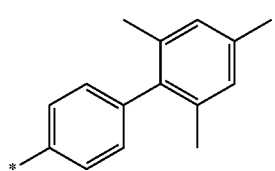
10-80 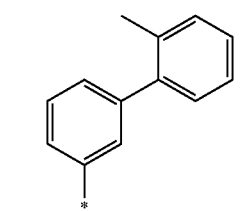
10-81 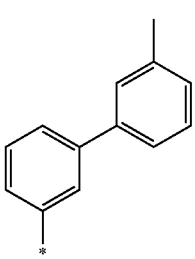
10-82 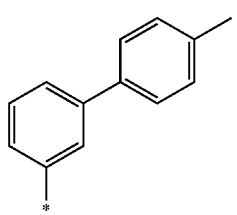
10-83 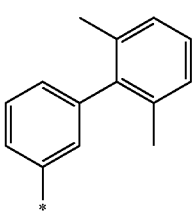
10-84 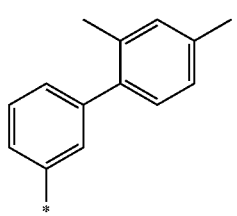
10-85 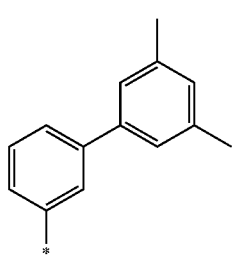
10-86 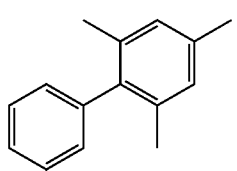
10-87 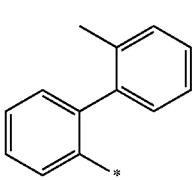

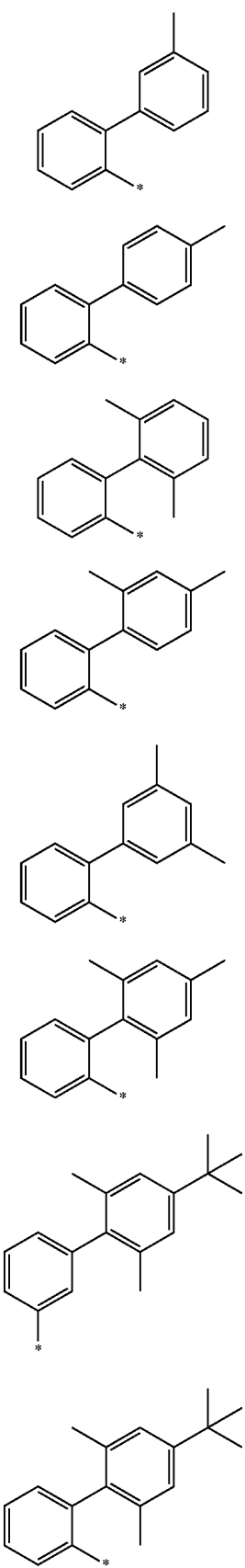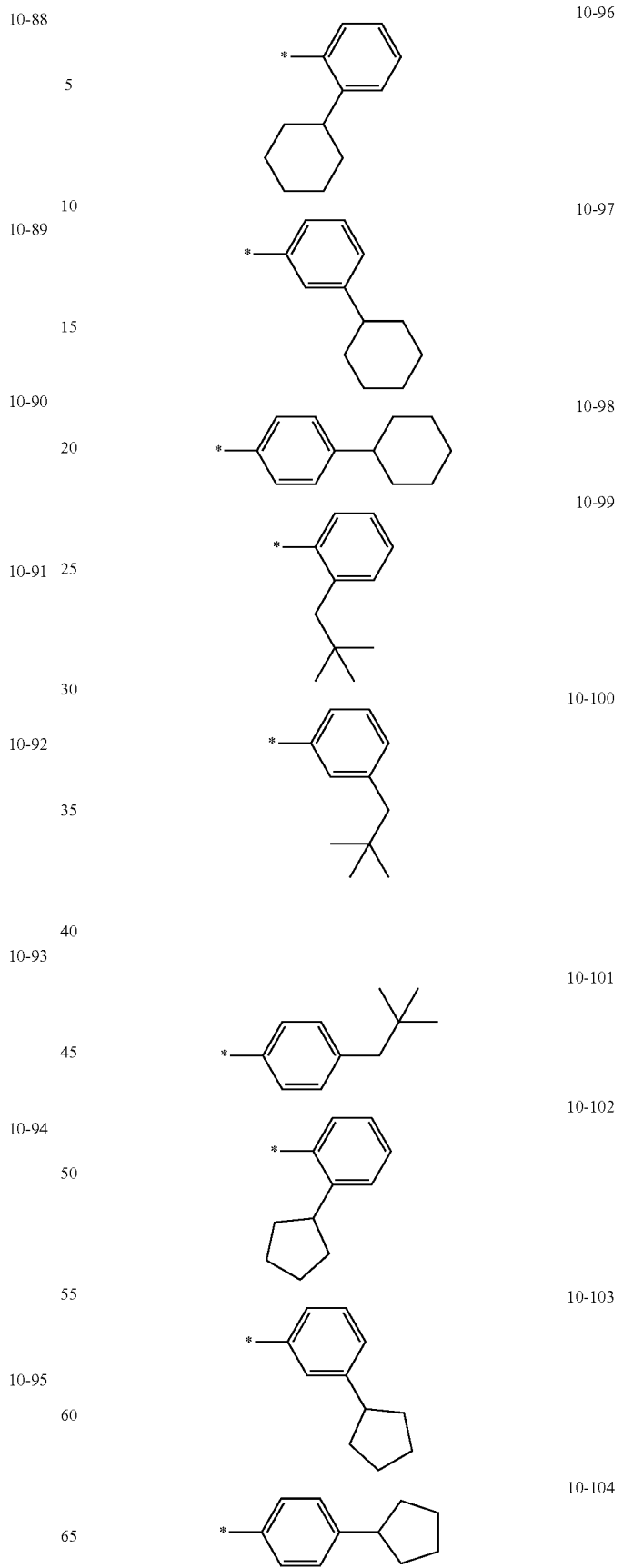

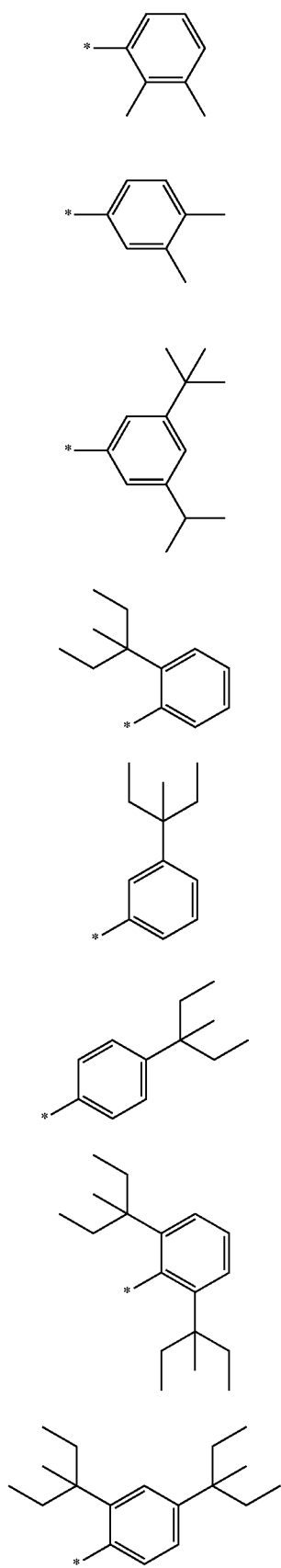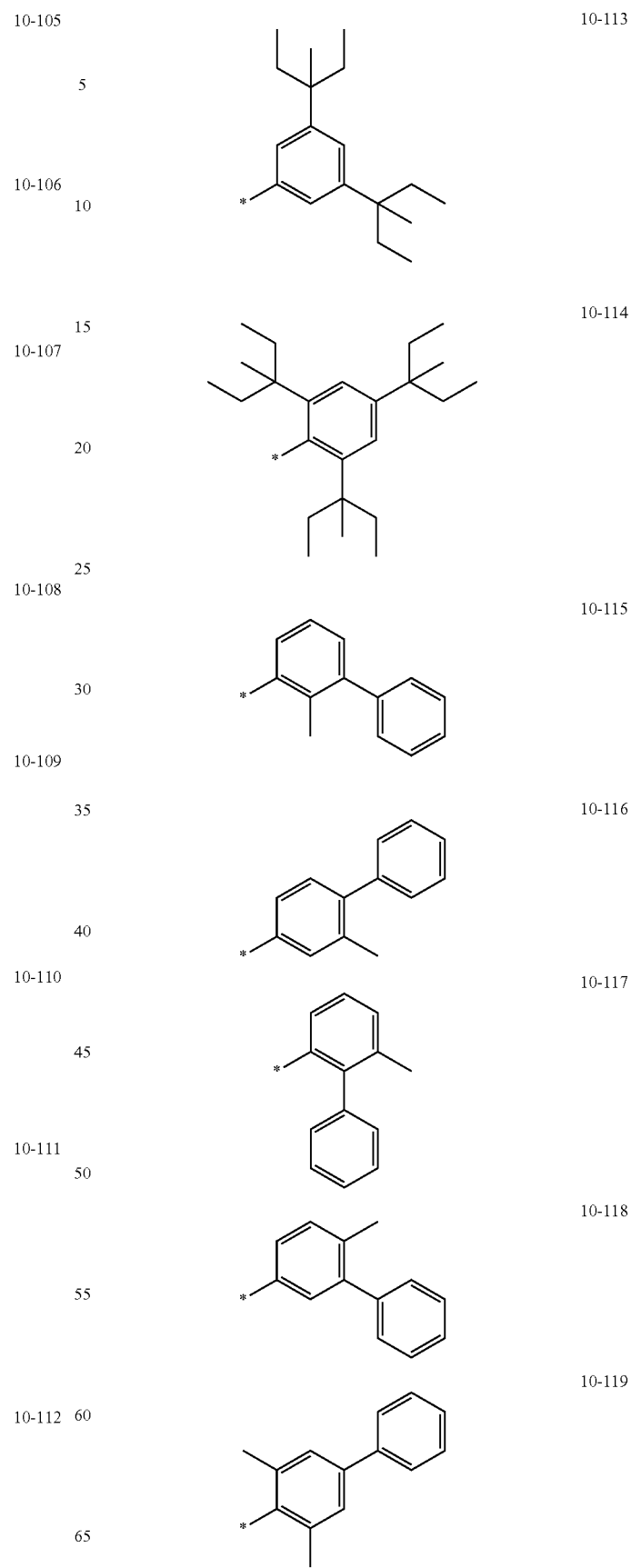

-continued
10-120
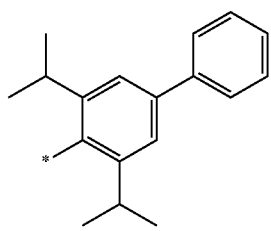
10-121
10-122
10-123
10-124
10-125
-continued
10-126
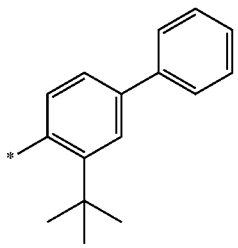
10-201
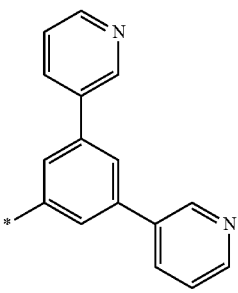
10-202
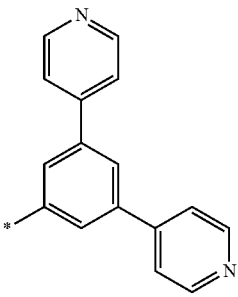
10-203
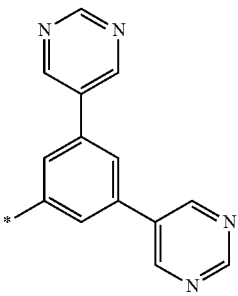
10-204
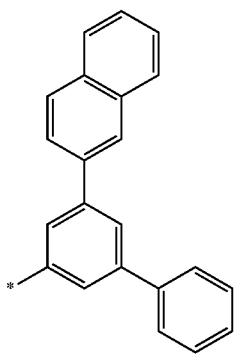

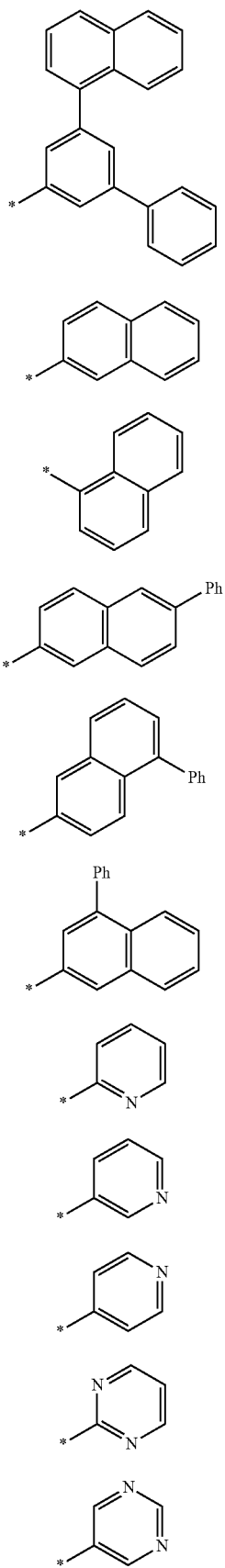
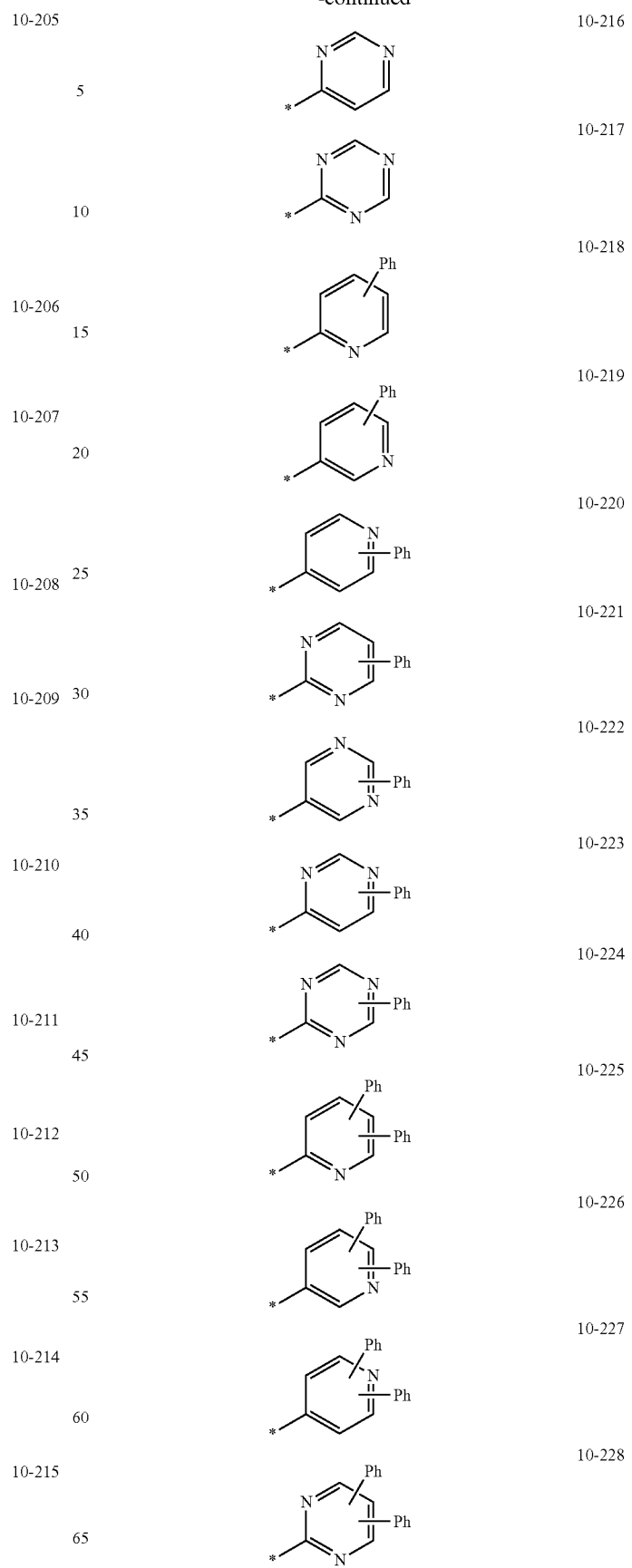

| | |
|---|---|
| 10-229 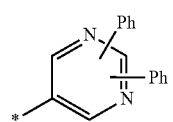 | 10-238 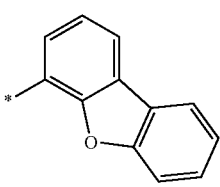 |
| 10-230 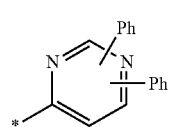 | 10-239 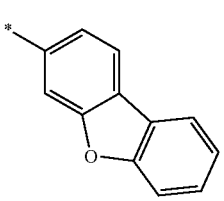 |
| 10-231 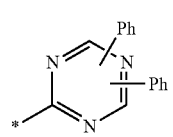 | 10-240 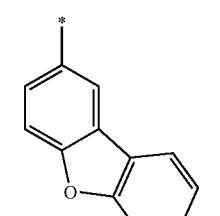 |
| 10-232 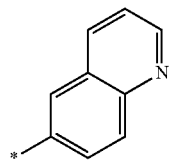 | 10-241 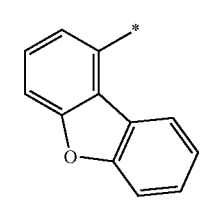 |
| 10-233 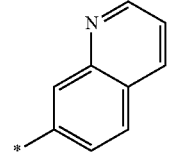 | 10-242 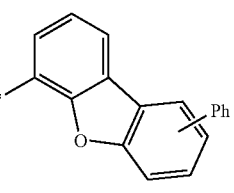 |
| 10-234 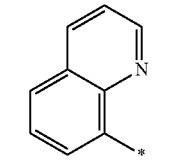 | 10-243 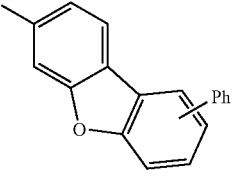 |
| 10-235 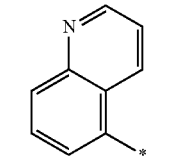 | 10-244 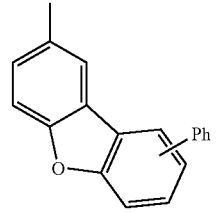 |
| 10-236 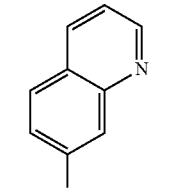 | 10-245 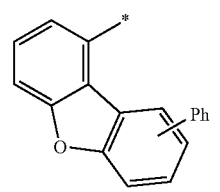 |
| 10-237 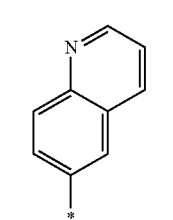 | |

-continued
10-246 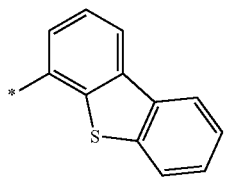
10-247 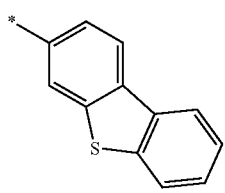
10-248 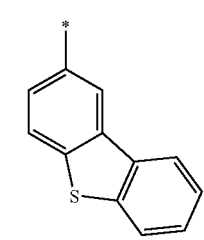
10-249 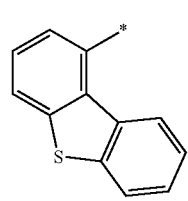
10-250 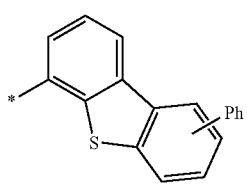
10-251 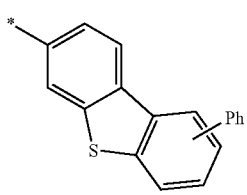
10-252 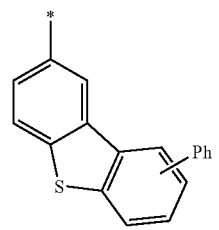
10-253 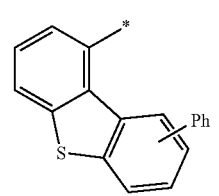
-continued
10-254 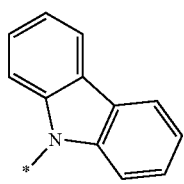
10-255 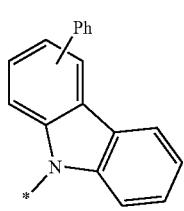
10-256 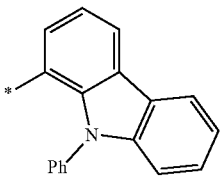
10-257 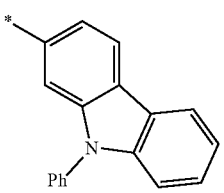
10-258 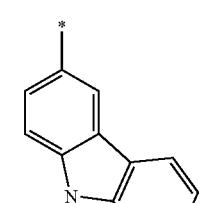
10-259 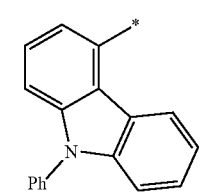
10-260 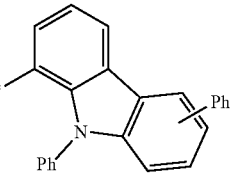
10-261 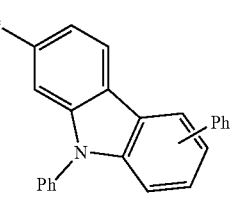

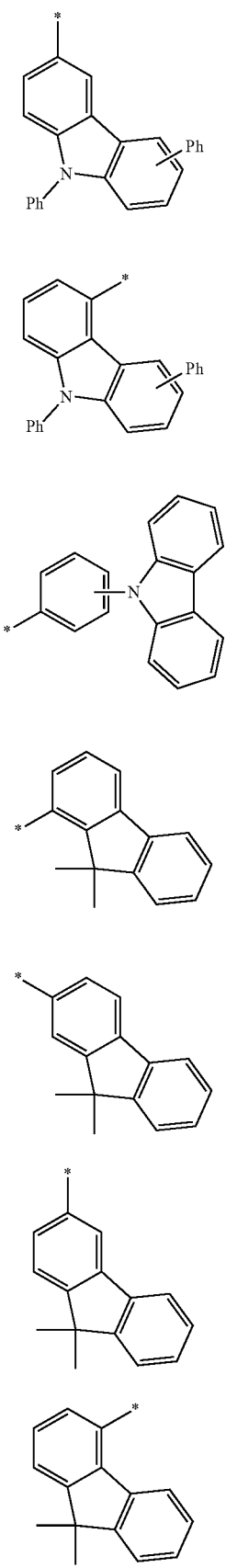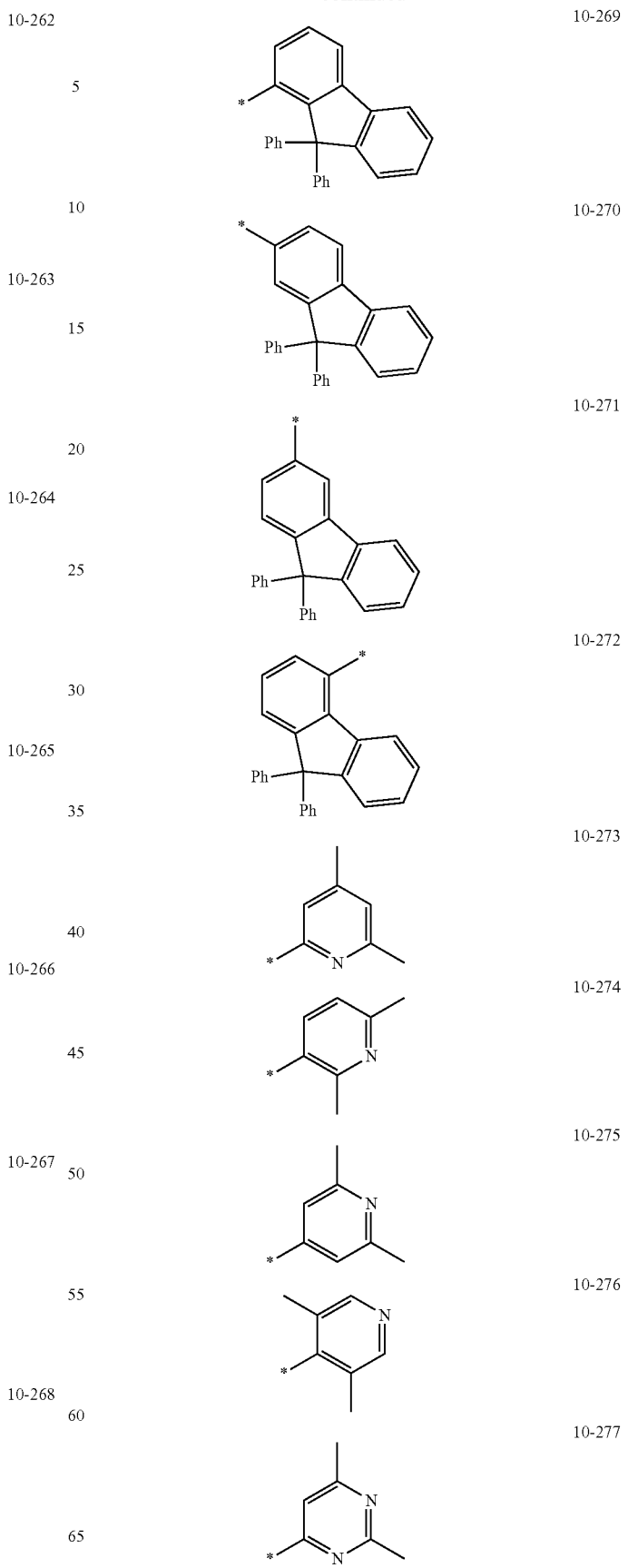

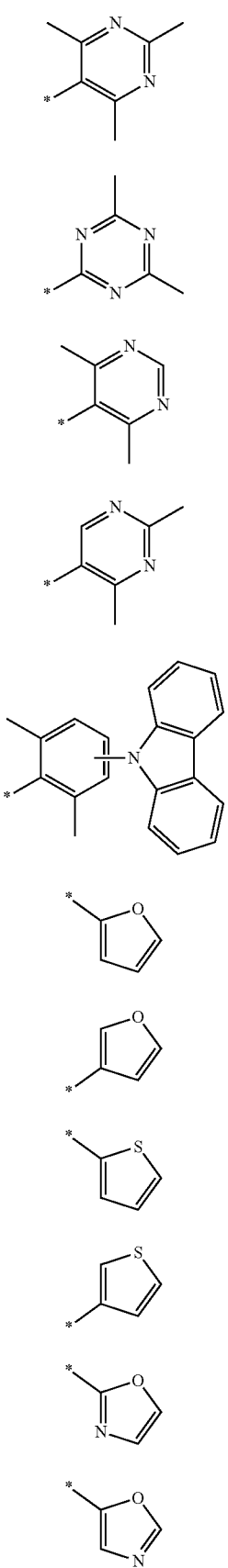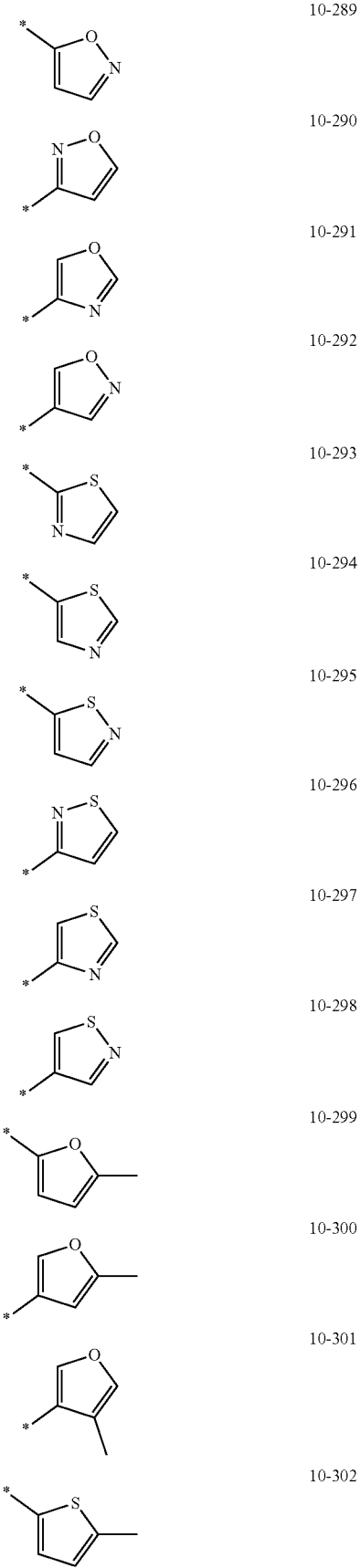

10-303 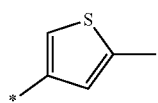
10-304 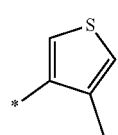
10-305 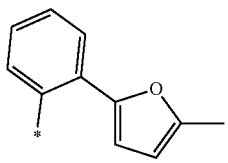
10-306 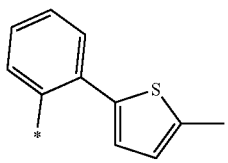
10-307 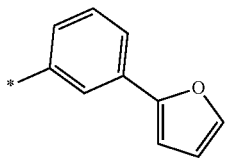
10-308 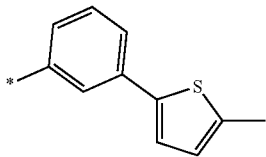
10-309 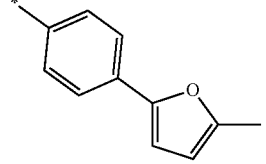
10-310 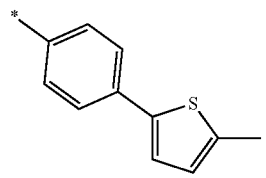
10-311 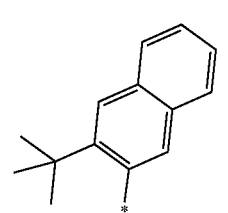
10-312 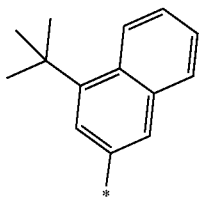
10-313 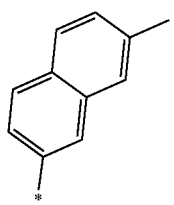
10-314 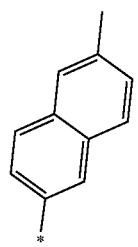
10-315 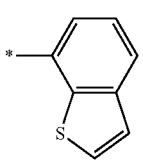
10-316 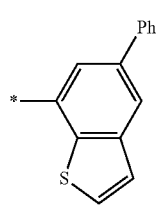
10-317 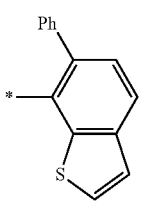
10-318 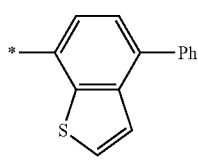
10-319 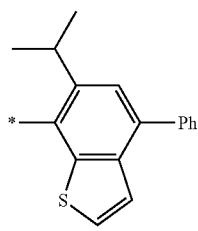

10-320 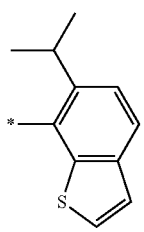
10-321 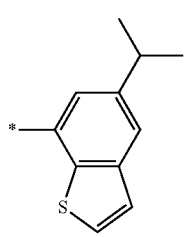
10-322 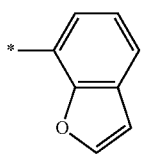
10-323 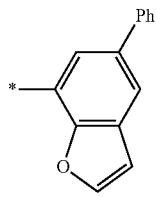
10-324 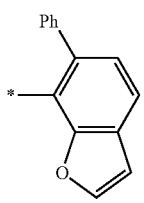
10-325 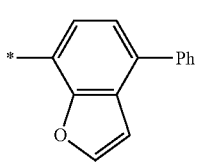
10-326 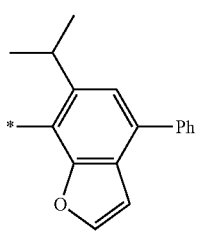
10-327 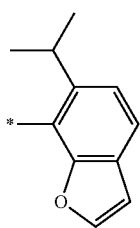
10-328 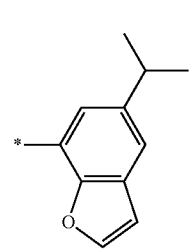
10-329 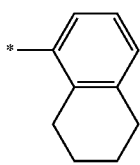
10-330 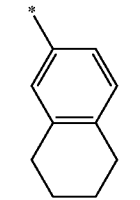
10-331 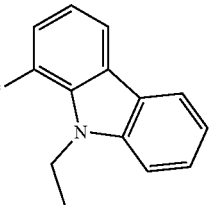
10-332 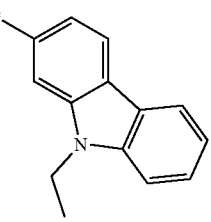
10-333 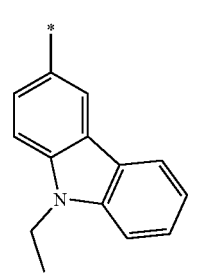

10-334 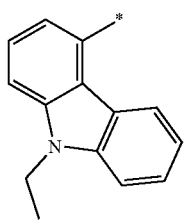

10-335 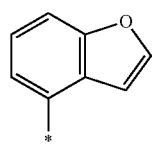

10-336 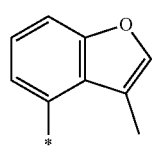

10-337 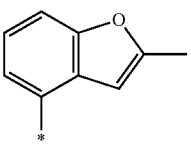

10-338 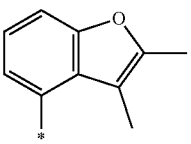

10-339 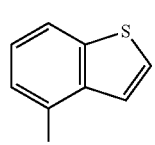

10-340 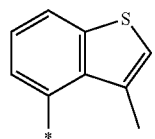

10-341 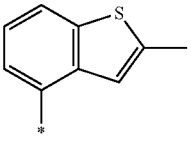

10-342 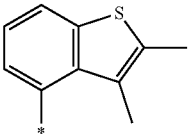

10-343 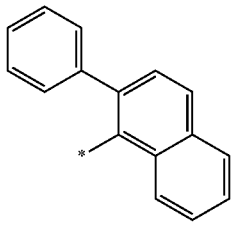

* in Formulae 9-1 to 9-39, 9-201 to 9-233, 10-1 to 10-126, and 10-201 to 10-343 indicates a binding site to a neighboring atom, Ph is a phenyl group, TMS is a trimethylsilyl group, and TMG is a trimethylgermyl group.

The "group represented by one of Formulae 9-1 to 9-39 in which at least one hydrogen is substituted with deuterium" and the "group represented by one of Formulae 9-201 to 9-233 in which at least one hydrogen is substituted with deuterium" may each be, for example, a group represented by one of Formulae 9-501 to 9-514 and 9-601 to 9-635:

9-501 

9-502 

9-503 

9-504 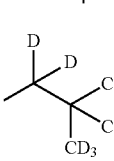

9-505 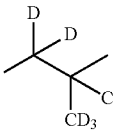

9-506 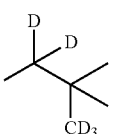

9-507 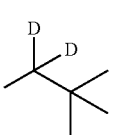

9-508 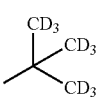

9-509 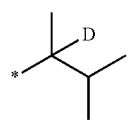
9-510 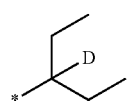
9-511 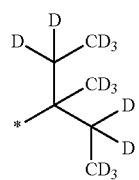
9-512 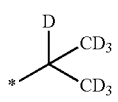
9-513 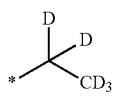
9-514 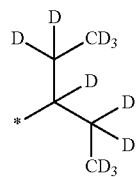
9-601 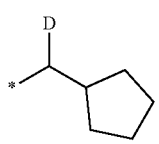
9-602 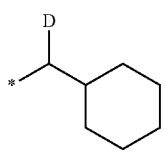
9-603 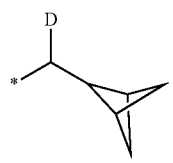
9-604 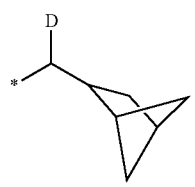
9-605 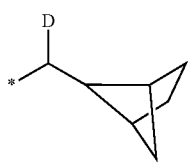
9-606 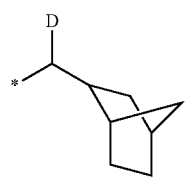
9-607 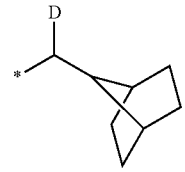
9-608 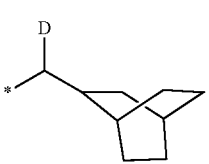
9-609 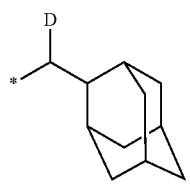
9-610 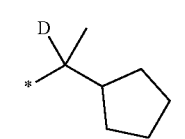
9-611 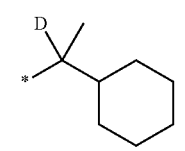
9-612 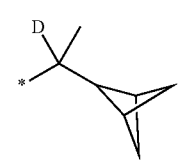
9-613 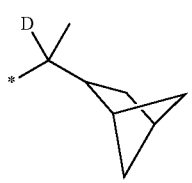

| | |
|---|---|
| 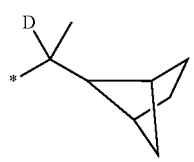 | 9-614 |
| 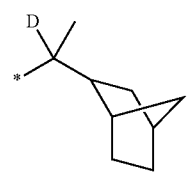 | 9-615 |
| 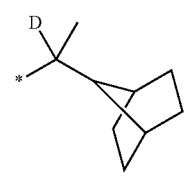 | 9-616 |
| 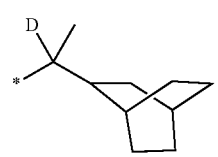 | 9-617 |
| 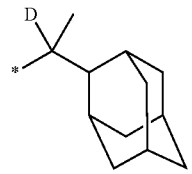 | 9-618 |
| 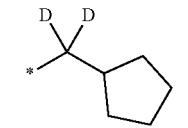 | 9-619 |
| 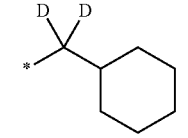 | 9-620 |
| 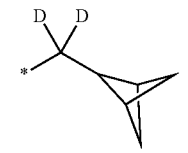 | 9-621 |
| 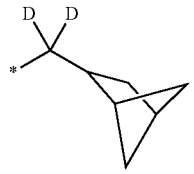 | 9-622 |
| 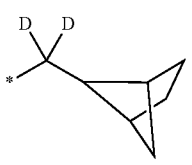 | 9-623 |
| 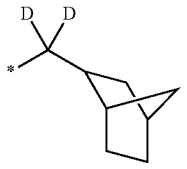 | 9-624 |
| 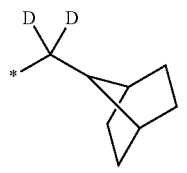 | 9-625 |
| 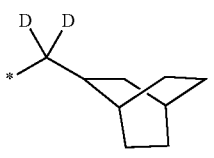 | 9-626 |
| 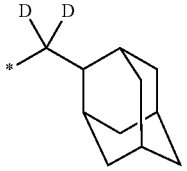 | 9-627 |
| 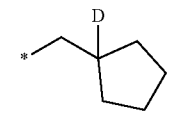 | 9-628 |
| 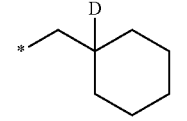 | 9-629 |
| 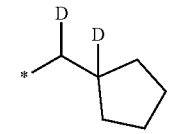 | 9-630 |
| 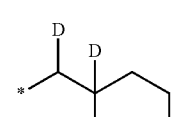 | 9-631 |
| 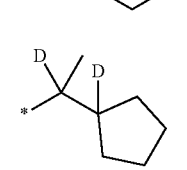 | 9-632 |

9-633 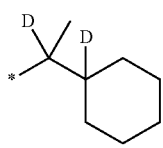

9-634 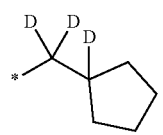

9-635 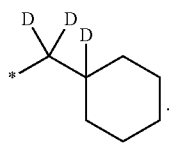

The "group represented by one of Formulae 9-1 to 9-39 in which at least one hydrogen is substituted with —F" and the "group represented by one of Formulae 9-201 to 9-233 in which at least one hydrogen is substituted with —F" may each be, for example, a group represented by one of Formulae 9-701 to 9-710:

9-701 

9-702 

9-703 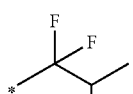

9-704 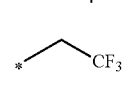

9-705 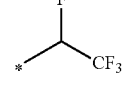

9-706 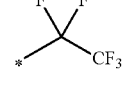

9-707 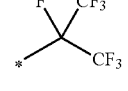

9-708 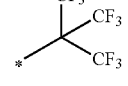

9-709 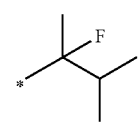

9-710 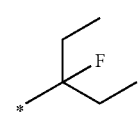

The "group represented by one of Formulae 10-1 to 10-126 in which at least one hydrogen is substituted with deuterium" and the "group represented by one of Formulae 10-201 to 10-343 in which at least one hydrogen is substituted with deuterium" may each be, for example, a group represented by one of Formulae 10-501 to 10-553:

10-501 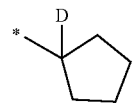

10-502 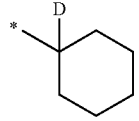

10-503 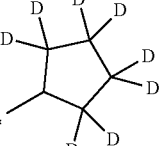

10-504 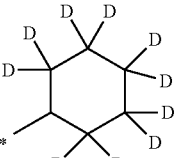

10-505 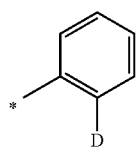

10-506 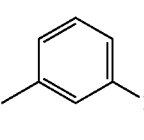

10-507 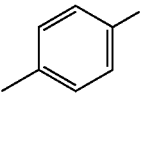

10-508 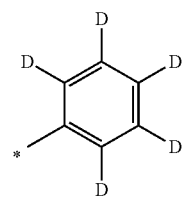
10-509 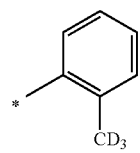
10-510 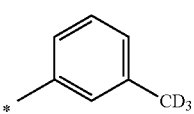
10-511 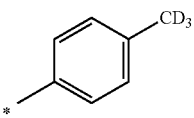
10-512 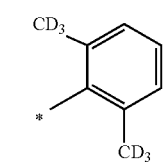
10-513 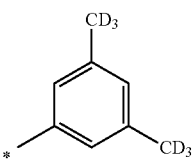
10-514 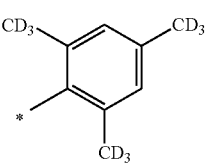
10-515 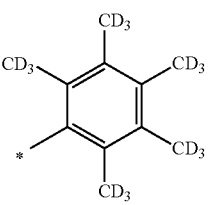
10-516 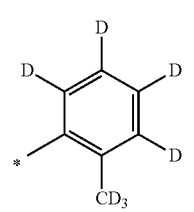
10-517 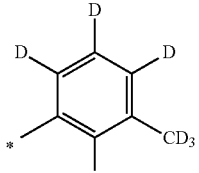
10-518 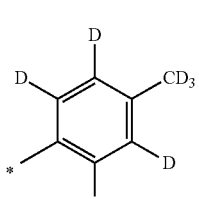
10-519 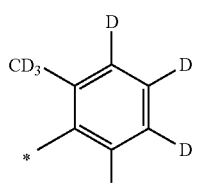
10-520 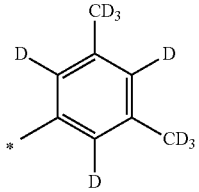
10-521 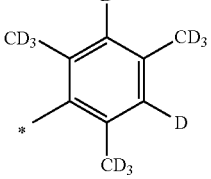
10-522 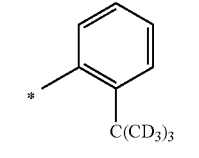
10-523 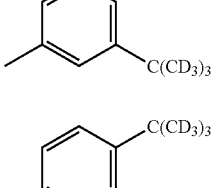
10-524 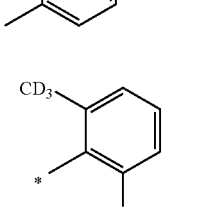
10-525 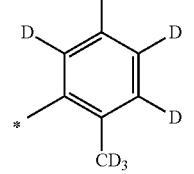

10-526
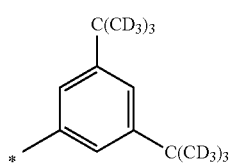
10-527
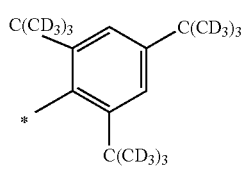
10-528
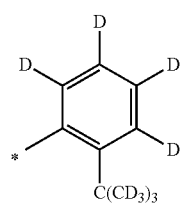
10-529
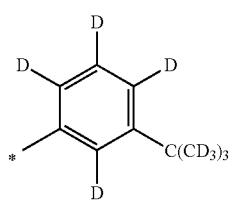
10-530
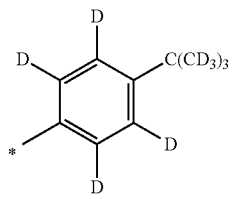
10-531
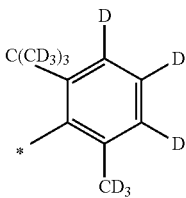
10-532
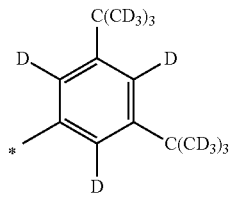
10-533
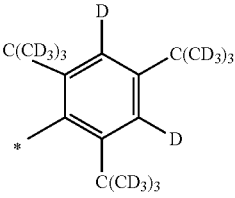
10-534
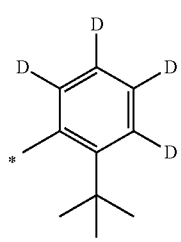
10-535
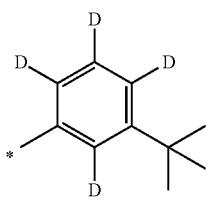
10-536
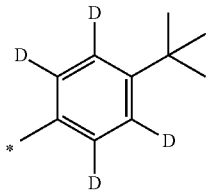
10-537
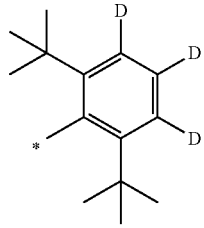
10-538
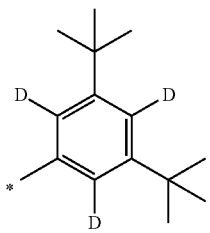
10-540
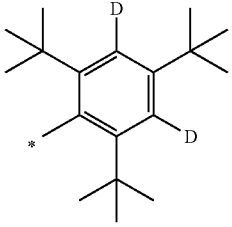
10-541
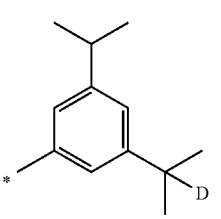

10-542 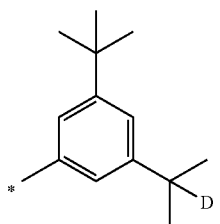
10-543 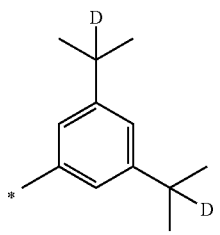
10-544 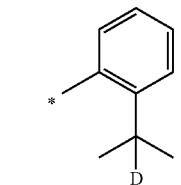
10-545 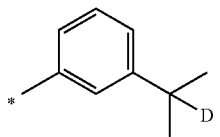
10-546 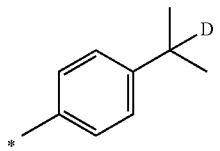
10-547 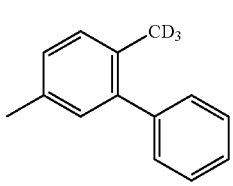
10-548 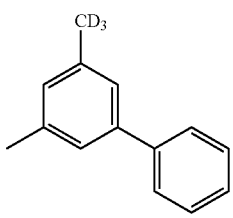
10-549 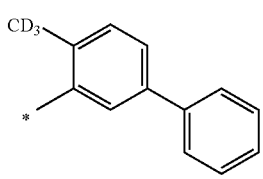
10-550 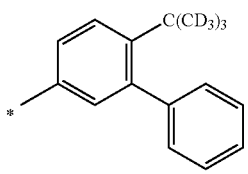
10-551 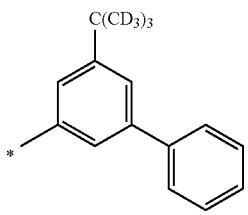
10-552 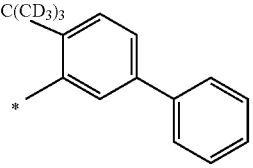
10-553 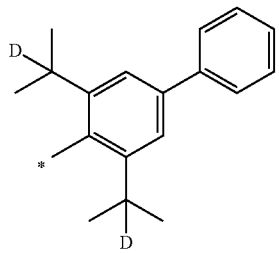
The "group represented by one of Formulae 10-1 to 10-126 in which at least one hydrogen is substituted with —F" and the "group represented by one of Formulae 10-201 to 10-343 in which at least one hydrogen is substituted with —F" may each be, for example, a group represented by one of Formulae 10-601 to 10-617:
10-601 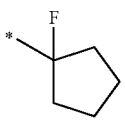
10-602 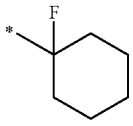
10-603 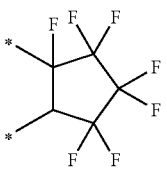

10-604 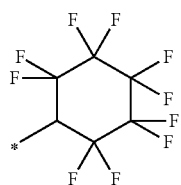

10-605 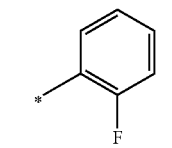

10-606 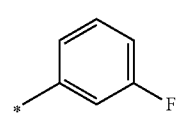

10-607 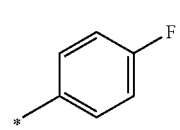

10-608 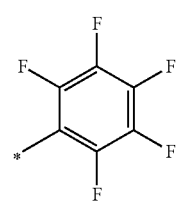

10-609 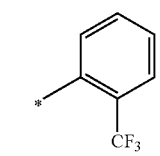

10-610 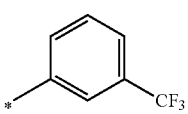

10-611 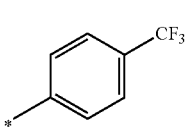

10-612 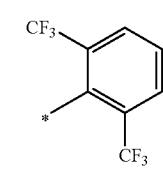

10-613 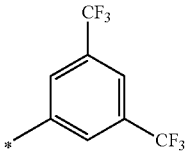

10-614 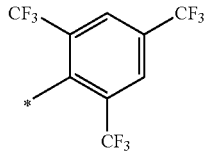

10-615 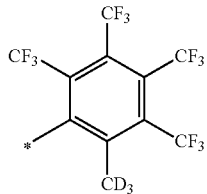

10-616 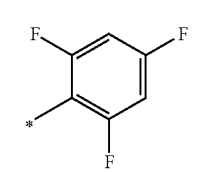

10-617 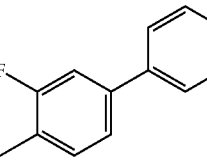

In one or more embodiments, in Formula 1,
1) $R_2$ may include at least one fluoro group (—F);
2) $R_3$ may include at least one fluoro group (—F);
3) $R_4$ may include at least one fluoro group (—F);
4) $R_5$ may include at least one fluoro group (—F);
5) $R_6$ may include at least one fluoro group (—F);
6) $R_7$ may include at least one fluoro group (—F);
7) $R_8$ may include at least one fluoro group (—F);
8) $R_4$ and $R_5$ may each include at least one fluoro group (—F);
9) $R_4$ and $R_6$ may each include at least one fluoro group (—F);
10) $R_5$ and $R_6$ may each include at least one fluoro group (—F);
11) $R_3$ and $R_4$ may each include at least one fluoro group (—F); or
12) $R_3$ and $R_6$ may each include at least one fluoro group (—F).

In one or more embodiments, regarding Formula 1, one or two of $R_1$ to $R_8$ may each independently include at least one fluoro group (—F), and
at least one of $R_1$ to $R_8$ i) may not include a fluoro group (—F), and ii) may not be hydrogen.

In one or more embodiments, $A_{20}$ in Formula 1 may be a $C_1$-$C_{20}$ alkyl group, a $C_3$-$C_{10}$ cycloalkyl group, or a $C_2$-$C_{10}$ heterocycloalkyl group, each unsubstituted or substituted with deuterium, a $C_1$-$C_{20}$ alkyl group, a $C_3$-$C_{10}$ cycloalkyl group, a $C_2$-$C_{10}$ heterocycloalkyl group, or any combination thereof.

In one or more embodiments, $A_{20}$ in Formula 1 may be a $C_1$-$C_{20}$ alkyl group, unsubstituted or substituted with deuterium, a $C_1$-$C_{20}$ alkyl group, or any combination thereof.

In one or more embodiments, d2 in Formula 1 may be 2.

In one or more embodiments, $A_{20}$ in Formula 1 may be a $C_1$-$C_{20}$ alkyl group, unsubstituted or substituted with deuterium, a $C_1$-$C_{20}$ alkyl group, or any combination thereof, and d2 may be 2.

In one or more embodiments, the organometallic compound represented by Formula 1 may have at least one deuterium.

In one or more embodiments, at least one of $R_1$ to $R_8$ of Formula 1 may have at least one deuterium.

In one or more embodiments, at least one of $R_{20}$ in number of d2 may have at least one deuterium.

In one or more embodiments, at least one of $R_{20}$ in number of d2 may be a deuterium-containing $C_1$-$C_{20}$ alkyl group, a deuterium-containing $C_3$-$C_{10}$ cycloalkyl group, or a deuterium-containing $C_2$-$C_{10}$ heterocycloalkyl group, each unsubstituted or substituted with a $C_1$-$C_{20}$ alkyl group, a $C_3$-$C_{10}$ cycloalkyl group, a $C_2$-$C_{10}$ heterocycloalkyl group, or any combination thereof.

In one or more embodiments, a group represented by

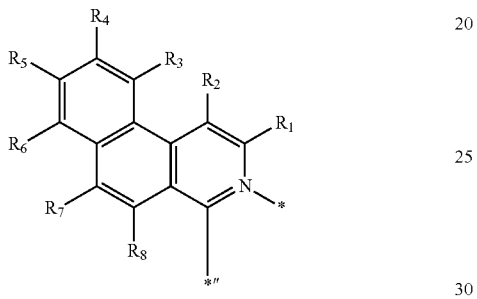

in Formula 1 may be a group represented by one of Formulae CY1 to CY108:

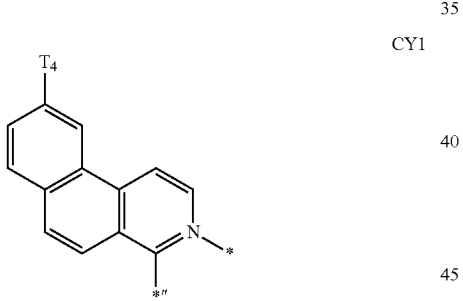
CY1

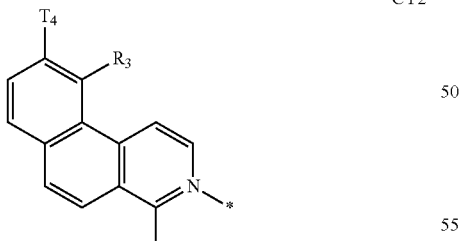
CY2

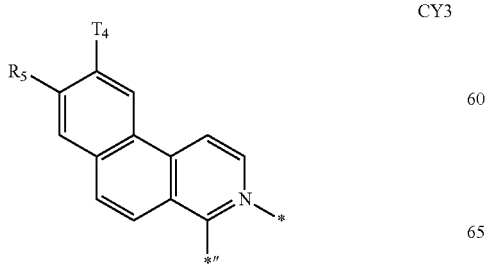
CY3

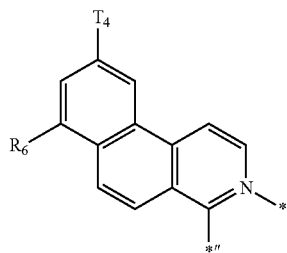
CY4

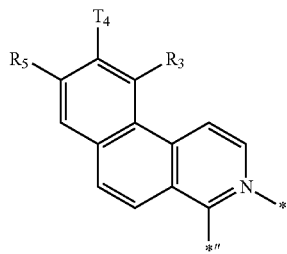
CY5

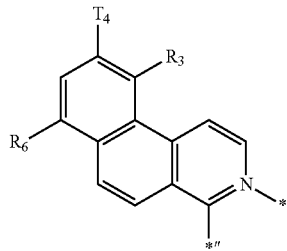
CY6

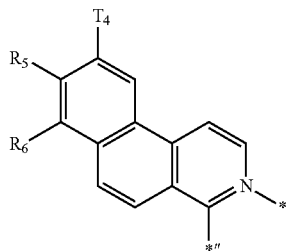
CY7

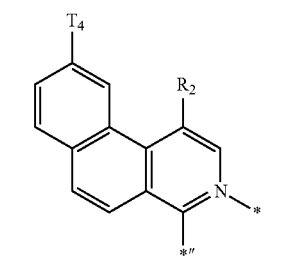
CY8

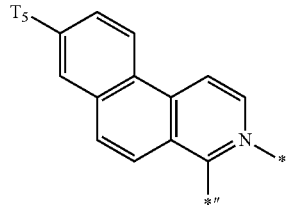
CY9

CY10
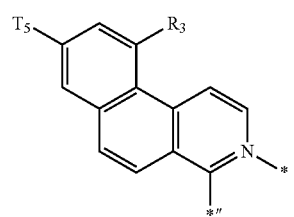
CY11
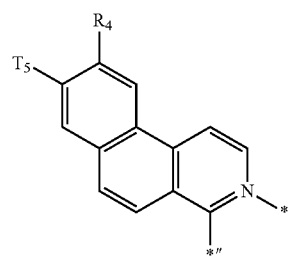
CY12
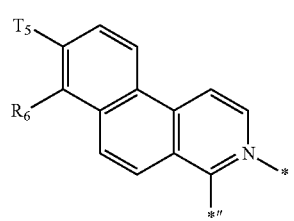
CY13
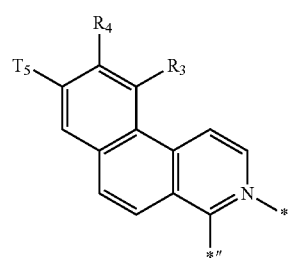
CY14
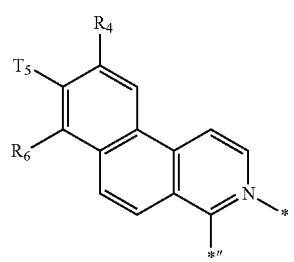
CY15
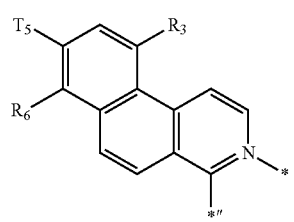
CY16
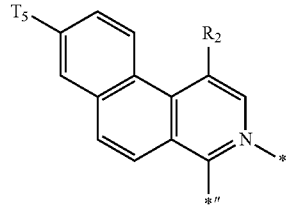
CY17
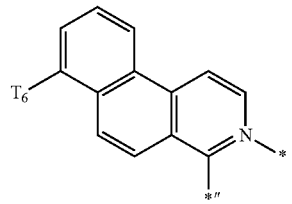
CY18
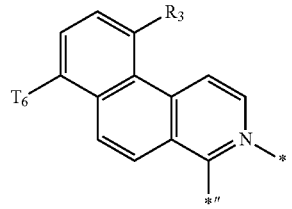
CY19
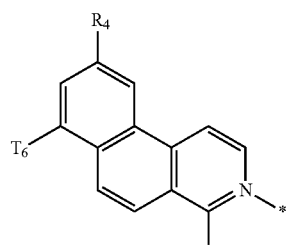
CY20
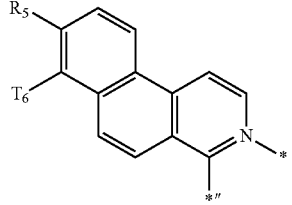
CY21
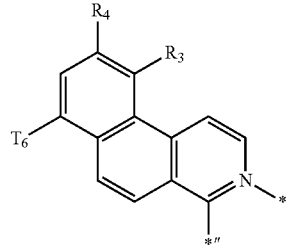
CY22
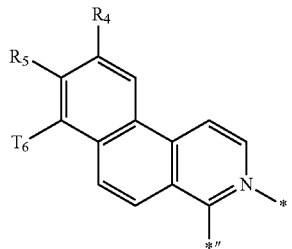

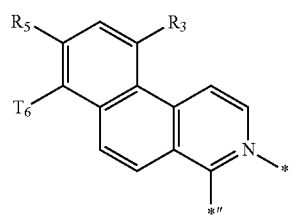
CY23
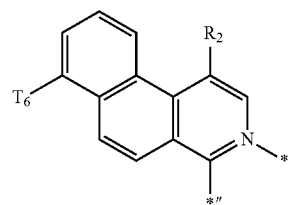
CY24
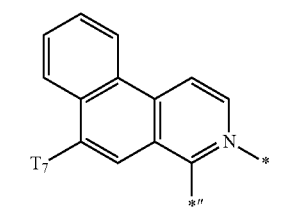
CY25
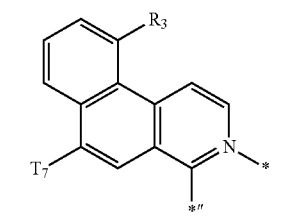
CY26
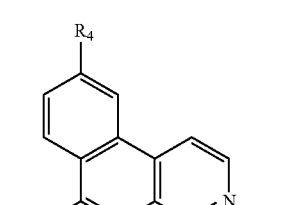
CY27

CY28
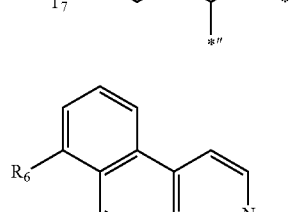
CY29
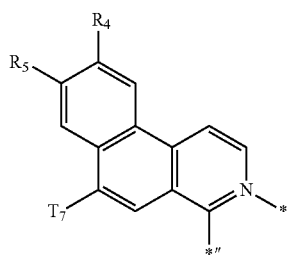
CY30
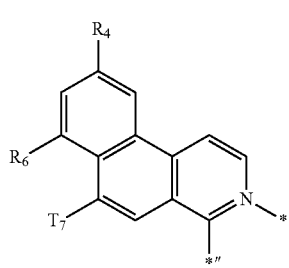
CY31
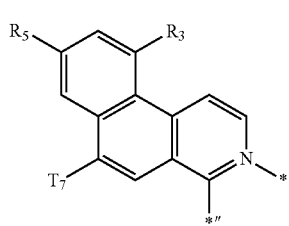
CY32
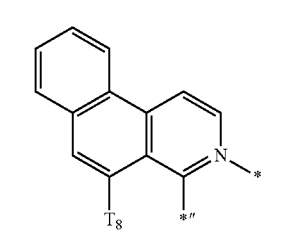
CY33
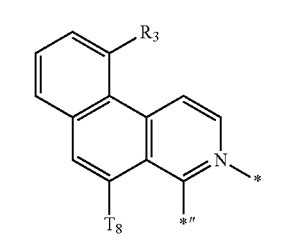
CY34
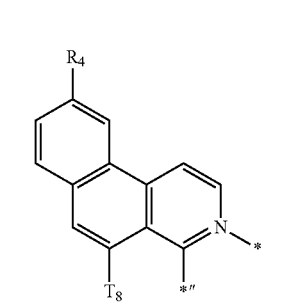
CY35

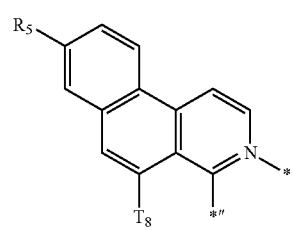 CY36
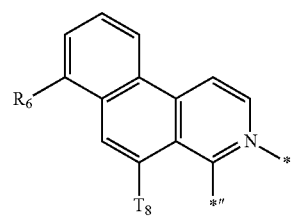 CY37
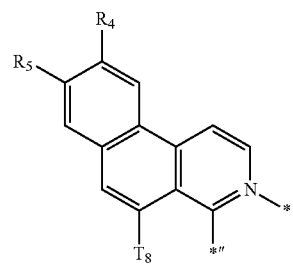 CY38
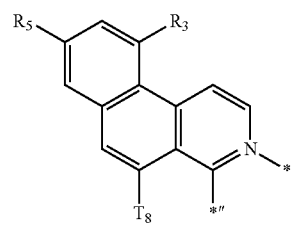 CY39
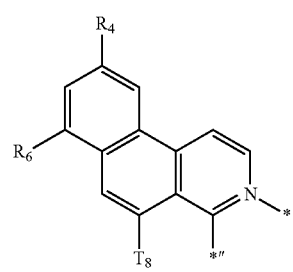 CY40
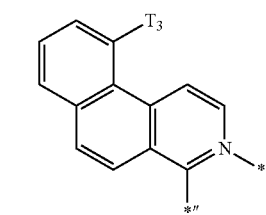 CY41
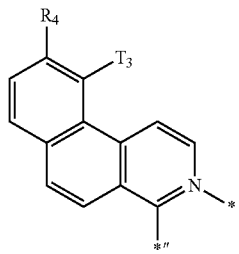 CY42
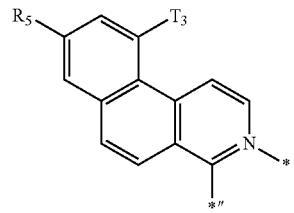 CY43
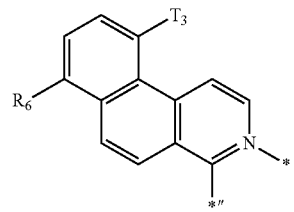 CY44
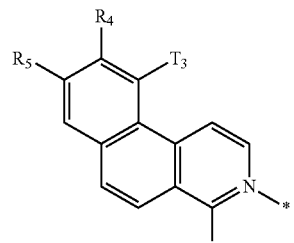 CY45
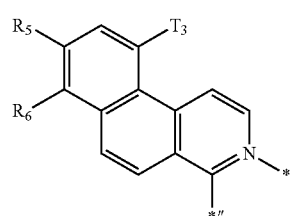 CY46
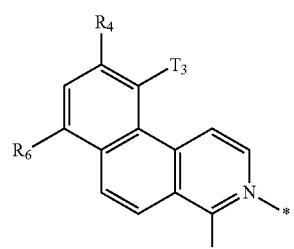 CY47
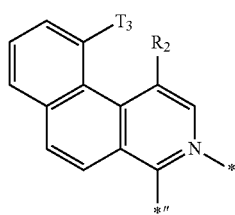 CY48

-continued
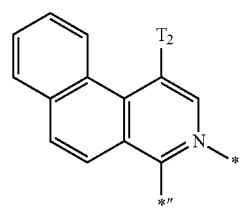
CY49
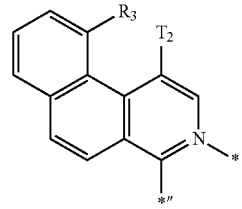
CY50
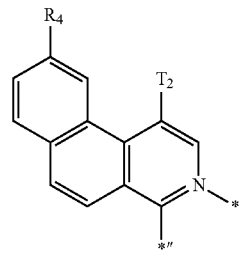
CY51
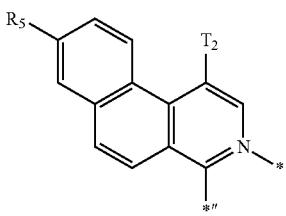
CY52
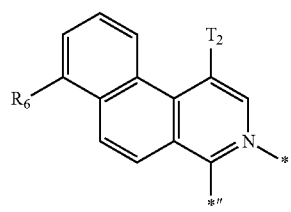
CY53
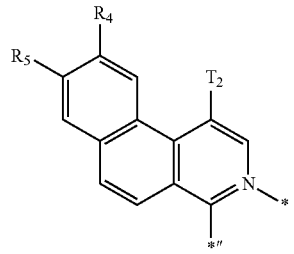
CY54
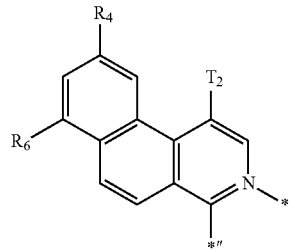
CY55
-continued
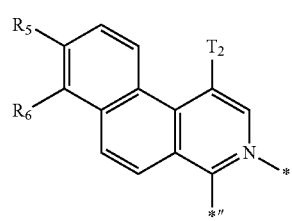
CY56
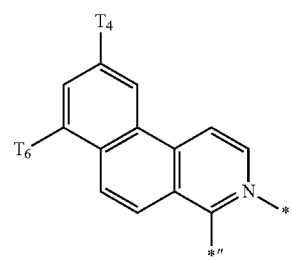
CY57
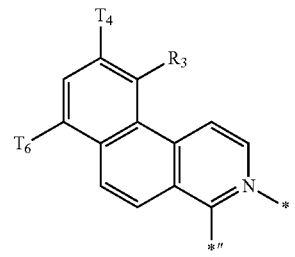
CY58
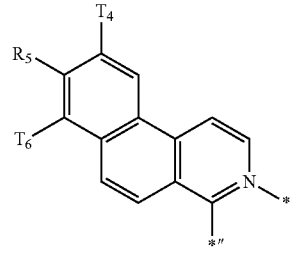
CY59
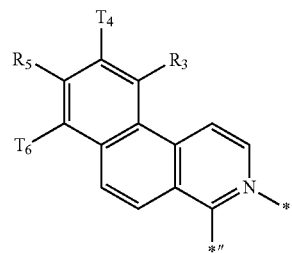
CY60
CY61

CY62
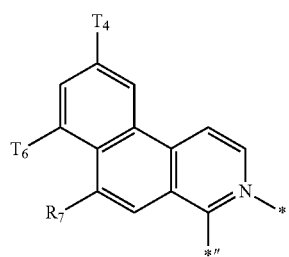
CY63
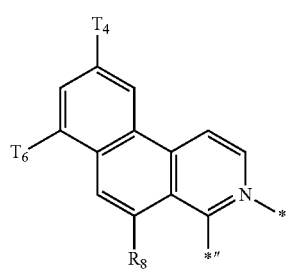
CY64
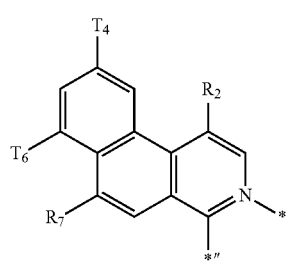
CY65
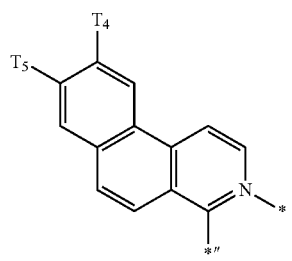
CY66
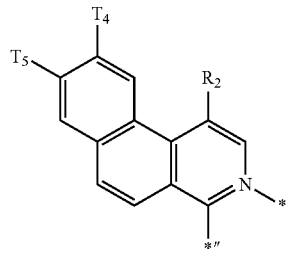
CY67
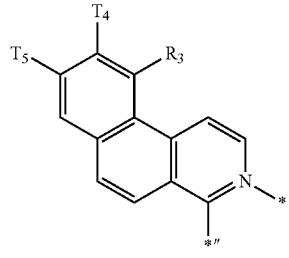
CY68
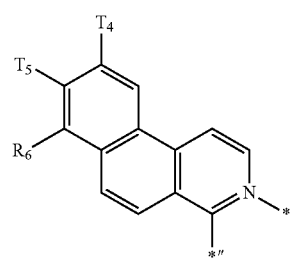
CY69
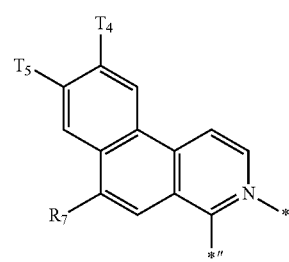
CY70
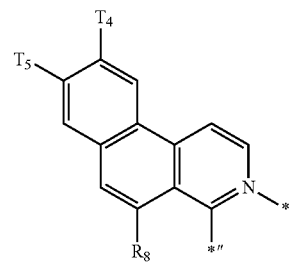
CY71
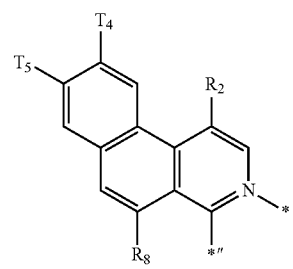
CY72
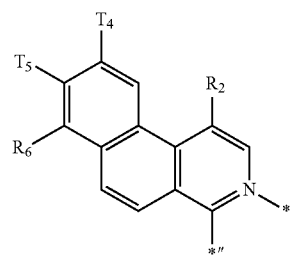
CY73
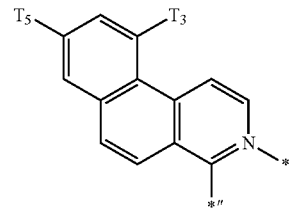

-continued
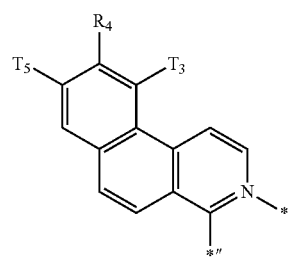
CY74
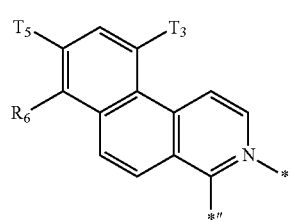
CY75
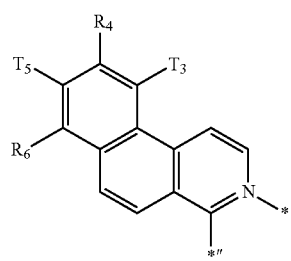
CY76
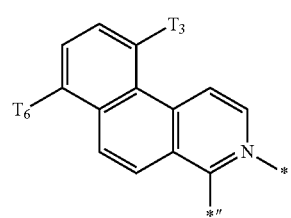
CY77
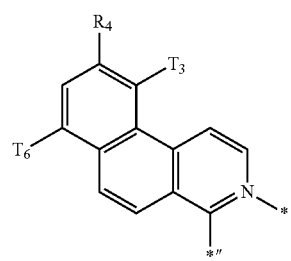
CY78
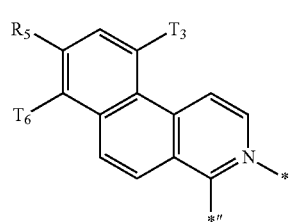
CY79
-continued
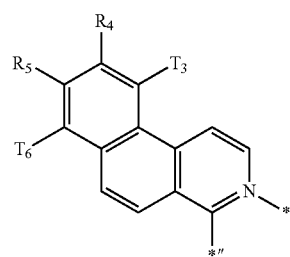
CY80
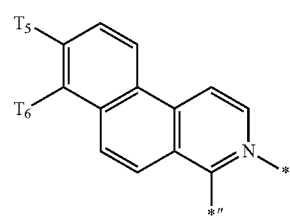
CY81
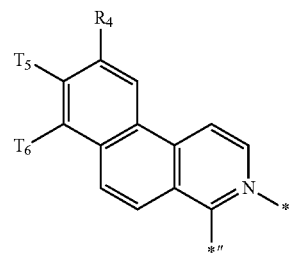
CY82
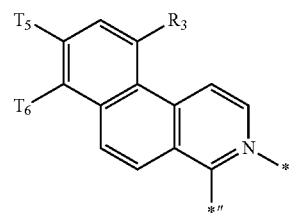
CY83
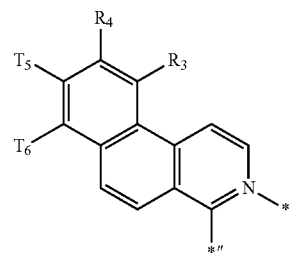
CY84
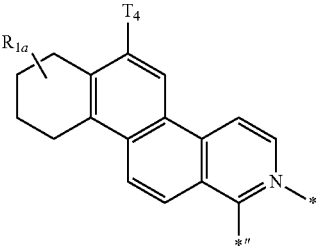
CY85

CY86 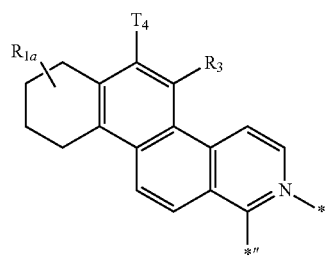
CY87 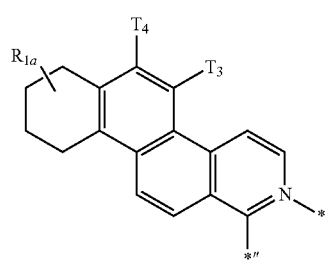
CY88 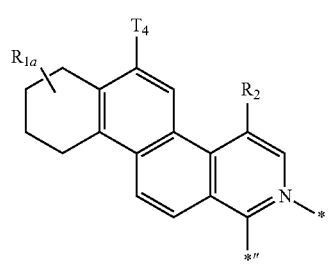
CY89 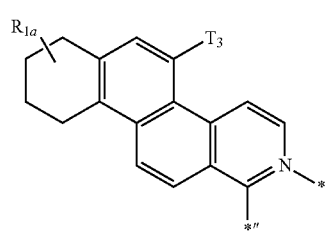
CY90 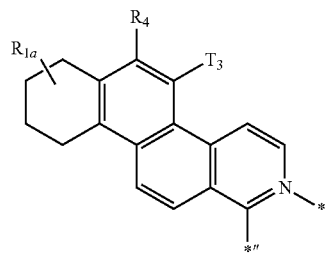
CY91 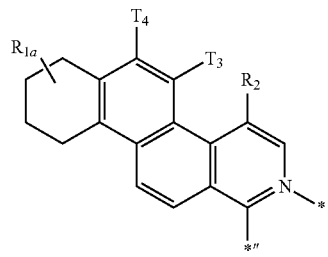
CY92 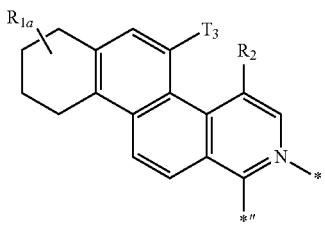
CY93 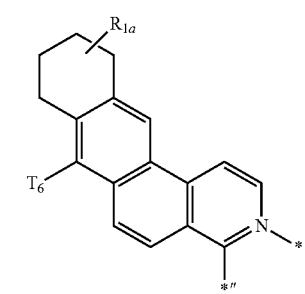
CY94 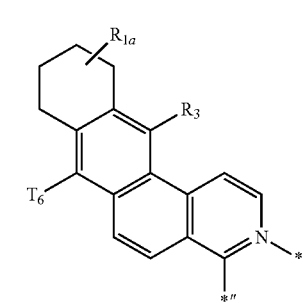
CY95 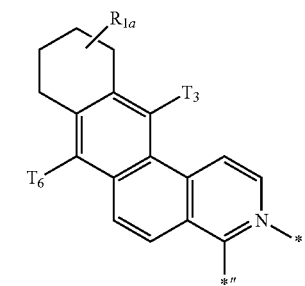
CY96 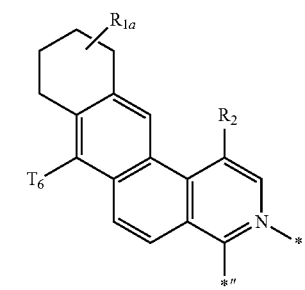

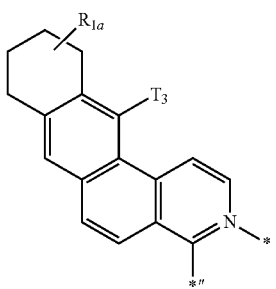
CY97
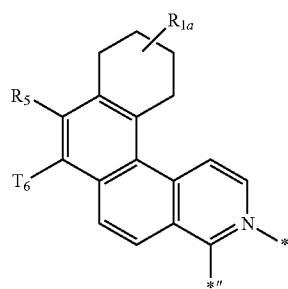
CY102
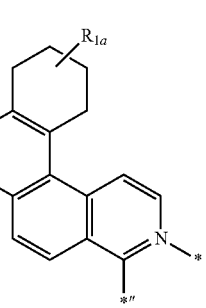
CY98
CY103
CY99
CY104
CY100
CY105
CY101
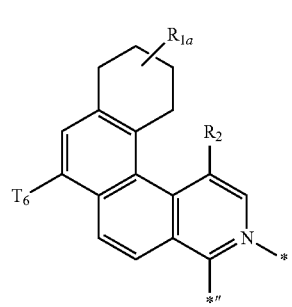
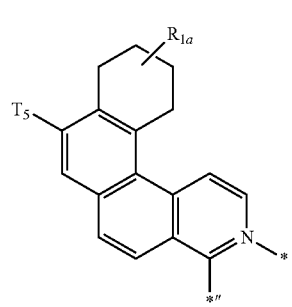
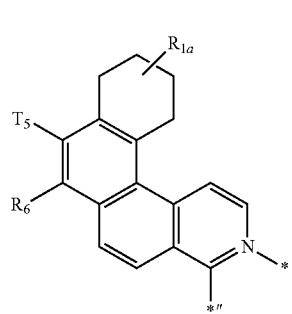
CY106

-continued

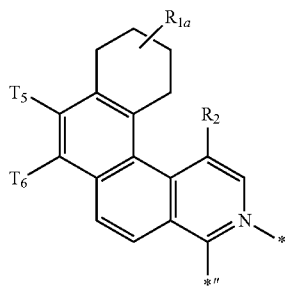
CY107

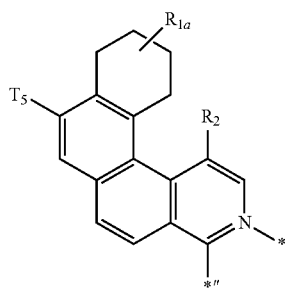
CY108

In Formulae CY1 to CY108, $T_2$ to $T_8$ may each independently be:

a fluoro group (—F); or a fluorinated $C_1$-$C_{20}$ alkyl group, a fluorinated $C_3$-$C_{10}$ cycloalkyl group, a fluorinated $C_2$-$C_{10}$ heterocycloalkyl group, or a fluorinated phenyl group, each unsubstituted or substituted with deuterium, a $C_1$-$C_{20}$ alkyl group, a $C_3$-$C_{10}$ cycloalkyl group, a $C_2$-$C_{10}$ heterocycloalkyl group, a phenyl group, or any combination thereof;

each of $R_2$ to $R_8$ are the same as described above, and $R_2$ to $R_8$ may not be hydrogen, \* indicates a binding site to Ir in Formula 1, \*''' indicates a binding site to a neighboring atom in Formula 1.

For example, $R_2$ to $R_8$ and $R_{1a}$ in Formulae CY1 to CY108 may each independently be:

deuterium; or a $C_1$-$C_{20}$ alkyl group, a $C_3$-$C_{10}$ cycloalkyl group, a $C_2$-$C_{10}$ heterocycloalkyl group, or a phenyl group, each unsubstituted or substituted with deuterium, a $C_1$-$C_{20}$ alkyl group, a $C_3$-$C_{10}$ cycloalkyl group, a $C_2$-$C_{10}$ heterocycloalkyl group, a phenyl group, or any combination thereof.

In one or more embodiments, the group represented by

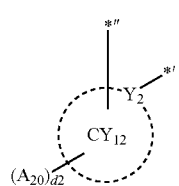

in Formula 1 may be a group represented by one of Formulae A(1) to A(7):

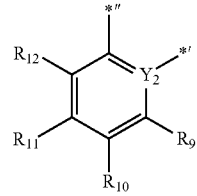
A(1)

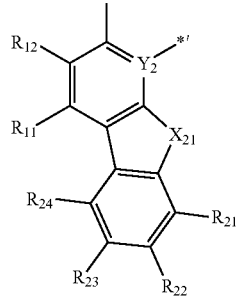
A(2)

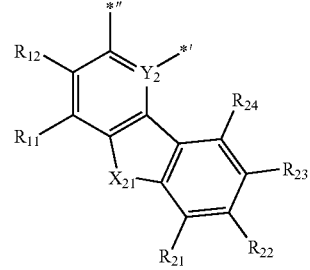
A(3)

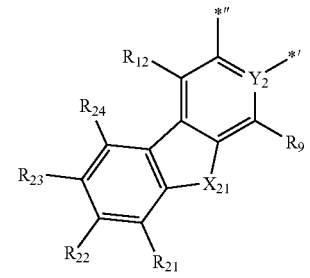
A(4)

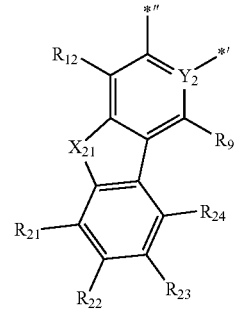
A(5)

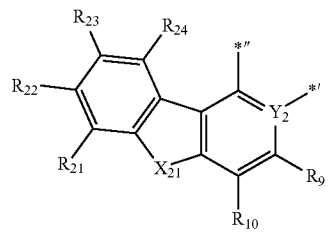
A(6)

A(7)

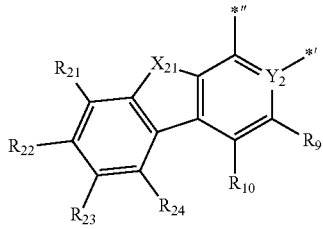

In Formulae A(1) to A(7), $Y_2$ is C, $X_{21}$ is O, S, $N(R_{25})$, $C(R_{25})(R_{26})$, or $Si(R_{25})(R_2)$, each of $R_9$ to $R_{12}$ and $R_{21}$ to $R_{2e}$ are the same as described in connection with $A_{20}$,

*' indicates a binding site to Ir in Formula 1, and

*'' indicates a binding site to a neighboring atom in Formula 1.

For example, $R_9$ and $R_{11}$ in Formula A(1) may each independently be a $C_1$-$C_{20}$ alkyl group, a $C_3$-$C_{10}$ cycloalkyl group, a $C_2$-$C_{10}$ heterocycloalkyl group, or a phenyl group, each unsubstituted or substituted with deuterium, a $C_1$-$C_{20}$ alkyl group, a $C_3$-$C_{10}$ cycloalkyl group, a $C_2$-$C_{10}$ heterocycloalkyl group, a phenyl group, or any combination thereof.

In one or more embodiments, $R_9$ and $R_{11}$ in Formula A(1) may each independently be a $C_1$-$C_{20}$ alkyl group, unsubstituted or substituted with deuterium, a $C_1$-$C_{20}$ alkyl group, or any combination thereof.

In one or more embodiments, $R_{10}$ and $R_{12}$ in Formula A(1) may each independently be hydrogen or deuterium.

In one or more embodiments, $R_9$ and $R_{11}$ in Formula A(1) may be identical to each other.

In one or more embodiments, $R_9$ and $R_{11}$ in Formula A(1) may be different from each other.

In one or more embodiments, $R_9$ and $R_{11}$ in Formula A(1) may be different from each other, and the number of carbon included in $R_{11}$ may be greater than the number of carbon included in $R_9$.

In one or more embodiments, i) at least one of $R_9$ to $R_{12}$ in Formula A(1), ii) $R_{11}$, $R_{12}$, one of $R_{21}$ to $R_{26}$, or any combination thereof in Formulae A(2) and A(3), iii) $R_9$, $R_{12}$, one of $R_{21}$ to $R_{26}$, or any combination thereof in Formulae A(4) and A(5), and iv) $R_9$, $R_{10}$, one of $R_{21}$ to $R_{28}$, or any combination thereof in Formulae A(6) and A(7), may each independently be a deuterium-containing $C_1$-$C_{20}$ alkyl group, a deuterium-containing $C_3$-$C_{10}$ cycloalkyl group, or a deuterium-containing $C_2$-$C_{10}$ heterocycloalkyl group, each unsubstituted or substituted with a $C_1$-$C_{20}$ alkyl group, a $C_3$-$C_{10}$ cycloalkyl group, a $C_2$-$C_{10}$ heterocycloalkyl group, or any combination thereof.

In one or more embodiments, at least one of $R_9$ and $R_{11}$ in Formula A(1) (for example, $R_9$ and $R_1$, in Formula A(1)) may each independently be a deuterium-containing $C_1$-$C_{20}$ alkyl group, a deuterium-containing $C_3$-$C_{10}$ cycloalkyl group, or a deuterium-containing $C_2$-$C_{10}$ heterocycloalkyl group, each unsubstituted or substituted with a $C_1$-$C_{20}$ alkyl group, a $C_3$-$C_{10}$ cycloalkyl group, a $C_2$-$C_{10}$ heterocycloalkyl group, or any combination thereof.

In one or more embodiments, the group represented by

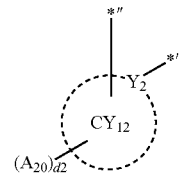

in Formula 1 may be a group represented by Formula A(1) or A(5).

In one or more embodiments, the number of carbon included in the group represented by *—$C(A_1)(A_2)(A_3)$ in Formula 1 may be 5 or more, and/or the number of carbon included in the group represented by *—$C(A_4)(A_5)(A_6)$ in Formula 1 may be 5 or more.

In one or more embodiments, $A_1$, $A_2$, and $A_5$ of the group represented by *—$C(A_1)(A_2)(A_3)$ in Formula 1 may be linked to each other to form a $C_5$-$C_{60}$ carbocyclic group which is unsubstituted or substituted with at least one $R_{1a}$ or a $C_1$-$C_{60}$ heterocyclic group which is unsubstituted or substituted with at least one $R_{1a}$. That is, the group represented by *—$C(A_1)(A_2)(A_3)$ in Formula 1 may be a $C_5$-$C_{60}$ carbocyclic group which is unsubstituted or substituted with at least one $R_{1a}$ or a $C_1$-$C_{60}$ heterocyclic group which is unsubstituted or substituted with at least one $R_{1a}$ (for example, an adamantane group, a norbornene group, a bicyclo[1.1.1]pentane group, a bicyclo[2.1.1]hexane group, a bicyclo[2.2.1]heptane group (a norbornane group), a bicyclo[2.2.2]octane group, a cyclopentane group, a cyclohexane group, or a cyclohexene group, each unsubstituted or substituted with at least one $R_{1a}$).

In one or more embodiments, $A_4$, $A_5$, and $A_6$ of the group represented by *—$C(A_4)(A_5)(A_6)$ in Formula 1 may be linked to each other to form a $C_5$-$C_{60}$ carbocyclic group which is unsubstituted or substituted with at least one $R_{1a}$ or a $C_1$-$C_{60}$ heterocyclic group which is unsubstituted or substituted with at least one $R_{1a}$. That is, the group represented by *—$C(A_4)(A_5)(A_6)$ in Formula 1 may be a $C_5$-$C_{60}$ carbocyclic group which is unsubstituted or substituted with at least one $R_1$, or a $C_1$-$C_{60}$ heterocyclic group which is unsubstituted or substituted with at least one $R_{1a}$ (for example, an adamantane group, a norbornene group, a bicyclo[1.1.1]pentane group, a bicyclo[2.1.1]hexane group, a bicyclo[2.2.1]heptane group (a norbornane group), a bicyclo[2.2.2]octane group, a cyclopentane group, a cyclohexane group, or a cyclohexene group, each unsubstituted or substituted with at least one $R_{1a}$).

In one or more embodiments, in Formula 1, a group represented by *—$C(A_1)(A_2)(A_3)$ may be identical to a group represented by *—$C(A_4)(A_5)(A_6)$.

In one or more embodiments, in Formula 1, a group represented by *—$C(A_1)(A_2)(A_3)$ may be different from a group represented by *—$C(A_4)(A_5)(A_6)$.

In one or more embodiments, the first compound may include at least one of Compounds 1 to 53:

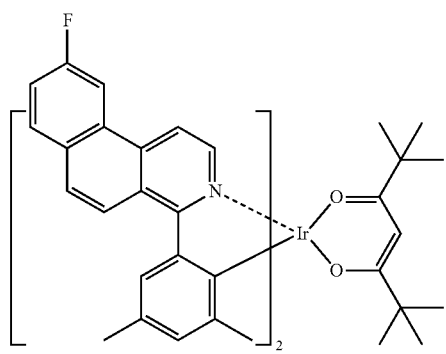
1
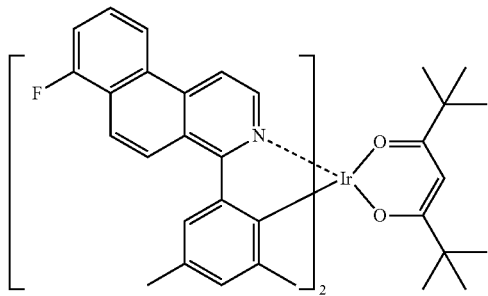
2
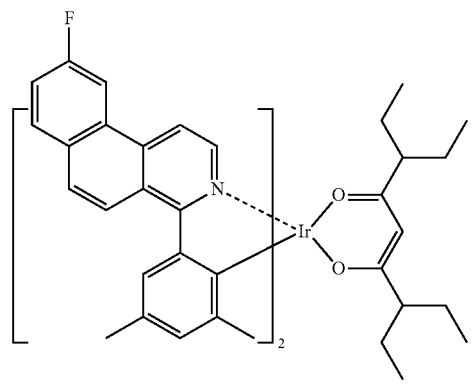
3
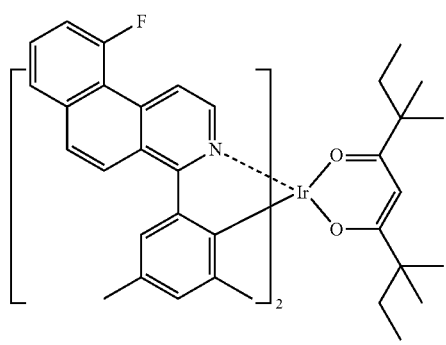
4
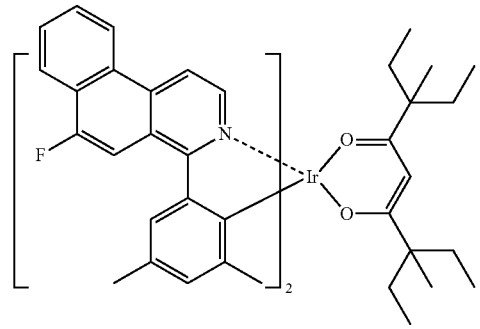
5
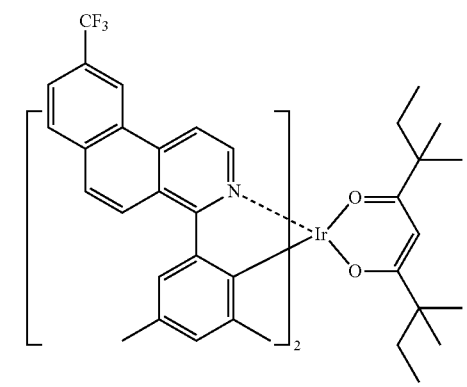
6
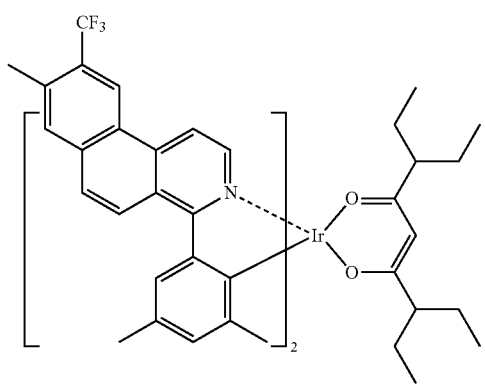
7
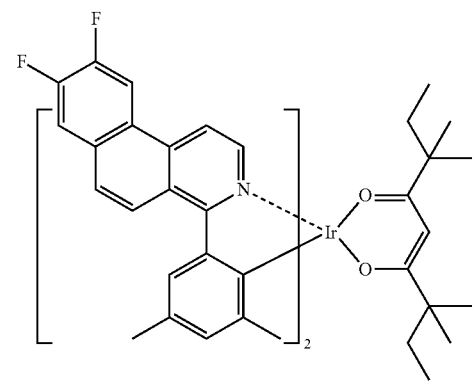
8

9
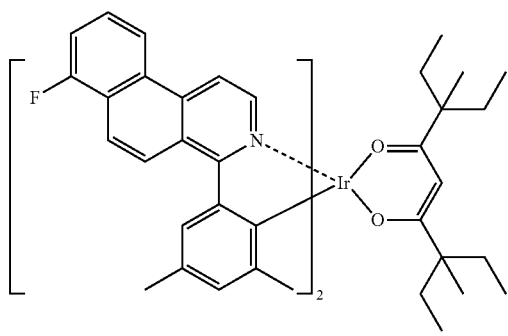
10
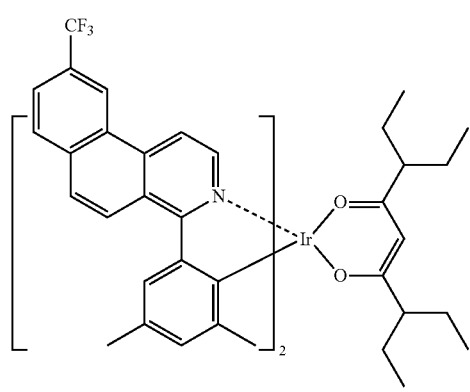
11
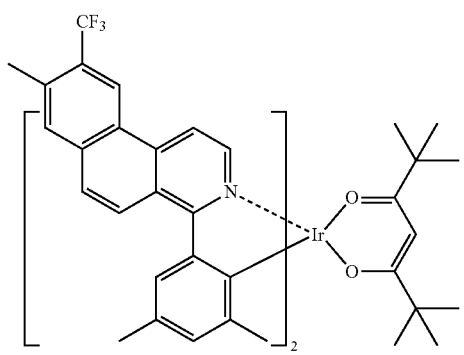
12
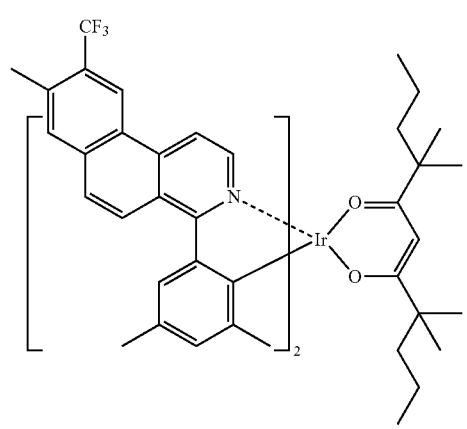
13
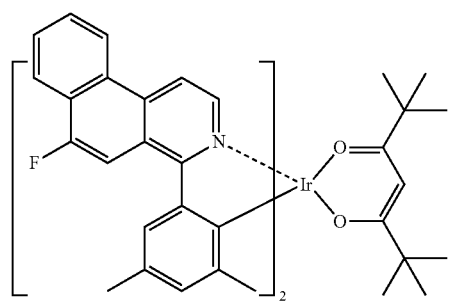
14
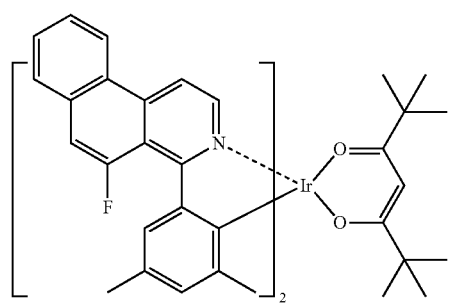
15
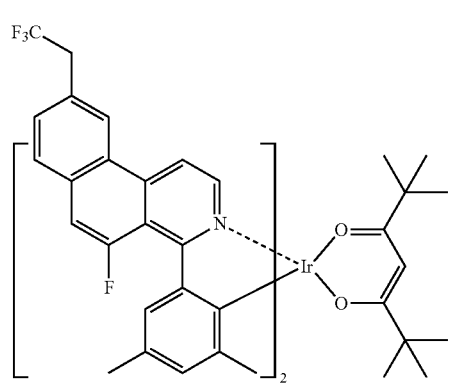
16
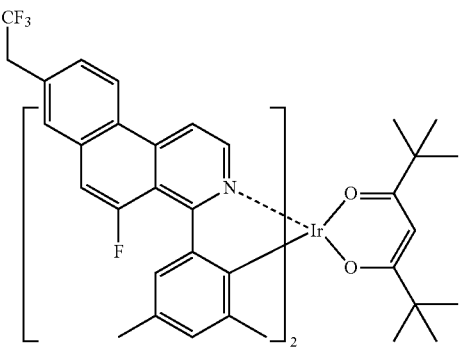

-continued
17
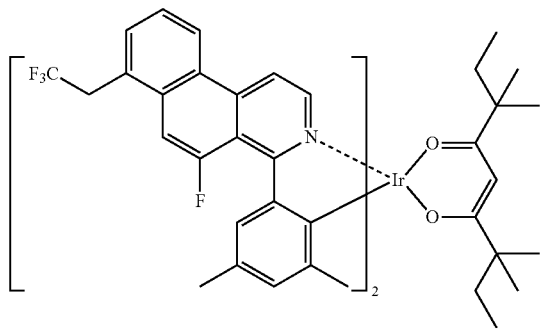
18
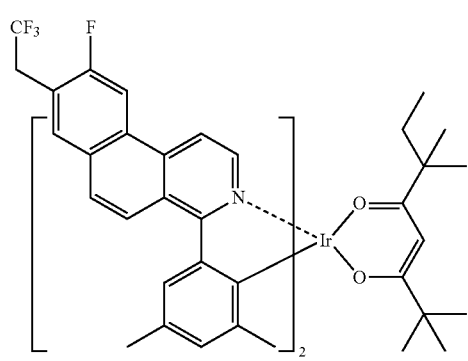
19
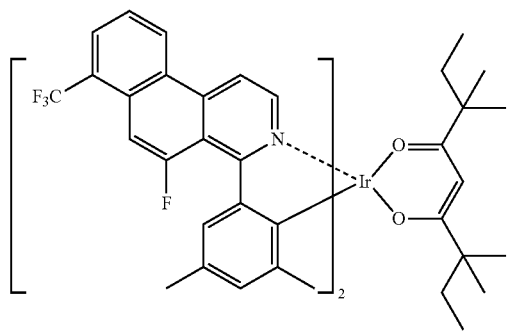
20
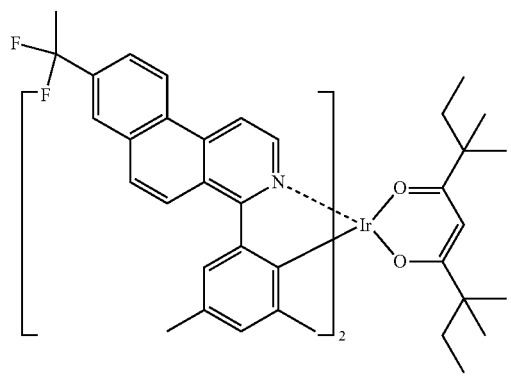
-continued
21
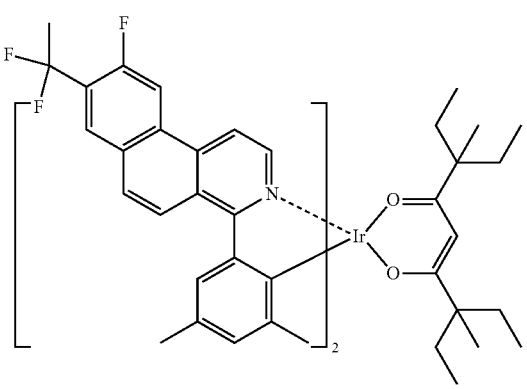
22
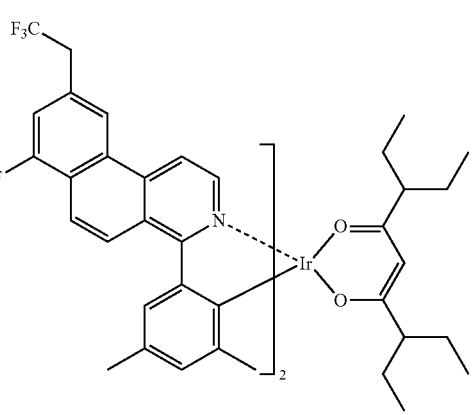
23
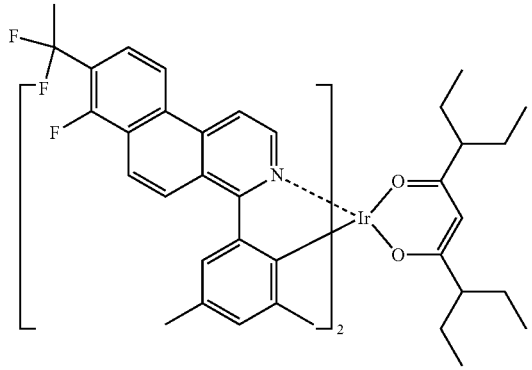
24
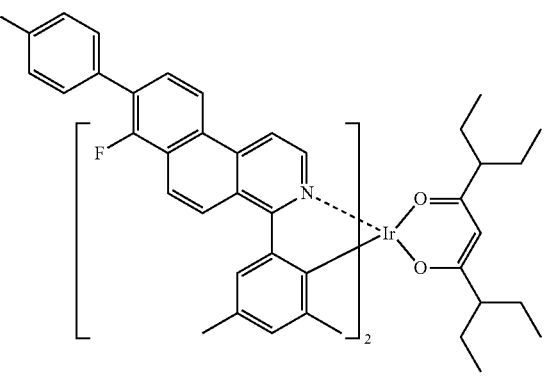

25
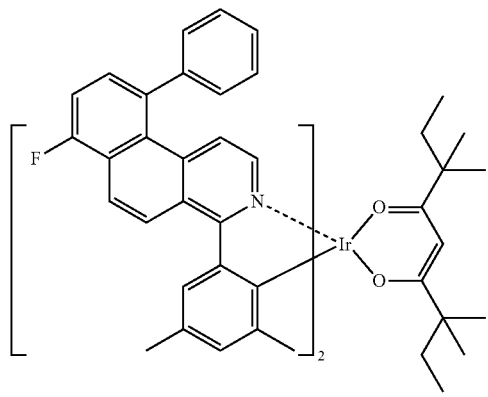
26
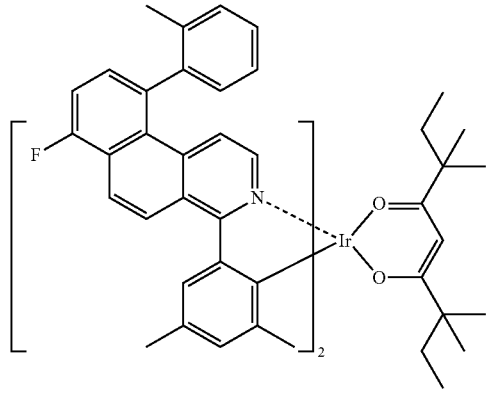
27
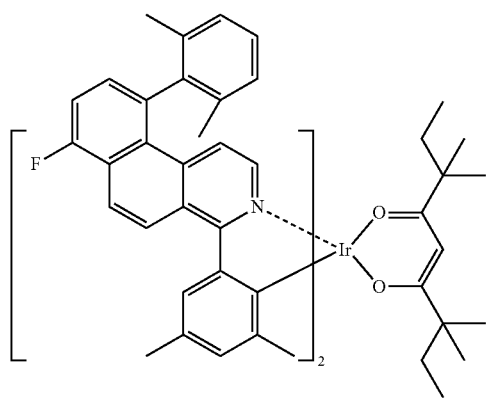
28
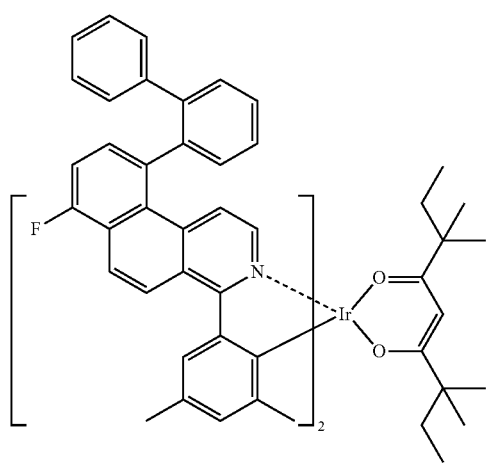
29
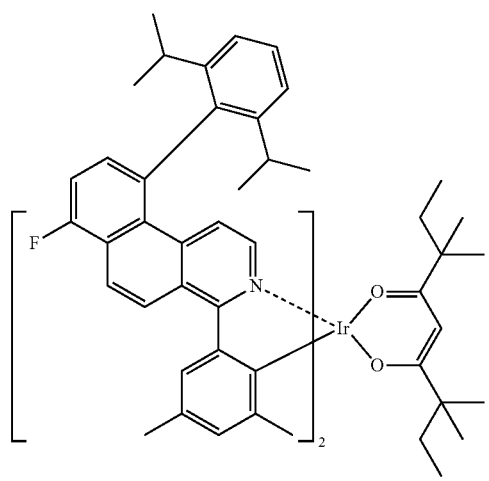
30
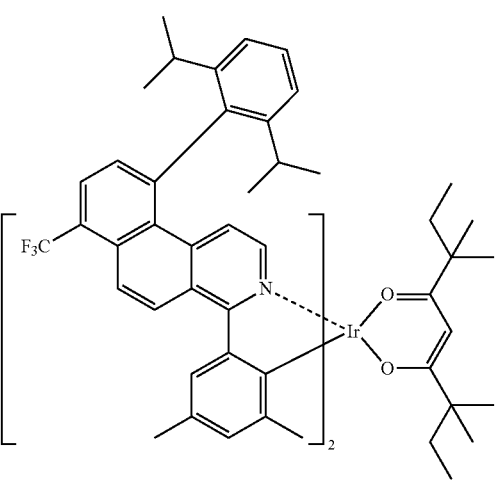
31
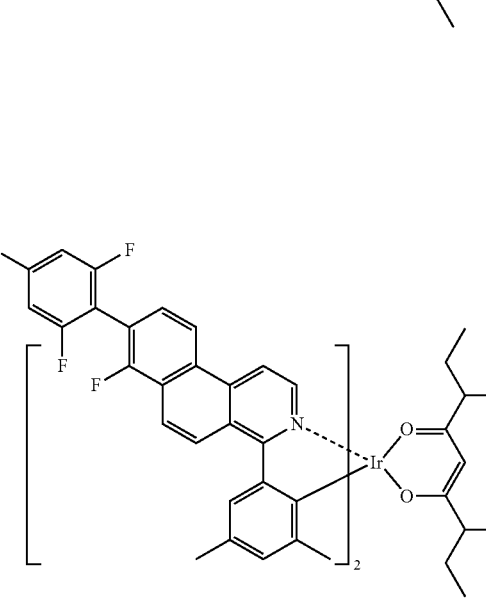

32
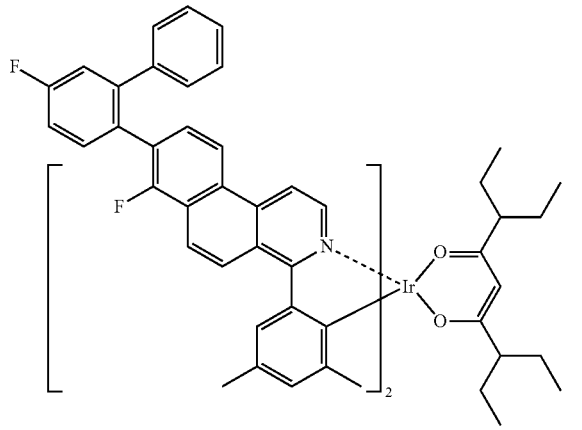
33
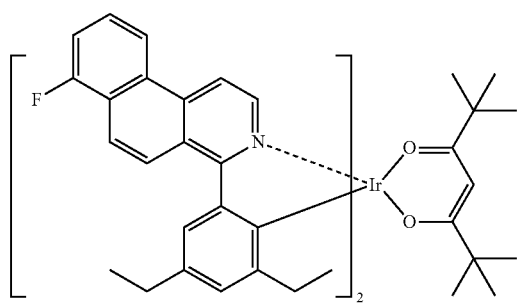
34
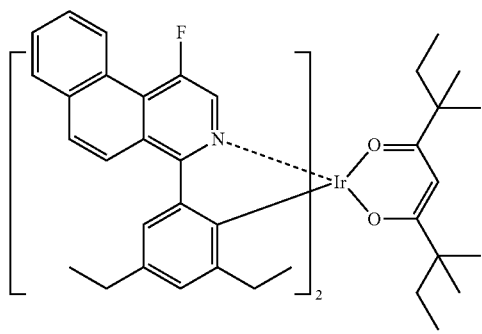
35
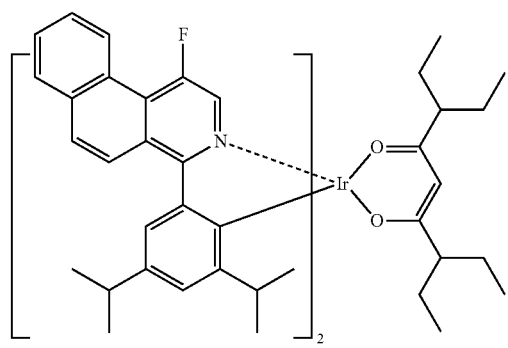
36
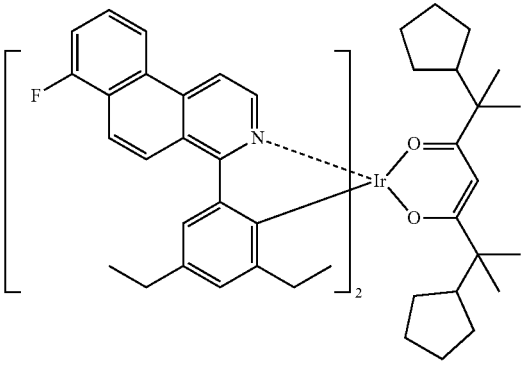
37
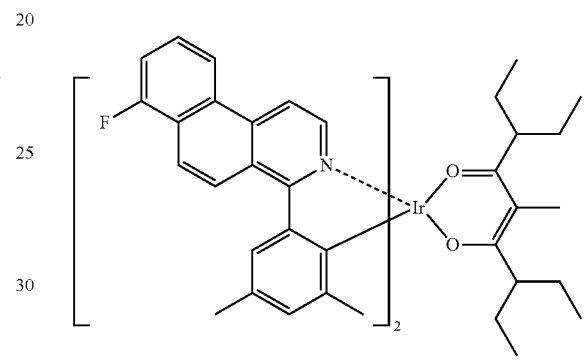
38
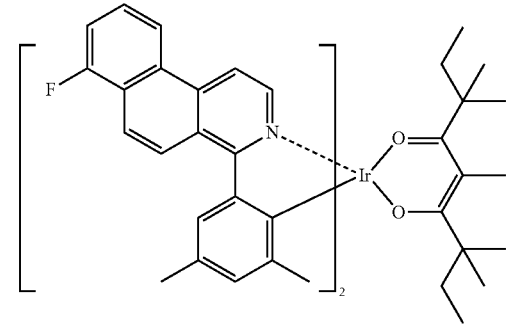
39
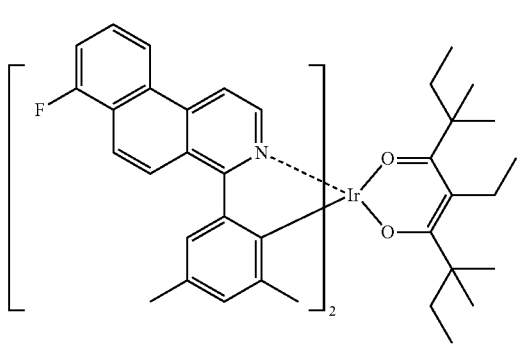

40
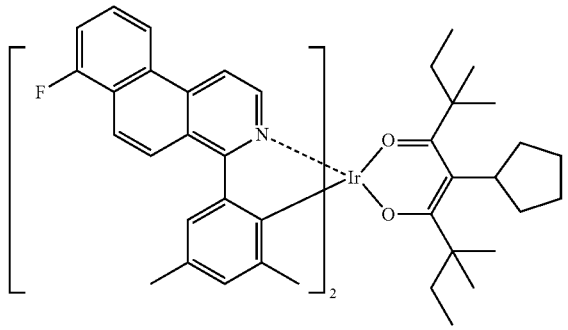
41
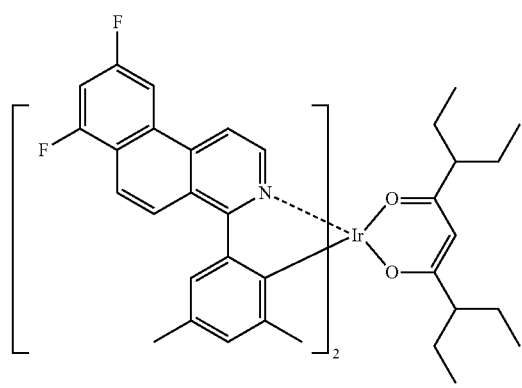
42
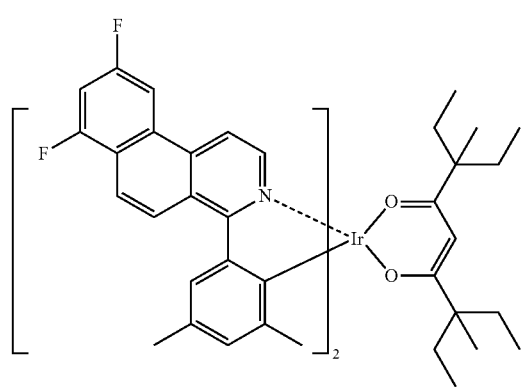
43
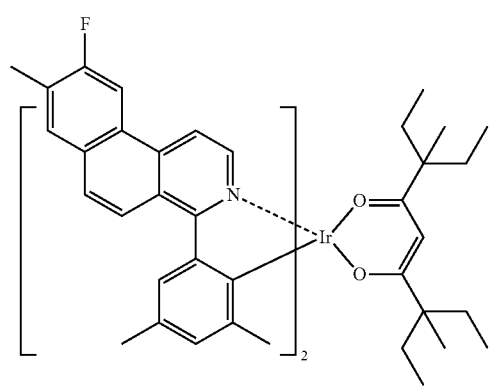
44
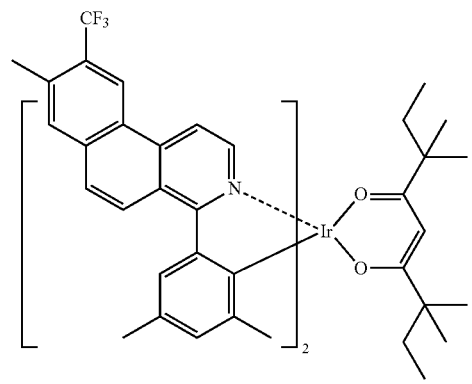
45
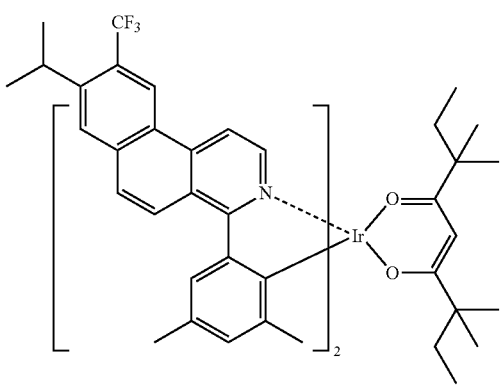
46
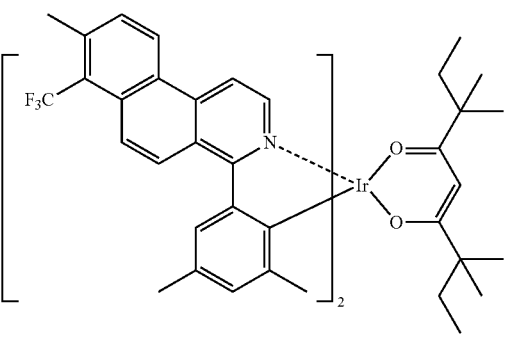
47
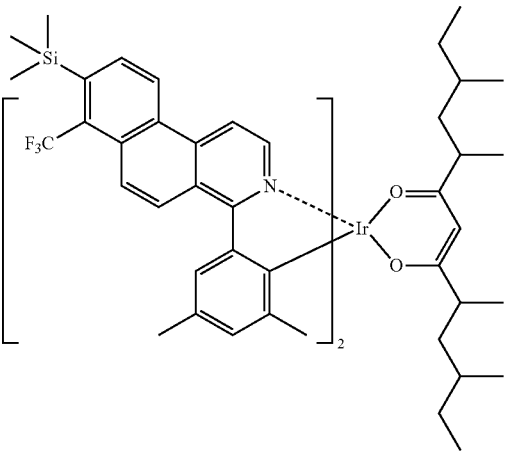

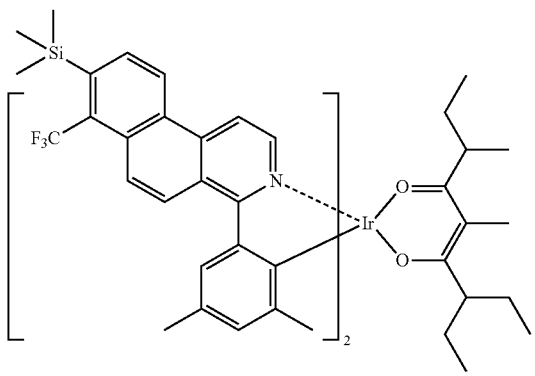

48

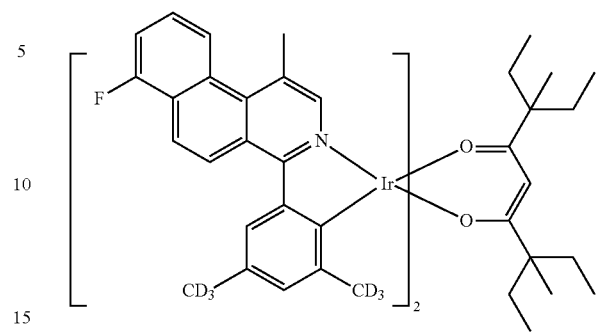

52

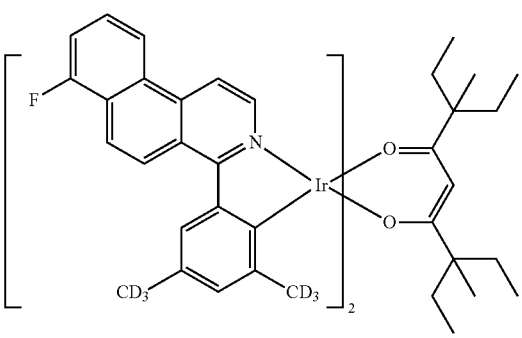

49

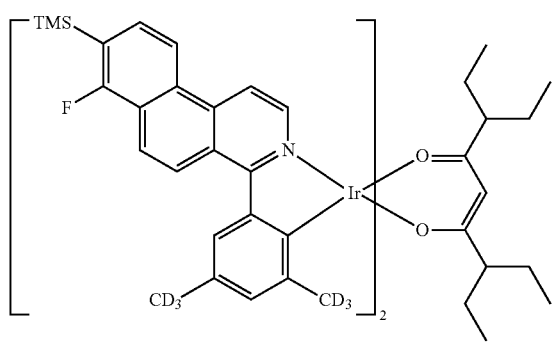

50

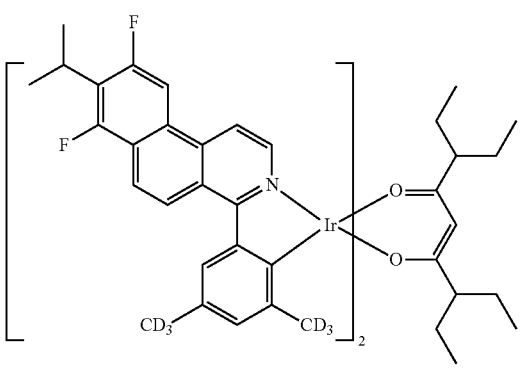

51

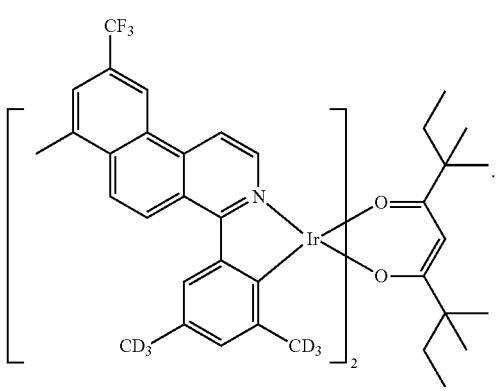

53

The first compound may include an organometallic compound represented by Formula 1. In an organometallic compound represented by Formula 1, 1) ring $CY_{11}$ (see Formula 1') is, as illustrated in Formula 1, a condensed cyclic group in which two benzene groups are condensed with one pyridine group, and 2) at least one of $R_1$ to $R_8$, $A_{20}$ includes at least one a fluoro group (—F). Accordingly, the transition dipole moment of the organometallic compounds may be increased, and the conjugation length of the organometallic compounds is relatively increased and structural rigidity thereof is increased, leading to a decrease in non-radiative transition. Thus, an electronic device, for example, an organic light-emitting device, including the organometallic compound represented by Formula 1 may have high external quantum efficiency (EQE), and thus, may have high luminescence efficiency.

101

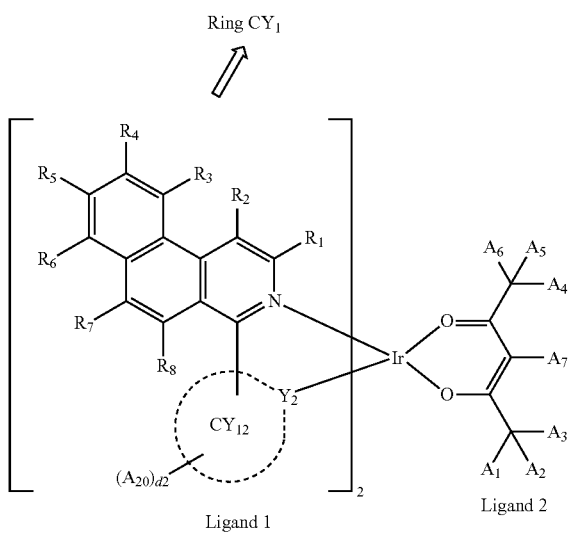

Formula 1'

Ring CY$_1$

Ligand 1    Ligand 2

In one or more embodiments, when at least one of A$_1$ to A$_6$ in Formula 1 is each independently be a substituted or unsubstituted C$_2$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_2$-C$_{10}$ heterocycloalkyl group, a substituted or unsubstituted C$_3$-C$_{10}$ cycloalkenyl group, a substituted or unsubstituted C$_2$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, or a substituted or unsubstituted monovalent non-aromatic condensed heteropolycyclic group (that is, when at least one of A$_1$ to A$_6$ in Formula 1 has two or more carbons), an electron donating capability of Ligand 2 (see Formula 1') in Formula 1 may be improved, and thus, an interaction between Ligand 1 and Ligand 2 in Formula 1 may be enhanced. Thus, the organometallic compound represented by Formula 1 may have improved luminescent transition characteristics, improved optical orientation characteristics, and improved structural rigidity. Accordingly, an electronic device, for example, an organic light-emitting device, including the organometallic compound represented by Formula 1 may have high luminescence efficiency and a long lifespan.

In one or more embodiments, when A$_1$ to A$_6$ in Formula 1 are each independently a substituted or unsubstituted C$_1$-C$_{60}$ alkyl group, a substituted or unsubstituted C$_2$-C$_{10}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_2$-C$_{10}$ heterocycloalkyl group, a substituted or unsubstituted C$_3$-C$_{10}$ cycloalkenyl group, a substituted or unsubstituted C$_2$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, or a substituted or unsubstituted monovalent

102 non-aromatic condensed heteropolycyclic group (that is, when A$_1$ to A$_6$ in Formula 1 each have one or more carbons), carbons bound to each A$_1$ to A$_6$ in Formula 1 as described above may not include an α-proton, and in this regard, the organometallic compound represented by Formula 1 may have a stable chemical structure with minimal occurrence of a side reaction before/after synthesis, and at the same time, an intermolecular interaction of the organometallic compound represented by Formula 1 may be minimized during the operation of an electronic device (for example, an organic light-emitting device) including the organometallic compound represented by Formula 1. Furthermore, an interaction between Ligand 1 and Ligand 2 in Formula 1 may be enhanced and thus, the organometallic compound represented by Formula 1 may have improved structural rigidity, a full width at half maximum (FWHM) in the photoluminescent spectrum or electroluminescent spectrum of the organometallic compound represented by Formula 1 may be reduced, and a vibronic state of the organometallic compound represented by Formula 1 may be reduced. Accordingly a non-radiative decay of the organometallic compound represented by Formula 1 can be reduced and thus an electronic device, for example, an organic light-emitting device, including the organometallic compound represented by Formula 1 may have high luminescence efficiency and long lifespan.

A method of synthesizing the first compound represented by Formula 1 may be apparent to one of ordinary skill in the art by referring to Synthesis Examples provided herein.

Description of Formula 2

In Formula 2, Ar$_1$ may be a C$_5$-C$_{60}$ carbocyclic group unsubstituted or substituted with at least one R$_{61}$ or a C$_1$-C$_{60}$ heterocyclic group unsubstituted or substituted with at least one R$_{61}$, in Formula 2, Ar$_2$ may be a π electron-depleted nitrogen-containing C$_1$-C$_{60}$ cyclic group unsubstituted or substituted with at least one R$_{62}$, in Formula 2, Ar$_5$ may not be present or may be a single bond, a C$_5$-C$_{60}$ carbocyclic group unsubstituted or substituted with at least one R$_{65}$, or a C$_1$-C$_{60}$ heterocyclic group unsubstituted or substituted with at least one R$_{65}$, in Formula 2, n may be 1, 2, or 3, and when n is 1, Ar$_5$ may not be present, in Formula 2, a1 and a2 may each independently be an integer from 0 to 5, and the sum of a1 and a2 may be 1 or greater, in Formula 2, ring CY$_2$ and ring CY$_3$ may each independently be a C$_5$-C$_{60}$ carbocyclic group or a C$_1$-C$_{60}$ heterocyclic group, and ring CY$_2$ and ring CY$_3$ may optionally be bound to each other via or a C$_5$-C$_{60}$ carbocyclic group unsubstituted or substituted with at least one R$_{66}$ or a C$_1$-C$_{60}$ heterocyclic group unsubstituted or substituted with at least one R$_{66}$.

As used herein, the term "a π electron-depleted nitrogen-containing C$_1$-C$_{60}$ cyclic group" is a cyclic group having 1 to 60 carbon atoms and at least one *—N=*' as a ring-forming moiety. The examples of r electron-depleted nitrogen-containing C$_1$-C$_{60}$ cyclic group may include a) a first ring, b) a condensed ring in which at least first rings or c) a condensed ring in which at least one first ring and at least one second ring are condensed. The examples of the first ring and the second ring may be understood by referring the descriptions herein.

For example, the π electron-depleted nitrogen-containing C$_1$-C$_{60}$ cyclic group may be an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, an azadibenzofuran group, an azadibenzothiophene group, an azadibenzosilole group, a benzonaphthofuran group, a benzonaphthothiophene group, an indolophenanthrene group, a benzofuranophenanthrene group, a benzothienophenanthrene group, or a pyridopyrazine group.

As used herein, the term "a π electron-rich $C_3$-$C_{60}$ cyclic group" is a cyclic group having 3 to 60 carbon atoms and not having *—N=*' as a ring-forming moiety. The examples of π electron-rich $C_3$-$C_{60}$ cyclic group may include a) a second ring, or b) a condensed ring in which at least second rings. The examples of the second ring may be understood by referring the descriptions herein.

For example, the π electron-rich $C_3$-$C_{60}$ cyclic group may be a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, an indene group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, a benzosilolocarbazole group, a triindolobenzene group, an acridine group, a dihydroacridine group, a pyrrolophenanthrene group, a furanophenanthrene group, or a thienophenanthrene group.

In some embodiments, $Ar_1$ in Formula 2 may be a group derived from i) a first ring unsubstituted or substituted with at least one $R_{61}$, ii) a second ring unsubstituted or substituted with at least one $R_{61}$, iii) a condensed ring in which at least two first rings are condensed, unsubstituted or substituted with at least one $R_{61}$, iv) a condensed ring in which at least two second rings are condensed, unsubstituted or substituted with at least one $R_{61}$, or v) a condensed ring in which at least one first ring and at least one second ring are condensed, unsubstituted or substituted with at least one $R_{61}$, $Ar_2$ in Formula 2 may be a group derived from i) a first ring unsubstituted or substituted with at least one $R_{62}$, ii) a condensed ring in which at least two first rings are condensed, unsubstituted or substituted with at least one $R_{62}$, or iii) a condensed ring in which at least one first ring and at least one second ring are condensed, unsubstituted or substituted with at least one $R_{62}$, $Ar_5$ in Formula 2 may not be present or be a single bond or a group derived from i) a first ring unsubstituted or substituted with at least one $R_{65}$, ii) a second ring unsubstituted or substituted with at least one $R_{65}$, iii) a condensed ring in which at least two first rings are condensed, unsubstituted or substituted with at least one $R_{65}$, iv) a condensed ring in which at least two second rings are condensed, unsubstituted or substituted with at least one $R_{65}$, or v) a condensed ring in which at least one first ring and at least one second ring are condensed, unsubstituted or substituted with at least one $R_{65}$, ring $CY_2$ and ring $CY_3$ in Formula 2 may each independently be i) a first ring, ii) a second ring, iii) a condensed ring in which at least two first rings are condensed, iv) a condensed ring in which at least two second rings are condensed, or v) a condensed ring in which at least one first ring and at least one second ring are condensed, the first ring may be an imidazole group, a pyrazole group, a thiazole group, an isothiazole group, an oxazole group, an isoxazole group, a pyridine group, a pyrazine group, a pyridazine group, a pyrimidine group, a triazole group, a tetrazole group, an oxadiazole group, a triazine group, or a thiadiazole group, and the second ring may be a benzene group, a cyclopentadiene group, a pyrrole group, a furan group, a thiophene group, or a silole group.

In one or more embodiments, in Formula 2, $Ar_1$ may be a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, an indene group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, a benzosilolocarbazole group, a triindolobenzene group, an acridine group, a dihydroacridine group, an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, an azadibenzofuran group, an azadibenzothiophene group, or an azadibenzosilole group, each unsubstituted or substituted with at least one $R_{61}$.

In one or more embodiments, $Ar_2$ in Formula 2 may be an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, an azadibenzofuran group, an azadibenzothiophene group, an azadibenzosilole group, or a pyridopyrazine group, each unsubstituted or substituted with at least one $R_{62}$.

In one or more embodiments, ring $CY_2$ and ring $CY_3$ may each independently be a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, an indene group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, a benzosilolocarbazole group, a triindolobenzene group, an acridine group, a dihydroacridine group, an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, an azadibenzofuran group, an azadibenzothiophene group, or an azadibenzosilole group.

In one or more embodiments, in Formula 2, when n is 1, at least one of the ring $CY_2$ and the ring $CY_3$ may not be a benzene group.

In one or more embodiments, ring $CY_2$ and ring $CY_3$ in Formula 2 may each independently be a π electron-rich $C_3$-$C_{60}$ cyclic group.

In one or more embodiments, in Formula 2, when n is 1, at least one of the ring $CY_2$ and the ring $CY_3$ may be a) a condensed ring in which at least two first rings are condensed, b) a condensed ring in which at least two second rings are condensed, or c) a condensed ring in which at least one first ring and at least one second ring are condensed. The examples of the first ring and the second ring may be understood by referring the descriptions herein.

In one or more embodiments, the second compound may include a compound represented by Formula 2(1):

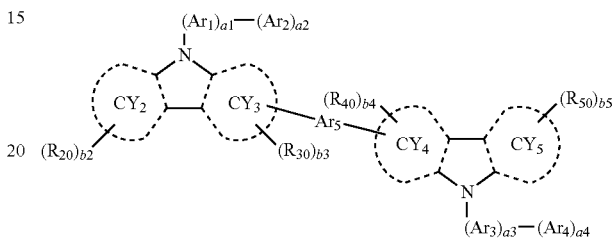

Formula 2(1)

wherein, in Formula 2(1), $Ar_5$ may be a single bond, a $C_5$-$C_{60}$ carbocyclic group unsubstituted or substituted with at least one $R_{65}$, or a $C_1$-$C_{60}$ heterocyclic group unsubstituted or substituted with at least one $R_{65}$, $Ar_1$, $Ar_2$, $Ar_5$, a1, a2, ring CY2, ring $CY_3$, $R_{20}$, $R_{30}$, b2, and b3 are respectively understood by referring to the descriptions of $Ar_1$, $Ar_2$, $Ar_5$, a1, a2, ring $CY_2$, ring $CY_3$, $R_{20}$, $R_{30}$, b2, and b3 provided herein, $Ar_3$ and $Ar_4$ are each understood by referring to the descriptions of $Ar_1$ provided herein, and a3, a4, ring CY4, ring CY5, $R_{40}$, $R_{50}$, b4, and b5 are respectively understood by referring to the descriptions of a1, a2, ring $CY_2$, ring $CY_3$, $R_{20}$, $R_{30}$, b2, and b3 provided herein.

For example, $Ar_5$ in Formula 2(1) may be a single bond.

In one or more embodiments, a group represented by

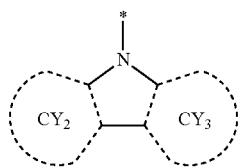

in Formulae 2 and 2(1) and a group represented by

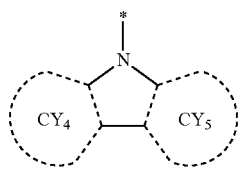

in Formula 2(1) may each independently be a group represented by one of Formulae 2-1 to 2-93:

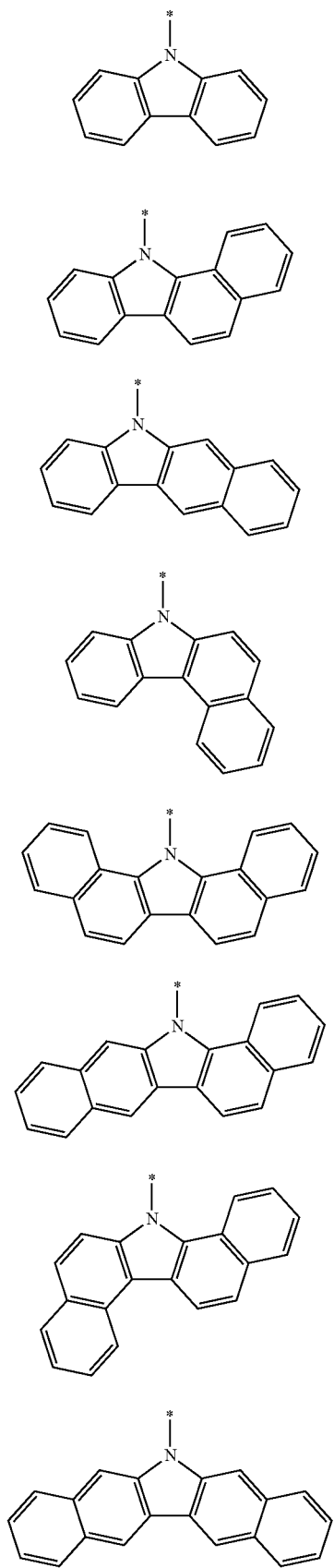
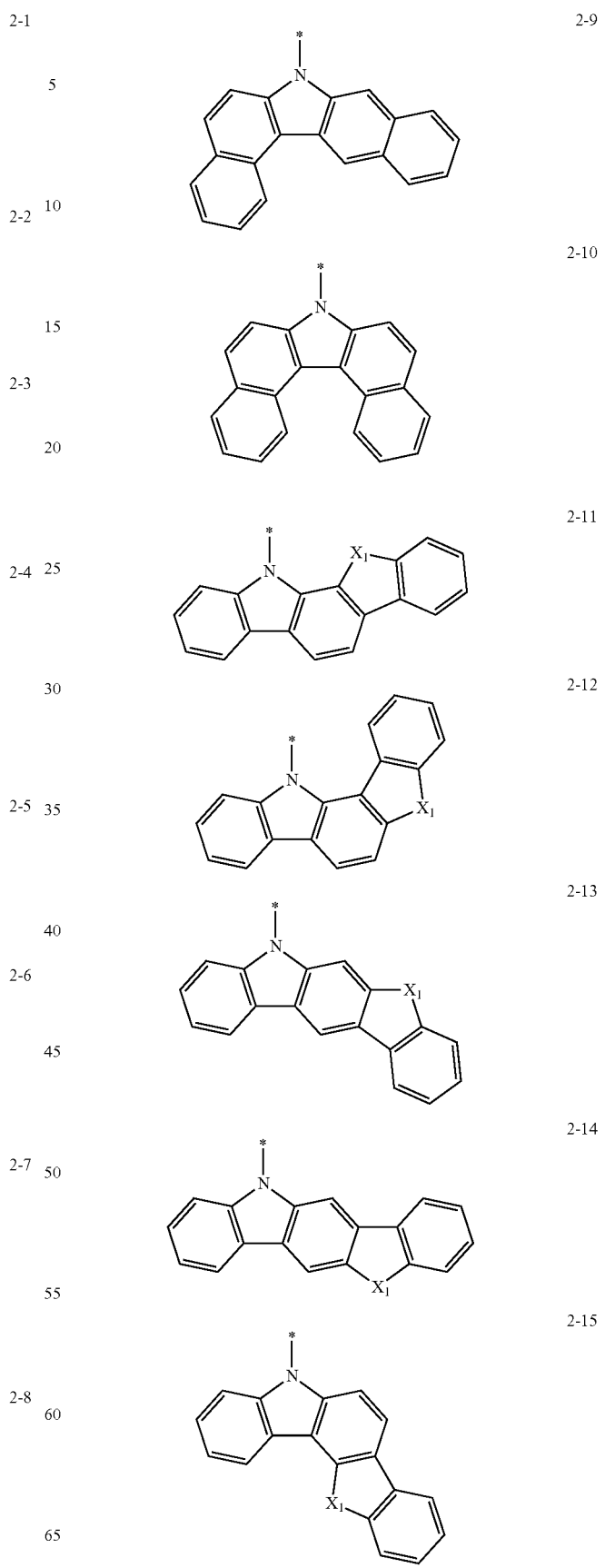

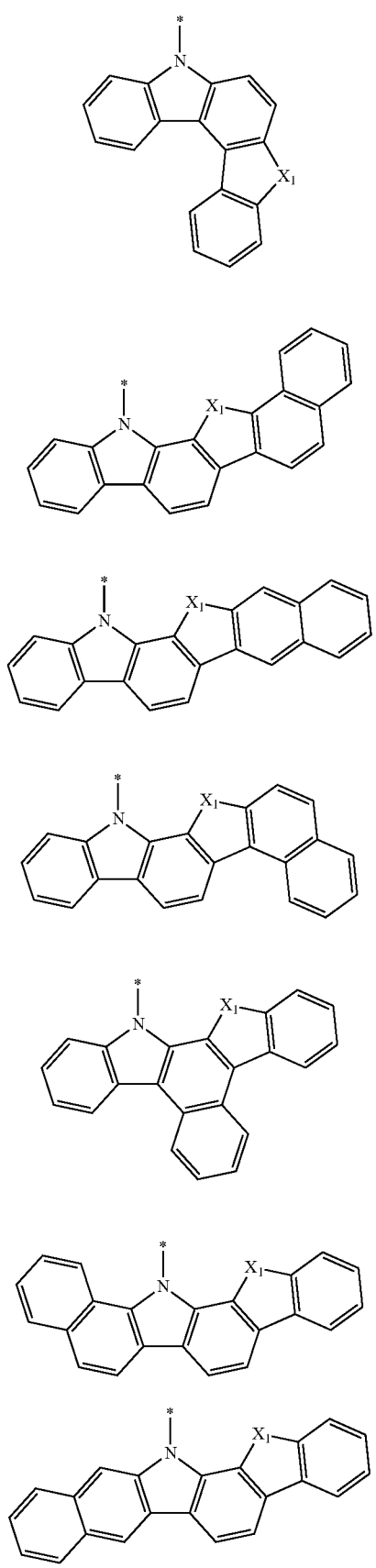
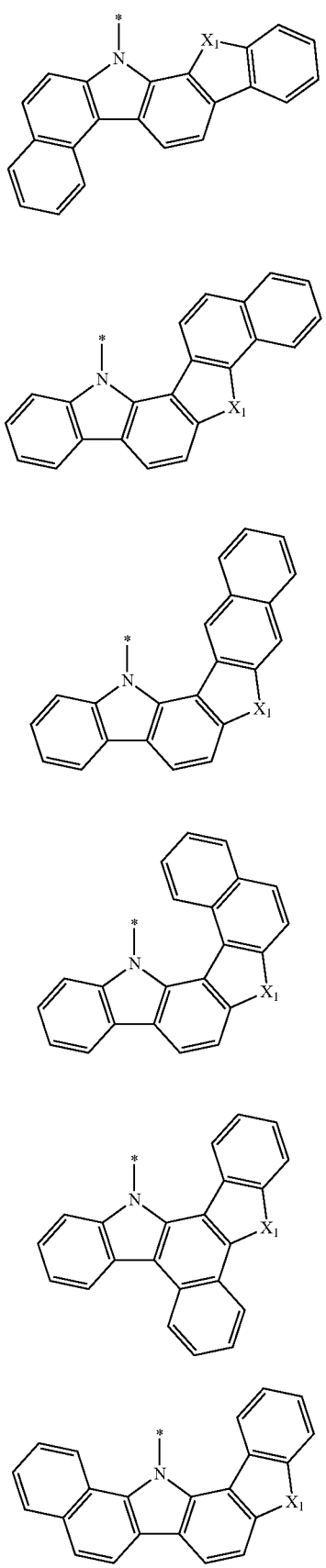

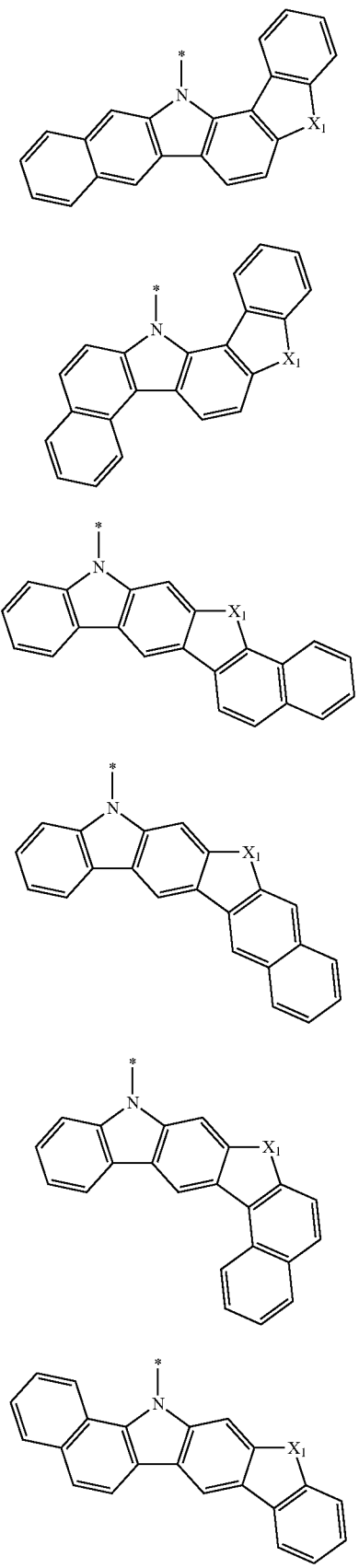
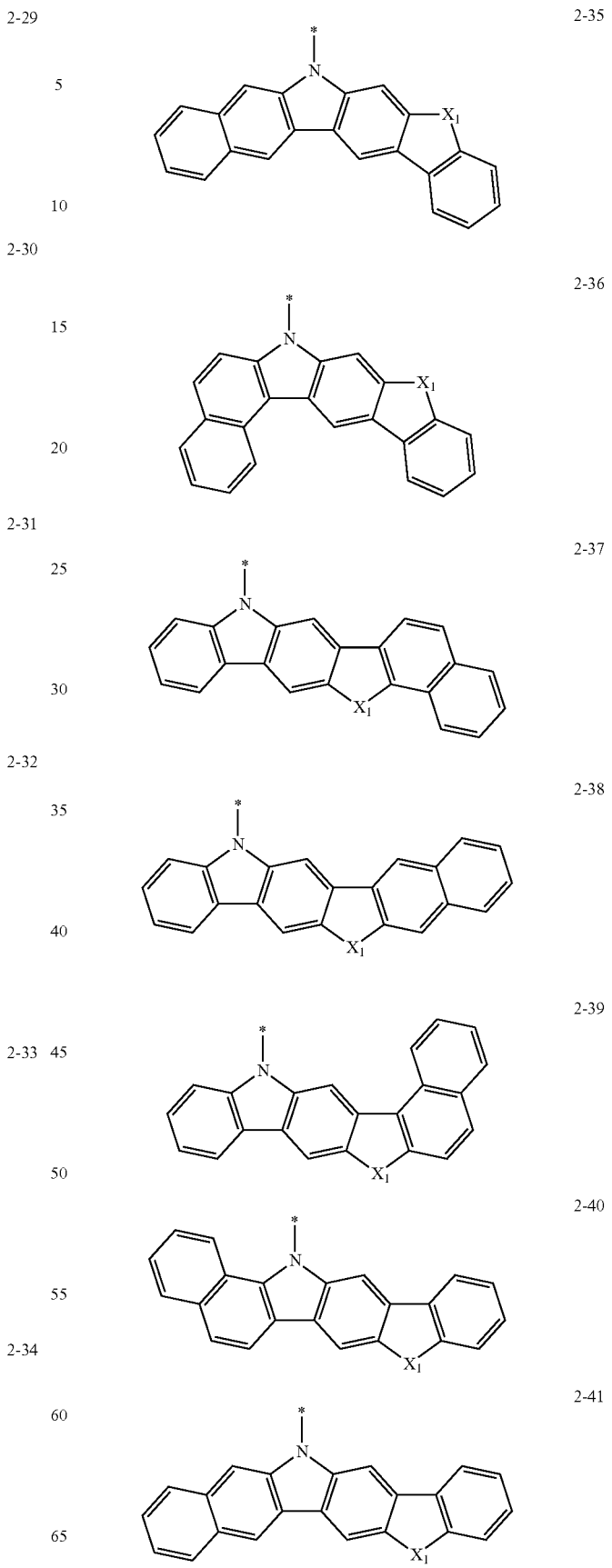

2-42
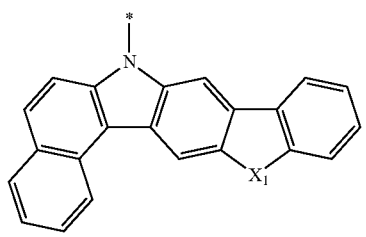
2-43
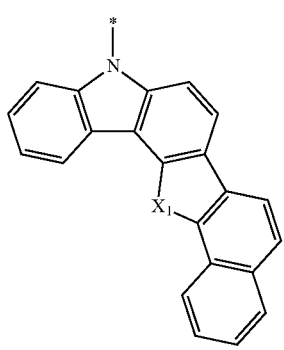
2-44
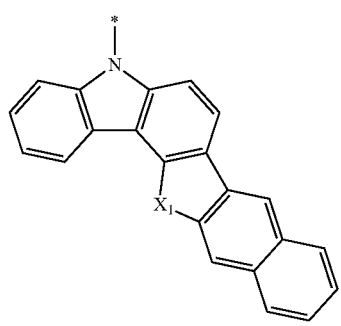
2-45
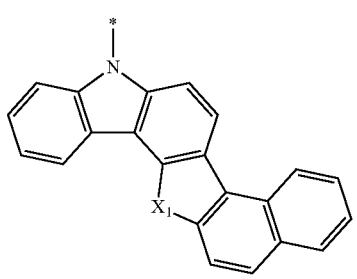
2-46
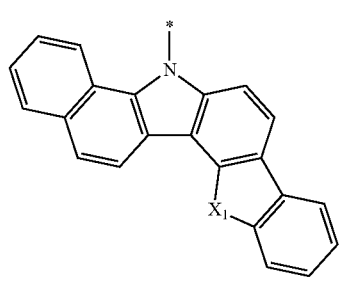
2-47
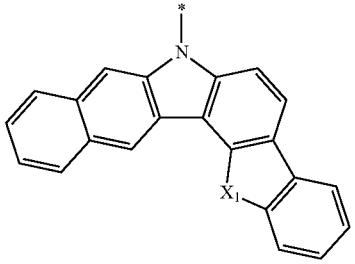
2-48
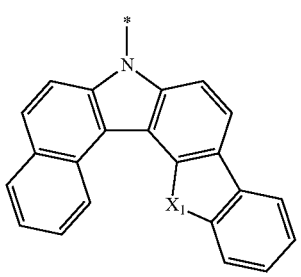
2-49
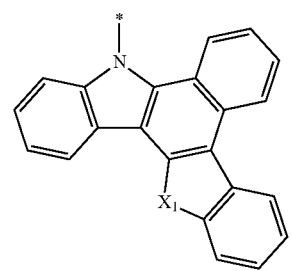
2-50
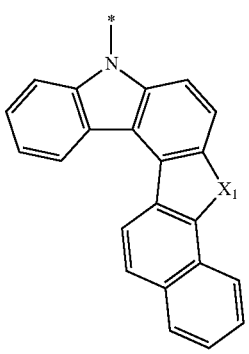
2-51
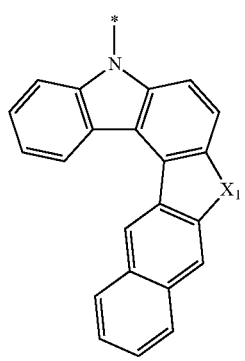

2-52
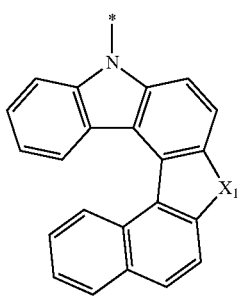
2-53
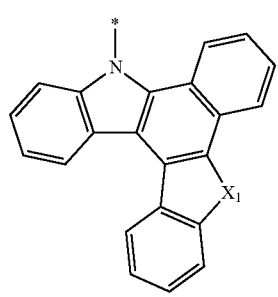
2-54
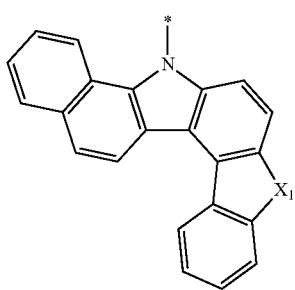
2-55
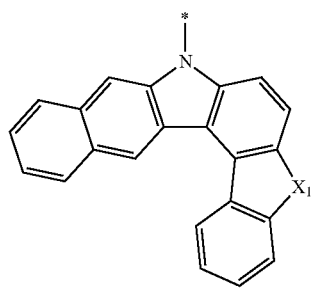
2-56
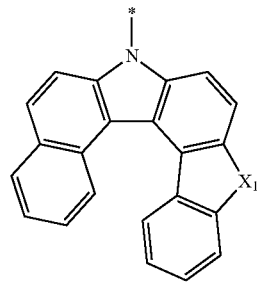
2-57
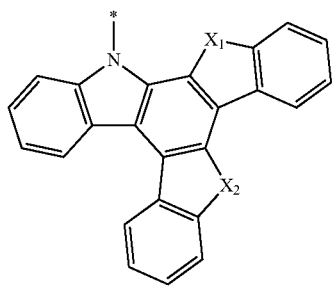
2-58
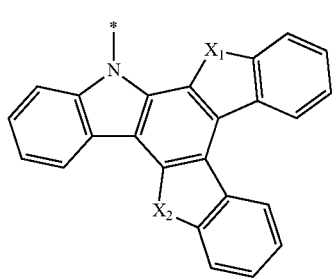
2-59
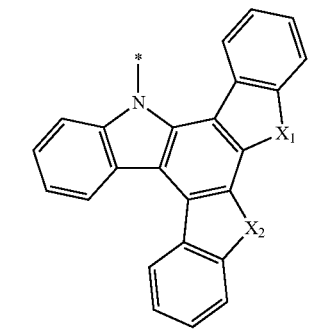
2-60
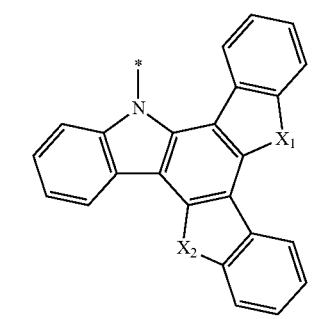
2-61
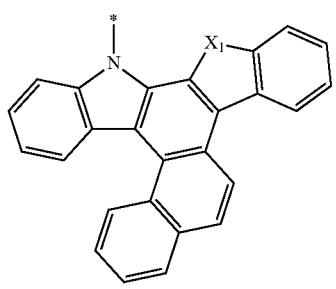

2-62
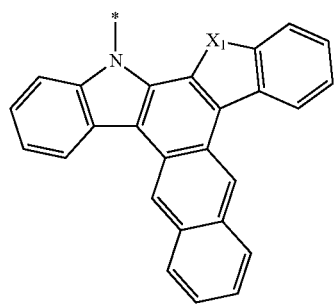
2-63
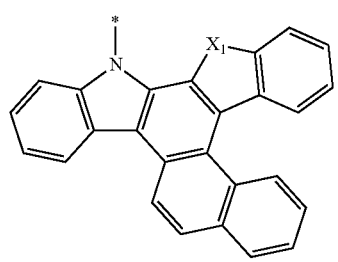
2-64
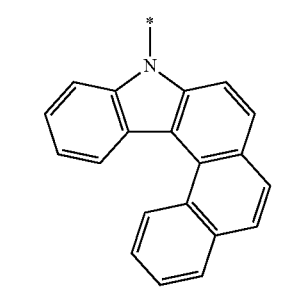
2-65
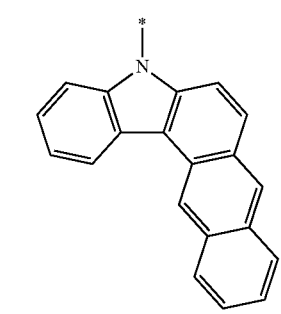
2-66
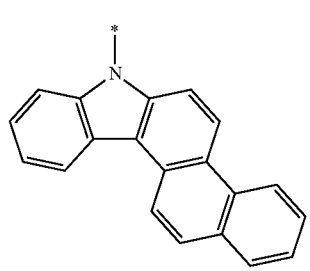
2-67
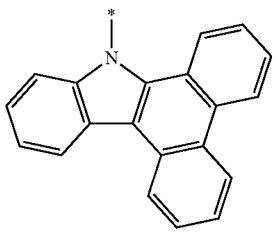
2-68
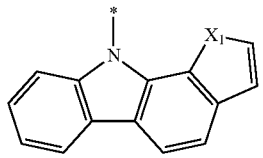
6-29
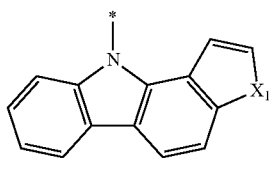
6-70
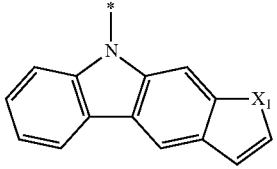
2-71
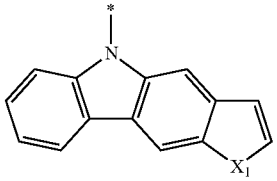
2-72
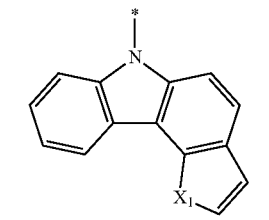
2-73
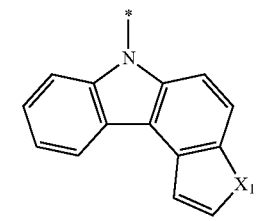
2-74
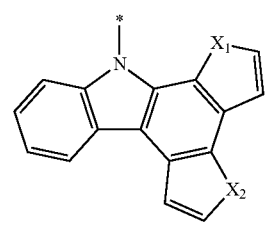

| 2-75 | 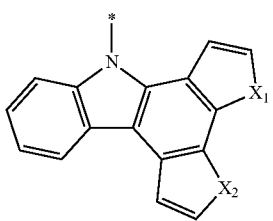 | 2-82 | 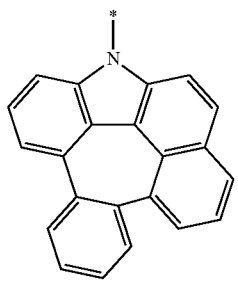 |
| 2-76 | 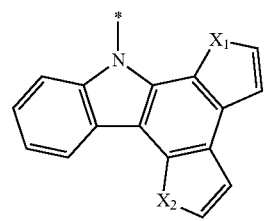 | 2-83 | 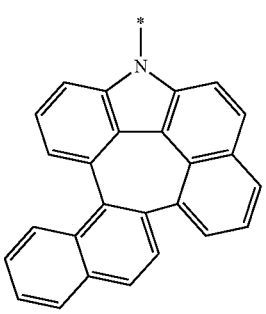 |
| 2-77 | 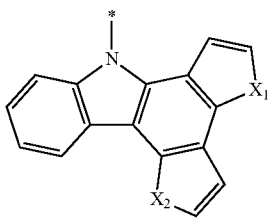 | 2-84 | 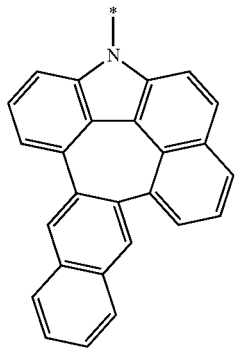 |
| 2-78 | 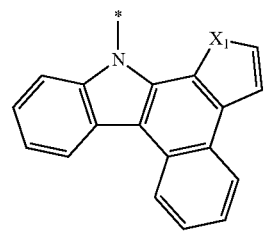 | 2-85 | 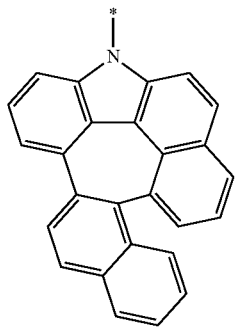 |
| 2-79 | 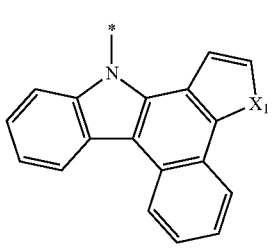 | 2-86 | 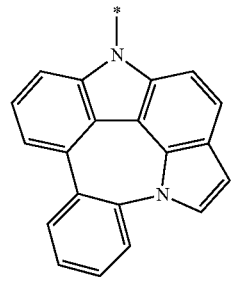 |
| 2-80 | 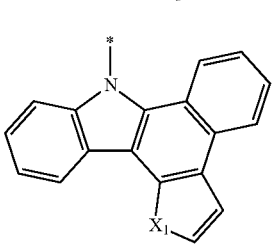 | | |
| 2-81 | 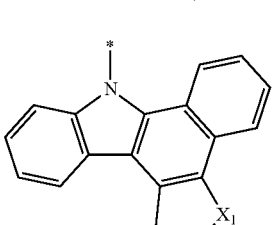 | | |

-continued
2-87
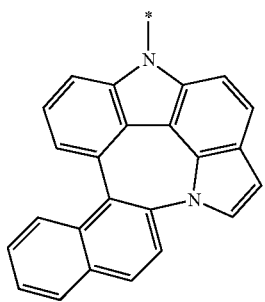
2-88
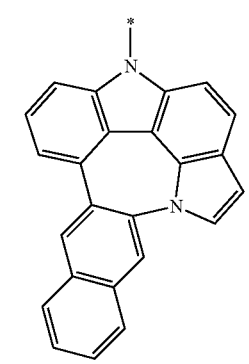
2-89
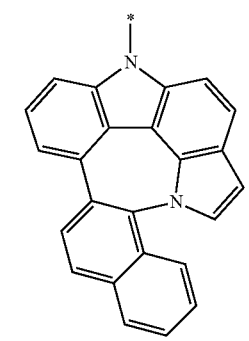
2-90
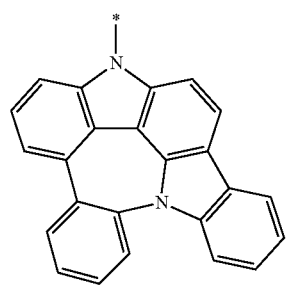
2-91
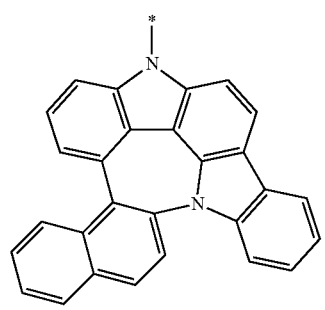
-continued
2-92
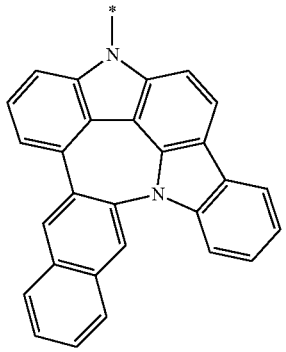
2-93
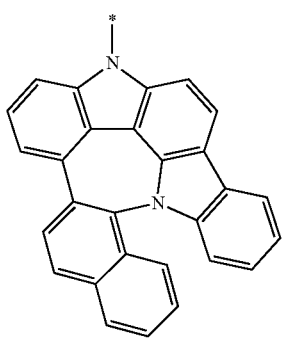
wherein, in Formulae 2-1 to 2-93,
$X_1$ may be O, S, $N(R_{31})$, $C(R_{31})(R_{32})$, or $Si(R_{31})(R_{32})$,
$X_2$ may be O, S, $N(R_{33})$, $C(R_{33})(R_{34})$, or $Si(R_{33})(R_4)$,
$R_{31}$ to $R_{34}$ may each be understood by referring to the description of $R_{30}$ provided herein, and
* in Formula 2 indicates a binding site to $Ar_1$ or $Ar_2$.
In some embodiments, in Formulae 2 and 2(1), $Ar_2$ may be a group represented by one of Formulae 5-1 to 5-31:
5-1
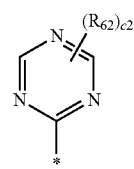
5-2
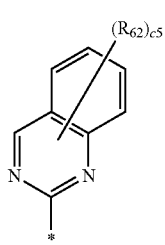
5-3
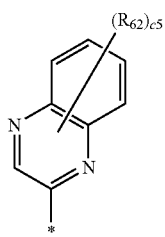

-continued
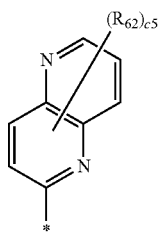 5-4
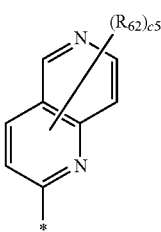 5-5
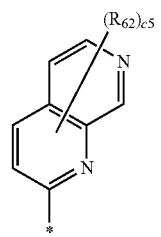 5-6
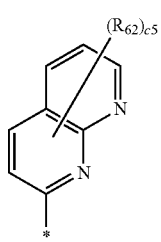 5-7
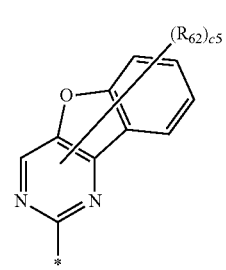 5-8
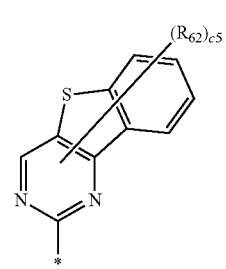 5-9
-continued
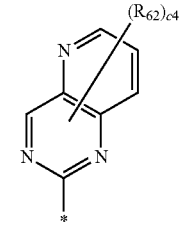 5-10
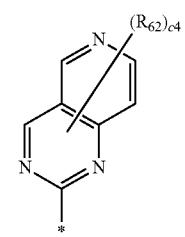 5-11
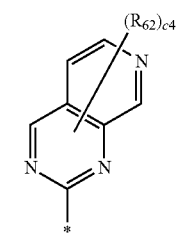 5-12
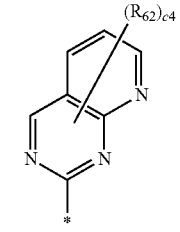 5-13
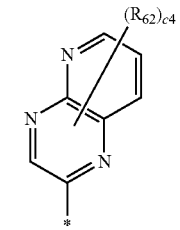 5-14
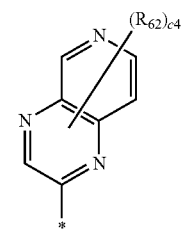 5-15

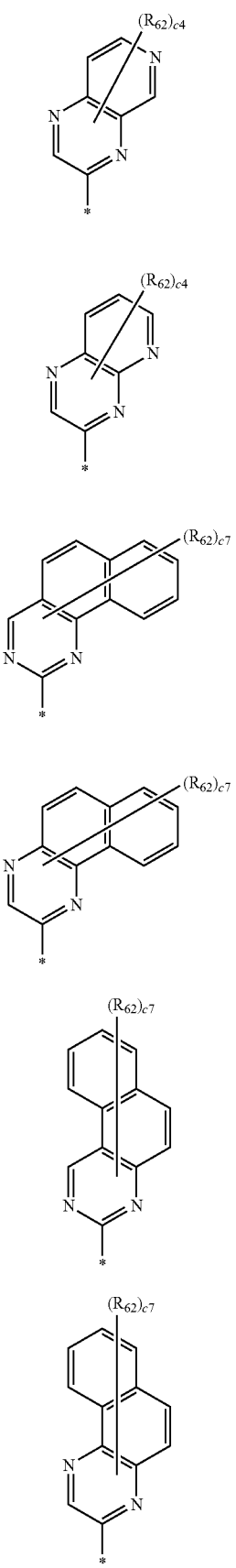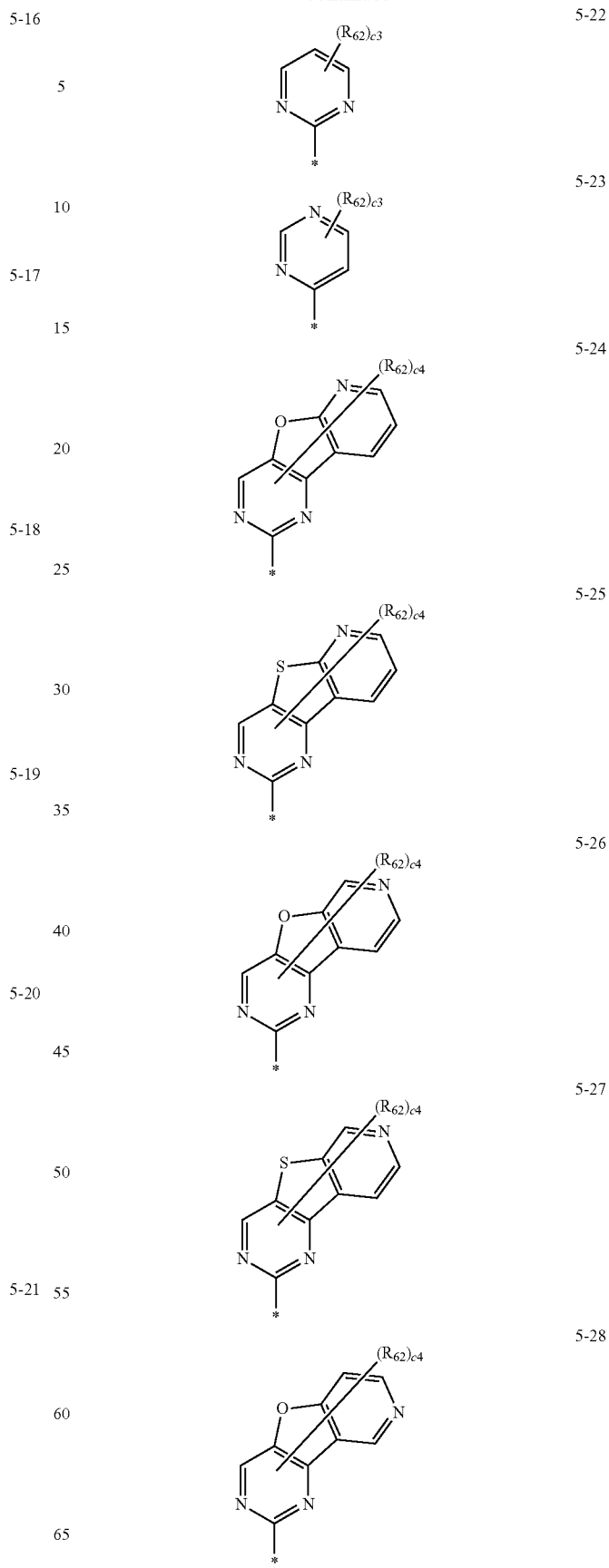

-continued

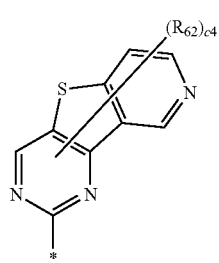

5-29

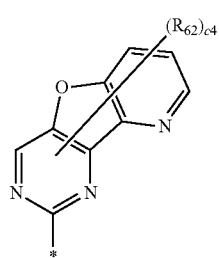

5-30

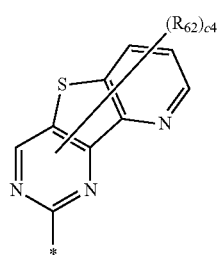

5-31 wherein, in Formulae 5-1 to 5-31,
$R_{62}$ may be understood by referring to the description of $R_{62}$ provided herein,
c2 may be an integer from 0 to 2,
c3 may be an integer from 0 to 3,
c4 may be an integer from 0 to 4,
c5 may be an integer from 0 to 5,
c7 may be an integer from 0 to 7, and
* indicates a binding site to $Ar_1$ or N in Formulae 2 and 2(1).

In Formulae 2 and 2(1), a1 and a2 each indicate the number of $Ar_1$(s) and $Ar_2$(s), respectively. a1 and a2 may each independently be an integer from 0 to 5, and the sum of a1 and a2 may be 1 or greater. When all is two or greater, at least two $Ar_1$ groups may be identical to or different from each other, and when a2 is two or greater, at least two $Ar_2$ groups may be identical to or different from each other. When a1 is 0, in Formula 2, *—$(Ar_1)_{a1}$—*' may be a single bond.

In some embodiments, in Formulae 2 and 2(1), a2 may not be 0.

In some embodiments, in Formulae 2 and 2(1), a2 may be 1 or 2.

In one or more embodiments, in Formulae 2 and 2(1), a2 may be 1 or 2 and $Ar_3$ and $Ar_4$ may each independently be a π electron-rich $C_3$-$C_{60}$ cyclic group (for example, a benzene group, a naphthalene group, a phenanthrene group, a carbazole group, a dibenzofuran group, a dibenzothiophene group, etc.) unsubstituted or substituted with deuterium, a $C_1$-$C_{20}$ alkyl group, a phenyl group, a biphenyl group, a terphenyl group, a naphthyl group, or any combination thereof.

In one or more embodiments, in Formula 2, n may be 1 or 2.

In Formula 2, $R_{20}$, $R_{30}$, $R_{61}$, $R_{62}$, $R_{65}$, and $R_{66}$ may each independently be hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{60}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —Ge($Q_3$)($Q_4$)($Q_5$), —B($Q_6$)($Q_7$), —P(=O)($Q_8$)($Q_9$), or —P($Q_8$)($Q_9$). $Q_1$ to $Q_9$ may respectively be understood by referring to the descriptions of $Q_1$ to $Q_9$ provided herein.

In some embodiments, in Formula 2, $R_{20}$, $R_{30}$, $R_{61}$, $R_{62}$, $R_{65}$, and $R_{66}$ may each independently be:
hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —SF$_5$, a $C_1$-$C_{20}$ alkyl group, or a $C_1$-$C_{20}$ alkoxy group;
a $C_1$-$C_{20}$ alkyl group or a $C_1$-$C_{20}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a deuterium-containing $C_1$-$C_{20}$ alkyl group, a fluorinated $C_1$-$C_{20}$ alkyl group, a cyclopentyl group, a cyclohexyl group, a cycloheptyl group, a cyclooctyl group, an adamantyl group, a norbomenyl group, a cyclopentenyl group, a cyclohexenyl group, a cycloheptenyl group, a bicyclo[1.1.1]pentyl group, a bicyclo[2.1.1]hexyl group, a bicyclo[2.2.1]heptyl group (a norbornanyl group), a bicyclo[2.2.2]octyl group, a ($C_1$-$C_{20}$ alkyl)cyclopentyl group, a ($C_1$-$C_{20}$ alkyl)cyclohexyl group, a ($C_1$-$C_{20}$ alkyl)cycloheptyl group, a ($C_1$-$C_{20}$ alkyl)cyclooctyl group, a ($C_1$-$C_{20}$ alkyl)adamantyl group, a ($C_1$-$C_{20}$ alkyl)norbomenyl group, a ($C_1$-$C_{20}$ alkyl)cyclopentenyl group, a ($C_1$-$C_{20}$ alkyl)cyclohexenyl group, a ($C_1$-$C_{20}$ alkyl)cycloheptenyl group, a ($C_1$-$C_{20}$ alkyl)bicyclo[1.1.1]pentyl group, a ($C_1$-$C_{20}$ alkyl)bicyclo[2.1.1]hexyl group, a ($C_1$-$C_{20}$ alkyl)bicyclo[2.2.1]heptyl group, a ($C_1$-$C_{20}$ alkyl)bicyclo[2.2.2]octyl group, a silolanyl group, a phenyl group, a ($C_1$-$C_{20}$ alkyl)phenyl group, a biphenyl group, a terphenyl group, a naphthyl group, a 1,2,3,4-tetrahydronaphthyl group, a pyridinyl group, a pyrimidinyl group, or any combination thereof;
a cyclopentyl group, a cyclohexyl group, a cycloheptyl group, a cyclooctyl group, an adamantyl group, a norbornenyl group, a cyclopentenyl group, a cyclohexenyl group, a cycloheptenyl group, a bicyclo[1.1.1]

pentyl group, a bicyclo[2.1.1]hexyl group, a bicyclo [2.2.1]heptyl group, a bicyclo[2.2.2]octyl group, a silolanyl group, a phenyl group, a ($C_1$-$C_{20}$ alkyl)phenyl group, a biphenyl group, a terphenyl group, a naphthyl group, a 1,2,3,4-tetrahydronaphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, or an azadibenzothiophenyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a deuterium-containing $C_1$-$C_{20}$ alkyl group, a fluorinated $C_1$-$C_{20}$ alkyl group, a $C_1$-$C_{20}$ alkoxy group, a cyclopentyl group, a cyclohexyl group, a cycloheptyl group, a cyclooctyl group, an adamantyl group, a norbornenyl group, a cyclopentenyl group, a cyclohexenyl group, a cycloheptenyl group, a bicyclo[1.1.1]pentyl group, a bicyclo[2.1.1] hexyl group, a bicyclo[2.2.1]heptyl group, a bicyclo [2.2.2]octyl group, a ($C_1$-$C_{20}$ alkyl)cyclopentyl group, a ($C_1$-$C_{20}$ alkyl)cyclohexyl group, a ($C_1$-$C_{20}$ alkyl) cycloheptyl group, a ($C_1$-$C_{20}$ alkyl)cyclooctyl group, a ($C_1$-$C_{20}$ alkyl)adamantyl group, a ($C_1$-$C_{20}$ alkyl)norbornenyl group, a ($C_1$-$C_{20}$ alkyl)cyclopentenyl group, a ($C_1$-$C_{20}$ alkyl)cyclohexenyl group, a ($C_1$-$C_{20}$ alkyl) cycloheptenyl group, a ($C_1$-$C_{20}$ alkyl)bicyclo[1.1.1] pentyl group, a ($C_1$-$C_{20}$ alkyl)bicyclo[2.1.1]hexyl group, a ($C_1$-$C_{20}$ alkyl)bicyclo[2.2.1]heptyl group, a ($C_1$-$C_{20}$ alkyl)bicyclo[2.2.2]octyl group, a silolanyl group, a phenyl group, a ($C_1$-$C_{20}$ alkyl)phenyl group, a biphenyl group, a terphenyl group, a naphthyl group, a 1,2,3,4-tetrahydronaphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, an azacarbazolyl group, an azadibenzofuranyl group, an azadibenzothiophenyl group, or any combination thereof; or —$N(Q_1)(Q_2)$, —$Si(Q_3)(Q_4)(Q_5)$, —$Ge(Q_3)(Q_4)(Q_5)$, —$B(Q_6)(Q_7)$, —$P(=O)(Q_8)(Q_9)$, or —$P(Q_8)(Q_9)$, $Q_1$ to $Q_6$ may each independently be:

—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$ or —$CD_2CDH_2$; or an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, a $C_1$-$C_{20}$ alkyl group, a phenyl group, or any combination thereof.

In Formula 2, b2 and b3 may each indicate the number of $R_{20}$(s) and $R_{30}$(s), respectively. b2 and b3 may each independently be an integer from 0 to 20. In some embodiments, b2 and b3 may each independently be an integer from 0 to 10. When b2 is two or greater, at least two $R_{20}$(s) may be identical to or different from each other, and when b3 is two or greater, at least two $R_{30}$(s) may be identical to or different from each other.

In one or more embodiments, $R_{20}$, $R_{30}$, $R_{61}$, $R_{62}$, $R_{65}$, and $R_{66}$ in Formulae 2 and 3 may each independently be:

hydrogen or deuterium;

a $C_1$-$C_{20}$ alkyl group or a $C_1$-$C_{20}$ alkoxy group, each unsubstituted or substituted with deuterium, a phenyl group, a naphthyl group, an anthracenyl group, a phenanthrenyl group, a triphenylenyl group, a fluorenyl group, a di($C_1$-$C_{10}$ alkyl)fluorenyl group, a di($C_6$-$C_{60}$ aryl)fluorenyl group, a dibenzosilolyl group, a di($C_1$-$C_{10}$ alkyl)dibenzosilolyl group, a di($C_6$-$C_{60}$ aryl)dibenzosilolyl group, a carbazolyl group, a ($C_1$-$C_{10}$ alkyl) carbazolyl group, a ($C_6$-$C_{60}$ aryl)carbazolyl group, a dibenzofuranyl group, a dibenzothiophenyl group, a biphenyl group, a terphenyl group, —$N(Q_{31})(Q_{32})$, or any combination thereof;

a π electron-rich $C_3$-$C_{60}$ cyclic group, unsubstituted or substituted with deuterium, a $C_1$-$C_{20}$ alkyl group, a $C_1$-$C_{20}$ alkoxy group, a phenyl group, a naphthyl group, an anthracenyl group, a phenanthrenyl group, a triphenylenyl group, a fluorenyl group, a di($C_1$-$C_{10}$ alkyl)

fluorenyl group, a di(C$_6$-C$_{60}$ aryl)fluorenyl group, a dibenzosilolyl group, a di(C$_1$-C$_{10}$ alkyl)dibenzosilolyl group, a di(C$_6$-C$_{60}$ aryl)dibenzosilolyl group, a carbazolyl group, a (C$_1$-C$_{10}$ alkyl)carbazolyl group, a (C$_6$-C$_{60}$ aryl)carbazolyl group, a dibenzofuranyl group, a dibenzothiophenyl group, a biphenyl group, a terphenyl group, —N(Q$_{31}$)(Q$_{32}$), or any combination thereof; or —N(Q$_1$)(Q$_2$). Herein, Q$_1$, Q$_2$, Q$_{31}$ and Q$_{32}$ are each independently the same as described herein.

In one or more embodiments, R$_{20}$, R$_{30}$, R$_{61}$, R$_{62}$, R$_{65}$, and R$_{66}$ in Formulae 2 and 3 may each independently be:

hydrogen or deuterium;

a C$_1$-C$_{20}$ alkyl group unsubstituted or substituted with deuterium, a phenyl group, a naphthyl group, an anthracenyl group, a phenanthrenyl group, a triphenylenyl group, a fluorenyl group, a di(C$_1$-C$_{10}$ alkyl)fluorenyl group, a di(C$_6$-C$_{60}$ aryl)fluorenyl group, a dibenzosilolyl group, a di(C$_1$-C$_{10}$ alkyl)dibenzosilolyl group, a di(C$_6$-C$_{60}$ aryl)dibenzosilolyl group, a carbazolyl group, a (C$_1$-C$_{10}$ alkyl)carbazolyl group, a (C$_6$-C$_{60}$ aryl)carbazolyl group, a dibenzofuranyl group, a dibenzothiophenyl group, a biphenyl group, a terphenyl group, —N(Q$_{31}$)(Q$_{32}$), or any combination thereof; or a phenyl group, a naphthyl group, an anthracenyl group, a phenanthrenyl group, a triphenylenyl group, a fluorenyl group, a dibenzosilolyl group, a carbazolyl group, a dibenzofuranyl group, or a dibenzothiophenyl group, unsubstituted or substituted with deuterium, a C$_1$-C$_{20}$ alkyl group, a C$_1$-C$_{20}$ alkoxy group, a phenyl group, a naphthyl group, an anthracenyl group, a phenanthrenyl group, a triphenylenyl group, a fluorenyl group, a di(C$_1$-C$_{10}$ alkyl)fluorenyl group, a di(C$_6$-C$_{60}$ aryl)fluorenyl group, a dibenzosilolyl group, a di(C$_1$-C$_{10}$ alkyl)dibenzosilolyl group, a di(C$_6$-C$_{60}$ aryl)dibenzosilolyl group, a carbazolyl group, a (C$_1$-C$_{10}$ alkyl)carbazolyl group, a (C$_6$-C$_{60}$ aryl)carbazolyl group, a dibenzofuranyl group, a dibenzothiophenyl group, a biphenyl group, a terphenyl group, —N(Q$_{31}$)(Q$_{32}$), or any combination thereof. Herein, Q$_{31}$ and Q$_{32}$ are each independently the same as described herein.

In some embodiments, the second compound represented by Formula 2 may include at least one of Compounds H1 to H90, but embodiments are not limited thereto:

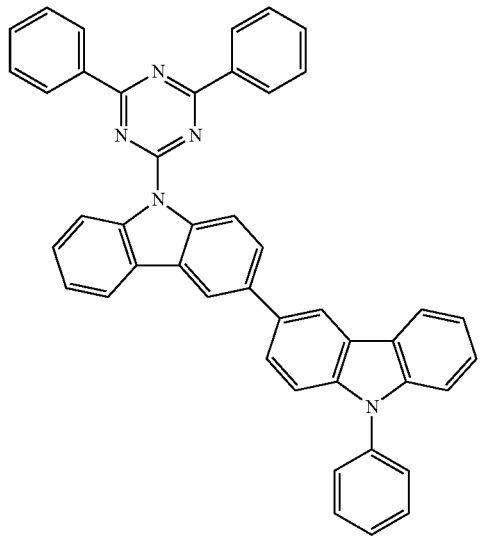

H1

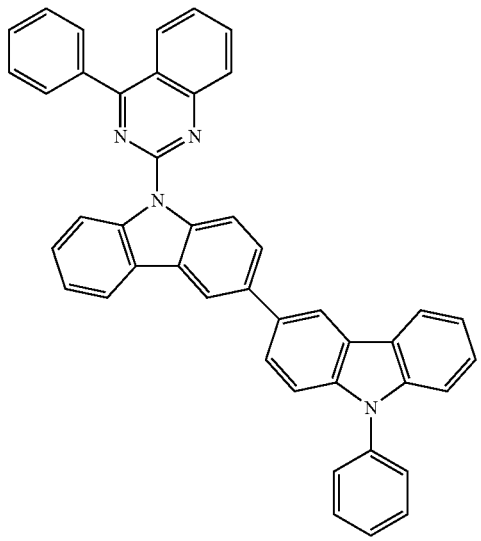

H2

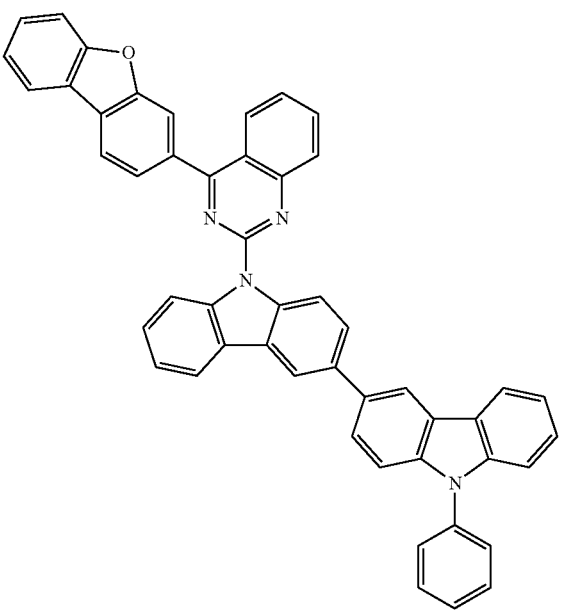

H3

H4
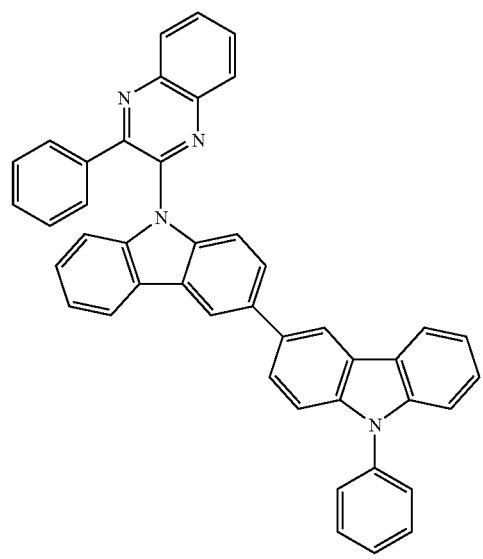
H5
H6
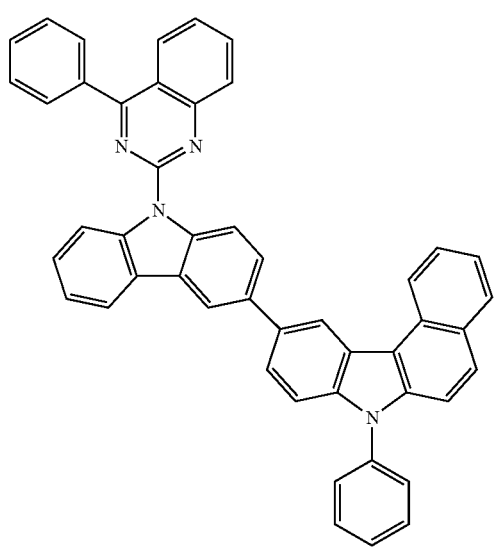
H7
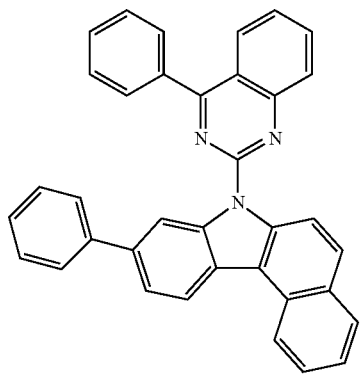
H8
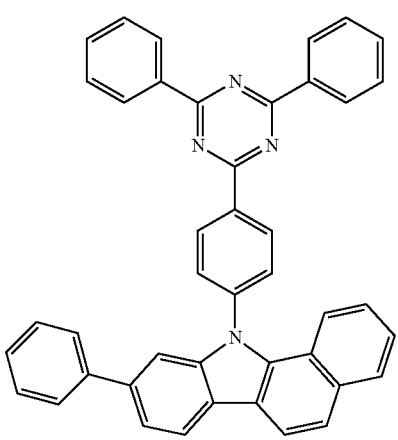
H9
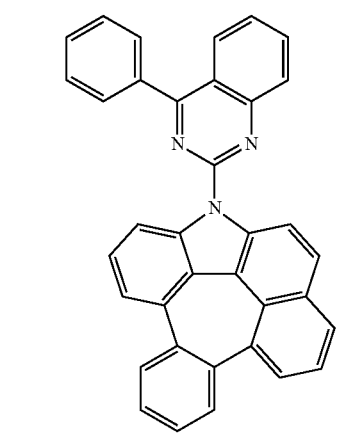

135
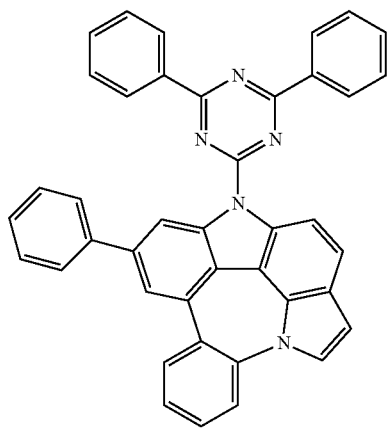
H10
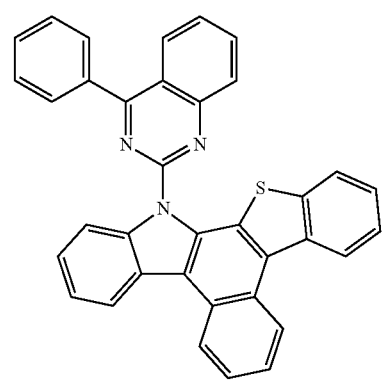
H11
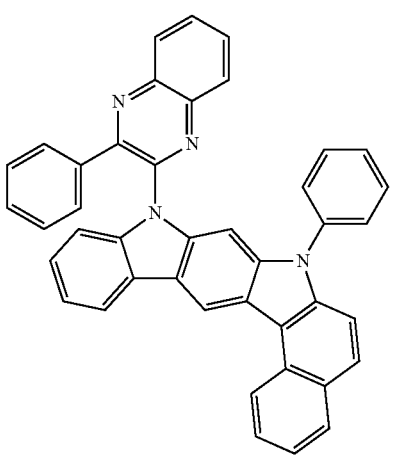
H12
136
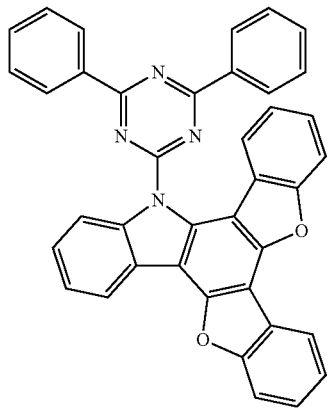
H13
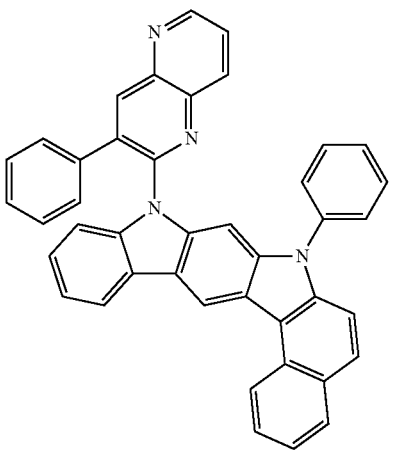
H14
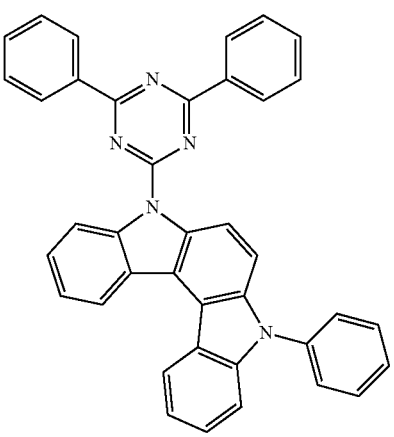
H15

137
-continued
H16
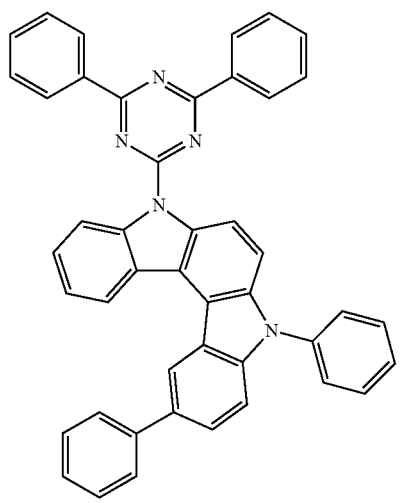
H17
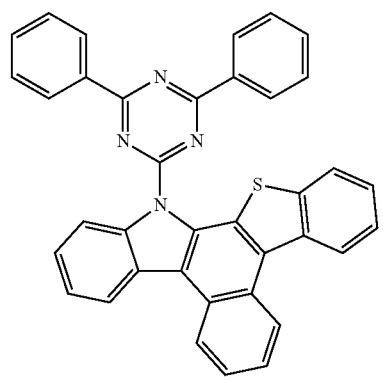
H18
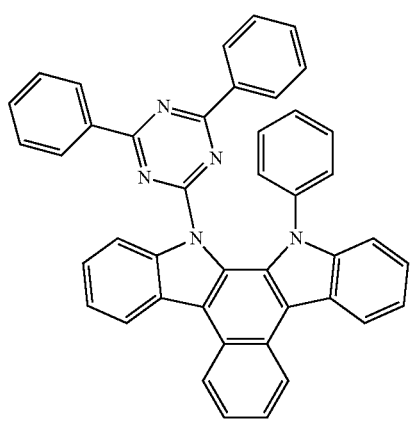
138
-continued
H19
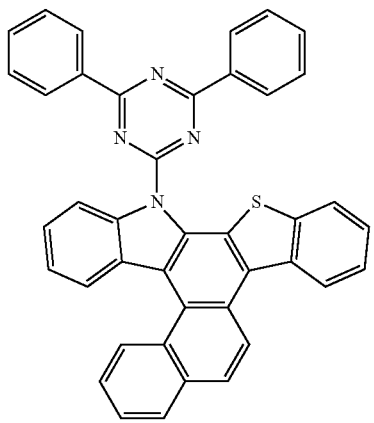
H20
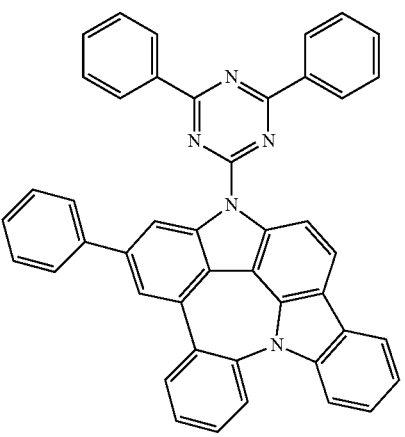
H21
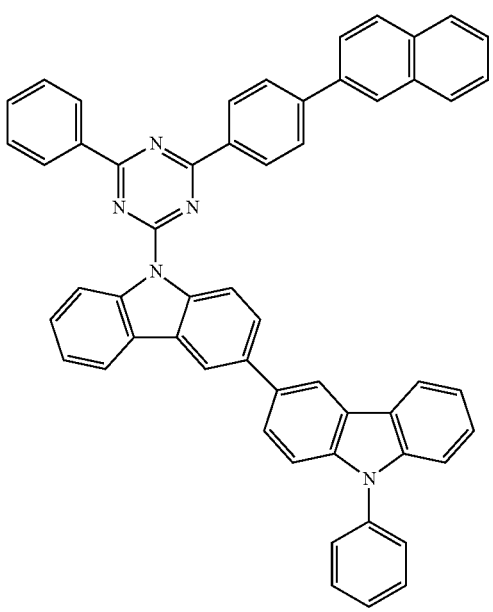

139
-continued
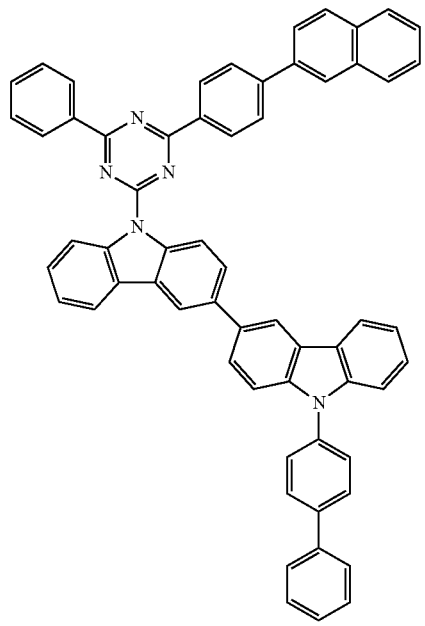
H22
140
-continued
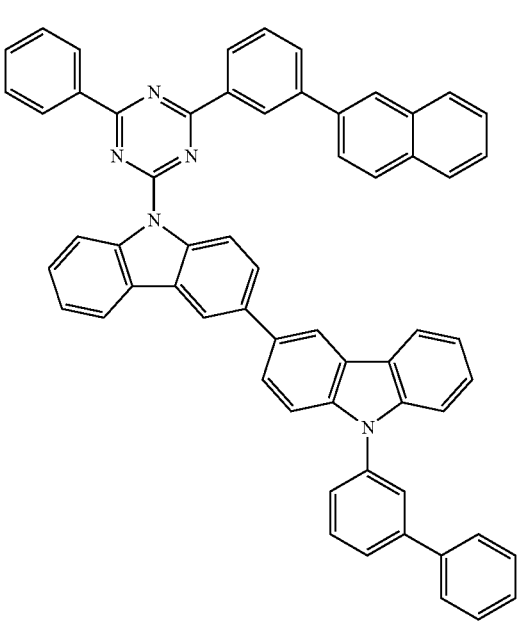
H24
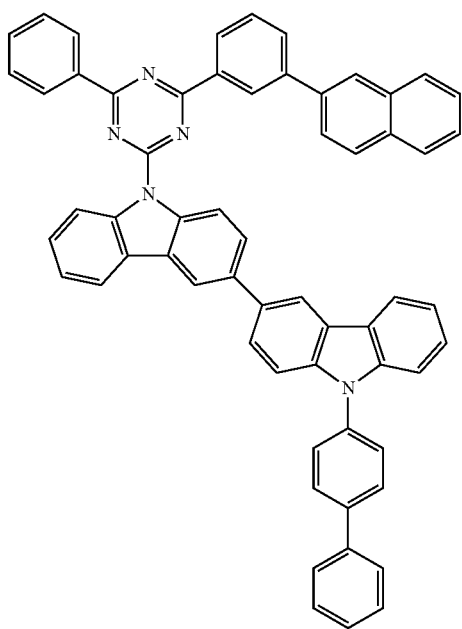
H23
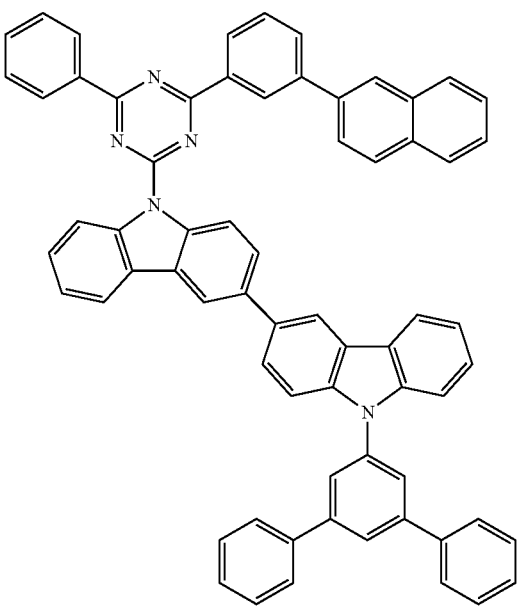
H25

H26
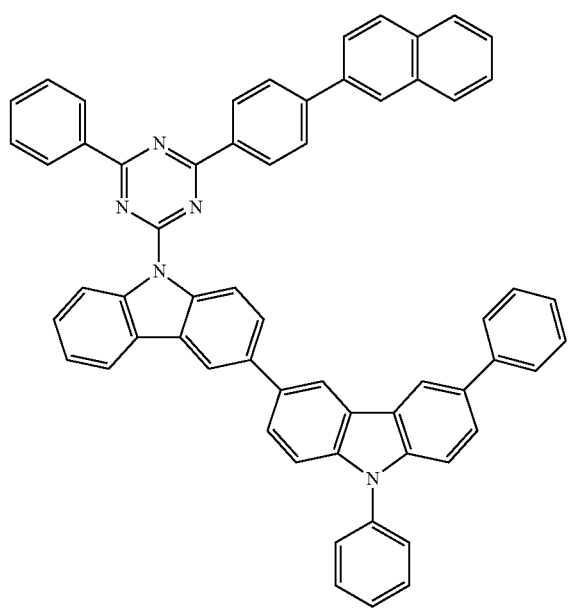
H28
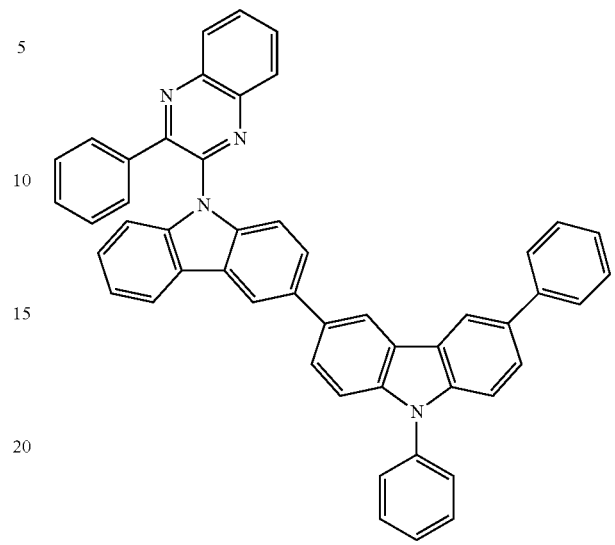
H27
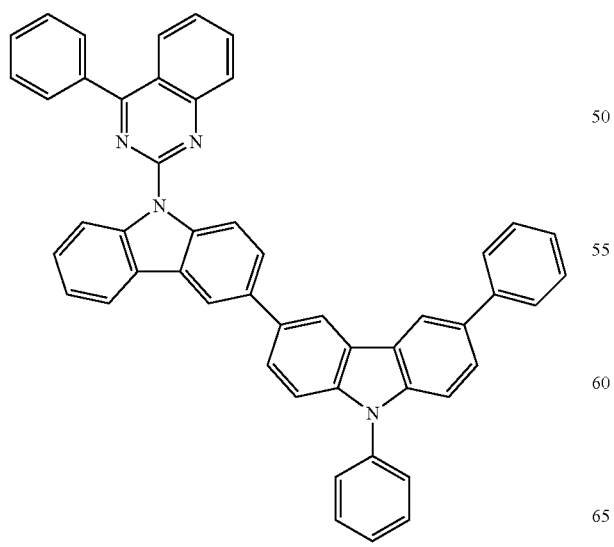
H29
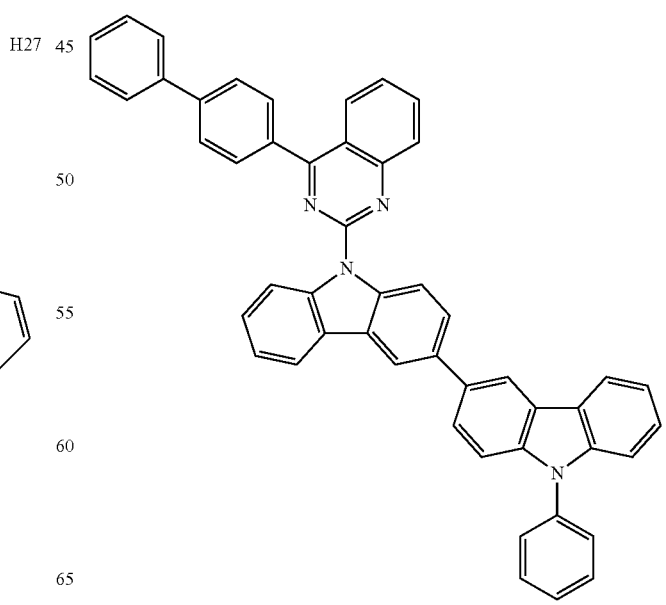

H30
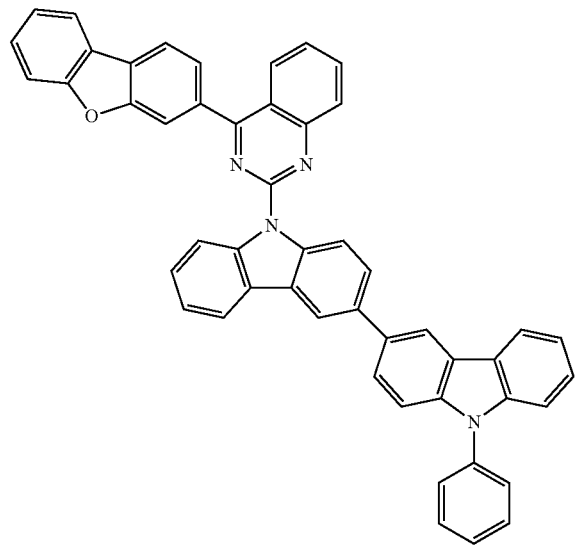
H31
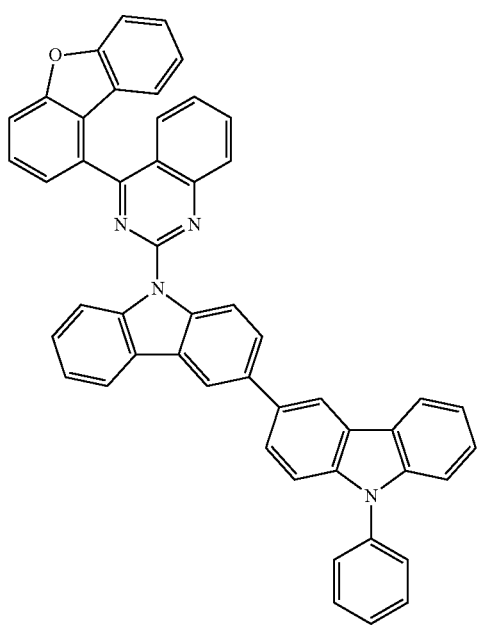
H32
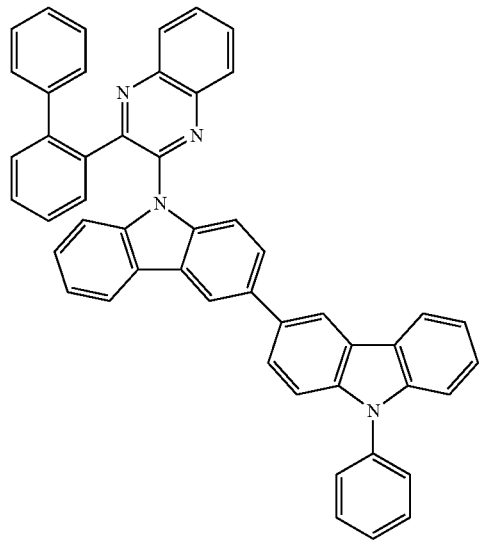
H33
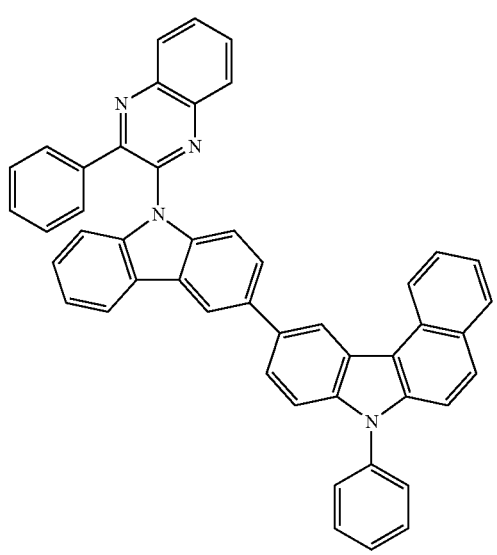
H34
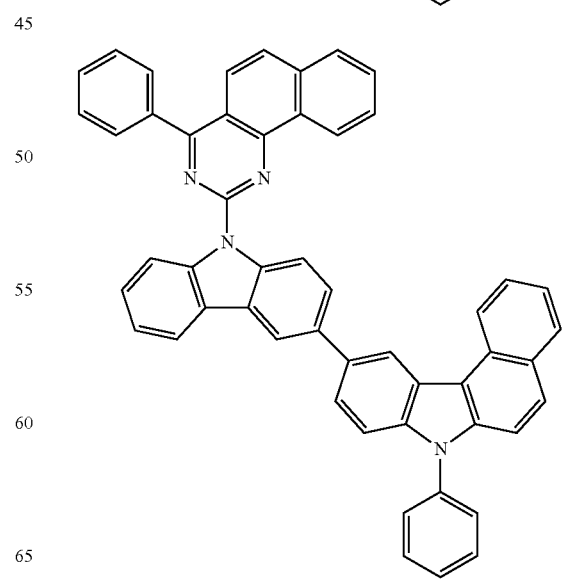

145
-continued
H35
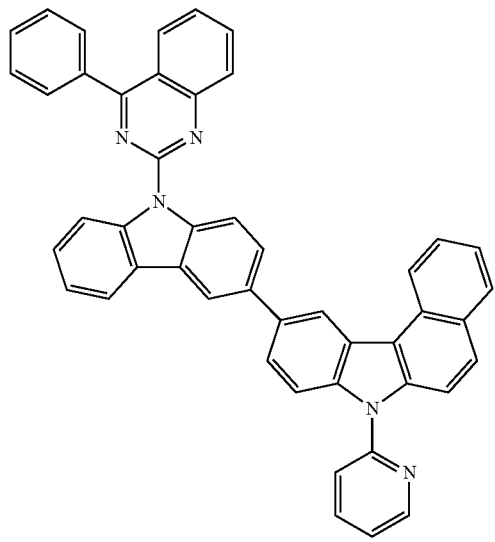
H36
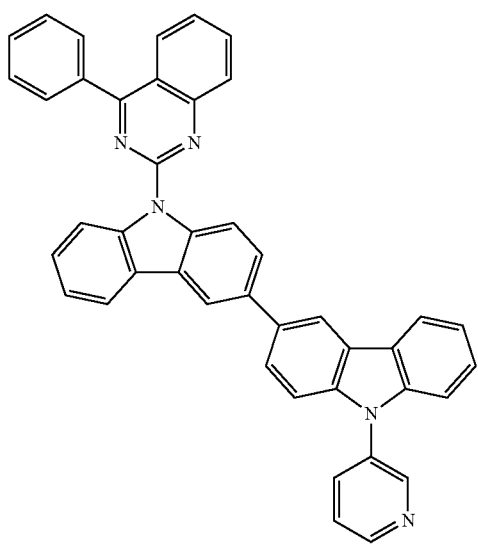
H37
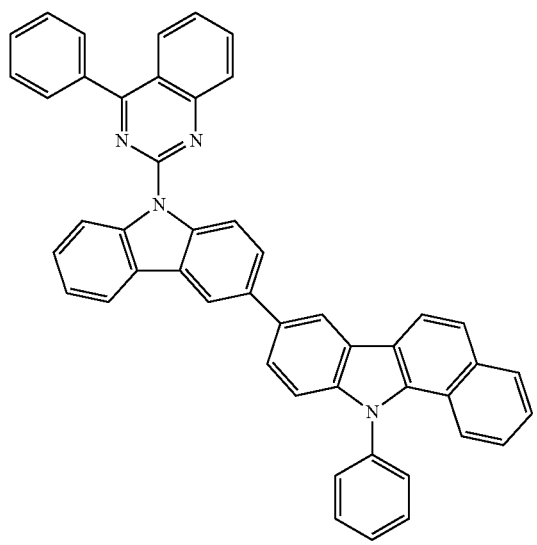
146
-continued
H38
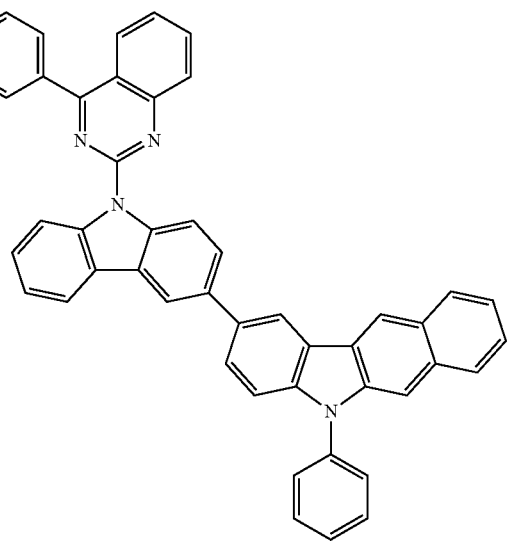
H39
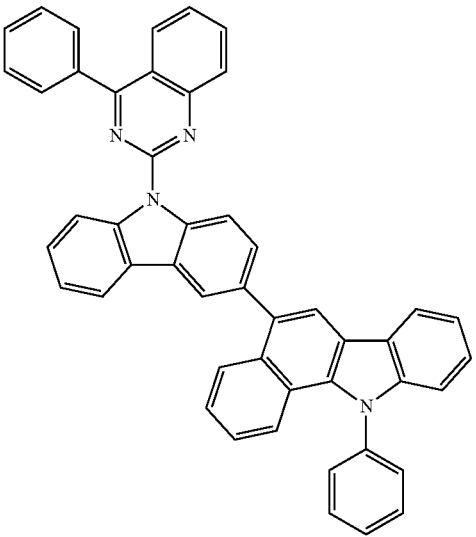

H40
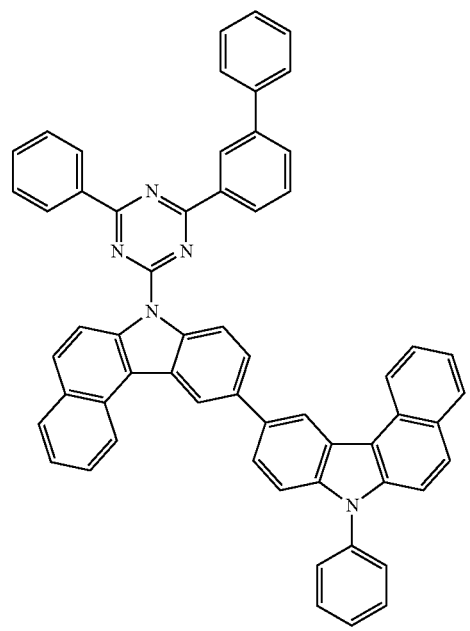
H41
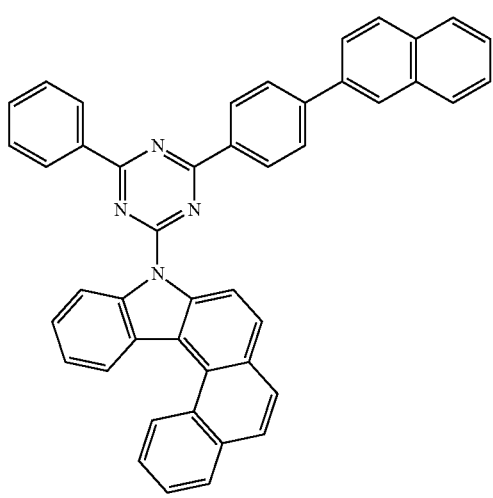
H42
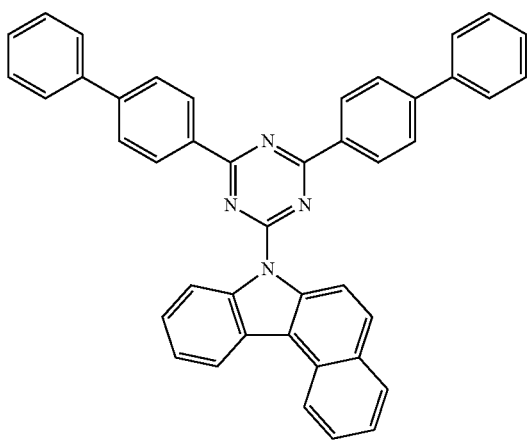
H43
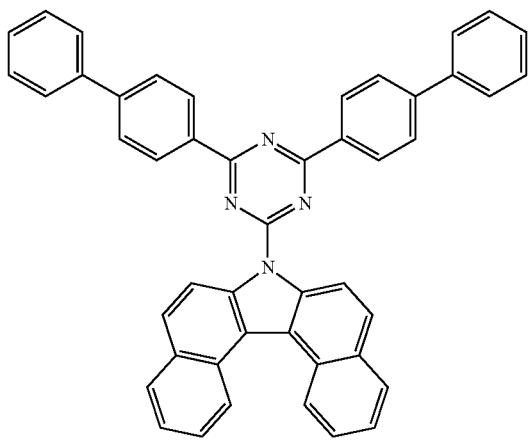
H44
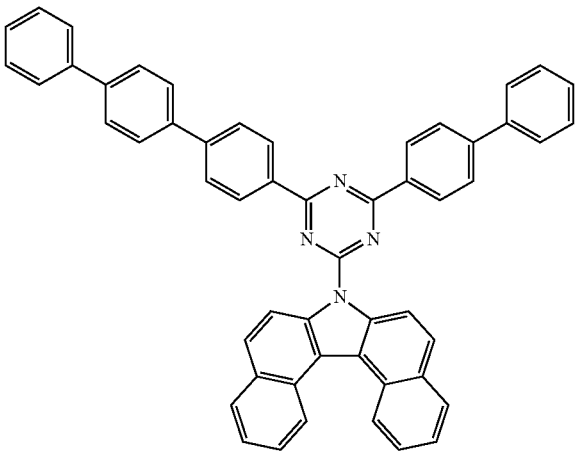
H45
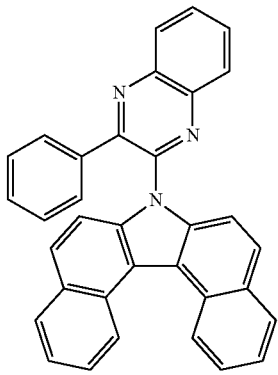

149
-continued
150
-continued
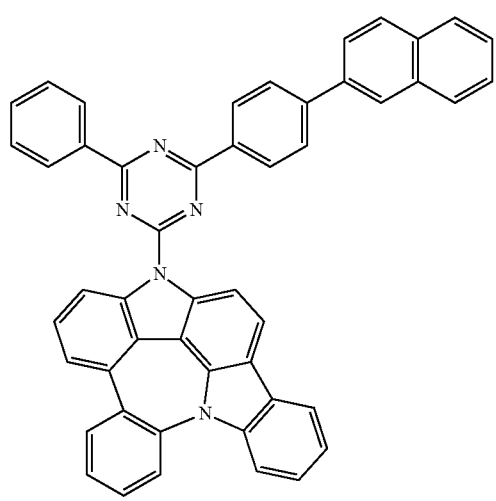
H46
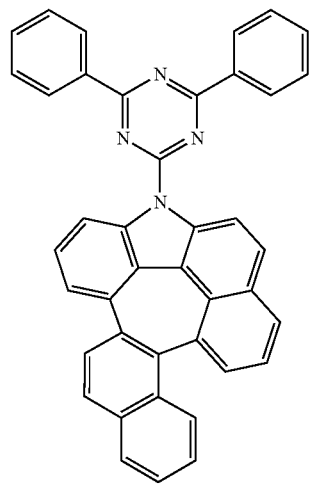
H49
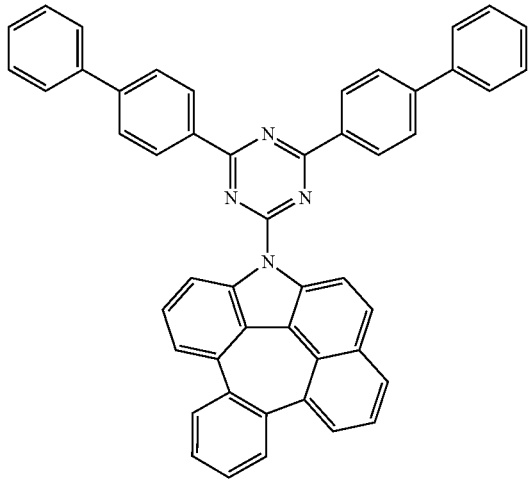
H47
H50
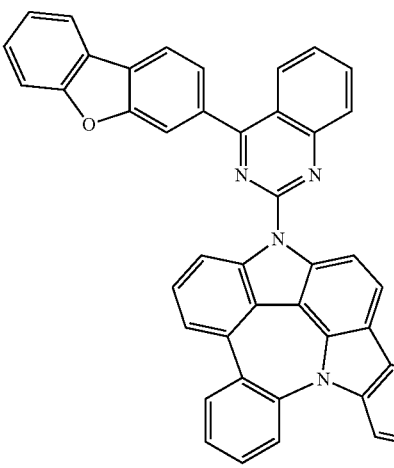
H48
H51

H52
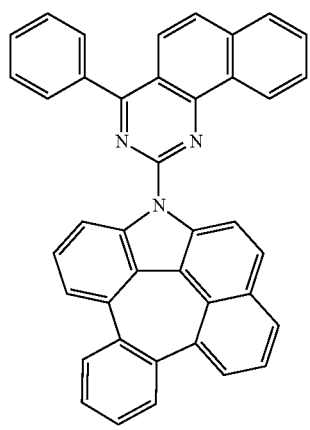
H53
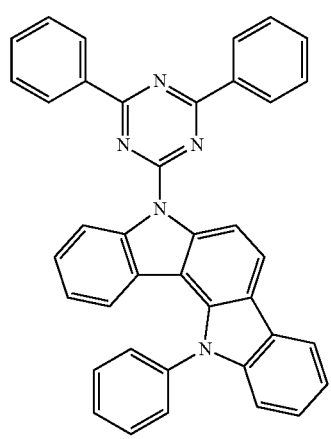
H54
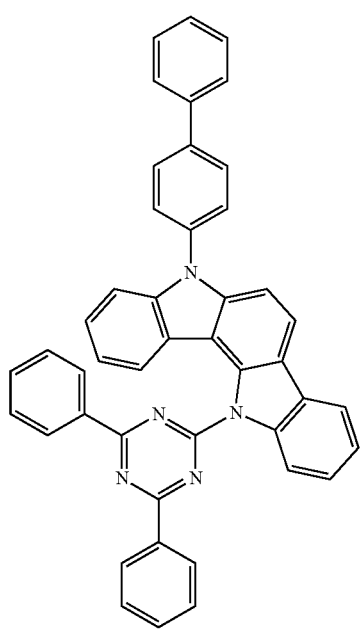
H55
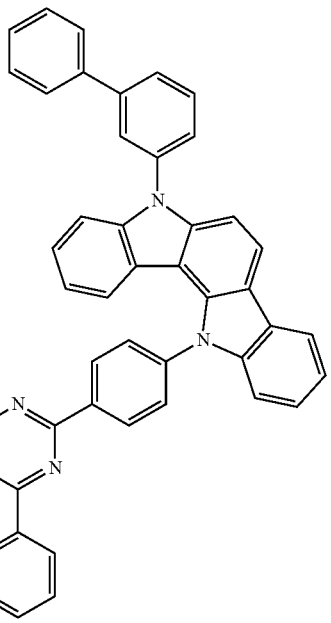
H56
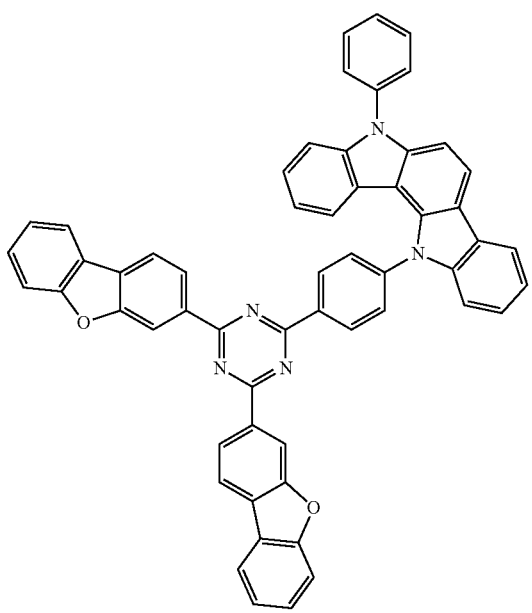

153
-continued
H57
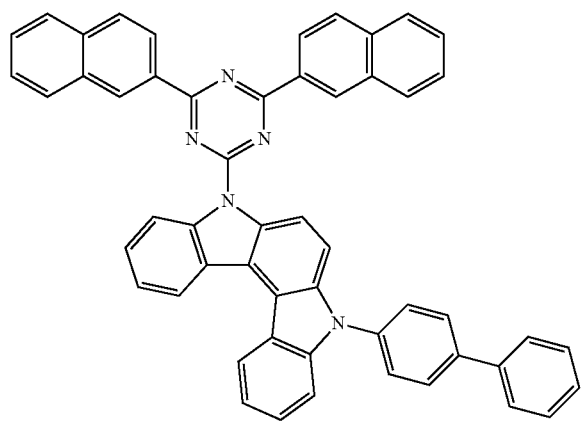
H58
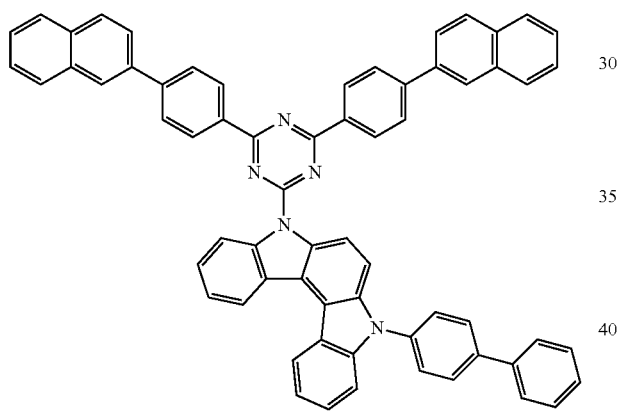
H59
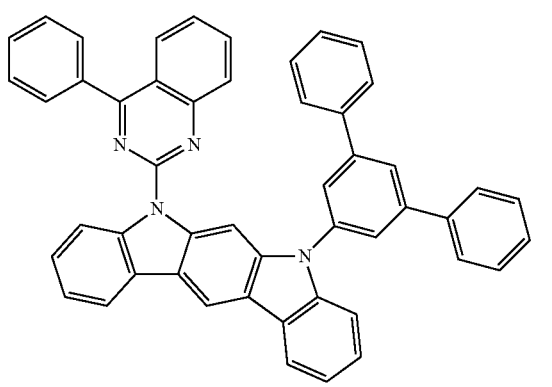
154
-continued
H60
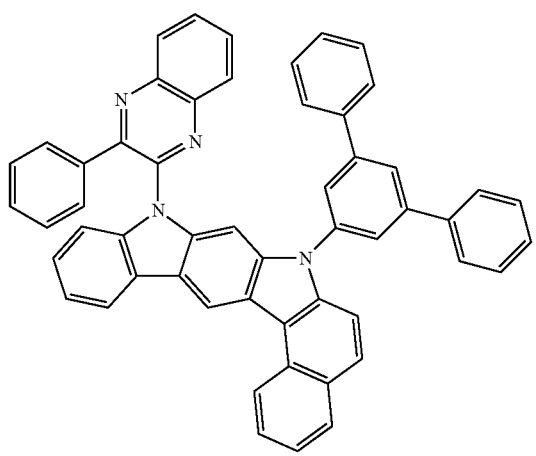
H61
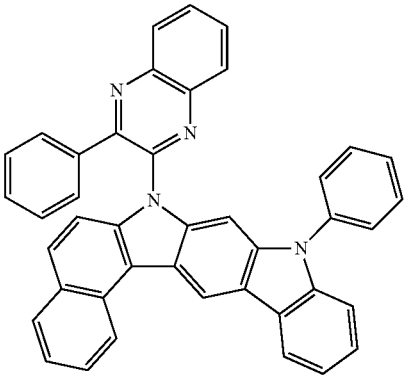
H62
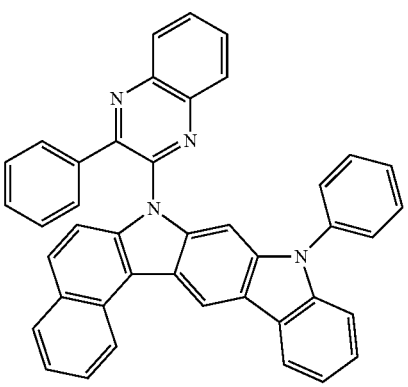

155
-continued
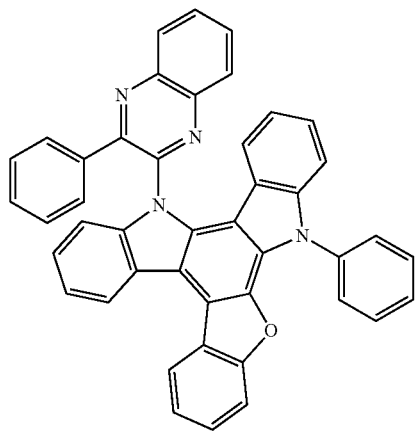
H63
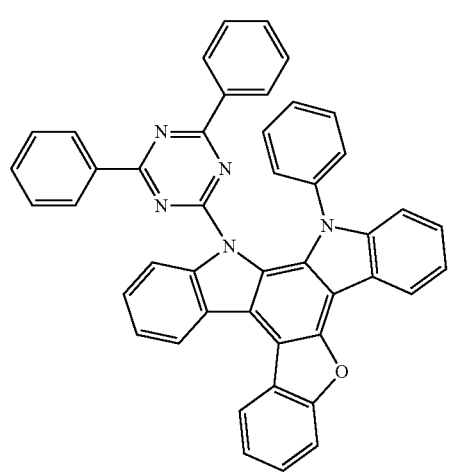
H64
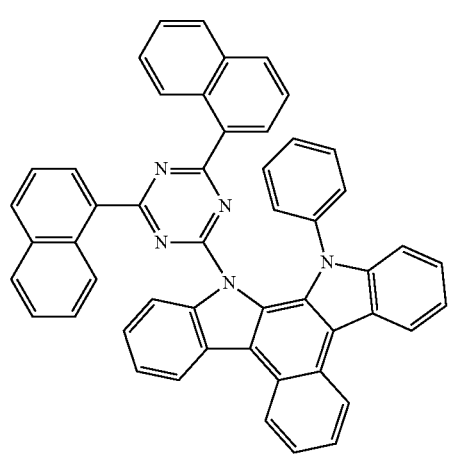
H65
156
-continued
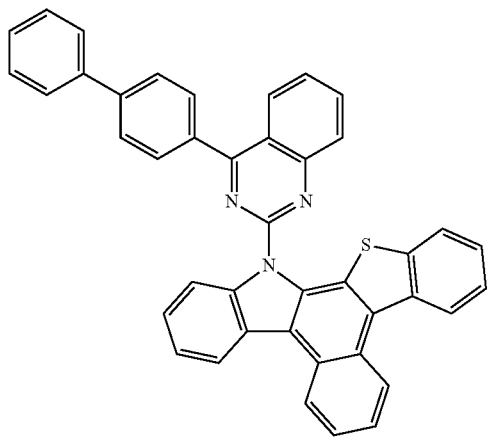
H66
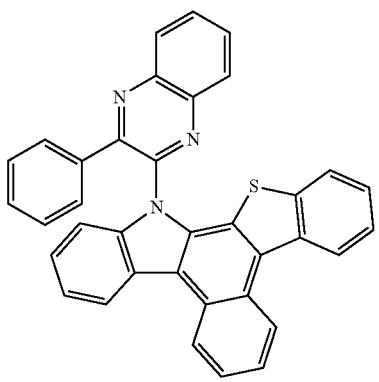
H67
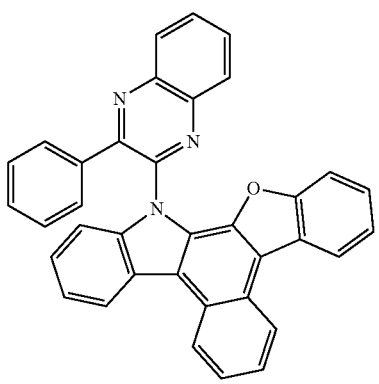
H68
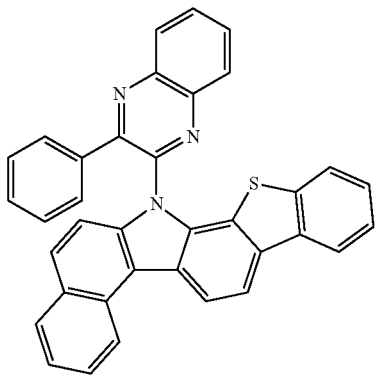
H69

H70
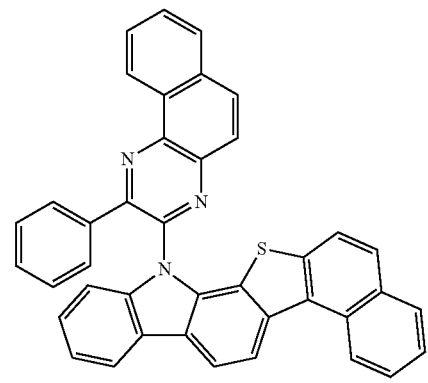
H71
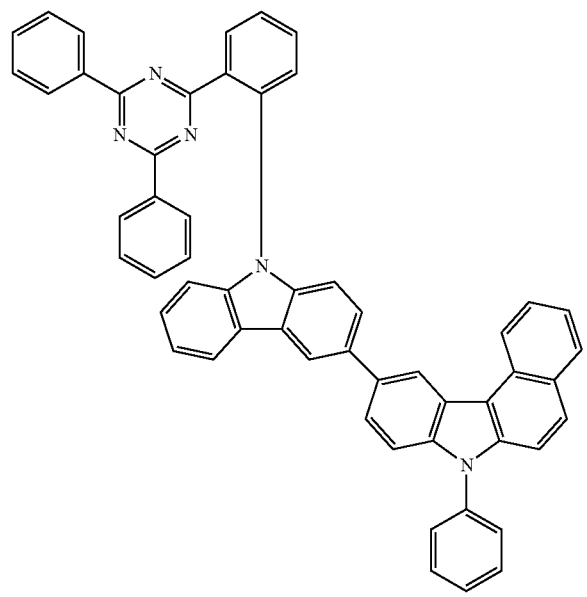
H72
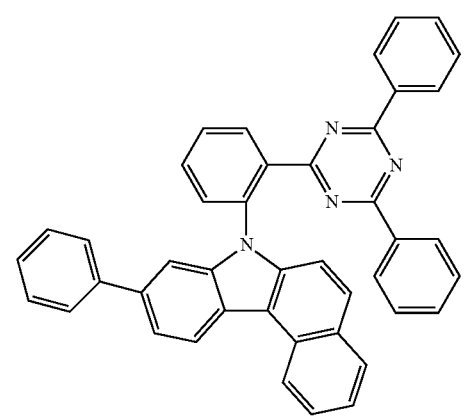
H73
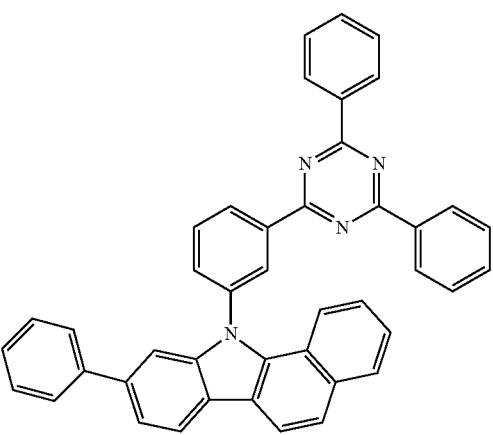
H74
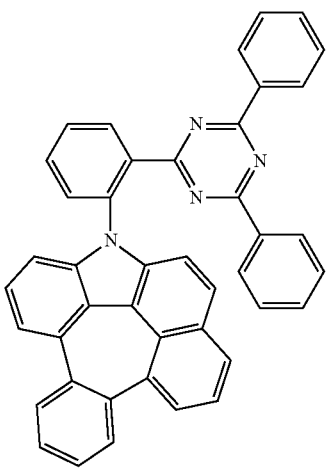
H75
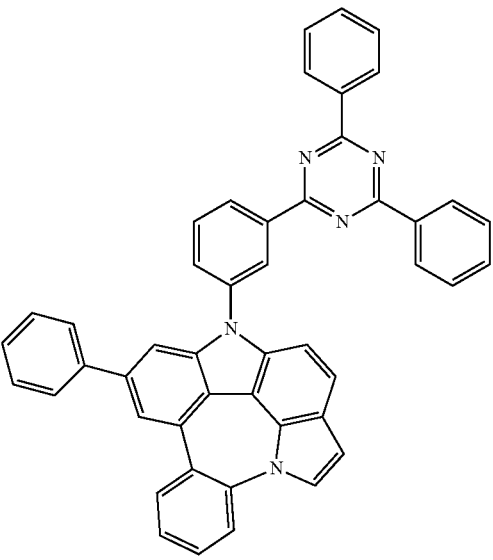

-continued
H76
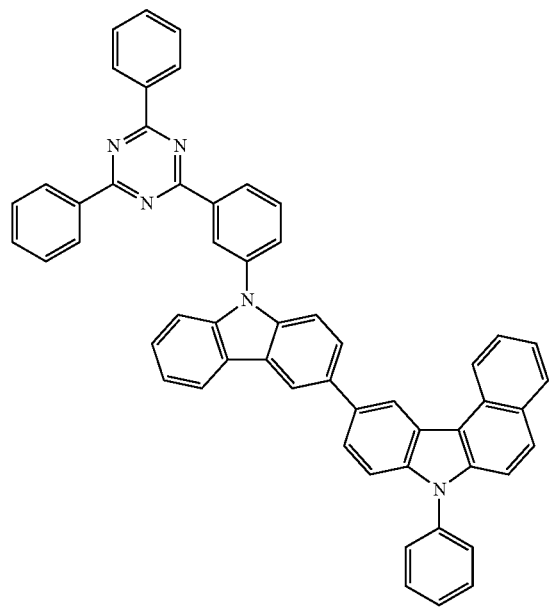
H77
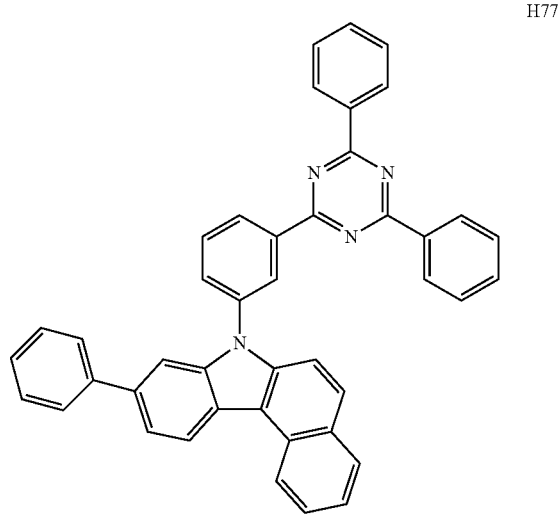
H78
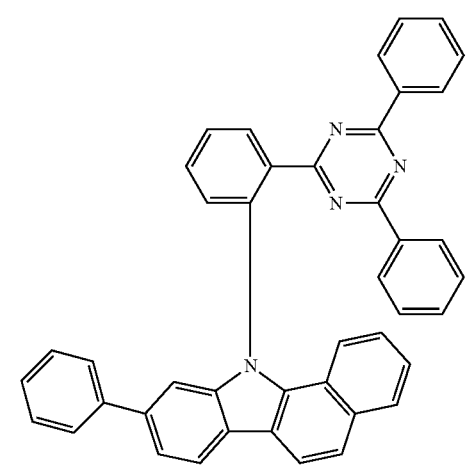
H79
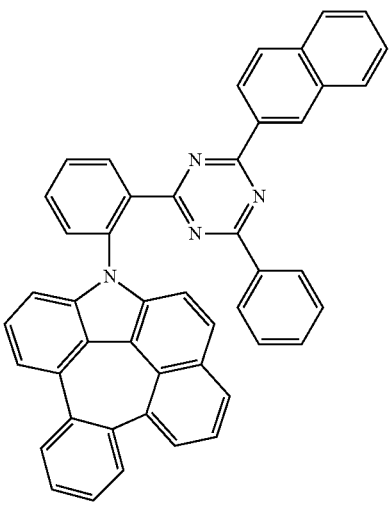
H80
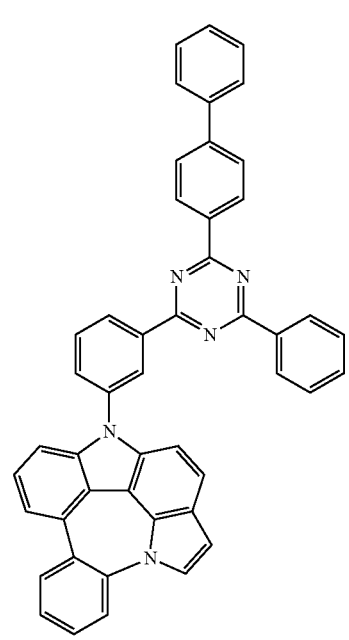
H81
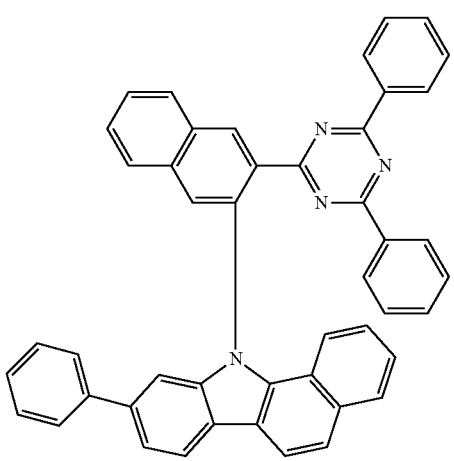

-continued
H82
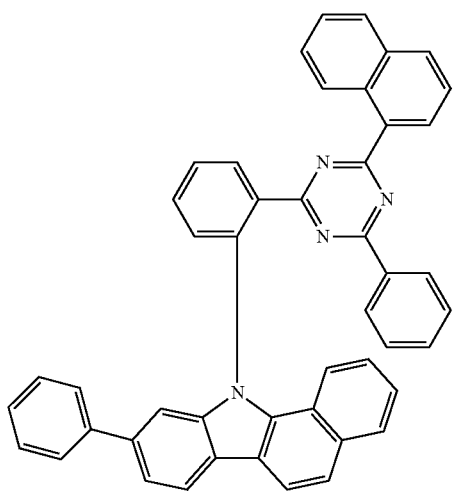
H83
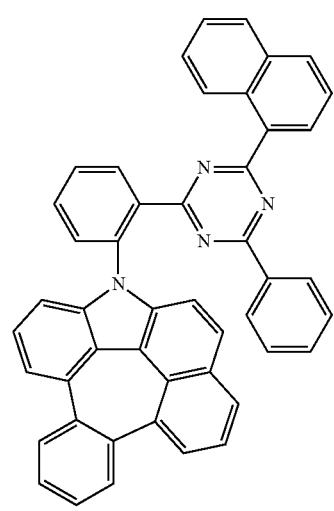
H84
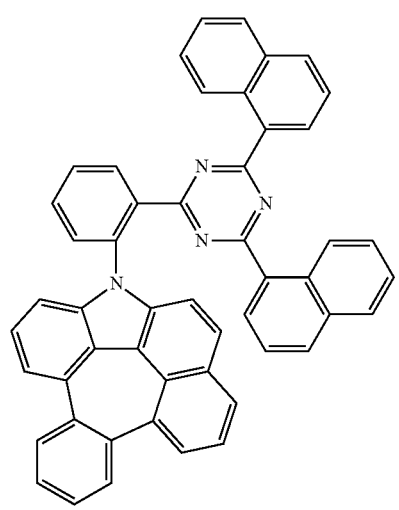
-continued
H85
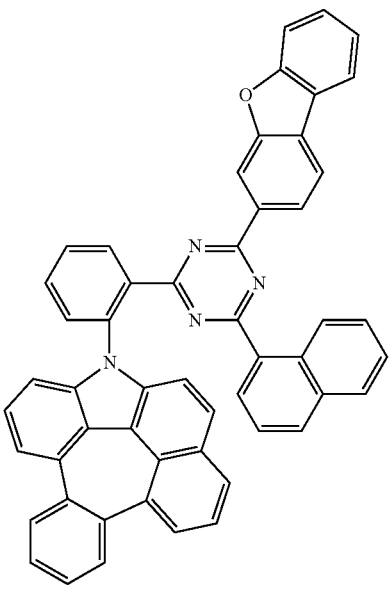
H86
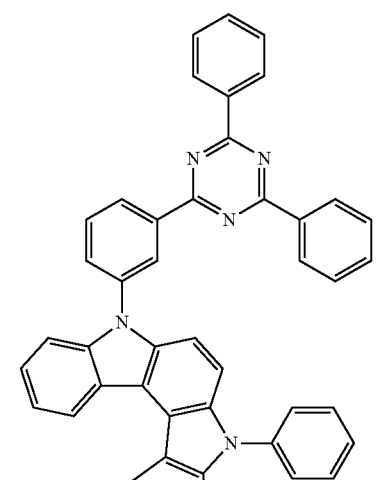
H87
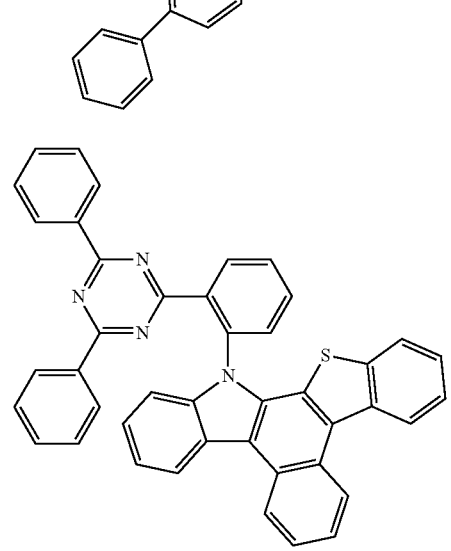

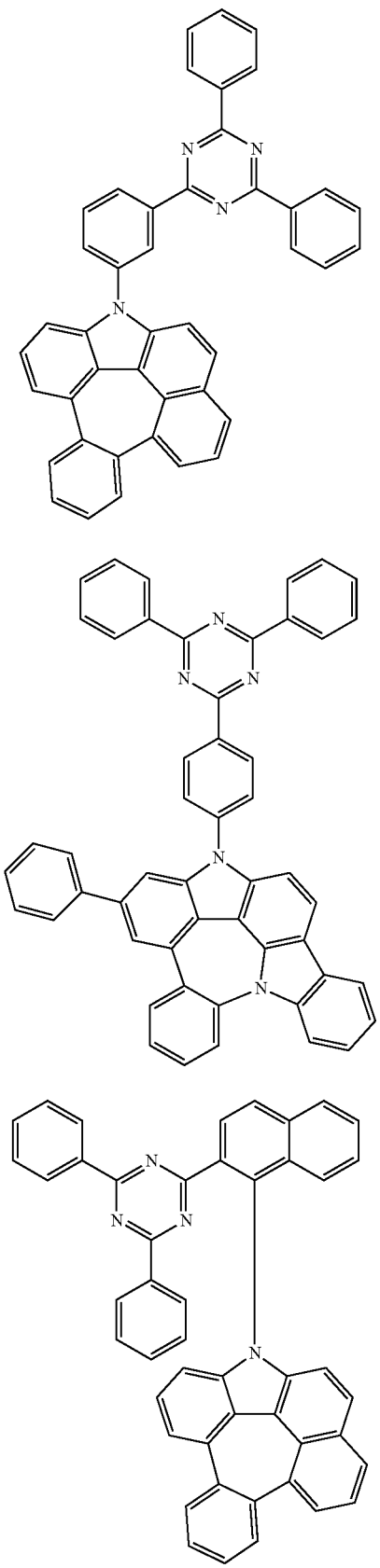

An electronic device, for example, an organic light-emitting device, including the second may have high external quantum efficiency (EQE) and long lifespan.

In Formulae 1 and 2, 1) two or more of $R_1$ to $R_8$ and $A_{20}$ may be optionally linked to each other to form a $C_5$-$C_{60}$ carbocyclic group which is unsubstituted or substituted with at least one $R_{1a}$ or a $C_1$-$C_{60}$ heterocyclic group which is unsubstituted or substituted with at least one $R_{1a}$, 2) two or more of $A_1$ to $A_7$ may be optionally linked to each other to form a $C_5$-$C_{60}$ carbocyclic group which is unsubstituted or substituted with at least one $R_{1a}$ or a $C_1$-$C_{60}$ heterocyclic group which is unsubstituted or substituted with at least one $R_{1a}$ and 3) two or more of ring CY2, ring $CY_3$, $R_{20}$ and $R_{30}$ may be optionally linked to each other to form a $C_5$-$C_{60}$ carbocyclic group which is unsubstituted or substituted with at least one $R_{1a}$ or a $C_1$-$C_{60}$ heterocyclic group which is unsubstituted or substituted with at least one $R_{1a}$. Herein, $R_{1a}$ may be understood by referring to the description of $A_T$.

The term "$C_5$-$C_{60}$ carbocyclic group" as used herein refers to a saturated or unsaturated cyclic group including 5 to 60 carbon atoms only as ring-forming atoms. The $C_5$-$C_{60}$ carbocyclic group may be a monocyclic group or a polycyclic group.

The phrase "a $C_5$-$C_{60}$ carbocyclic group (which is unsubstituted or substituted with at least one $R_{1a}$)" may include, for example, an adamantane group, a norbornene group, a bicyclo[1.1.1]pentane group, a bicyclo[2.1.1]hexane group, a bicyclo[2.2.1]heptane group (a norbornane group), a bicyclo[2.2.2]octane group, a cyclopentane group, a cyclohexane group, a cyclohexene group, a benzene group, a naphthalene group, an anthracene group, a phenanthrene group, a triphenylene group, a pyrene group, a chrysene group, cyclopentadiene group, a fluorene group, and a 1,2,3,4-tetrahydronaphthalene group, each being unsubstituted or substituted with at least one $R_{1a}$.

The term "$C_1$-$C_{60}$ heterocyclic group" as used herein refers to saturated or unsaturated cyclic group including 1 to 60 carbon atoms and at least one heteroatom selected from N, O, P, Si, and S as ring-forming atoms. The $C_1$-$C_{60}$ heterocyclic group may be a monocyclic group or a polycyclic group.

The phrase "a $C_1$-$C_{60}$ heterocyclic group (which is unsubstituted or substituted with at least one $R_{1a}$)" may include a thiophene group, a furan group, a pyrrole group, a silole group, a borole group, a phosphole group, a selenophene group, a germole group, a benzothiophene group, a benzofuran group, an indole group, an indene group, a benzosilole group, a benzoborole group, a benzophosphole group, a benzoselenophene group, a benzogermole group, a dibenzothiophene group, a dibenzofuran group, a carbazole group, a dibenzosilole group, a dibenzoborole group, a dibenzophosphole group, a dibenzoselenophene group, a dibenzogermole group, a dibenzothiophene 5-oxide group, 9H-fluorene-9-one group, a dibenzothiophene 5,5-dioxide group, an azabenzothiophene group, an azabenzofuran group, an azaindole group, an azaindene group, an azabenzosilole group, an azabenzoborole group, an azabenzophosphole group, an azabenzoselenophene group, an azabenzogermole group, an azadibenzothiophene group, an azadibenzofuran group, an azacarbazole group, an azafluorene group, an azadibenzosilole group, an azadibenzoborole group, an azadibenzophosphole group, an azadibenzoselenophene group, an azadibenzogermole group, an azadibenzothiophene 5-oxide group, an aza-9H-fluorene-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, and a 5,6,7,8-tetrahydroquinoline group, each being unsubstituted or substituted with at least one $R_{1a}$.

The term "$C_1$-$C_{60}$ alkyl group" as used herein refers to a linear or branched saturated aliphatic hydrocarbon monovalent group having 1 to 60 carbon atoms. The term "$C_1$-$C_{60}$ alkylene group" as used herein refers to a divalent group having substantially the same structure as the $C_1$-$C_{60}$ alkyl group.

Examples of the $C_1$-$C_{60}$ alkyl group, the $C_1$-$C_{20}$ alkyl group, and/or the $C_1$-$C_{10}$ alkyl group are a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an iso-nonyl group, a sec-nonyl group, a tert-nonyl group, an n-decyl group, an iso-decyl group, a sec-decyl group, and a tert-decyl group, each unsubstituted or substituted with a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, or any combination thereof. For example, Formula 9-33 may be a branched $C_6$ alkyl group, and may be a tert-butyl group that is substituted with two methyl groups.

The term "$C_1$-$C_{60}$ alkoxy group" as used herein refers to a monovalent group represented by —$OA_{101}$ (wherein $A_{101}$ is a $C_1$-$C_{60}$ alkyl group). Examples of the $C_1$-$C_{60}$ alkoxy group, the $C_1$-$C_{20}$ alkoxy group, or the $C_1$-$C_{10}$ alkoxy group are a methoxy group, an ethoxy group, a propoxy group, a butoxy group, or a pentoxy group.

The term "$C_3$-$C_{10}$ cycloalkyl group" as used herein refers to a monovalent monocyclic saturated hydrocarbon group including 3 to 10 carbon atoms. The term "$C_3$-$C_{10}$ cycloalkylene group" as used herein refers to a divalent group having substantially the same structure as the $C_3$-$C_{10}$ cycloalkyl group.

Examples of the $C_3$-$C_{10}$ cycloalkyl group are a cyclopropyl group, a cyclobutyl group, a cyclopentyl group, a cyclohexyl group, a cycloheptyl group, a cyclooctyl group, an adamantyl group, a bicyclo[1.1.1]pentyl group (bicyclo[1.1.1]pentyl), a bicyclo[2.1.1]hexyl group (bicyclo[2.1.1]hexyl), a bicyclo[2.2.1]heptyl group (bicyclo[2.2.1]heptyl)(a norbornanyl group), and a bicyclo[2.2.2]octyl group.

The term "$C_2$-$C_{10}$ heterocycloalkyl group" as used herein refers to a monovalent saturated monocyclic group having at least one heteroatom selected from N, O, P, Si Se, B, Ge, or S as a ring-forming atom and 2 to 10 carbon atoms, and non-limiting examples thereof include a tetrahydrofuranyl group, and a tetrahydrothiophenyl group. The term "$C_2$-$C_{10}$ heterocycloalkylene group" as used herein refers to a divalent group having the same structure as the $C_2$-$C_{10}$ heterocycloalkyl group.

Examples of the $C_2$-$C_{10}$ heterocycloalkyl group are a silolanyl group, a silinanyl group, a tetrahydrofuranyl group, a tetrahydro-2H-pyranyl group, and a tetrahydrothiophenyl group.

The term "deuterium-containing $C_1$-$C_{60}$ alkyl group (or, deuterium-containing $C_1$-$C_{20}$ alkyl group, a deuterium-containing $C_2$-$C_{20}$ alkyl group, or the like)" as used herein refers to a $C_1$-$C_{60}$ alkyl group substituted with at least one deuterium (or a $C_1$-$C_{20}$ alkyl group substituted with at least one deuterium, a $C_2$-$C_{20}$ alkyl substituted with at least one deuterium, or the like). For example, the term "the deuterium-containing C, alkyl group (that is, a deuterium-containing methyl group)" as used herein includes —$CD_3$, —$CD_2H$, and —$CDH_2$.

The term "deuterium-containing $C_3$-$C_{10}$ cycloalkyl group" as used herein refers to a $C_3$-$C_{10}$ cycloalkyl group substituted with at least one deuterium. Examples of the "deuterium-containing $C_3$-$C_{10}$ cycloalkyl group" are provided in connection with, for example, Formula 10-501.

The terms "fluorinated $C_1$-$C_{60}$ alkyl group (or a fluorinated $C_1$-$C_{20}$ alkyl group, or the like)", "fluorinated $C_3$-$C_{10}$ cycloalkyl group", "fluorinated $C_2$-$C_{10}$ heterocycloalkyl group" or "fluorinated phenyl group" as used herein refer to a $C_1$-$C_{60}$ alkyl group (or, $C_1$-$C_{20}$ alkyl group, or the like) substituted with at least one a fluoro group (—F), a $C_3$-$C_{10}$ cycloalkyl group substituted with at least one a fluoro group (—F), a $C_2$-$C_{10}$ heterocycloalkyl group substituted with at least one a fluoro group (—F), and a phenyl group substituted with at least one a fluoro group (—F), respectively. For example, the term "the fluorinated C, alkyl group (that is, the fluorinated methyl group)" includes —$CF_3$, —$CF_2H$, and —$CFH_2$. The "fluorinated $C_1$-$C_{60}$ alkyl group (or the fluorinated $C_1$-$C_{20}$ alkyl group, or the like)", "the fluorinated $C_3$-$C_{10}$ cycloalkyl group", or "the fluorinated $C_2$-$C_{10}$ heterocycloalkyl group" may be i) a fully fluorinated $C_1$-$C_{60}$ alkyl group (or, fully fluorinated $C_1$-$C_{20}$ alkyl group, or the like), a fully fluorinated $C_3$-$C_{10}$ cycloalkyl group, or a fully fluorinated $C_2$-$C_{10}$ heterocycloalkyl group, each group in which all hydrogen are substituted with a fluoro group, or ii) a partially fluorinated $C_1$-$C_{10}$ alkyl group (or, a partially fluorinated $C_1$-$C_{20}$ alkyl group, or the like), a partially fluorinated $C_3$-$C_{10}$ cycloalkyl group, or a partially fluorinated $C_2$-$C_{10}$ heterocycloalkyl group, each group in which some hydrogen are substituted with a fluoro group.

The term "($C_1$-$C_2$ alkyl)'X' group" as used herein refers to a 'X' group substituted with at least one $C_1$-$C_{20}$ alkyl group. For example, the term "($C_1$-$C_{20}$ alkyl)$C_3$-$C_{10}$ cycloalkyl group" as used herein refers to a $C_3$-$C_{10}$ cycloalkyl group substituted with at least one $C_1$-$C_{20}$ alkyl group and the term "($C_1$-$C_{20}$ alkyl)phenyl group" as used herein refers to a phenyl group substituted with at least one $C_1$-$C_{20}$ alkyl group.

The terms "an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, and an azadibenzothiophene 5,5-dioxide group" respectively refer to a heterocyclic group having the same backbone as "an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, 9H-fluorene-9-one group, and a dibenzothiophene 5,5-dioxide group" in which at least one carbon atoms constituting the cyclic groups is substituted with a nitrogen.

The term "$C_2$-$C_{60}$ alkenyl group" as used herein refers to a group formed by including at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having substantially the same structure as the $C_2$-$C_{60}$ alkenyl group.

The term "$C_2$-$C_{60}$ alkynyl group" as used herein refers to a group formed by including at least one carbon-carbon triple bond in the middle or at the terminus of the $C_2$-$C_{60}$ alkyl group. Examples thereof include an ethenyl group and a propenyl group. The term "$C_2$-$C_{60}$ alkynylene group" as used herein refers to a divalent group having substantially the same structure as the $C_2$-$C_{60}$ alkynyl group.

The term "$C_3$-$C_{10}$ cycloalkenyl group" as used herein refers to a monovalent monocyclic group including 3 to 10 carbon atoms and at least one carbon-carbon double bond in its ring, wherein the molecular structure as a whole is non-aromatic. Examples thereof include a cyclopentenyl group, a cyclohexenyl group, and a cycloheptenyl group. The term "$C_3$-$C_{10}$ cycloalkenylene group" as used herein refers to a divalent group having substantially the same structure as the $C_3$-$C_{10}$ cycloalkenyl group.

The term "$C_2$-$C_{10}$ heterocycloalkenyl group" as used herein refers to a monovalent monocyclic group including at least one heteroatom selected from N, O, P, Si, and S as a ring-forming atom, 1 to 10 carbon atoms, and at least one double bond in its ring. Examples of the $C_2$-$C_{10}$ heterocycloalkenyl group include a 2,3-dihydrofuranyl group and a 2,3-dihydrothiophenyl group. The term "$C_1$-$C_{10}$ heterocycloalkylene group" as used herein refers to a divalent group having substantially the same structure as the $C_2$-$C_{10}$ heterocycloalkenyl group.

The term "$C_6$-$C_{60}$ aryl group" as used herein refers to a monovalent group having a carbocylic aromatic system having 6 to 60 carbon atoms. The term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and a $C_6$-$C_{60}$ arylene group each include at least two rings, the at least two rings may be fused.

The term "$C_1$-$C_{60}$ heteroaryl group" as used herein refers to a monovalent group having a heterocyclic aromatic system having at least one heteroatom selected from N, O, P, Si, and S as a ring-forming atom and 1 to 60 carbon atoms. The term "$C_1$-$C_{60}$ heteroarylene group" as used herein refers to a divalent group having a heterocyclic aromatic system having at least one heteroatom selected from N, O, P, and S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include at least two rings, the at least two rings may be fused.

The term "$C_6$-$C_{60}$ aryloxy group" as used herein indicates —$OA_{102}$ (wherein $A_{102}$ is a $C_6$-$C_{60}$ aryl group). The term "$C_6$-$C_{60}$ arylthio group" as used herein indicates —$SA_{103}$ (wherein $A_{103}$ is a $C_6$-$C_{60}$ aryl group).

The term "monovalent non-aromatic condensed polycyclic group" as used herein refers to a monovalent group that has two or more condensed rings and only carbon atoms (e.g., the number of carbon atoms may be in a range of 8 to 60) as ring-forming atoms, wherein the molecular structure as a whole is non-aromatic. Examples of the monovalent non-aromatic condensed polycyclic group include a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group that has two or more condensed rings and a heteroatom selected from N, O, P, Si, and S and carbon atoms (e.g., the number of carbon atoms may be in a range of 1 to 60) as ring-forming atoms, wherein the molecular structure as a whole is non-aromatic. Examples of the monovalent non-aromatic condensed heteropolycyclic group include a carbazolyl group. The term "divalent non-aromatic condensed heteropolycyclic group" as used herein refers to a divalent group having substantially the same structure as the monovalent non-aromatic condensed heteropolycyclic group.

The term "$C_1$-$C_{60}$ cyclic group" includes the $C_5$-$C_{60}$ carbocyclic group and the $C_1$-$C_{60}$ heterocyclic group.

A substituent of the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, substituted $C_6$-$C_{60}$ aryloxy group, the substituted $C_6$-$C_{60}$ arylthio group, substituted $C_1$-$C_{60}$ heteroaryl group, the substituted monovalent non-aromatic condensed polycyclic group, and the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_7$-$C_{60}$ alkyl aryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —Ge($Q_{13}$)($Q_{14}$)($Q_{15}$), —B($Q_{16}$)($Q_{17}$), —P(=O)($Q_{18}$)($Q_{19}$), —P($Q_{18}$)($Q_{19}$), or any combination thereof;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a monovalent non-aromatic condensed polycyclic group, or a monovalent non-aromatic condensed heteropolycyclic group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —Ge($Q_{23}$)($Q_{24}$)($Q_{25}$), —B($Q_{26}$)($Q_{27}$), —P(=O)($Q_{28}$)($Q_{29}$), —P($Q_{28}$)($Q_{29}$), or any combination thereof;

—N($Q_{31}$)($Q_{32}$), —Si($Q_{33}$)($Q_{34}$)($Q_{35}$), —Ge($Q_{33}$)($Q_{34}$)($Q_{35}$), —B($Q_{36}$)($Q_{37}$), —P(=O)($Q_{38}$)($Q_{39}$), or —P($Q_{38}$)($Q_{39}$); or any combination thereof.

In the present specification, $Q_1$ to $Q_6$, $Q_1$ to $Q_{19}$, $Q_{21}$ to $Q_{29}$, and $Q_{31}$ to $Q_{39}$ may each independently be hydrogen; deuterium; —F; —Cl; —Br; —I; a hydroxyl group; a cyano group; a nitro group; an amidino group; a hydrazine group; a hydrazone group; a carboxylic acid group or a salt thereof; a sulfonic acid group or a salt thereof; a phosphoric acid group or a salt thereof; a $C_1$-$C_{60}$ alkyl group, unsubstituted or substituted with deuterium, a $C_1$-$C_{60}$ alkyl group, a $C_6$-$C_{60}$ aryl group, or any combination thereof; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_2$-$C_{10}$ heterocycloalkyl group; a $C_3$-$C_{10}$ cycloalkenyl group; a $C_2$-$C_{10}$ heterocycloalkenyl group; a $C_6$-$C_{60}$ aryl group, unsubstituted or substituted with deuterium, a $C_1$-$C_{60}$ alkyl group, a $C_5$-$C_{60}$ aryl group, or any combination thereof; a $C_6$-$C_{60}$ aryloxy group; a $C_6$-$C_{60}$ arylthio group; a $C_1$-$C_{60}$ heteroaryl group; a monovalent non-aromatic condensed polycyclic group; or a monovalent non-aromatic condensed heteropolycyclic group.

For example, in the present specification, $Q_1$ to $Q_6$, $Q_{11}$ to $Q_{19}$, $Q_{21}$ to $Q_{29}$, and $Q_{31}$ to $Q_{39}$ may each independently be —$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, or —$CD_2CDH_2$; or an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, a $C_1$-$C_{10}$ alkyl group, a phenyl group, or any combination thereof.

Thus, a composition including the first compound and the second compound may be suitable for use in an organic layer of an organic light-emitting device, e.g., as an emission layer material in the organic layer. Therefore, according to another aspect, an organic light-emitting device may include a first electrode; a second electrode; and an organic layer disposed between the first electrode and the second electrode and including an emission layer, wherein the organic layer includes the composition.

Since the organic light-emitting device includes the composition including the first and second compounds, the organic light-emitting device may have a low driving voltage, high external quantum efficiency, and long lifespan.

The composition may be used in a pair of electrodes of an organic light-emitting device. In some embodiments, the composition may be included in the emission layer. In this embodiment, the first compound may serve as a dopant, and the second compound may serve as a host. For example, a content of the second compound may be greater than a content of the first compound. The emission layer may emit red light, e.g., red light having a maximum emission wavelength of 550 nanometers (nm) or longer (e.g., about 550 nm to about 900 nm).

The first electrode may be an anode, which is a hole injection electrode, and the second electrode may be a cathode, which is an electron injection electrode. In some embodiments, the first electrode may be a cathode, which is an electron injection electrode, and the second electrode may be an anode, which is a hole injection electrode.

For example, in the organic light-emitting device, the first electrode may be an anode, the second electrode may be a cathode, and the organic layer may further include a hole transport region between the first electrode and the emission layer and an electron transport region between the emission layer and the second electrode, wherein the hole transport region may include a hole injection layer, a hole transport layer, an electron blocking layer, a buffer layer, or a combination thereof, and the electron transport region may include a hole blocking layer, an electron transport layer, an electron injection layer, or a combination thereof.

The term "organic layer" as used herein refers to a single and/or a plurality of layers between the first electrode and the second electrode in an organic light-emitting device. The "organic layer" may include not only organic compounds but also organometallic complexes including metals.

The FIGURE illustrates a schematic cross-sectional view of an organic light-emitting device 10 according to an embodiment. Hereinafter, a structure of an organic light-emitting device according to one or more embodiments and a method of manufacturing the organic light-emitting device will be described with reference to the FIGURE. The organic light-emitting device 10 may include a first electrode 11, an organic layer 15, and a second electrode 19, which may be sequentially layered in this stated order.

A substrate may be additionally disposed under the first electrode 11 or on the second electrode 19. The substrate may be a conventional substrate used in organic light-emitting devices, e.g., a glass substrate or a transparent plastic substrate, each having excellent mechanical strength, thermal stability, transparency, surface smoothness, ease of handling, and water repellency.

The first electrode 11 may be formed by depositing or sputtering, onto the substrate, a material for forming the first electrode 11. The first electrode 11 may be an anode. The material for forming the first electrode 11 may be selected from materials with a high work function for easy hole injection. The first electrode 11 may be a reflective electrode, a semi-transmissive electrode, or a transmissive electrode. The material for forming the first electrode 11 may be selected from indium tin oxide (ITO), indium zinc oxide (IZO), tin oxide ($SnO_2$), and zinc oxide (ZnO). In some embodiments, the material for forming the first electrode 11 may be a metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including a plurality of layers. In some embodiments, the first electrode 11 may have a triple-layered structure of ITO/Ag/ITO, but embodiments are not limited thereto.

The organic layer 15 may be on the first electrode 11.

The organic layer 15 may include a hole transport region, an emission layer, and an electron transport region.

The hole transport region may be between the first electrode 11 and the emission layer.

The hole transport region may include a hole injection layer, a hole transport layer, an electron blocking layer, a buffer layer, or a combination thereof.

The hole transport region may include a hole injection layer only or a hole transport layer only. In some embodiments, the hole transport region may include a hole injection layer and a hole transport layer which are sequentially stacked on the first electrode 11. In some embodiments, the hole transport region may include a hole injection layer, a hole transport layer, and an electron blocking layer, which are sequentially stacked on the first electrode 11.

When the hole transport region includes a hole injection layer, the hole injection layer may be formed on the first electrode 11 by using one or more suitable methods, such as vacuum deposition, spin coating, casting, and Langmuir-Blodgett (LB) deposition.

When a hole injection layer is formed by vacuum-deposition, for example, the vacuum deposition may be performed at a temperature in a range of about 100° C. to about 500° C., at a vacuum pressure in a range of about $10^{-8}$ torr to about $10^{-3}$ torr, and at a rate in a range of about 0.01 Angstroms per second (Å/sec) to about 100 Å/sec, though the conditions may vary depending on a compound used as a hole injection material and a structure and thermal properties of a desired hole injection layer, but embodiments are not limited thereto.

When a hole injection layer is formed by spin coating, the spin coating may be performed at a rate in a range of about 2,000 revolutions per minute (rpm) to about 5,000 rpm and at a temperature in a range of about 80° C. to 200° C. to facilitate removal of a solvent after the spin coating, though the conditions may vary depending on a compound used as a hole injection material and a structure and thermal properties of a desired hole injection layer, but embodiments are not limited thereto.

The conditions for forming a hole transport layer and an electron blocking layer may be inferred from the conditions for forming the hole injection layer.

The hole transport region may include m-MTDATA, TDATA, 2-TNATA, NPB, 3-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor-sulfonic acid (PANI/CSA), polyaniline)/poly(4-styrenesulfonate (PANI/PSS), a compound represented by Formula 201, a compound represented by Formula 202, or any combination thereof:

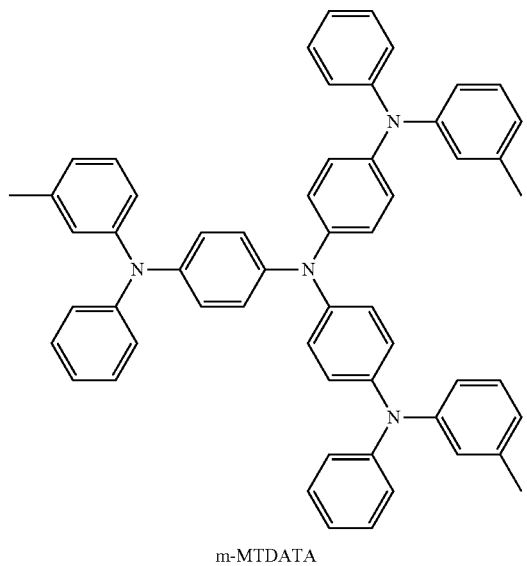

m-MTDATA

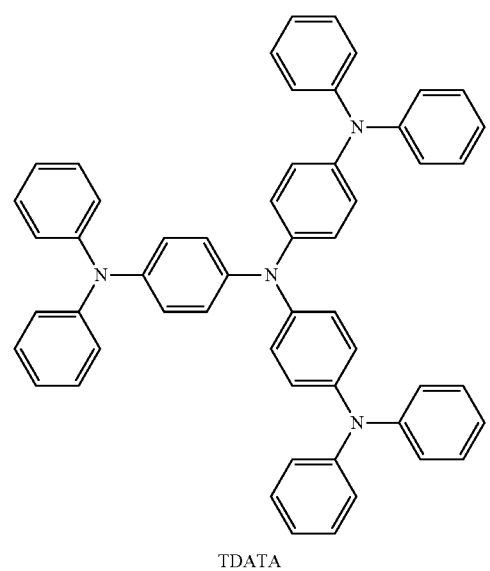

TDATA

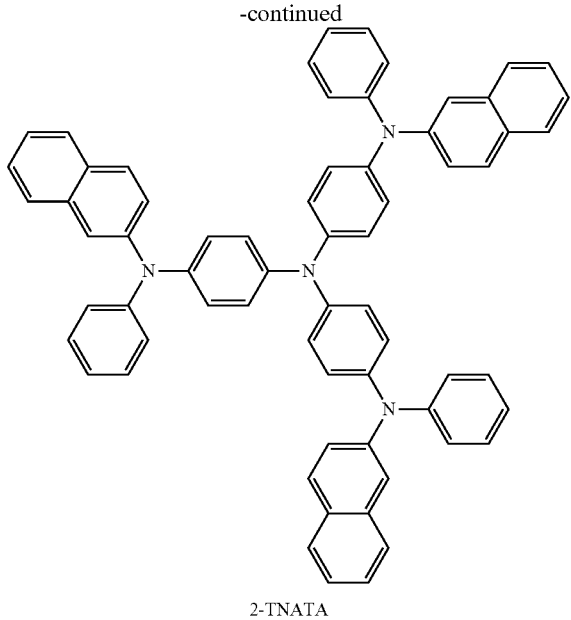
2-TNATA
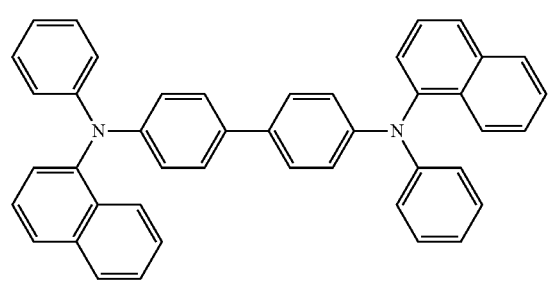
NPB
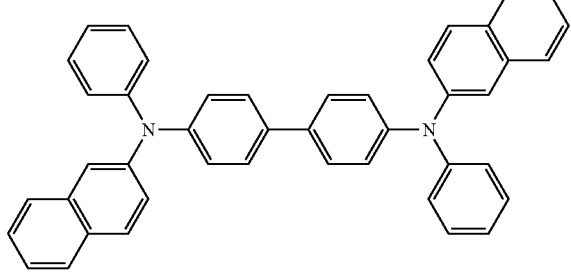
β-NPB
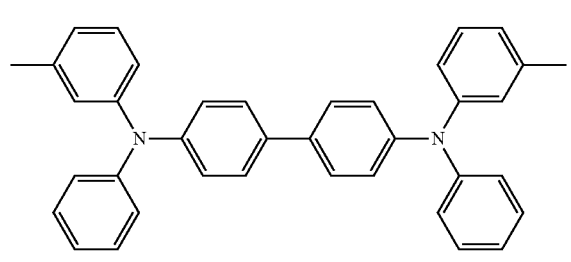
TPD
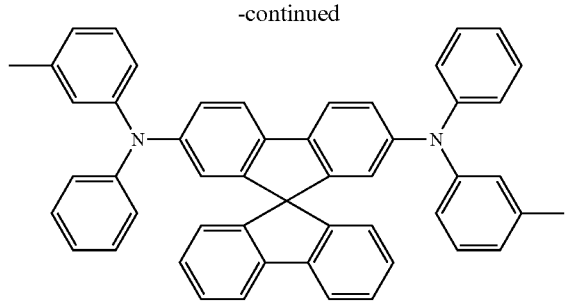
Spiro-TPD
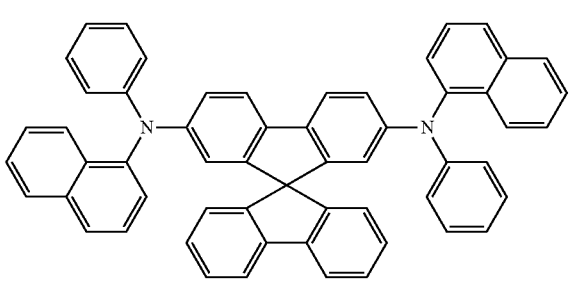
Spiro-NPB
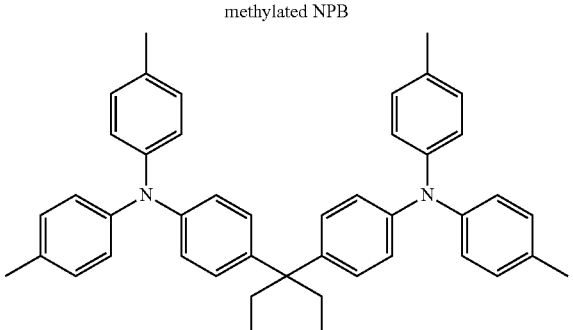
methylated NPB
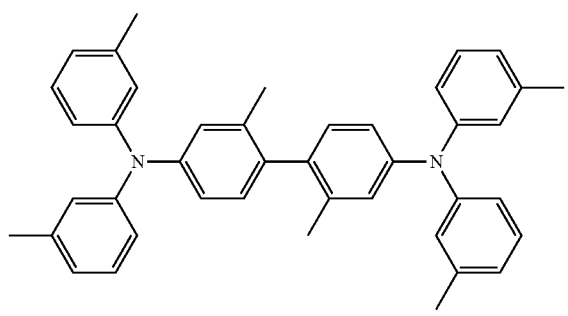
TAPC
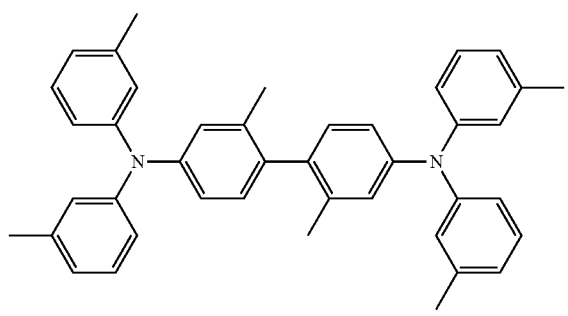
HMTPD Formula 201

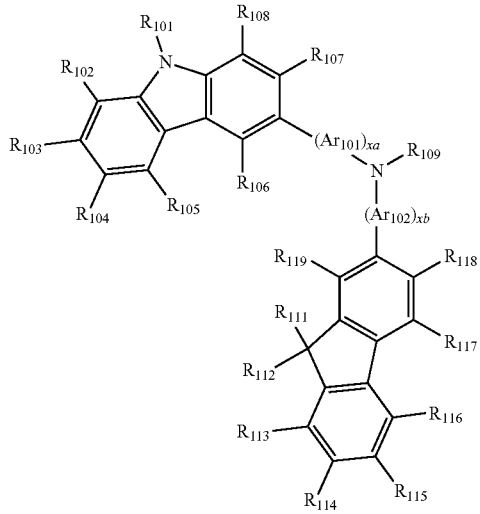

Formula 202

Ar$_{101}$ and Ar$_{102}$ in Formula 201 may each independently be a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or any combination thereof.

The designations xa and xb in Formula 201 may each independently be an integer from 0 to 5, or 0, 1 or 2. For example, xa may be 1 and xb may be 0, but xa and xb are not limited thereto.

$R_{101}$ to $R_{10}$, $R_{111}$ to $R_{119}$ and $R_{121}$ to $R_{124}$ in Formulae 201 and 202 may each independently be:

hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group (for example, a methyl group, an ethyl group, a propyl group, a butyl group, a pentyl group, or a hexyl group), or a $C_1$-$C_{10}$ alkoxy group (for example, a methoxy group, an ethoxy group, a propoxy group, a butoxy group, or a pentoxy group);

a $C_1$-$C_{10}$ alkyl group or a $C_1$-$C_{10}$ alkoxy group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, or any combination thereof; or a phenyl group, a naphthyl group, an anthracenyl group, a fluorenyl group, or a pyrenyl group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, or any combination thereof.

$R_{10}$ in Formula 201 may be a phenyl group, a naphthyl group, an anthracenyl group, or a pyridinyl group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyridinyl group, or any combination thereof.

In some embodiments, the compound represented by Formula 201 may be represented by Formula 201A:

Formula 201A

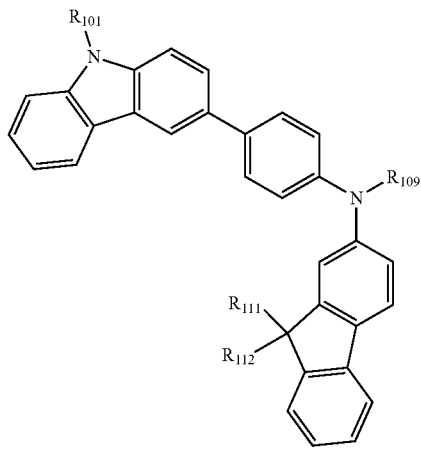

wherein, in Formula 201A, $R_{101}$, $R_{111}$, $R_{112}$, and $R_{109}$ may respectively be understood by referring to the descriptions of $R_{101}$, $R_{111}$, $R_{112}$, and $R_{109}$ provided herein.

In some embodiments, the hole transport regions may include at least one of Compounds HT1 to HT20:

HT1
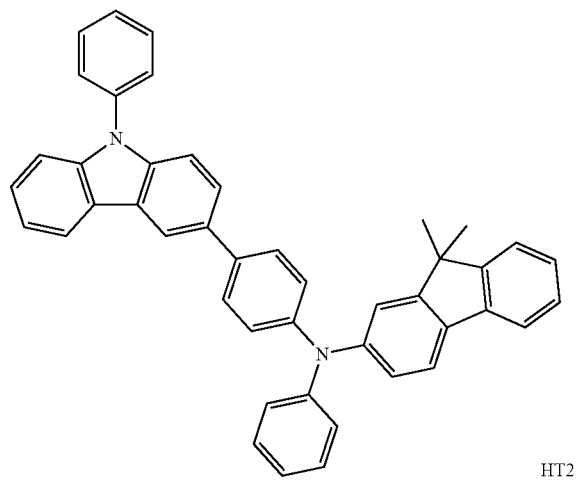
HT2
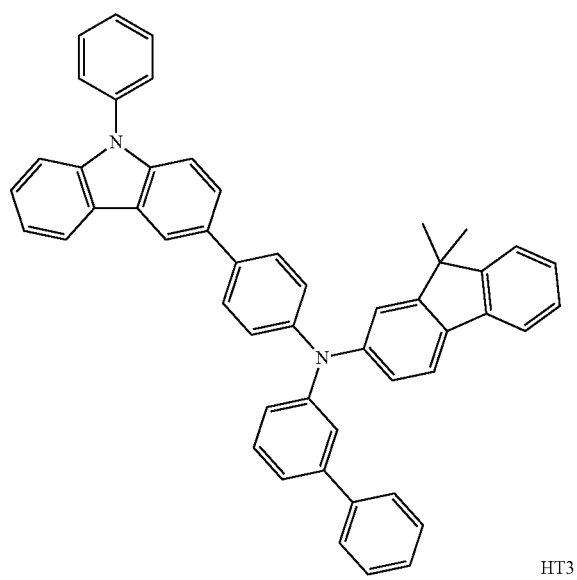
HT3
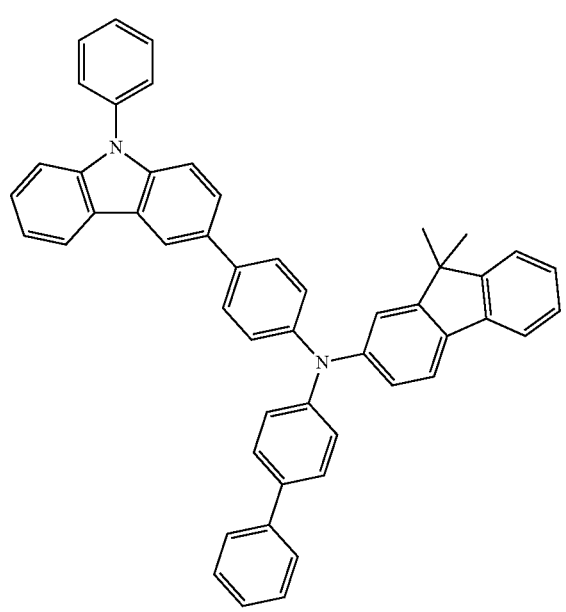
HT4
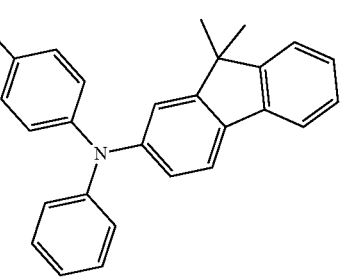
HT5
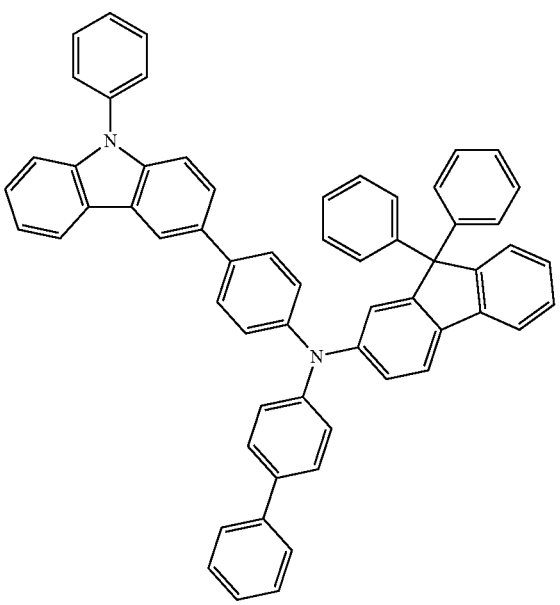

HT6
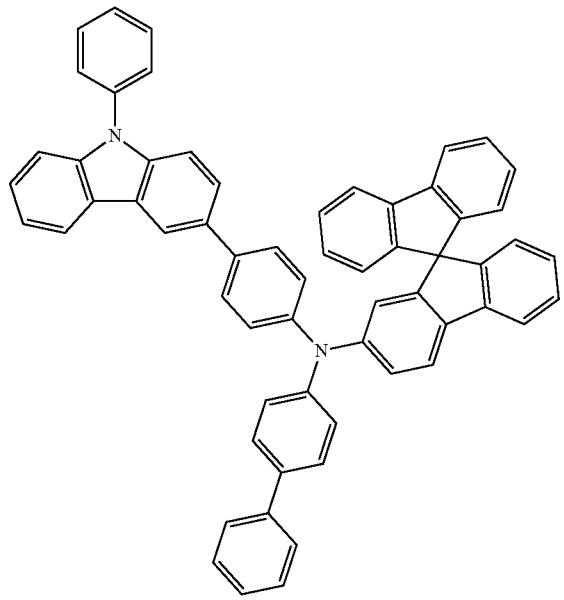
HT8
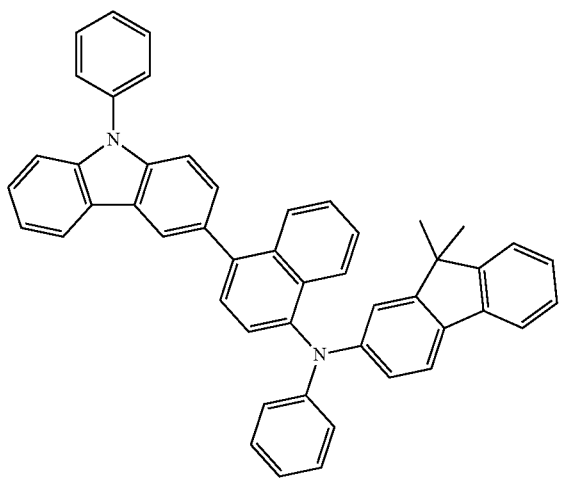
HT9
HT7
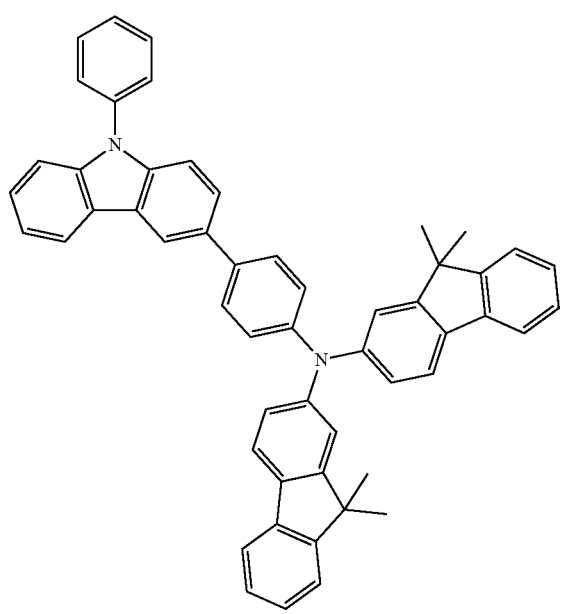
HT10
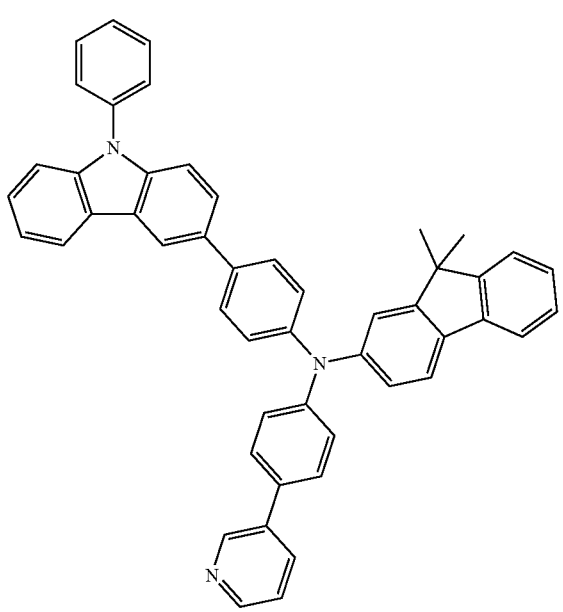

HT11
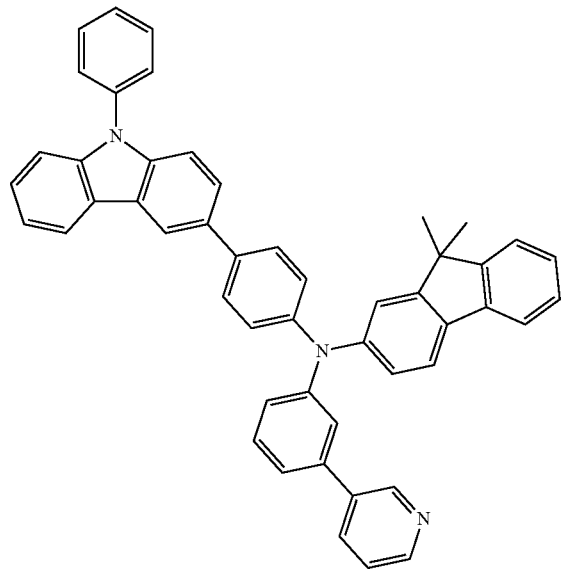
HT12
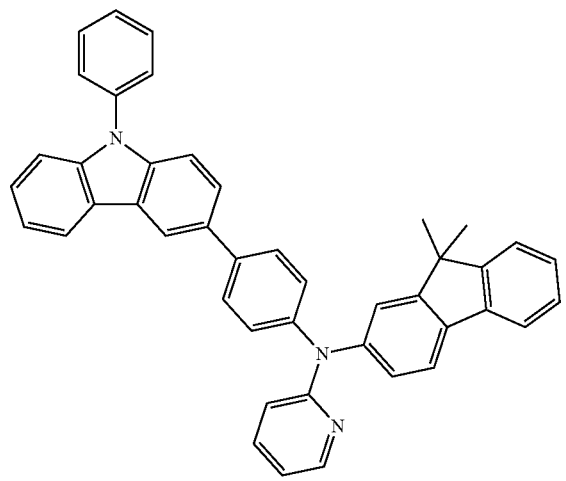
HT13
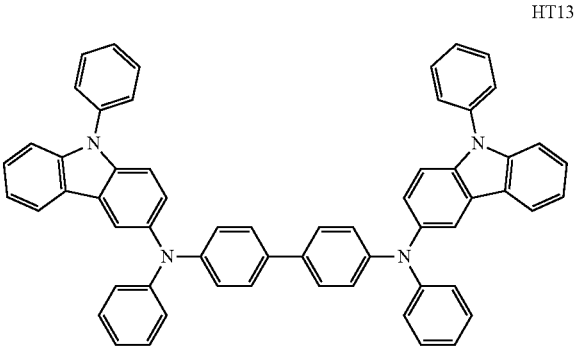
HT14
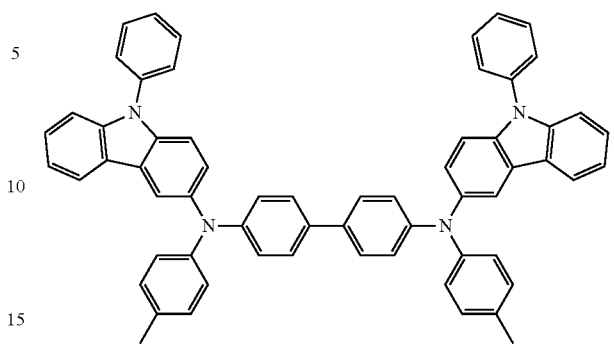
HT15
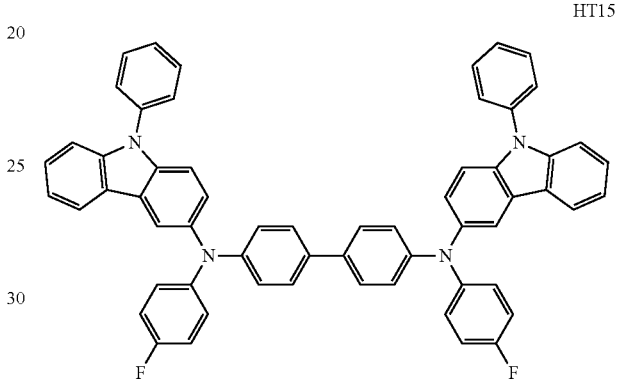
HT16
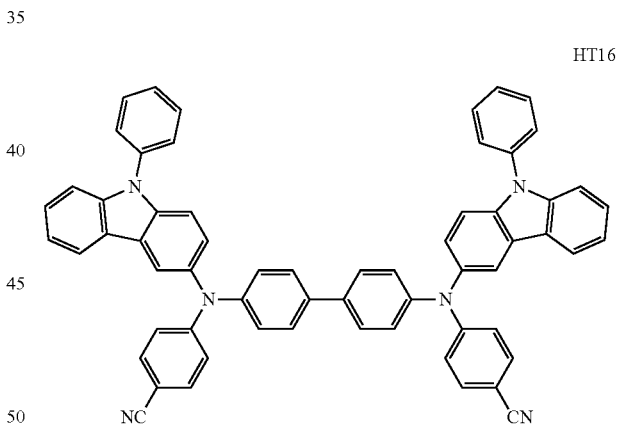
HT17
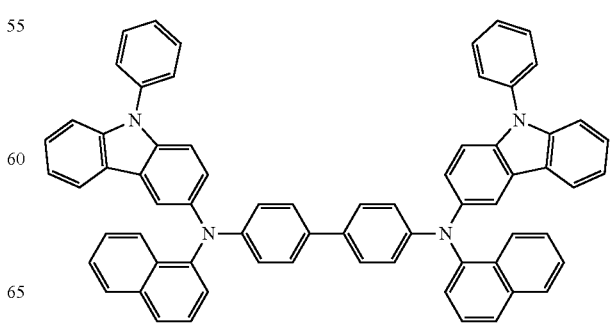

-continued

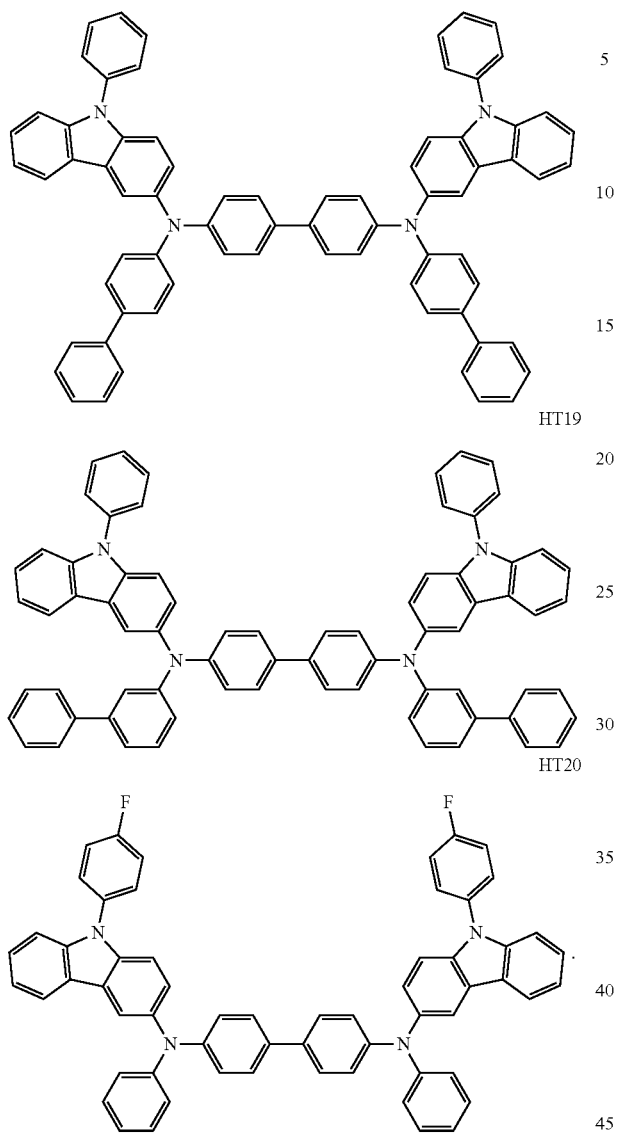

HT18

HT19

HT20

The thickness of the hole transport region may be in a range of about 100 Angstroms (Å) to about 10,000 Å, for example, about 100 Å to about 1,000 Å. When the hole transport region includes a hole injection layer, a hole transport layer, or any combination thereof, the thickness of the hole injection layer may be in a range of about 100 Å to about 10,000 Å, for example, about 100 Å to about 1,000 Å, the thickness of the hole transport layer may be in a range of about 50 Å to about 2,000 Å, for example, about 100 Å to about 1,500 Å. When the thicknesses of the hole transport region, the hole injection layer, and the hole transport layer are within any of these ranges, excellent hole transport characteristics may be obtained without a substantial increase in driving voltage.

The hole transport region may include a charge generating material as well as the aforementioned materials, to improve conductive properties of the hole transport region. The charge generating material may be substantially homogeneously or non-homogeneously dispersed in the hole transport region.

The charge-generation material may be, for example, a p-dopant. The p-dopant may be a quinone derivative, a metal oxide, a cyano group-containing compound, or any combination thereof, but embodiments of the present disclosure are not limited thereto. Examples of the p-dopant are a quinone derivative, such as tetracyanoquinodimethane (TCNQ), 2,3,5,6-tetrafluoro-tetracyano-1,4-benzoquinone dimethane (F4-TCNQ), or F6-TCNNQ; a metal oxide, such as a tungsten oxide or a molybdenum oxide; a cyano group-containing compound, such as Compound HT-D1 below; or any combination thereof.

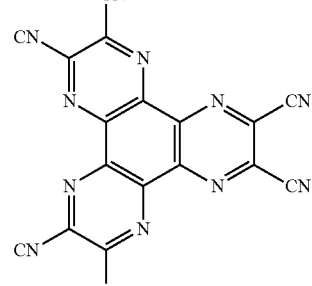

HT-D1

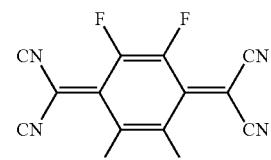

F4-TCNQ

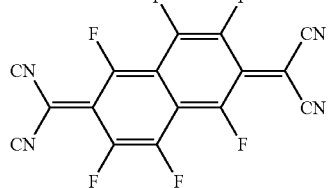

F6-TCNNQ

The hole transport region may include a buffer layer.

Also, the buffer layer may compensate for an optical resonance distance according to a wavelength of light emitted from the emission layer, and thus, efficiency of a formed organic light-emitting device may be improved.

Meanwhile, when the hole transport region includes an electron blocking layer, a material for the electron blocking layer may be a material for the hole transport region described above, a material for a host to be explained later, or any combination thereof. For example, when the hole transport region includes an electron blocking layer, a material for the electron blocking layer may be mCP.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a material that is used to form the hole transport layer.

The emission layer may include a composition including the first and second compounds described herein.

In one or more embodiments, the emission layer may include a host and a dopant, wherein the dopant may include the first compound, and the host may include the second compound.

In addition, the emission layer may further include a dopant and/or a host, other than the composition described herein.

When the organic light-emitting device 10 is a full-color organic light-emitting device, the emission layer may be patterned into a red emission layer, a green emission layer, and/or a blue emission layer. In some embodiments, the emission layer may have a structure in which the red emission layer, the green emission layer, and/or the blue emission layer are layered to emit white light. In some embodiments, the structure of the emission layer may vary.

When the emission layer includes the host and the dopant, an amount of the dopant may be selected from a range of about 0.01 parts to about 15 parts by weight based on about 100 parts by weight of the host, but embodiments are not limited thereto.

The thickness of the emission layer may be in a range of about 100 Å to about 1,000 Å, and in some embodiments, about 200 Å to about 600 Å. When the thickness of the emission layer is within any of these ranges, improved luminescence characteristics may be obtained without a substantial increase in driving voltage.

Next, an electron transport region may be formed on the emission layer.

The electron transport region may include a hole blocking layer, an electron transport layer, an electron injection layer, or a combination thereof.

In some embodiments, the electron transport region may have a hole blocking layer/an electron transport layer/an electron injection layer structure or an electron transport layer/an electron injection layer structure, but embodiments are not limited thereto. The electron transport layer may have a single-layered structure or a multi-layered structure including two or more different materials.

The conditions for forming a hole blocking layer, an electron transport layer, and an electron injection layer may be inferred based on the conditions for forming the hole injection layer.

When the electron transport region includes a hole blocking layer, the hole blocking layer may include, for example, at least one of BCP, Bphen, and BAlq:

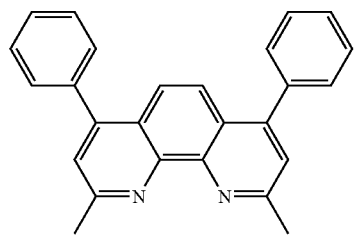

BCP

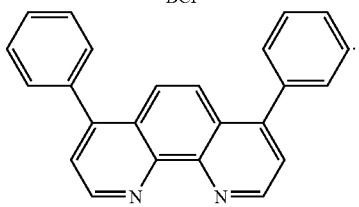

Bphen

In one or more embodiments, the hole blocking layer may include the host, a material for forming an electron transport layer to be described later, a material for forming an electron injection layer to be described later, or any combination thereof.

The thickness of the hole blocking layer may be in a range of about 20 Å to about 1,000 Å, for example, about 30 Å to about 300 Å. When the thickness of the hole blocking layer is within any of these ranges, excellent hole blocking characteristics may be obtained without a substantial increase in driving voltage.

The electron transport layer may include BCP, Bphen, TPBi, Alq$_3$, Balq, TAZ, NTAZ, or any combination thereof:

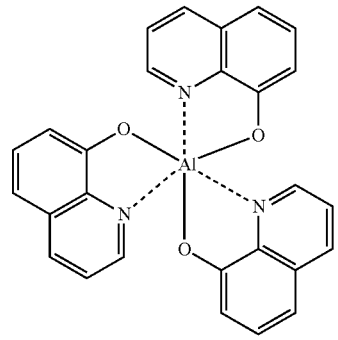

Alq$_3$

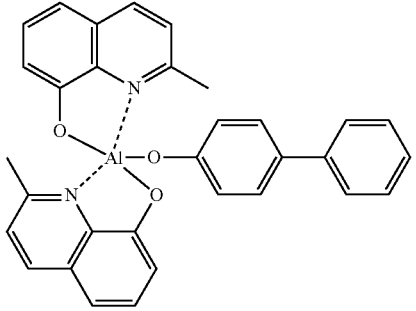

BAlq

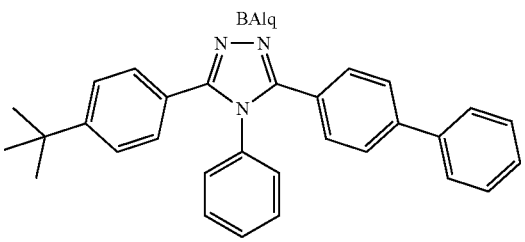

TAZ

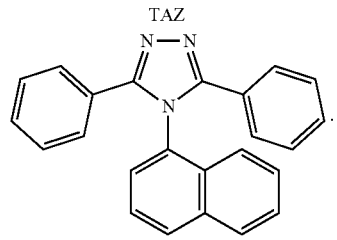

NTAZ

In some embodiments, the electron transport layer may include at least one of Compounds ET1 to ET25, but embodiments are not limited thereto:

ET1
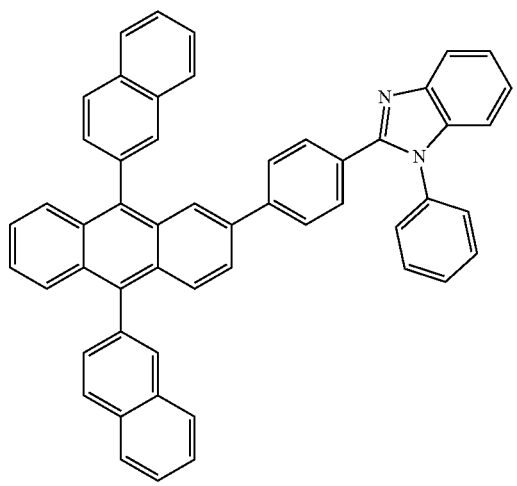
ET2
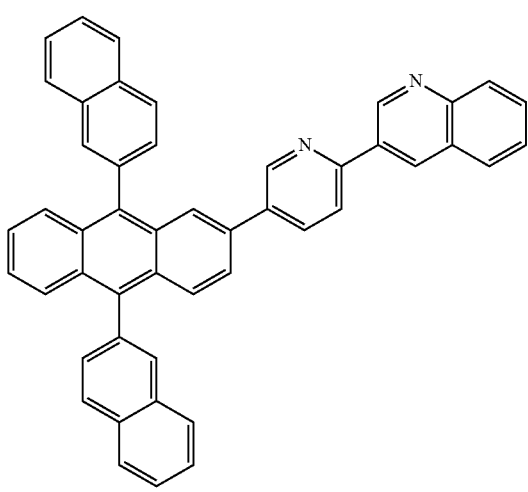
ET3
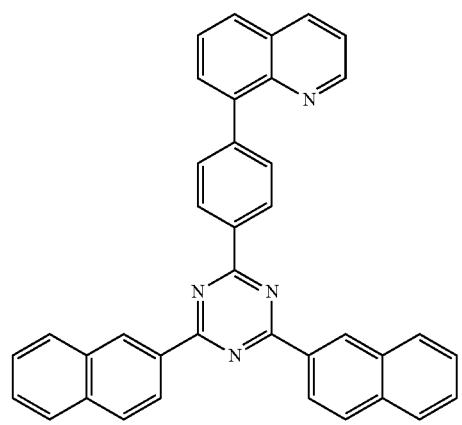
ET4
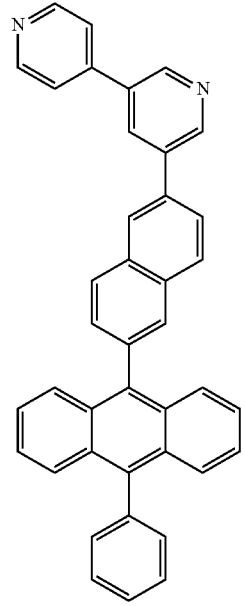
ET5
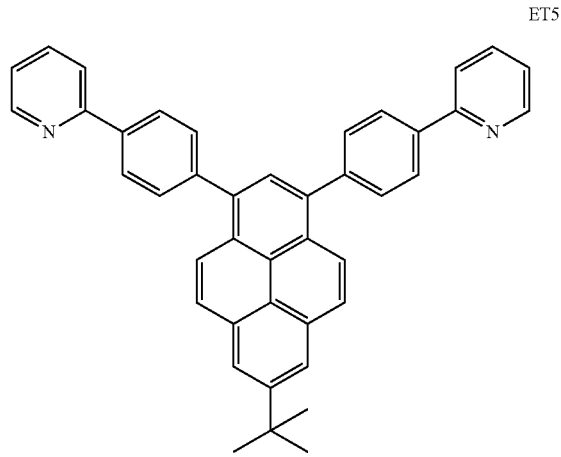
ET6
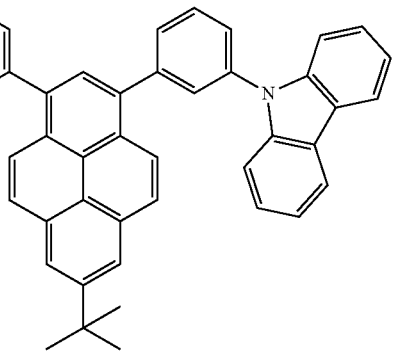

ET7
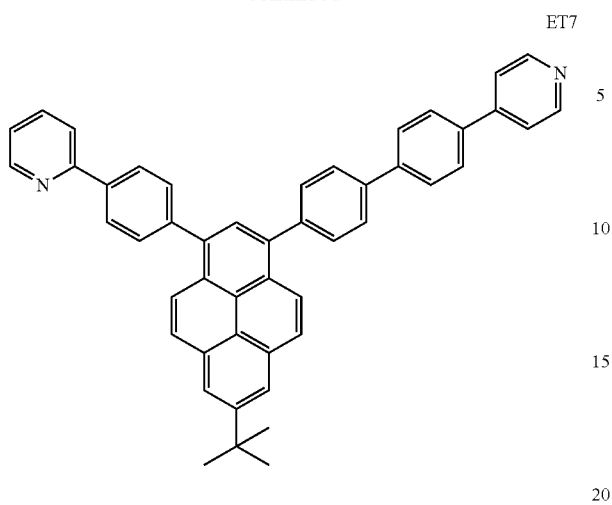
ET8
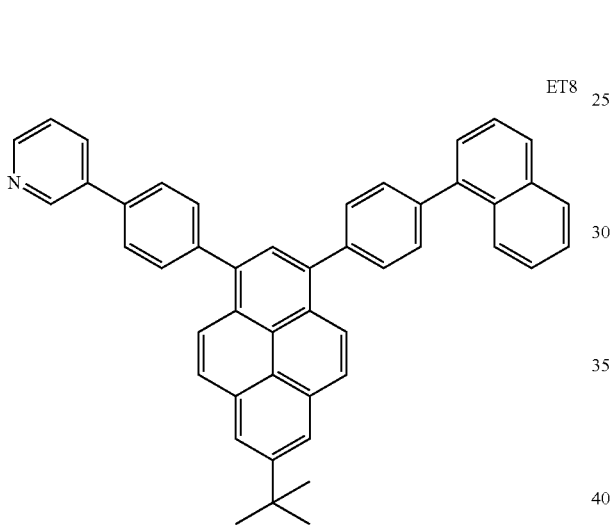
ET9
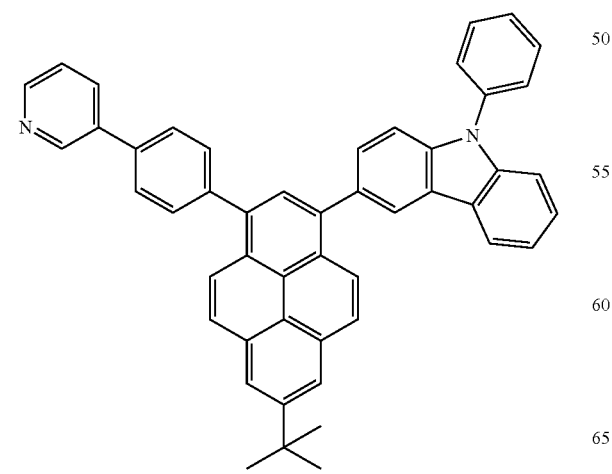
ET10
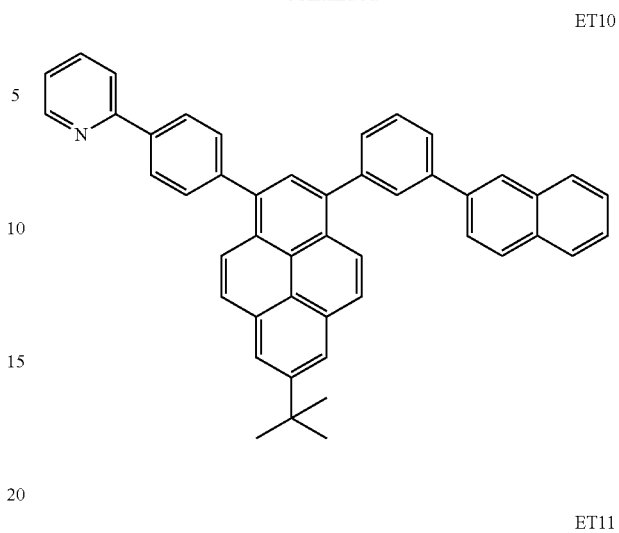
ET11
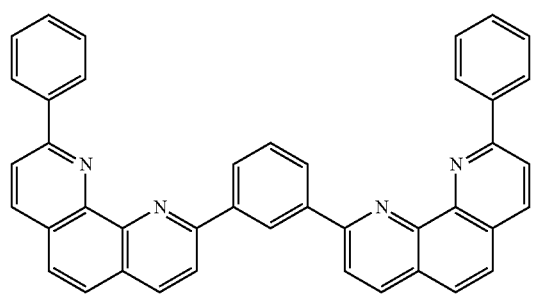
ET12
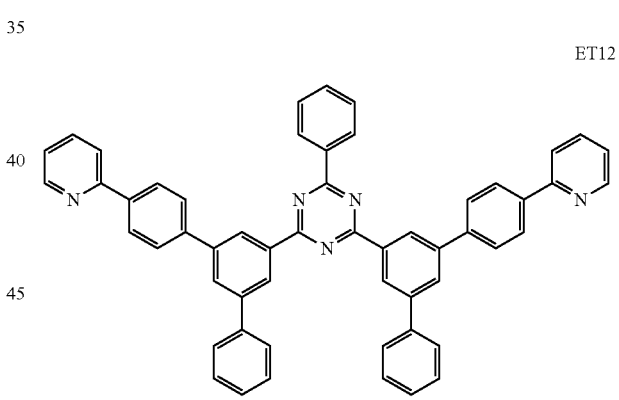
ET13
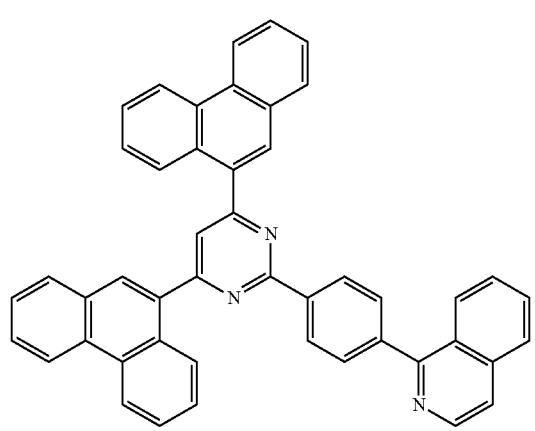

-continued
ET14
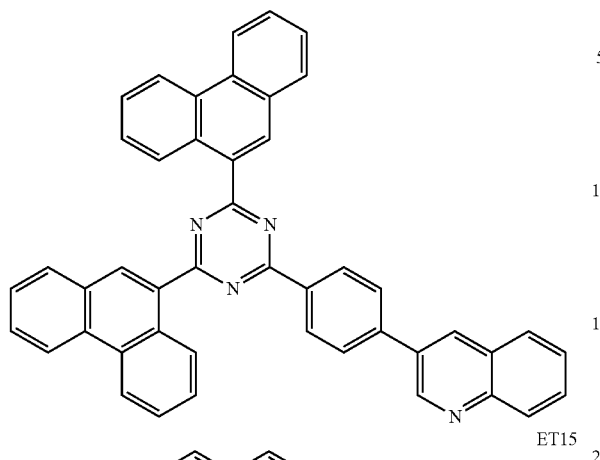
ET15
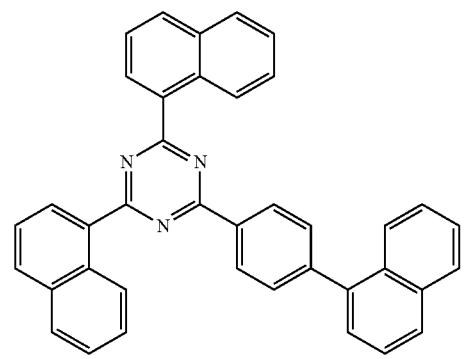
ET16
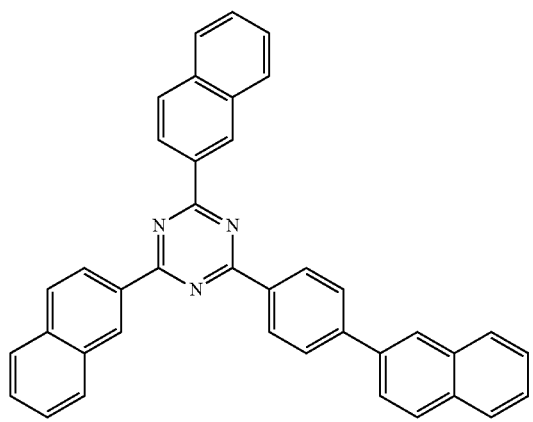
ET17
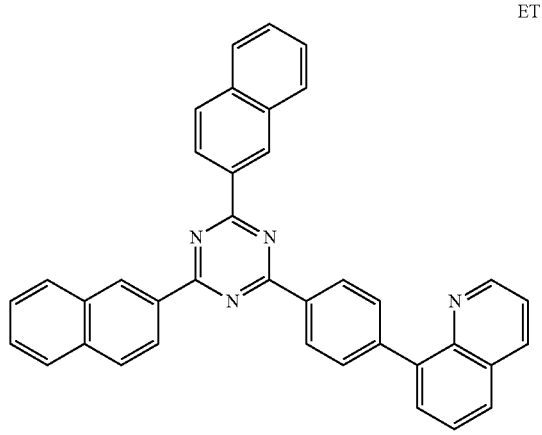
-continued
ET18
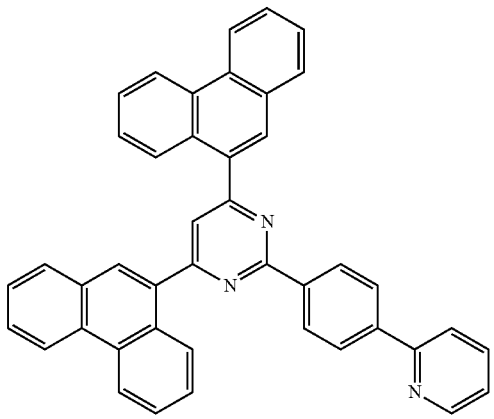
ET19
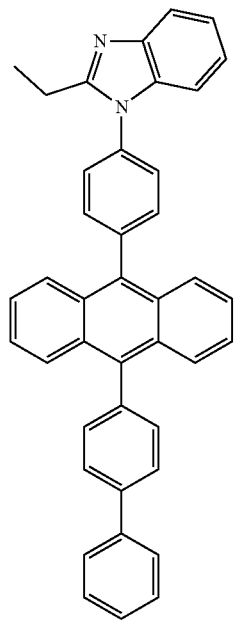
ET20
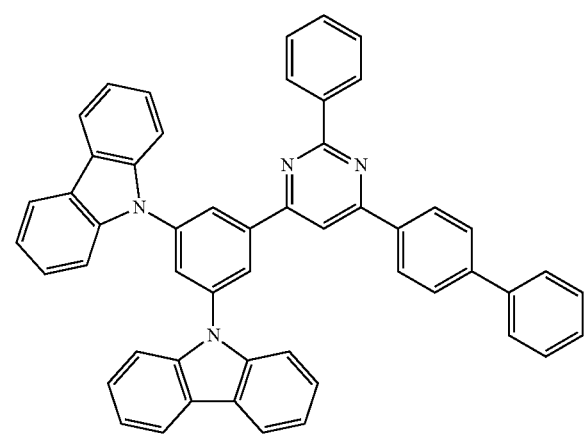

ET21

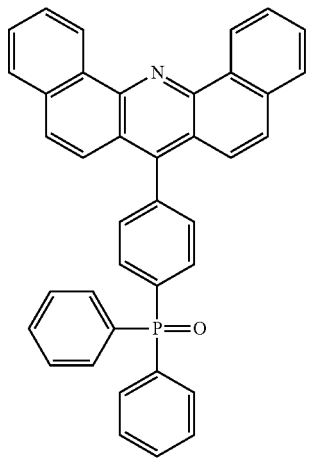

ET22

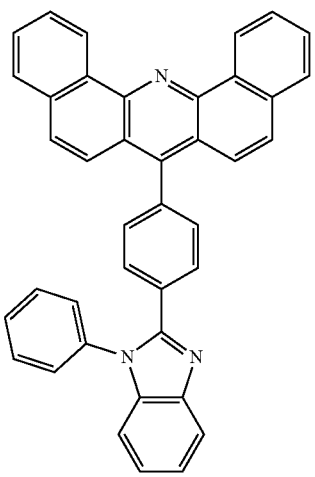

ET23

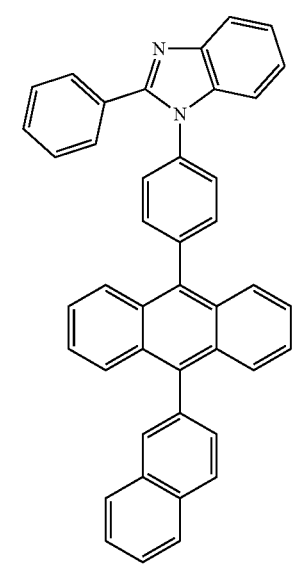

ET24

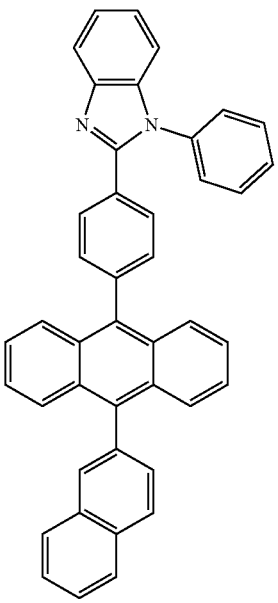

ET25

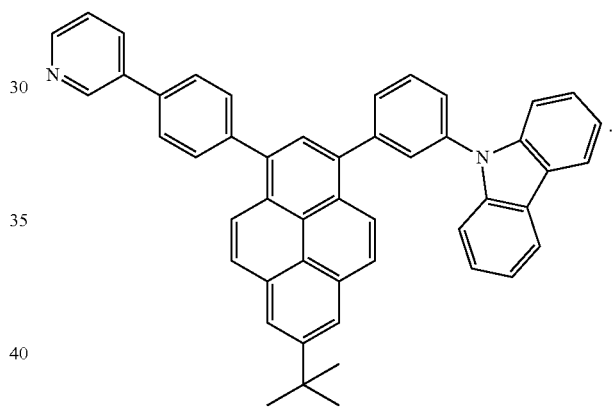

The thickness of the electron transport layer may be in a range of about 100 Å to about 1,000 Å, and in some embodiments, about 150 Å to about 500 Å. When the thickness of the electron transport layer is within any of these ranges, excellent electron transport characteristics may be obtained without a substantial increase in driving voltage.

The electron transport layer may further include a material containing metal, in addition to the materials described above.

The material containing metal may include a Li complex. The Li complex may include, e.g., Compound ET-D1 (LiQ), Compound ET-D2, or a combination thereof:

ET-D1

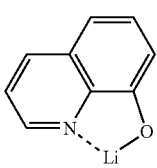

-continued

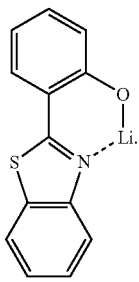

ET-D2

The electron transport region may include an electron injection layer that facilitates electron injection from the second electrode 19.

The electron injection layer may include LiF, NaCl, CsF, Li$_2$O, BaO, or any combination thereof.

The thickness of the electron injection layer may be in a range of about 1 Å to about 100 Å, and in some embodiments, about 3 Å to about 90 Å. When the thickness of the electron injection layer is within any of these ranges, excellent electron injection characteristics may be obtained without a substantial increase in driving voltage.

The second electrode 19 may be on the organic layer 15. The second electrode 19 may be a cathode. A material for forming the second electrode 19 may be a material with a relatively low work function, such as a metal, an alloy, an electrically conductive compound, and a mixture thereof. Examples of the material for forming the second electrode 19 may include lithium (Li), magnesium (Mg), aluminum (Al), aluminum-lithium (Al—Li), calcium (Ca), magnesium-indium (Mg—In), and magnesium-silver (Mg—Ag). In some embodiments, ITO or IZO may be used to form a transmissive second electrode 19 to manufacture a top emission light-emitting device. In some embodiments, the material for forming the second electrode 19 may vary.

Hereinbefore the organic light-emitting device 10 has been described with reference to the FIGURE, but embodiments are not limited thereto.

Hereinafter, a compound and an organic light-emitting device according to an embodiment will be described in detail with reference to Synthesis Examples and Examples, however, the present disclosure is not limited thereto. The wording "B was used instead of A" used in describing Synthesis Examples means that an amount of B used was identical to an amount of A used based on molar equivalence.

EXAMPLES

Synthesis Example 1 (Compound 3)

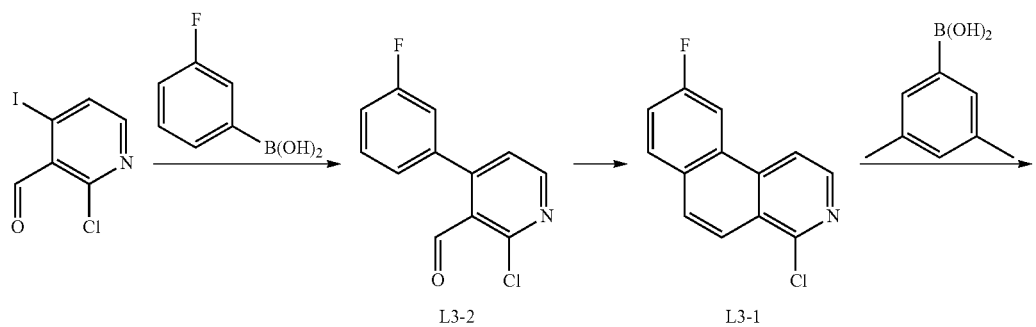

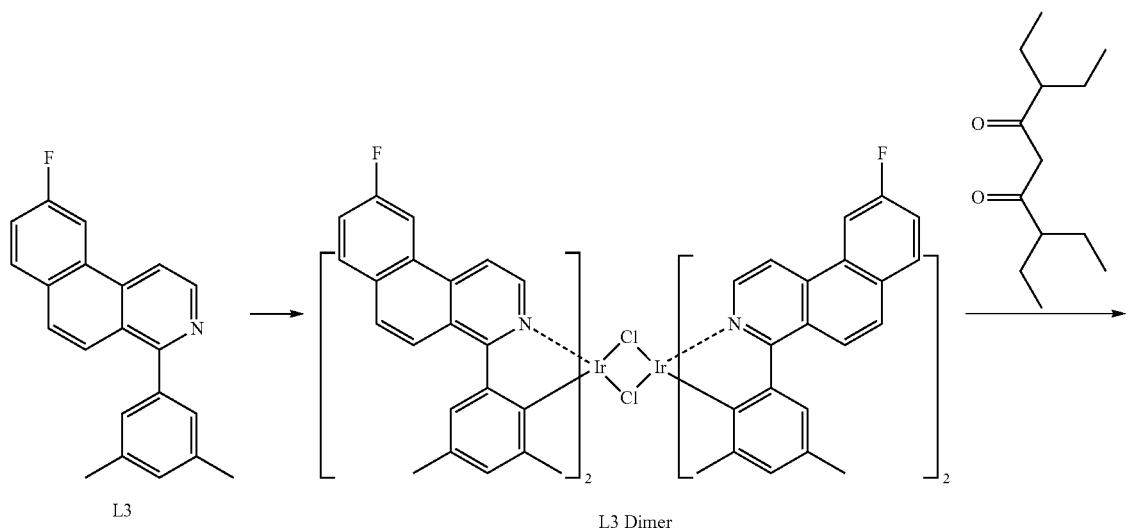

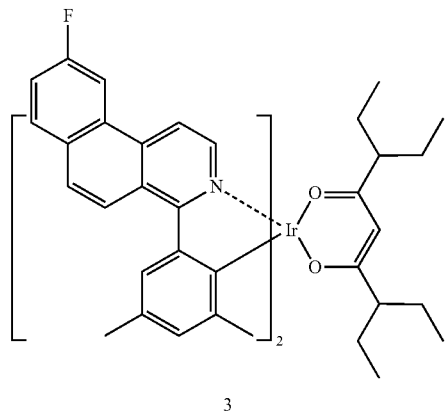

3

Synthesis of Intermediate L3-2

2.5 grams (g) (9.3 mmol) of 2-chloro-4-iodonicotinaldehyde was mixed with 100 milliliter (ml) of tetrahydrofuran and 30 ml of water, and 0.53 g (0.46 mmol) of Pd(PPh$_3$)$_4$, 1.3 g (9.3 mmol) of 3-fluorophenylboronic acid, and 3.2 g (23.0 mmol) of K$_2$CO$_3$ were added thereto, followed by heating under reflux at 80° C. for 24 hours. Once the reaction was complete, the reaction mixture was concentrated under reduced pressure, and dichloromethane and water were added thereto to extract an organic layer, which was then dried using magnesium sulfate and distilled under reduced pressure, followed by purification through column chromatography to obtain 1.1 g of Intermediate L3-2 (yield: 51%).

LCMS: m/z calcd for C$_{12}$H7ClFNO 235.02; Found 236.06.

Synthesis of Intermediate L3-1

5.8 g (17.0 mmol) of (methoxy methyl)triphenyl phosphonium chloride and 1.6 g (6.8 mmol) of Intermediate L3-2 were added to 50 ml of tetrahydrofuran and mixed. Then, at room temperature, 17 ml of 1.0 M potassium tert-butoxide solution (in THF) was slowly added dropwise thereto and stirred for 24 hours. Once the reaction was complete, water and ethyl acetate were added to the reaction mixture, and an organic layer was extracted therefrom, which was then dried using magnesium sulfate and distilled under reduced pressure. The resulting product was dried under reduced pressure, which was then mixed with 40 ml of dichloromethane. Then, 1.5 ml of methanesulfonic acid was slowly added to the mixture at room temperature, followed by stirring at room temperature for about 12 hours. Once the reaction was complete, a saturated sodium bicarbonate aqueous solution was added thereto to extract an organic layer, which was then dried using magnesium sulfate and distilled under reduced pressure, followed by purification through column chromatography to obtain 1.1 g of Intermediate L3-1 (yield: 72%).

LCMS: m/z calcd for C$_{13}$H7ClFN 231.03; Found 231.98.

Synthesis of Intermediate L3

0.7 g (3.0 mmol) of Intermediate L3-1 was mixed with 30 ml of THF and 10 ml of water, and 0.5 g (3.6 mmol) of 3,5-dimethylphenylboronic acid, 0.24 g (0.2 mmol) of Pd(PPh$_3$)$_4$, and 1.0 g (7.5 mmol) of K$_2$CO$_3$ were added thereto, followed by heating under reflux for one day. Once the reaction was complete, ethyl acetate and water were added thereto to extract an organic layer, which was then dried using magnesium sulfate and distilled under reduced pressure, followed by purification through column chromatography to obtain 0.72 g of Intermediate L3 (yield: 80%).

LCMS: m/z calcd for C$_{21}$H$_{16}$FN 301.13; Found 302.05.

Synthesis of Intermediate L3 Dimer 1.05 g (3.4 mmol) of Intermediate L3 and 0.6 g (1.6 mmol) of iridium chloride were mixed with 40 mL of ethoxyethanol and 15 mL of distilled water. Then, the mixture was heated under reflux for 24 hours. Once the reaction was complete, the temperature was dropped to room temperature, and the produced solid was filtered and sequentially washed with water, methanol, and hexane to a sufficient degree. The resulting solid was dried in a vacuum oven to obtain 1.0 g of Intermediate L3 dimer.

Synthesis of Compound 3

1.0 g (0.63 mmol) of Intermediate L3 Dimer, 0.96 g (4.5 mmol) of 3,7-diethylnonane-4,6-dione, and 0.48 g (4.5 mmol) of Na$_2$CO$_3$ were mixed with 40 mL of ethoxyethanol, followed by reaction by stirring at 90° C. for 24 hours. Once the reaction was complete, the temperature was cooled to room temperature, and the produced solid was filtered and purified through liquid chromatography to obtain 0.8 g of Compound 3 (yield: 65%).

LCMS: m/z calcd for C$_{55}$H$_{53}$F$_2$IrN$_2$O$_2$, 1004.37; Found 1005.25.

Synthesis Example 2 (Compound 9)

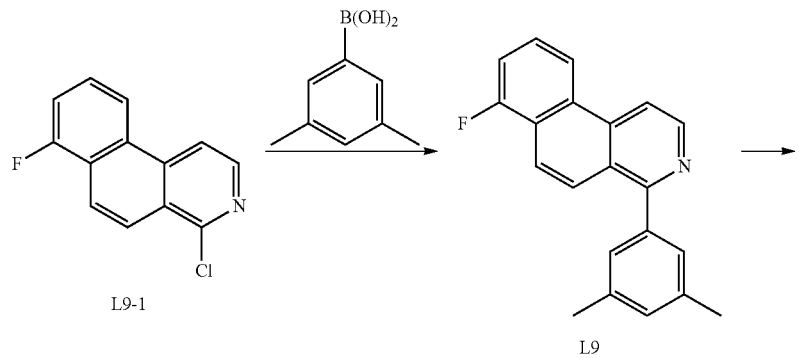

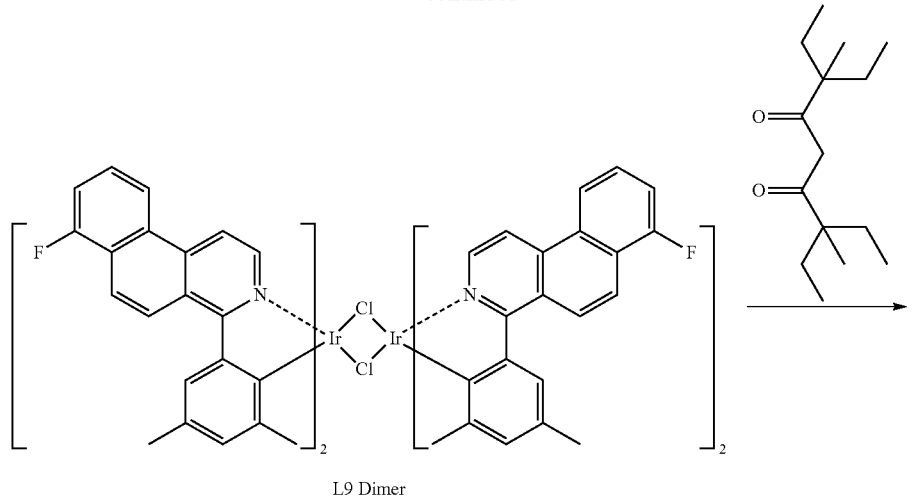

L9 Dimer

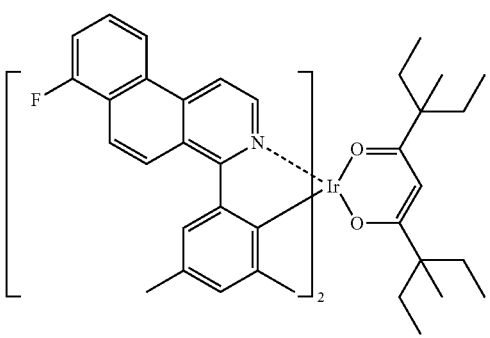

9

Synthesis of Intermediate L9

Intermediate L9 was synthesized in substantially the same manner as in Synthesis of Intermediate L3 in Synthesis Example 1, except that Intermediate L9-1 was used instead of Intermediate L3-1.

LC-MS m/z=303 (M+H)$^+$

Synthesis of Intermediate L9 Dimer

Intermediate L9 Dimer was synthesized in substantially the same manner as in Synthesis of Intermediate L3 Dimer in Synthesis Example 1, except that Intermediate L9 was used instead of Intermediate L3.

Synthesis of Compound 9

Compound 9 was synthesized in substantially the same manner as in Synthesis of Compound 3 in Synthesis Example 1, except that Intermediate L9 Dimer and 3,7-diethyl-3,7-dimethylnonane-4,6-dione were used instead of Intermediate L3 Dimer and 3,7-diethylnonane-4,6-dione.

LC-MS m/z=1035 (M+H)$^+$.

Synthesis Example 3 (Compound 10)

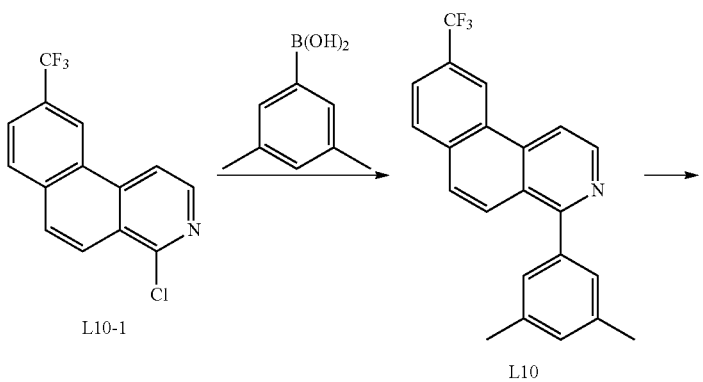

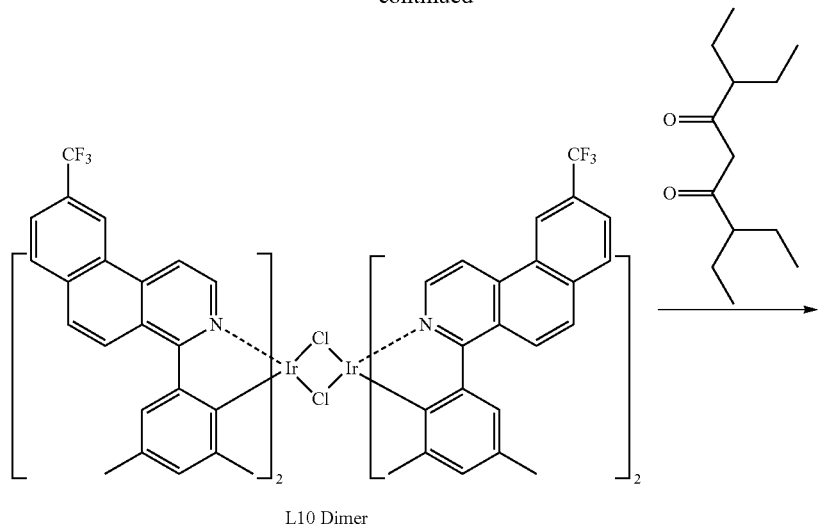

L10 Dimer

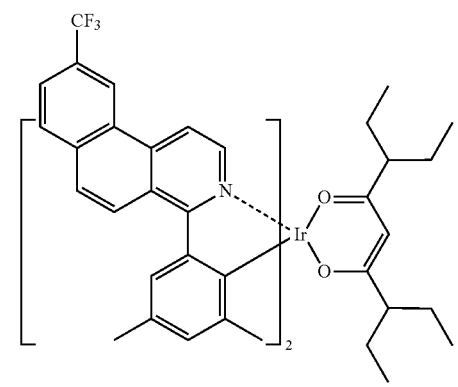

10

Synthesis of Intermediate L10

Intermediate L10 was synthesized in substantially the same manner as in Synthesis of Intermediate L3 in Synthesis Example 1, except that Intermediate L10-1 was used instead of Intermediate L3-1.

LCMS: m/z calcd for $C_{22}H_{16}F_3N$ 351.36; Found 352.21.

Synthesis of Intermediate L10 Dimer

Intermediate L10 Dimer was synthesized in substantially the same manner as in Synthesis of Intermediate L3 Dimer in Synthesis Example 1, except that Intermediate L10 was used instead of Intermediate L3.

Synthesis of Compound 10

Compound 10 was synthesized in substantially the same manner as in Synthesis of Compound 3 in Synthesis Example 1, except that Intermediate L10 Dimer was used instead of Intermediate L3 Dimer.

LCMS: m/z calcd for $C_{57}H_{53}F_6IrN_2O_2$ 1104.35; Found 1105.40.

Example 1

A glass substrate, on which an anode having an ITO/Ag/ITO (70 Å/1,000 Å/70 Å) structure was deposited, was cut to a size of 50 millimeters (mm)×50 mm×0.5 mm, sonicated in isopropyl alcohol and water for 5 minutes each, and cleaned by exposure to ultraviolet rays and ozone for 30 minutes. Subsequently, the glass substrate was mounted on a vacuum-deposition device.

2-TNATA was vacuum-deposited on the anode to form a hole injection layer having a thickness of 600 Å, and 4,4'-bis[N-(1-naphthyl)-N-phenylamino]biphenyl (hereinafter, referred as "NPB") was vacuum-deposited on the hole injection layer to form a hole transport layer having a thickness of 1,350 Å.

Subsequently, Compound H2 (host) and Compound 3 (dopant) were co-deposited on the hole transport layer at a weight ratio of 98:2 to form an emission layer having a thickness of 400 Å.

Then, BCP was vacuum-deposited on the emission layer to form a hole blocking layer having a thickness of 50 Å. $Alq_3$ was vacuum-deposited on the hole blocking layer to form an electron transport layer having a thickness of 350 Å. LiF was vacuum-deposited on the electron transport layer to form an electron injection layer having a thickness of 10 Å. Mg and Ag were co-deposited on the electron injection layer at a weight ratio of 90:10 to form a cathode having a thickness of 120 Å, thereby completing the manufacture of an organic light-emitting device (emitting red light).

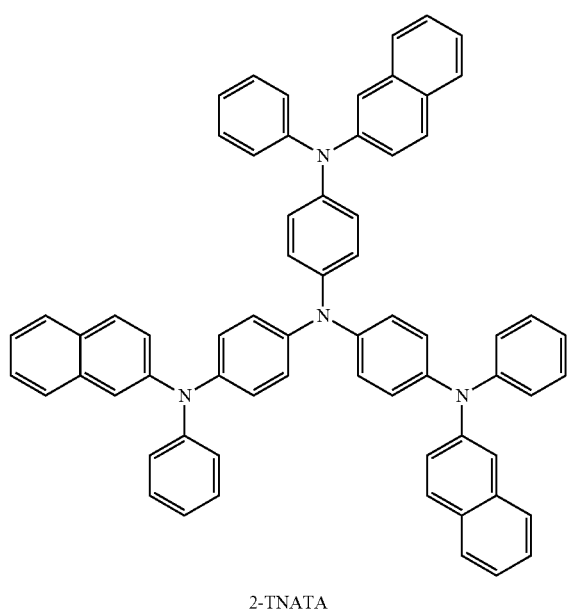

2-TNATA

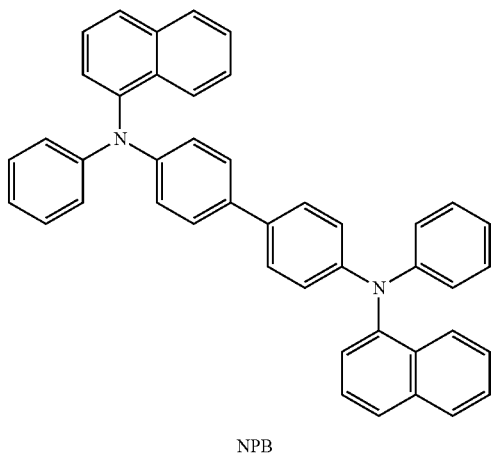

NPB

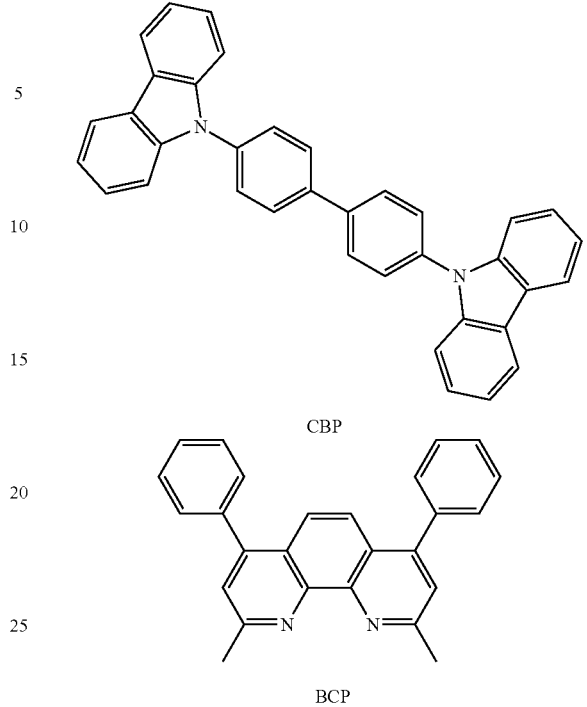

CBP

BCP

Examples 2 to 6 and Comparative Examples 1 and 3

Organic light-emitting devices were manufactured in substantially the same manner as in Example 1, except that the compounds shown in Tables 1 and 2 were used instead of Compound H2 and Compound 3 as a host and a dopant in the formation of an emission layer, respectively.

Evaluation Example 1: Evaluation of Characteristics of Organic Light-Emitting Device The driving voltage, current density, maximum of external quantum efficiency (Max EQE), FWHM of EL spectrum, emission color, color-coordinate, and lifespan ($LT_{97}$) of the organic light-emitting devices manufactured in Examples 1 to 6 and Comparative Examples 1 to 3 were evaluated. The results thereof are shown in Tables 1 and 2. A Keithley 2400 current voltmeter and a luminance meter (Minolta $C_5$-1000A) were used in the evaluation. The lifespan ($LT_{97}$) refers to time required for the initial luminance of 3,500 nit of the organic light-emitting device to reduce by 97%. Lifespan ($LT_{97}$) was shown in a relative value (%).

TABLE 1

| | Host Compound No. | Dopant Compound No. | Driving voltage (V) | Current density (mA/cm$^2$) | Max EQE (%) | FWHM (nm) | Emission color | Color coordinate (CIEx) | $LT_{97}$ (relative value, %) |
|---|---|---|---|---|---|---|---|---|---|
| Example 1 | H2 | 3 | 4.45 | 10.7 | 31.5 | 50.9 | Red | 0.665, 0.332 | 162 |
| Example 2 | H2 | 9 | 4.8 | 12.2 | 30.8 | 51.6 | Red | 0.679, 0.32 | 145 |
| Example 3 | H2 | 10 | 5.02 | 14.5 | 30.0 | 54.5 | Red | 0.673, 0.323 | 109 |
| Comparative Example 1 | H2 | A | 5.4 | 16.2 | 29.1 | 51.4 | Red | 0.677, 0.32 | 100 |
| Comparative Example 2 | H2 | B | 4.8 | 10.2 | 27.8 | 60.0 | Red | 0.647, 0.650 | 60 |

TABLE 2
| | Host Compound No. | Dopant Compound No. | Driving voltage (V) | Current density (mA/cm$^2$) | Max EQE (%) | FWHM (nm) | Emission color | Color coordinate (CIEx) | LT$_{97}$ (relative value, %) |
|---|---|---|---|---|---|---|---|---|---|
| Example 4 | H12 | 3 | 3.9 | 11.3 | 29.8 | 50.7 | Red | 0.667, 0.332 | 162 |
| Example 5 | H12 | 9 | 4.2 | 12.7 | 29.7 | 51 | Red | 0.680, 0.320 | 144 |
| Example 6 | H12 | 10 | 4.38 | 15.0 | 29 | 53.5 | Red | 0.674, 0.323 | 116 |
| Comparative Example 3 | H12 | A | 4.6 | 16.9 | 27.1 | 55.8 | Red | 0.678, 0.320 | 100 |
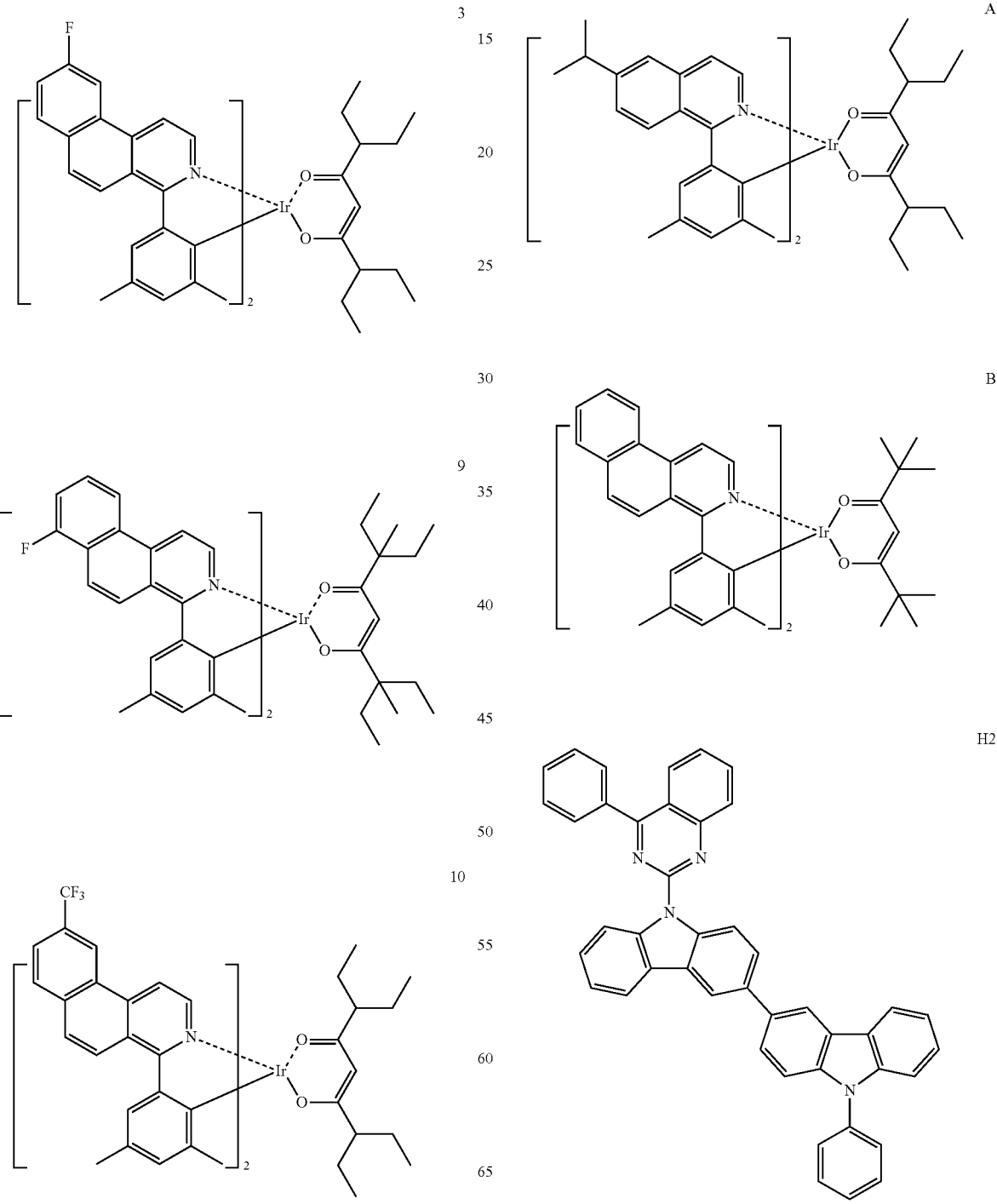

H12

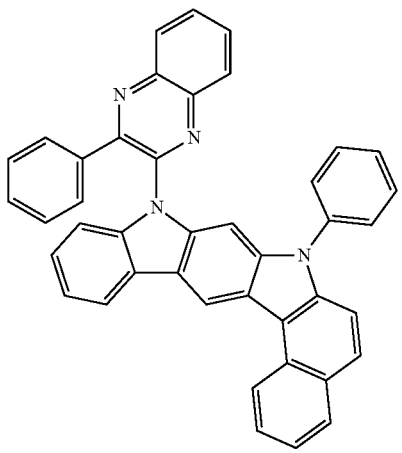

As shown in Tables 1 and 2, it was found that the organic light-emitting devices according to Examples 1 to 3 had improved driving voltage, improved EQE, and improved lifespan characteristics, as compared with the organic light-emitting devices according to Comparative Examples 1 and 2, and the organic light-emitting devices according to Examples 4 to 6 had improved driving voltage, improved EQE, and improved lifespan characteristics, as compared with the organic light-emitting devices according to Comparative Example 3.

As apparent from the foregoing description, the composition may have excellent electrical characteristics and stability. Thus, an electronic device, e.g., an organic light-emitting device, including the composition may have improved driving voltage, improved EQE, and improved lifespan characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope as defined by the following claims.

What is claimed is:

1. A composition comprising a first compound and a second compound, wherein the first compound comprises a compound represented by Formula 1, and the second compound comprises a compound represented by Formula 2:

Formula 1

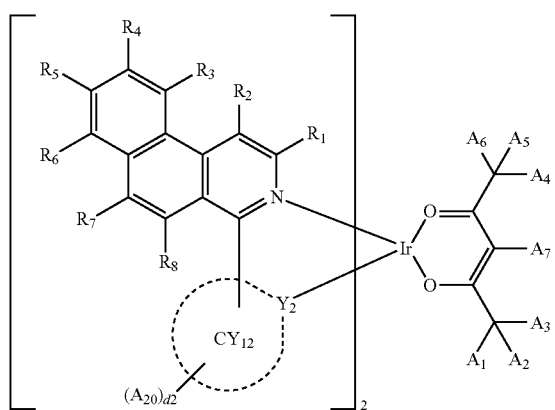

Formula 2

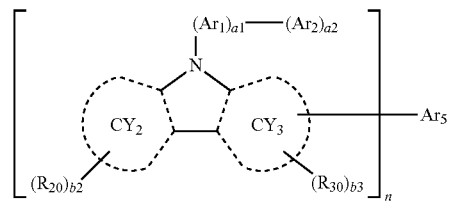

$Y_2$ in Formula 1 is C,
a group represented by

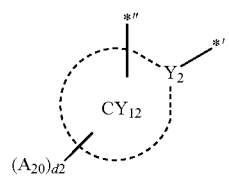

in Formula 1 is a group represented by Formula A(1):

A(1)

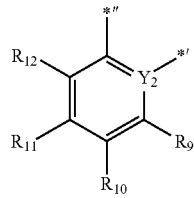

wherein, in Formula A(1), $R_9$ and $R_{11}$ are each independently a $C_1$-$C_{20}$ alkyl group, a $C_3$-$C_{10}$ cycloalkyl group, a $C_2$-$C_{10}$ heterocycloalkyl group, or a phenyl group, each unsubstituted or substituted with deuterium, a $C_1$-$C_{20}$ alkyl group, a $C_3$-$C_{10}$ cycloalkyl group, a $C_2$-$C_{10}$ heterocycloalkyl group, a phenyl group, or any combination thereof, and $R_{10}$ and $R_{12}$ are each independently hydrogen or deuterium, *' indicates a binding site to Ir in Formula 1, and *'' indicates a binding site to a neighboring atom in Formula 1, $Ar_1$ in Formula 2 is a $C_5$-$C_6$ carbocyclic group unsubstituted or substituted with at least one $R_{61}$ or a $C_1$-$C_6$ heterocyclic group unsubstituted or substituted with at least one $R_{61}$, $Ar_2$ in Formula 2 is a π electron-depleted nitrogen-containing $C_1$-$C_6$ cyclic group unsubstituted or substituted with at least one $R_{62}$, $Ar_5$ in Formula 2 is not present or is a single bond, a $C_5$-$C_6$ carbocyclic group unsubstituted or substituted with at least one $R_{65}$, or a $C_1$-$C_6$ heterocyclic group unsubstituted or substituted with at least one $R_{65}$, n in Formula 2 is 1, 2, or 3, and when n is 1, $Ar_5$ is not present, a1 and a2 in Formula 2 are each independently an integer from 0 to 5, and the sum of a1 and a2 is 1 or greater, ring $CY_2$ and ring $CY_3$ in Formula 2 are each independently a $C_5$-$C_6$ carbocyclic group or a $C_1$-$C_6$ heterocyclic group, and ring $CY_2$ and ring $CY_3$ are optionally bound to each other via a $C_5$-$C_6$ carbocyclic group unsubstituted or substituted with at least one $R_{66}$ or a $C_1$-$C_6$ heterocyclic group unsubstituted or substituted with at least one $R_6$, $R_1$ to $R_8$, $A_1$ to $A_7$, $R_{20}$, $R_{30}$, $R_{61}$, $R_{62}$, $R_{65}$, and $R_{66}$ in Formulae 1 and 2 are each independently hydrogen, deuterium, —F, —Cl, —Br, —I, —SF$_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —Ge($Q_3$)($Q_4$)($Q_5$), —B($Q_6$)($Q_7$), —P(=O)($Q_8$)($Q_9$), or —P($Q_8$)($Q_9$), b2 and b3 in Formula 2 are each independently an integer from 0 to 20, when b2 is 2 or more, two or more $R_{20}$(s) are identical to or different from each other, and when b3 is 2 or more, two or more $R_{30}$(s) are identical to or different from each other, provided that at least one of $R_1$ to $R_8$ is a fluoro (—F) group, two or more of $R_1$ to $R_8$ in Formula 1 are optionally linked to form a $C_5$-$C_{60}$ carbocyclic group which is unsubstituted or substituted with at least one $R_{1a}$ or a $C_1$-$C_{60}$ heterocyclic group which is unsubstituted or substituted with at least one $R_{1a}$, two or more of $A_1$ to $A_7$ in Formula 1 are optionally linked to form a $C_5$-$C_{60}$ carbocyclic group which is unsubstituted or substituted with at least one $R_{1a}$ or a $C_1$-$C_{60}$ heterocyclic group which is unsubstituted or substituted with at least one $R_{1a}$, two or more of ring $CY_2$, ring $CY_3$, $R_{20}$, and $R_{30}$ in Formula 2 are optionally linked to form a $C_5$-$C_{60}$ carbocyclic group which is unsubstituted or substituted with at least one $R_{1a}$ or a $C_1$-$C_{60}$ heterocyclic group which is unsubstituted or substituted with at least one $R_{1a}$, $R_{1a}$ is understood by referring to the description of $A_7$ provided above, and a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —Ge($Q_{13}$)($Q_{14}$)($Q_{15}$), —B($Q_{16}$)($Q_{17}$), —P(=O)($Q_{18}$)($Q_{19}$), —P($Q_{18}$)($Q_{19}$), or any combination thereof;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each unsubstituted or substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —Ge($Q_{23}$)($Q_{24}$)($Q_{25}$), —B($Q_{26}$)($Q_{27}$), —P(=O)($Q_{28}$)($Q_{29}$), —P($Q_{28}$)($Q_{29}$), or any combination thereof;

—N($Q_{31}$)($Q_{32}$), —Si($Q_{33}$)($Q_{34}$)($Q_{35}$), —Ge($Q_{33}$)($Q_{34}$)($Q_{35}$), —B($Q_{36}$)($Q_{37}$), —P(=O)($Q_{38}$)($Q_{39}$), or —P($Q_{38}$)($Q_{39}$); or any combination thereof, wherein $Q_1$ to $Q_9$, $Q_{11}$ to $Q_{19}$, $Q_{21}$ to $Q_{29}$, and $Q_{31}$ to $Q_{39}$ are each independently hydrogen; deuterium; —F; —Cl; —Br; —I; a hydroxyl group; a cyano group; a nitro group; an amidino group; a hydrazine group; a hydrazone group; a carboxylic acid group or a salt thereof; a sulfonic acid group or a salt thereof; a phosphoric acid group or a salt thereof; a $C_1$-$C_{60}$ alkyl group, unsubstituted or substituted with deuterium, a $C_1$-$C_{60}$ alkyl group, a $C_6$-$C_{60}$ aryl group, or any combination thereof; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_2$-$C_{10}$ heterocycloalkyl group; a $C_3$-$C_{10}$ cycloalkenyl group; a $C_2$-$C_{10}$ heterocycloalkenyl group; a $C_6$-$C_{60}$ aryl group, unsubstituted or substituted with deuterium, a $C_1$-$C_{60}$ alkyl group, a $C_6$-$C_{60}$ aryl group, or any combination thereof; a $C_6$-$C_{60}$ aryloxy group; a $C_6$-$C_{60}$ arylthio group; a $C_1$-$C_{60}$ heteroaryl group; a monovalent non-aromatic condensed polycyclic group; or a monovalent non-aromatic condensed heteropolycyclic group.

2. The composition of claim 1, wherein
$R_1$ to $R_8$ and $A_1$ to $A_7$ are each independently:
hydrogen, deuterium, or —F;
a $C_1$-$C_{20}$ alkyl group, a $C_3$-$C_{10}$ cycloalkyl group, a $C_2$-$C_{10}$ heterocycloalkyl group, or a phenyl group, each unsubstituted or substituted with deuterium, —F, a $C_1$-$C_{20}$ alkyl group, a $C_3$-$C_{10}$ cycloalkyl group, a $C_2$-$C_{10}$ heterocycloalkyl group, a phenyl group, or any combination thereof; or
—Si($Q_3$)($Q_4$)($Q_5$) or —Ge($Q_3$)($Q_4$)($Q_5$).

3. The composition of claim 1, wherein
at least one of $A_1$ to $A_6$ in Formula 1 is an unsubstituted or substituted $C_2$-$C_{60}$ alkyl group, an unsubstituted or substituted $C_3$-$C_{10}$ cycloalkyl group, or an unsubstituted or substituted $C_2$-$C_{10}$ heterocycloalkyl group.

4. The composition of claim 1, wherein
$A_1$ to $A_6$ are each independently an unsubstituted or substituted $C_1$-$C_{60}$ alkyl group, an unsubstituted or substituted $C_3$-$C_{10}$ cycloalkyl group, or an unsubstituted or substituted $C_2$-$C_{10}$ heterocycloalkyl group.

5. The composition of claim 1, wherein
a group represented by

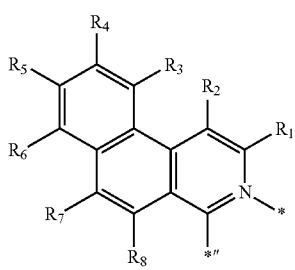

in Formula 1 is a group represented by one of Formulae CY1 to CY108:

CY1
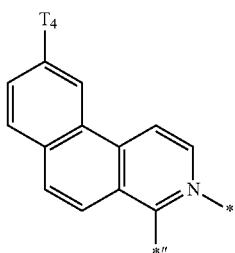

CY2
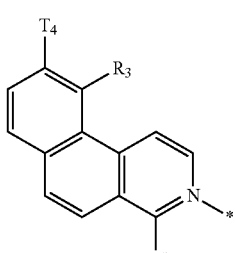

CY3
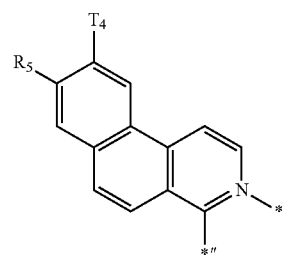

CY4
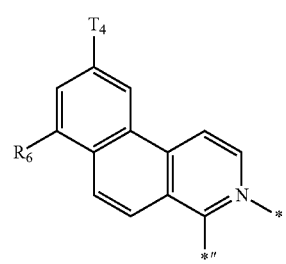

CY5
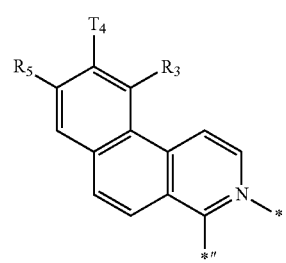

CY6
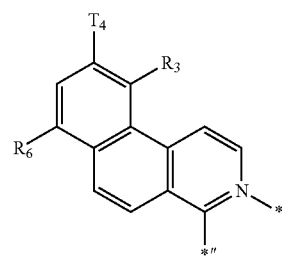

CY7
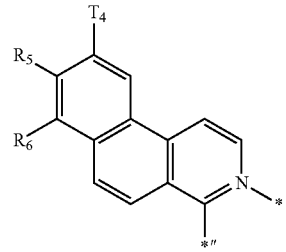

CY8
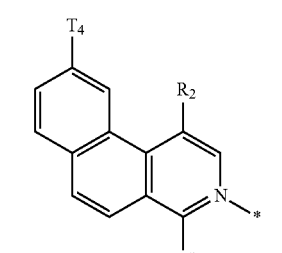

| | 213 -continued | | | 214 -continued | |
|---|---|---|---|---|---|
| | 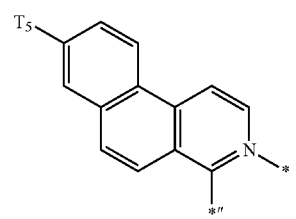 | CY9 | | 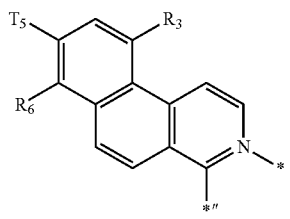 | CY15 |
| | 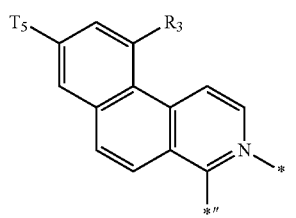 | CY10 | | 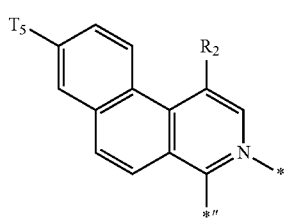 | CY16 |
| | 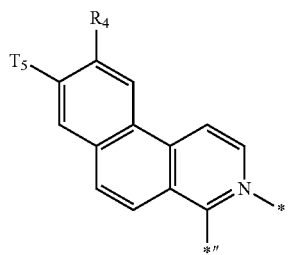 | CY11 | | 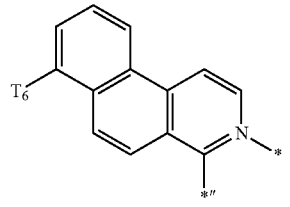 | CY17 |
| | 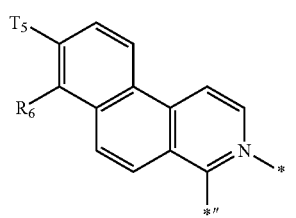 | CY12 | | 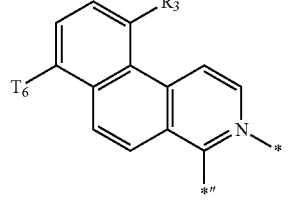 | CY18 |
| | 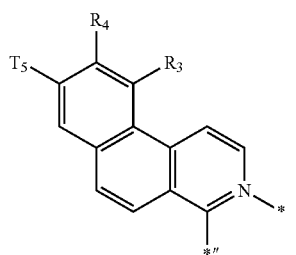 | CY13 | | 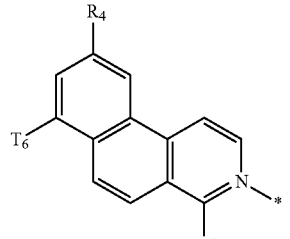 | CY19 |
| | | | | 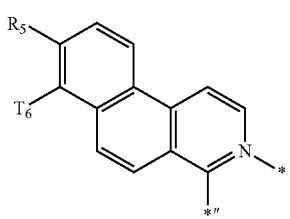 | CY20 |
| | 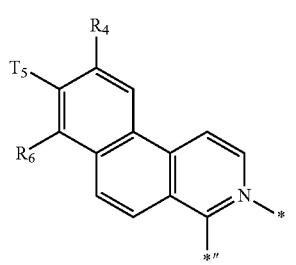 | CY14 | | 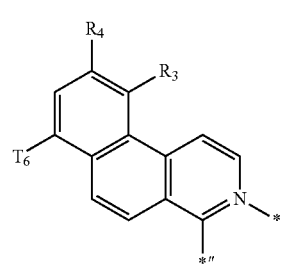 | CY21 |

-continued
CY22
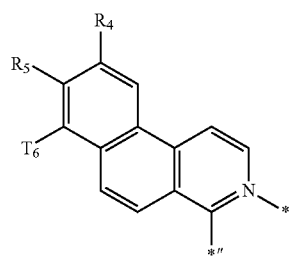
CY23
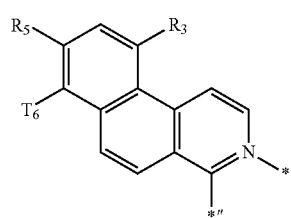
CY24
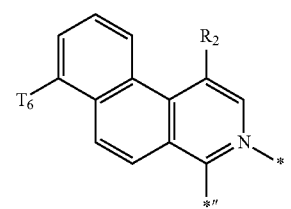
CY25
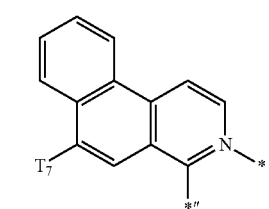
CY26
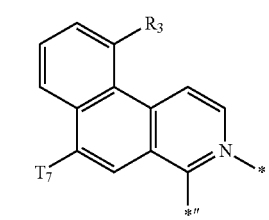
CY27
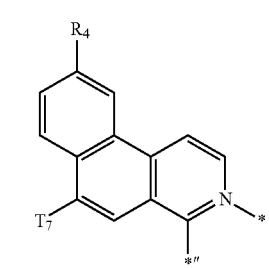
CY28
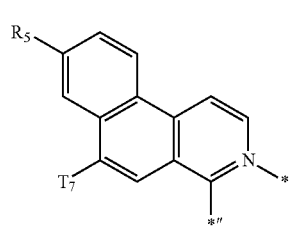
-continued
CY29
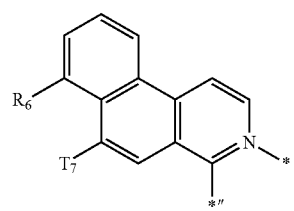
CY30
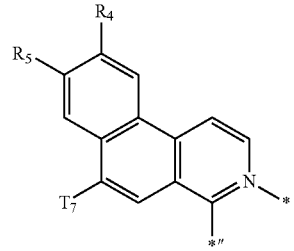
CY31
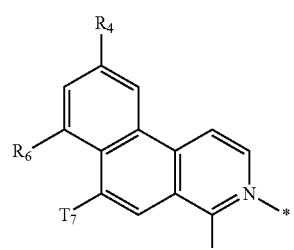
CY32
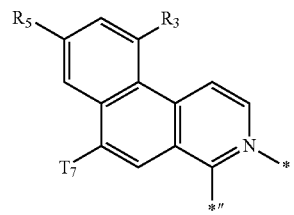
CY33
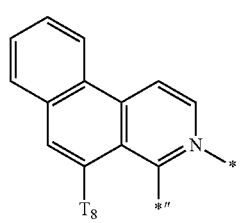
CY34
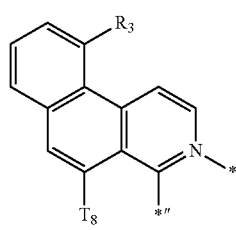

CY35 CY36 CY37 CY38 CY39 CY40

CY41 CY42 CY43 CY44 CY45 CY46 CY47

| | |
|---|---|
| 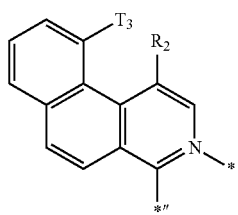 CY48 | 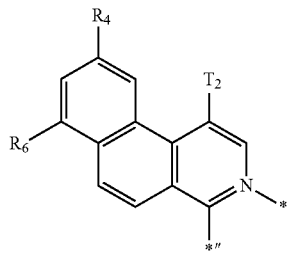 CY55 |
| 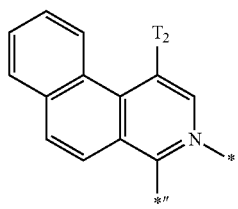 CY49 | 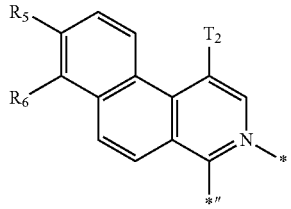 CY56 |
| 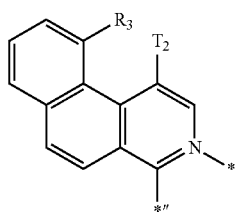 CY50 | 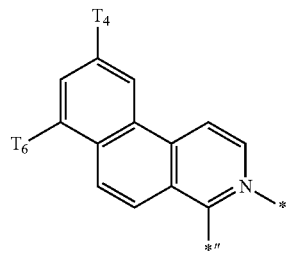 CY57 |
| 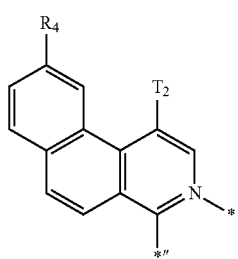 CY51 | 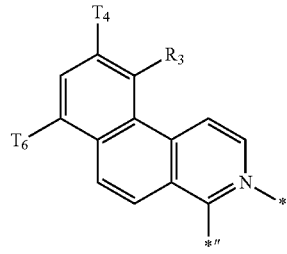 CY58 |
| 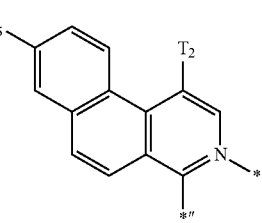 CY52 | 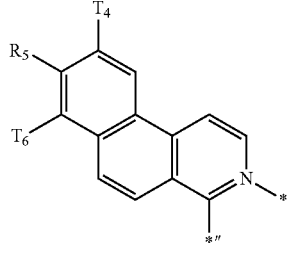 CY59 |
| 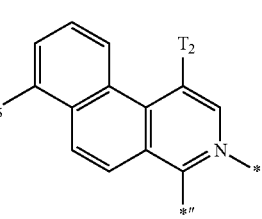 CY53 | 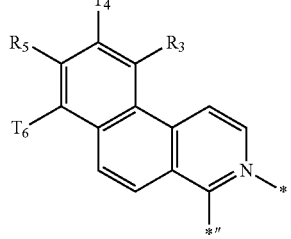 CY60 |
| 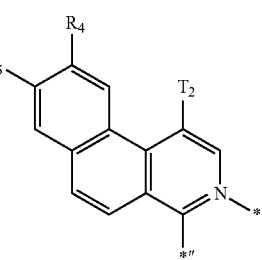 CY54 | |

-continued
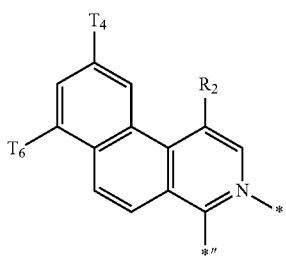
CY61
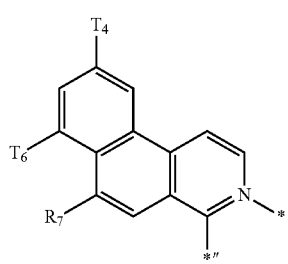
CY62
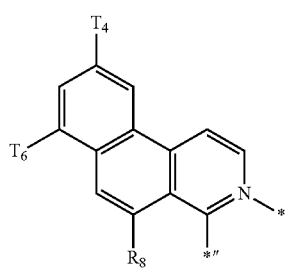
CY63
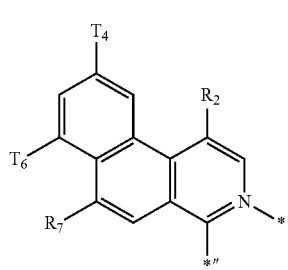
CY64
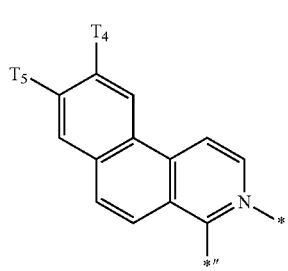
CY65
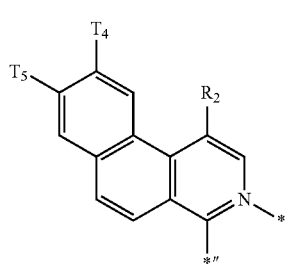
CY66
-continued
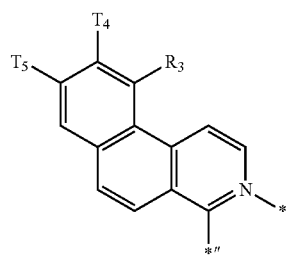
CY67
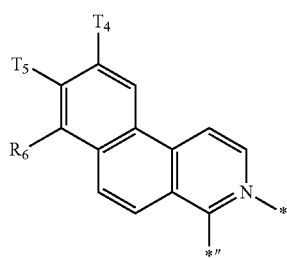
CY68
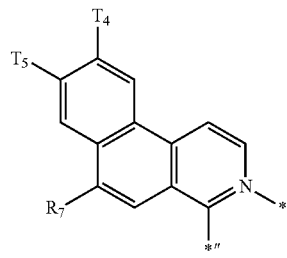
CY69
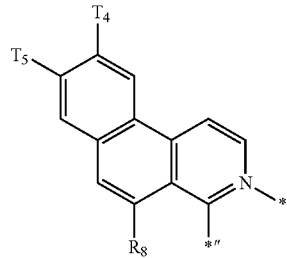
CY70
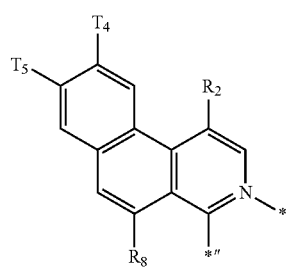
CY71
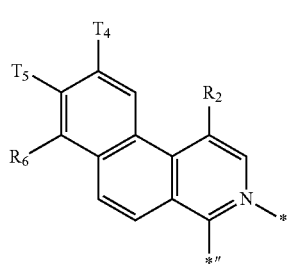
CY72

-continued

CY73
CY74
CY75
CY76
CY77
CY78
CY79
CY80
CY81
CY82
CY83
CY84
CY85

CY86
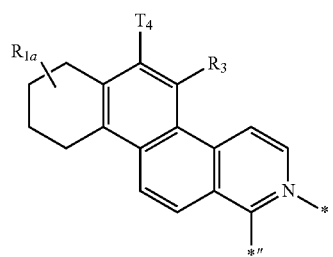
CY87
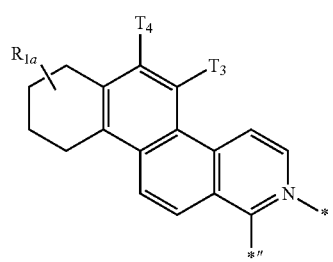
CY88
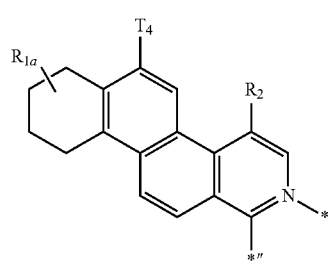
CY89
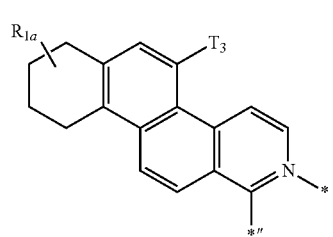
CY90
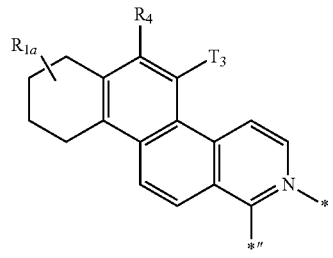
CY91
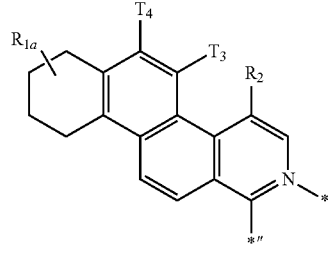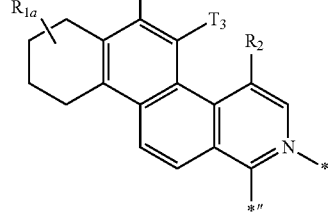
CY92
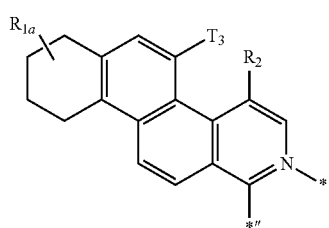
CY93
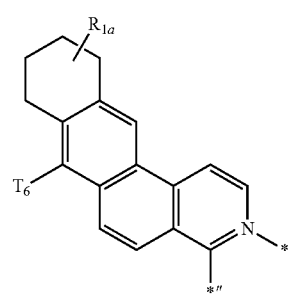
CY94
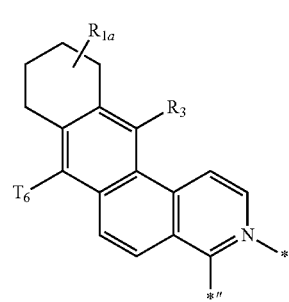
CY95
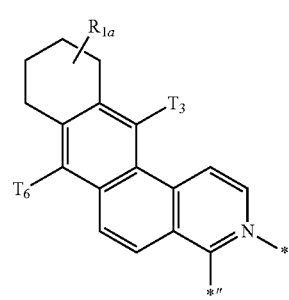
CY96
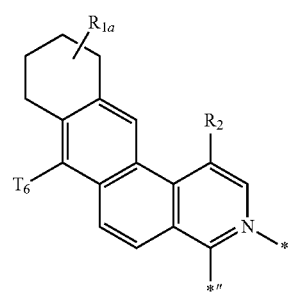

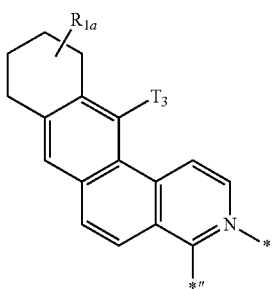 CY97
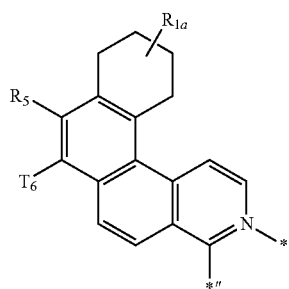 CY102
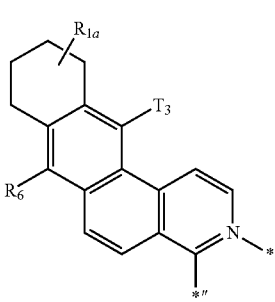 CY98
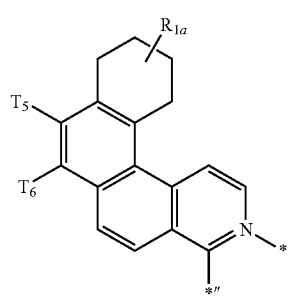 CY103
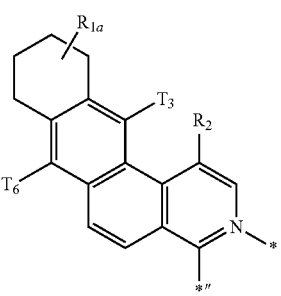 CY99
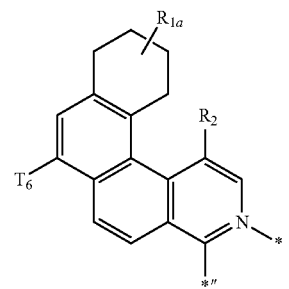 CY104
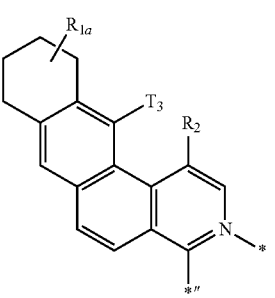 CY100
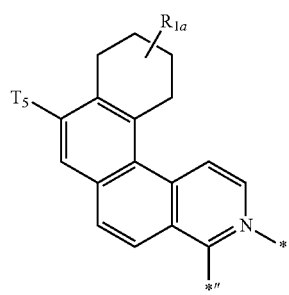 CY105
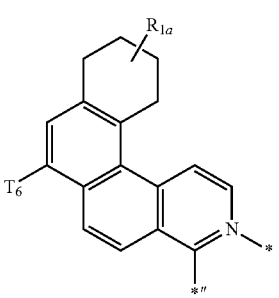 CY101
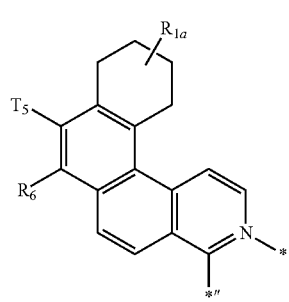 CY106

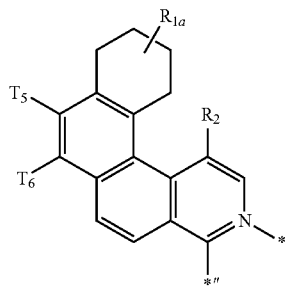

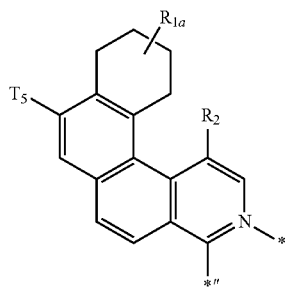

wherein, in Formulae CY1 to CY108, $T_2$ to $T_8$ are each a fluoro group (—F), each of $R_2$ to $R_8$ and $R_{1a}$ are the same as described in claim 1, provided that $R_2$ to $R_8$ are not hydrogen,

* indicates a binding site to Ir in Formula 1, and

*" indicates a binding site to a neighboring atom in Formula 1.

6. The composition of claim 1, wherein the first compound comprises at least one of Compounds 1 to 5, 8, 9, 13, 14, 25 to 29, 33 to 43 and 48 to 52:

1

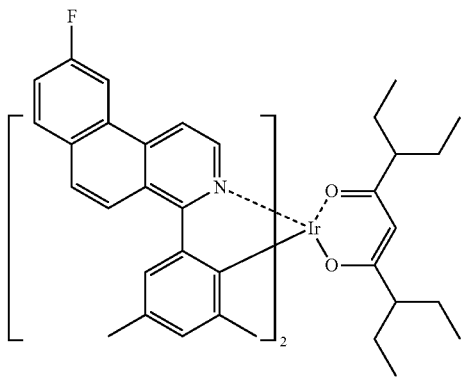

2

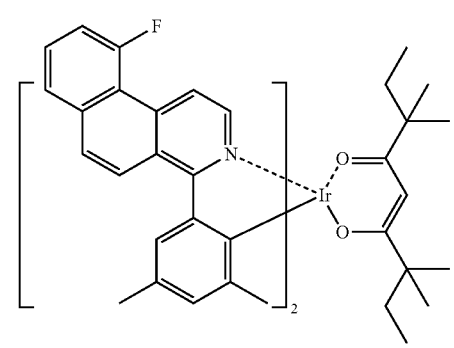

3

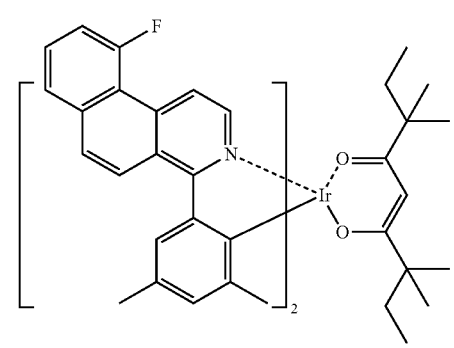

4

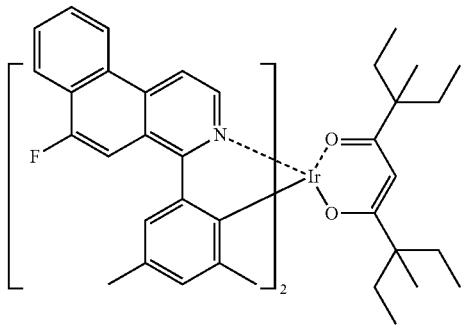

5

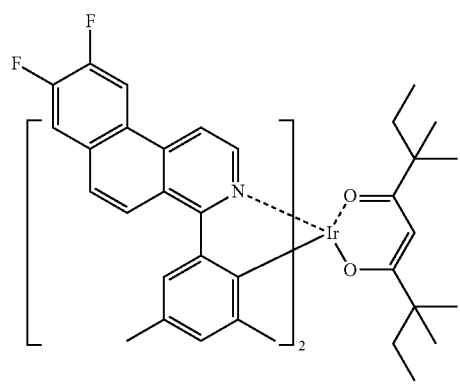

8

231
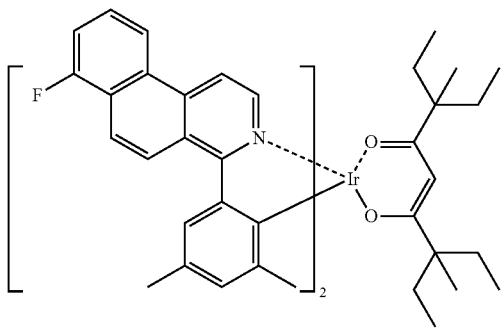
9
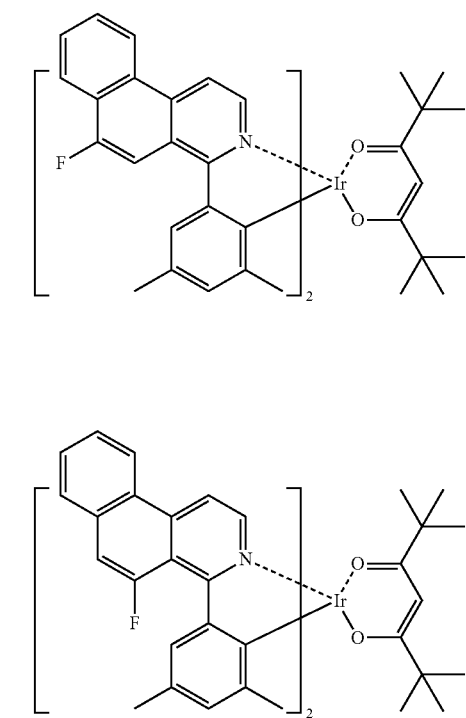
13
14
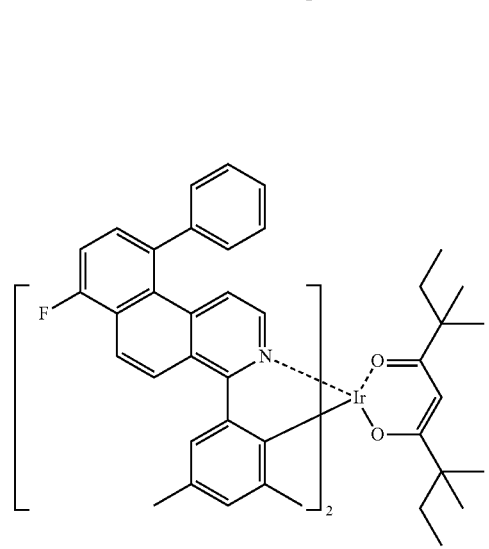
25
232
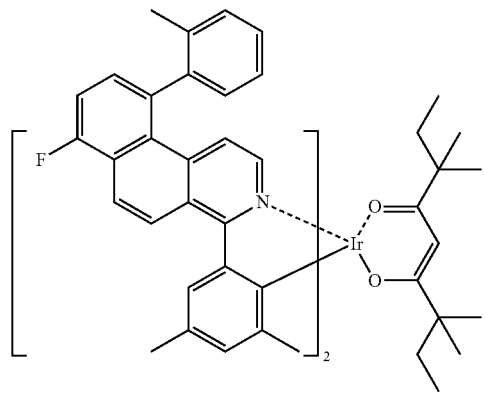
26
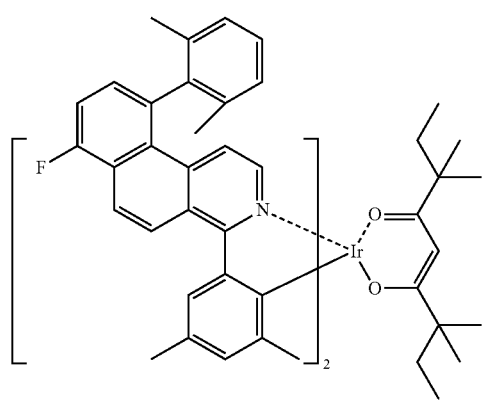
27
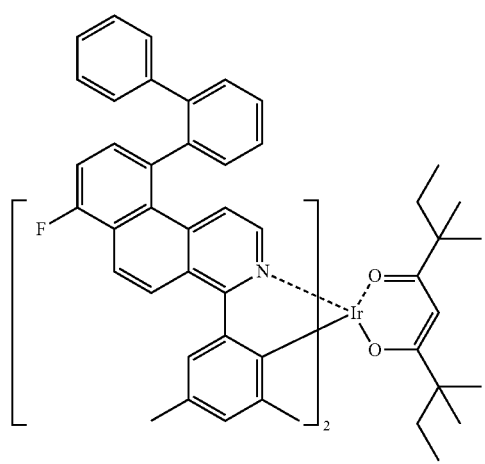
28

29
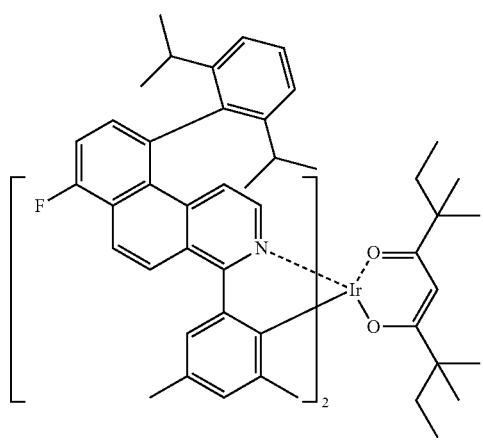
33
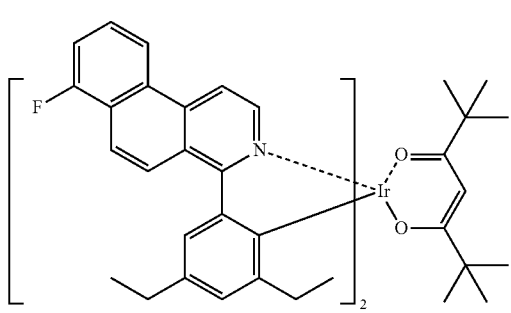
34
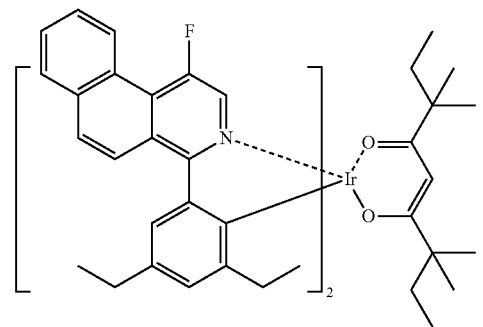
35
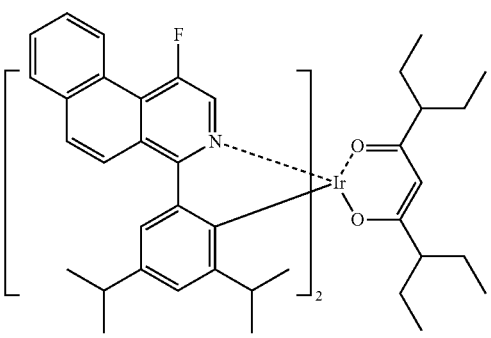
36
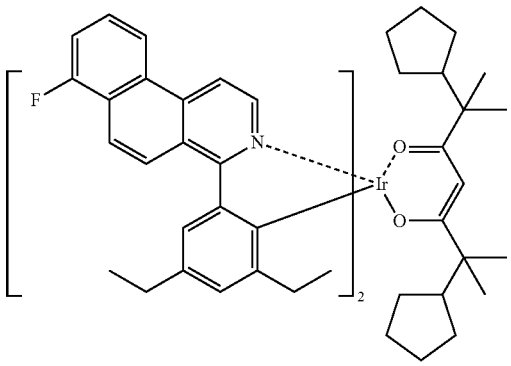
37
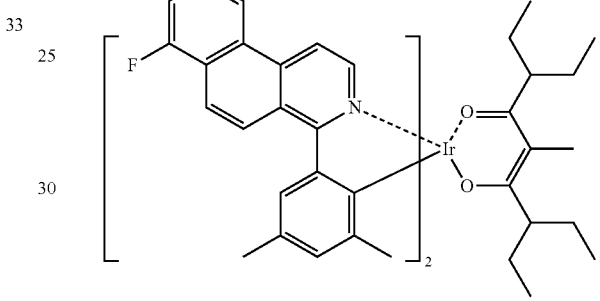
38
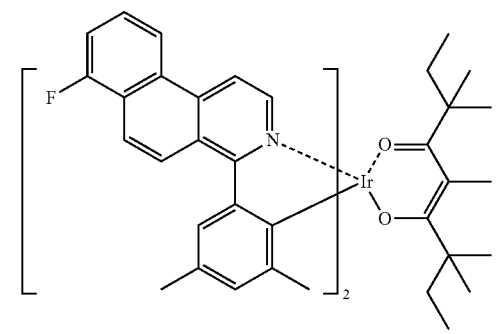
39
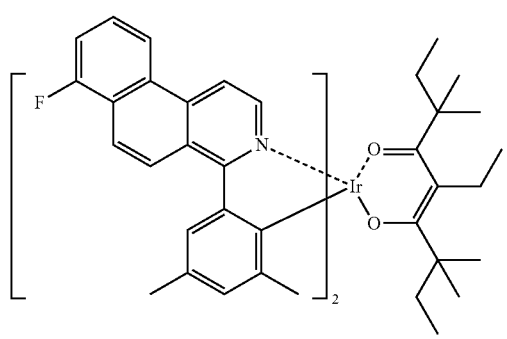

235
-continued
40
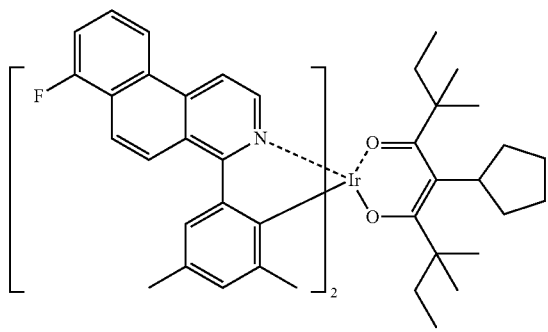
41
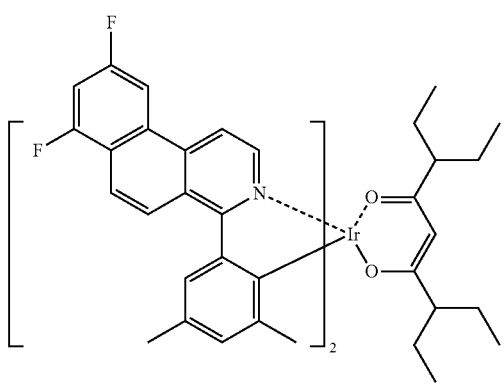
42
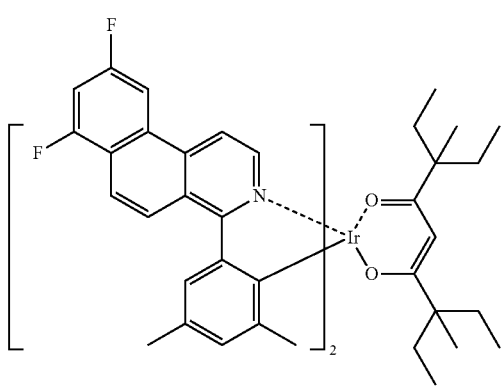
43
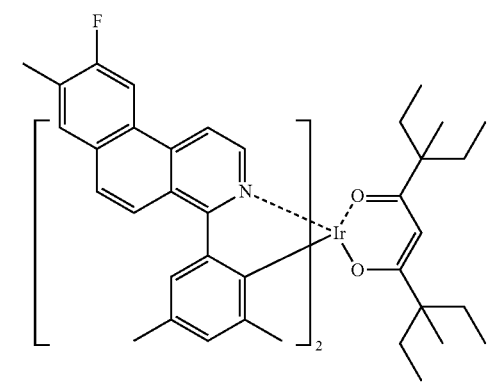
236
-continued
48
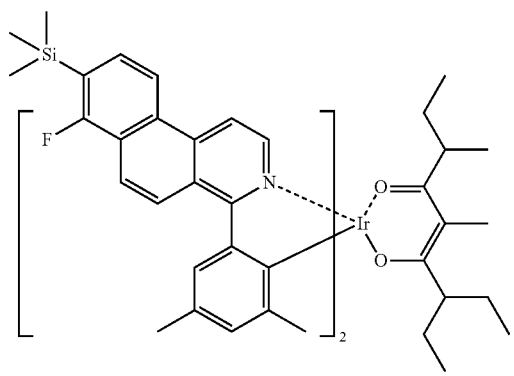
49
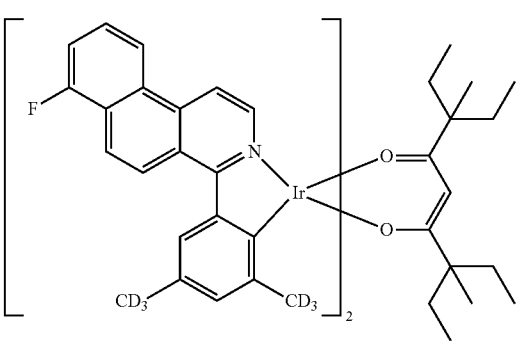
50
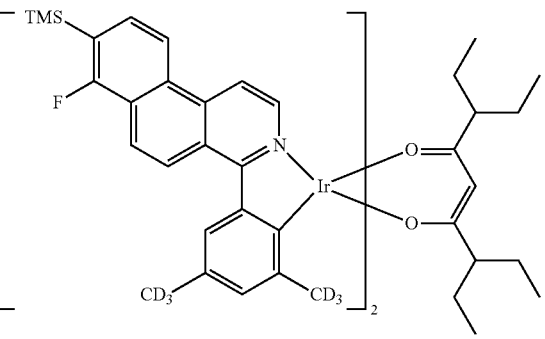
51
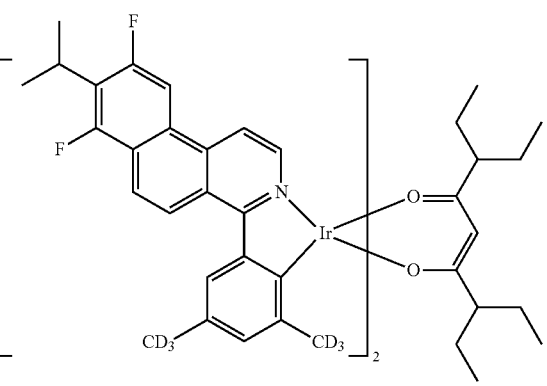

52

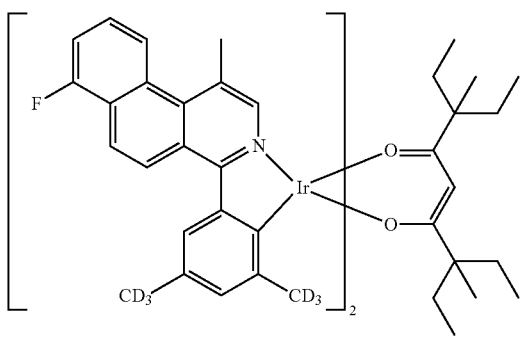

7. The composition of claim 1, wherein
Ar₁ in Formula 2 is a group derived from i) a first ring unsubstituted or substituted with at least one $R_{61}$, ii) a second ring unsubstituted or substituted with at least one $R_{61}$, iii) a condensed ring in which at least two first rings are condensed, unsubstituted or substituted with at least one $R_{61}$, iv) a condensed ring in which at least two second rings are condensed, unsubstituted or substituted with at least one $R_{61}$, or v) a condensed ring in which at least one first ring and at least one second ring are condensed, unsubstituted or substituted with at least one $R_{61}$, Ar₂ in Formula 2 is a group derived from i) a first ring unsubstituted or substituted with at least one $R_{62}$, ii) a condensed ring in which at least two first rings are condensed, unsubstituted or substituted with at least one $R_{62}$, or iii) a condensed ring in which at least one first ring and at least one second ring are condensed, unsubstituted or substituted with at least one $R_{62}$, Ar₅ in Formula 2 is not present, a single bond, or a group derived from i) a first ring unsubstituted or substituted with at least one $R_{65}$, ii) a second ring unsubstituted or substituted with at least one $R_{65}$, iii) a condensed ring in which at least two first rings are condensed, unsubstituted or substituted with at least one $R_{65}$, iv) a condensed ring in which at least two second rings are condensed, unsubstituted or substituted with at least one $R_{65}$, or v) a condensed ring in which at least one first ring and at least one second ring are condensed, unsubstituted or substituted with at least one $R_{65}$, ring $CY_2$ and ring $CY_3$ in Formula 2 are each independently i) a first ring, ii) a second ring, iii) a condensed ring in which at least two first rings are condensed, iv) a condensed ring in which at least two second rings are condensed, or v) a condensed ring in which at least one first ring and at least one second ring are condensed, the first ring is an imidazole group, a pyrazole group, a thiazole group, an isothiazole group, an oxazole group, an isoxazole group, a pyridine group, a pyrazine group, a pyridazine group, a pyrimidine group, a triazole group, a tetrazole group, an oxadiazole group, a triazine group, or a thiadiazole group, and the second ring is a benzene group, a cyclopentadiene group, a pyrrole group, a furan group, a thiophene group, or a silole group.

8. The composition of claim 1, wherein Ar₂ in Formula 2 is an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, an azadibenzofuran group, an azadibenzothiophene group, an azadibenzosilole group, or a pyridopyrazine group, each unsubstituted or substituted with at least one $R_{62}$.

9. The composition of claim 1, wherein a2 in Formula 2 is 1 or 2.

10. The composition of claim 1, wherein the second compound comprises a compound represented by Formula 2(1):

Formula 2(1)

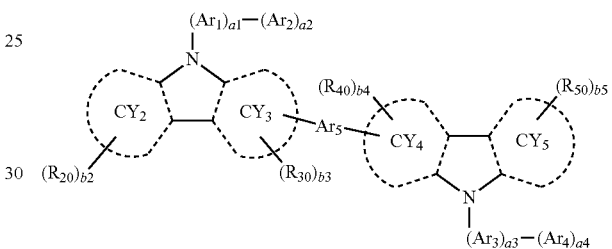

wherein, in Formula 2(1),

Ar₅ is a single bond, a $C_5$-$C_6$, carbocyclic group unsubstituted or substituted with at least one $R_{65}$, or a $C_1$-$C_6$ heterocyclic group unsubstituted or substituted with at least one $R_{65}$, Ar₁, Ar₂, a1, a2, ring $CY_2$, ring $CY_3$, $R_{1a}$, $R_{20}$, $R_{30}$, b2, and b3 are respectively understood by referring to the descriptions of Ar₁, Ar₂, a1, a2, ring $CY_2$, ring $CY_3$, $R_{1a}$, $R_{20}$, $R_{30}$, b2, and b3 in claim 1, Ar₃ and Ar₄ are each independently a $C_5$-$C_6$ carbocyclic group unsubstituted or substituted with at least one $R_{61}$ or a $C_1$-$C_6$ heterocyclic group unsubstituted or substituted with at least one $R_{61}$, a3 and a4 are each independently an integer from 0 to 5, and the sum of a3 and a4 is 1 or greater, ring $CY_4$ and ring $CY_5$ are each independently a $C_5$-$C_6$, carbocyclic group or a $C_1$-$C_{60}$ heterocyclic group, and ring CY4 and ring $CY_5$ are optionally bound to each other via a $C_5$-$C_6$ carbocyclic group unsubstituted or substituted with at least one $R_{66}$ or a $C_1$-$C_6$ heterocyclic group unsubstituted or substituted with at least one $R_{66}$, two or more of ring CY4, ring $CY_5$, $R_{40}$, and $R_{50}$ are optionally linked to form a $C_5$-$C_6$, carbocyclic group which is unsubstituted or substituted with at least one $R_{1a}$ or a $C_1$-$C_6$, heterocyclic group which is unsubstituted or substituted with at least one $R_{1a}$, $R_{40}$ and $R_{50}$ are each independently hydrogen, deuterium, —F, —Cl, —Br, —I, —SF₅, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —Ge($Q_3$)($Q_4$)($Q_5$), —B($Q_6$)($Q_7$), —P(=O)($Q_8$)($Q_9$), or —P($Q_8$)($Q_9$), and b4 and b5 in Formula 2 are each independently an integer from 0 to 20, when b4 is 2 or more, two or more $R_{40}$(s) are identical to or different from each other, and when b5 is 2 or more, two or more $R_{50}$(s) are identical to or different from each other, a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —Ge($Q_{13}$)($Q_{14}$)($Q_{15}$), —B($Q_{16}$)($Q_{17}$), —P(=O)($Q_{18}$)($Q_{19}$), —P($Q_{18}$)($Q_{19}$), or any combination thereof;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —Ge($Q_{23}$)($Q_{24}$)($Q_{25}$), —B($Q_{26}$)($Q_{27}$), —P(=O)($Q_{28}$)($Q_{29}$), —P($Q_{28}$)($Q_{29}$), or any combination thereof;

—N($Q_{31}$)($Q_{32}$), —Si($Q_{33}$)($Q_{34}$)($Q_{35}$), —Ge($Q_{33}$)($Q_{34}$)($Q_{35}$), —B($Q_{36}$)($Q_{37}$), —P(=O)($Q_{38}$)($Q_{39}$), or —P($Q_{38}$)($Q_{39}$); or any combination thereof, wherein $Q_1$ to $Q_9$, $Q_{11}$ to $Q_{19}$, $Q_{21}$ to $Q_{29}$, and $Q_{31}$ to $Q_{39}$ are each independently hydrogen; deuterium; —F; —Cl; —Br; —I; a hydroxyl group; a cyano group; a nitro group; an amidino group; a hydrazine group; a hydrazone group; a carboxylic acid group or a salt thereof; a sulfonic acid group or a salt thereof; a phosphoric acid group or a salt thereof; a $C_1$-$C_{60}$ alkyl group, unsubstituted or substituted with deuterium, a $C_1$-$C_{60}$ alkyl group, a $C_6$-$C_{60}$ aryl group, or any combination thereof; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_2$-$C_{10}$ heterocycloalkyl group; a $C_3$-$C_{10}$ cycloalkenyl group; a $C_2$-$C_{10}$ heterocycloalkenyl group; a $C_6$-$C_{60}$ aryl group, unsubstituted or substituted with deuterium, a $C_1$-$C_{60}$ alkyl group, a $C_6$-$C_{60}$ aryl group, or any combination thereof; a $C_6$-$C_{60}$ aryloxy group; a $C_6$-$C_{60}$ arylthio group; a $C_1$-$C_{60}$ heteroaryl group; a monovalent non-aromatic condensed polycyclic group; or a monovalent non-aromatic condensed heteropolycyclic group.

11. The composition of claim 1, wherein a group represented by

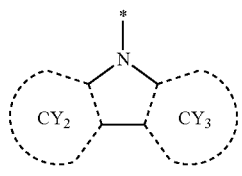

in Formula 2 is a group represented by one of Formulae 2-1 to 2-93:

2-1

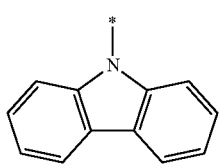

241
-continued
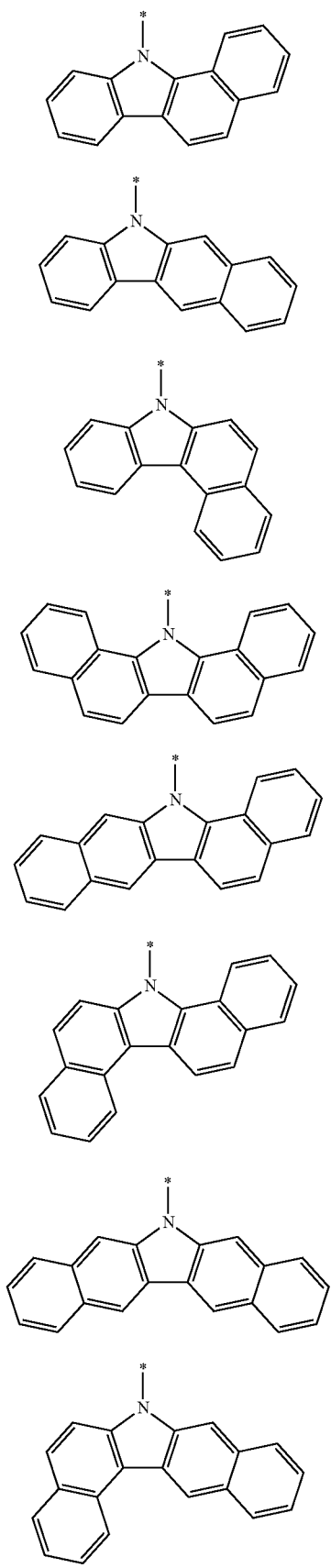
2-2
2-3
2-4
2-5
2-6
2-7
2-8
2-9
242
-continued
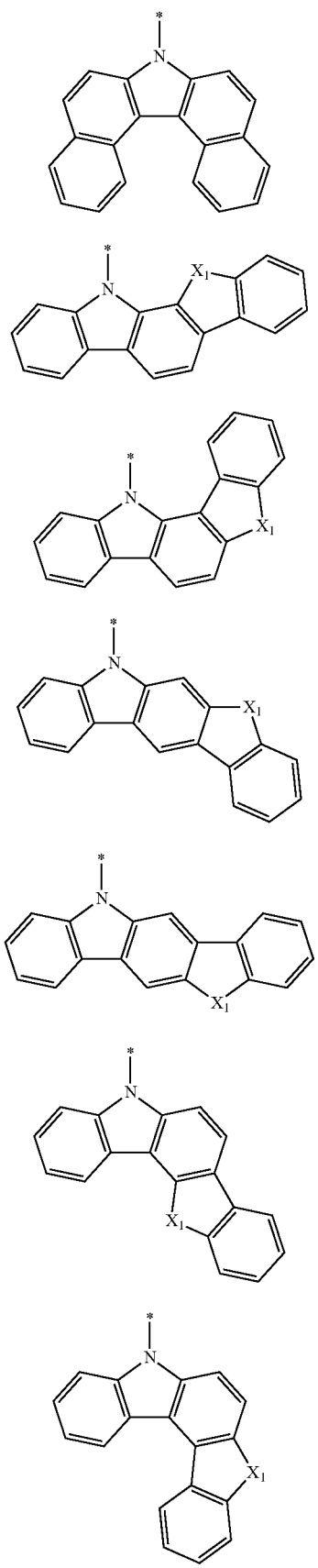
2-10
2-11
2-12
2-13
2-14
2-15
2-16

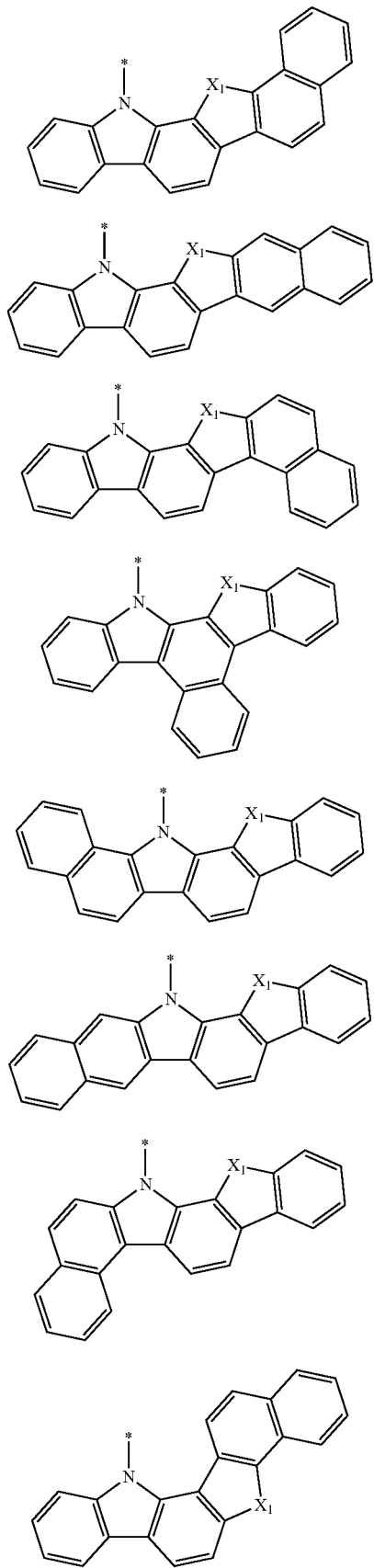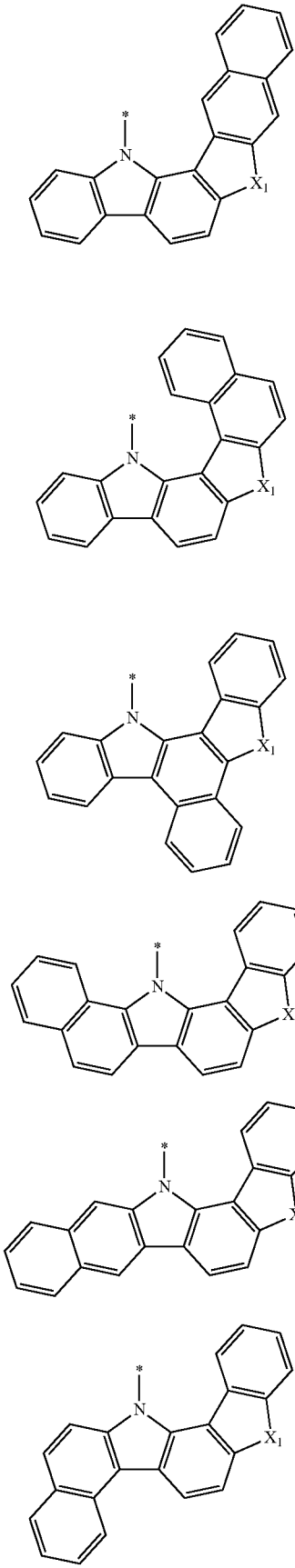

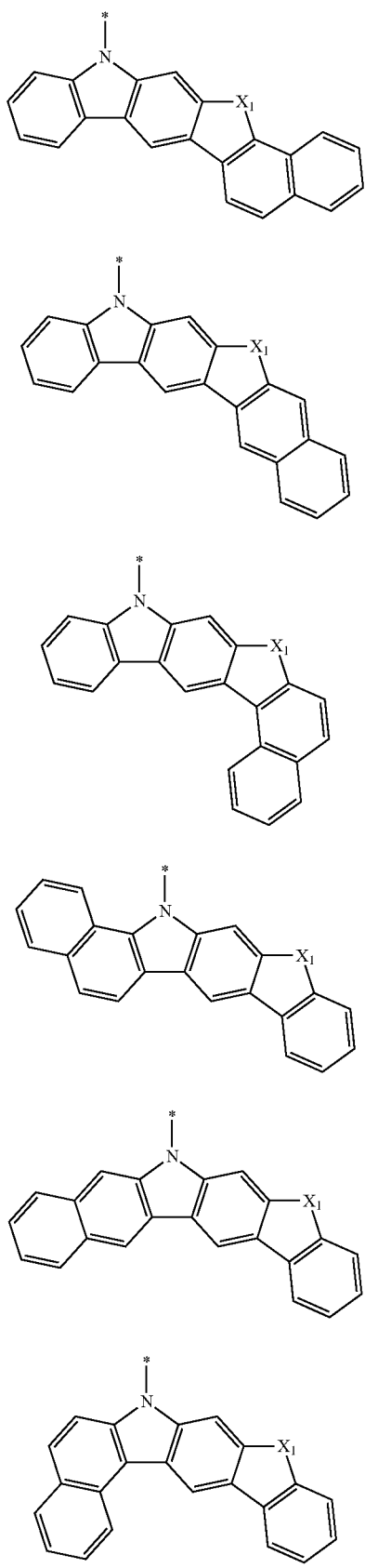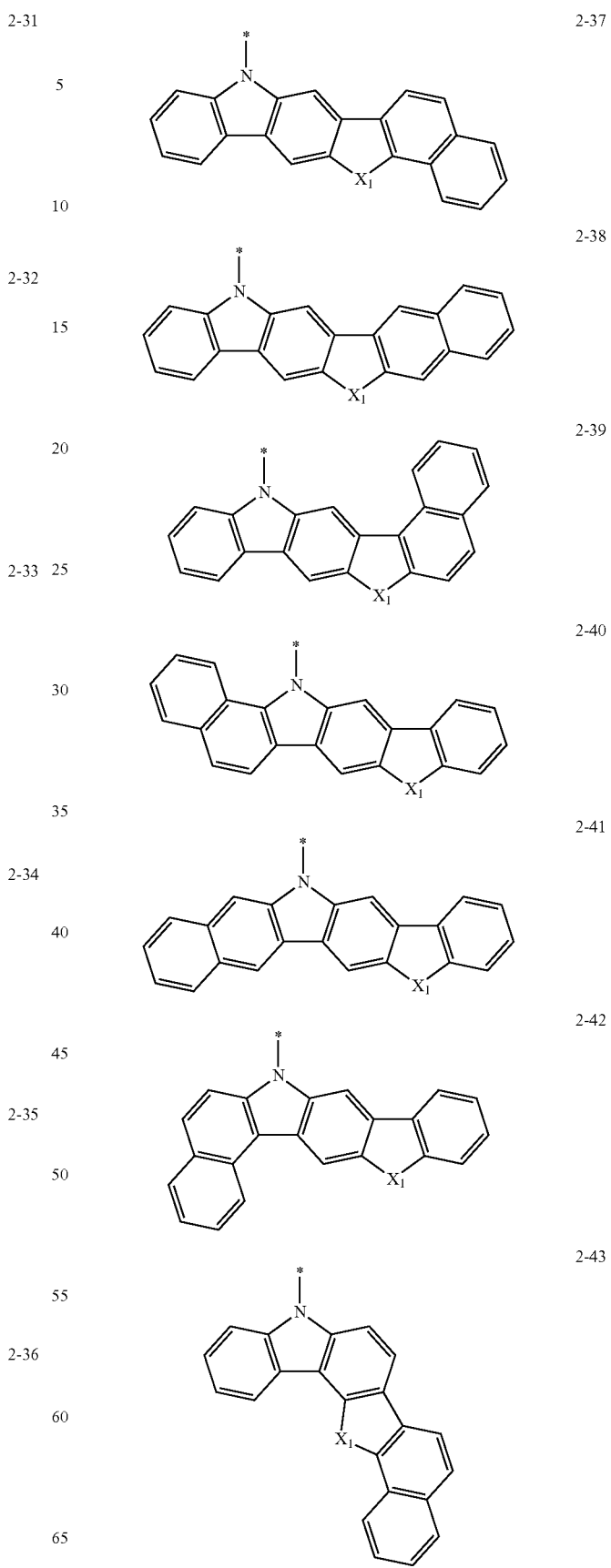

2-44
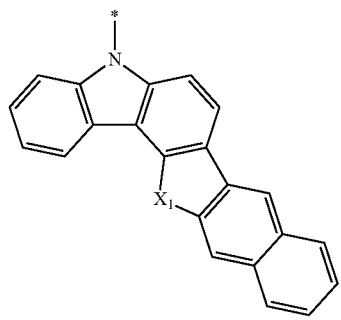
2-45
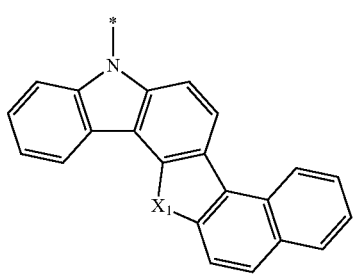
2-46
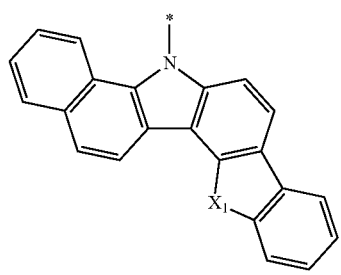
2-47
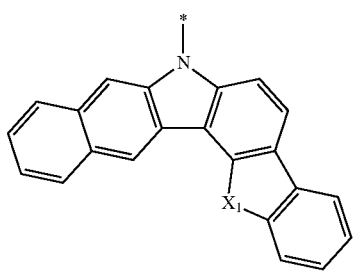
2-48
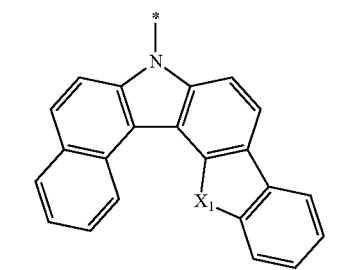
2-49
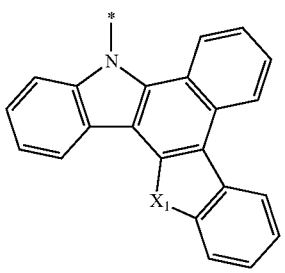
2-50
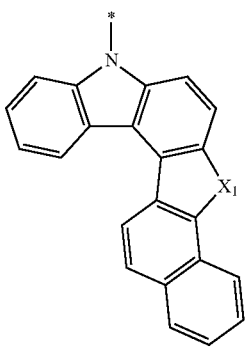
2-51
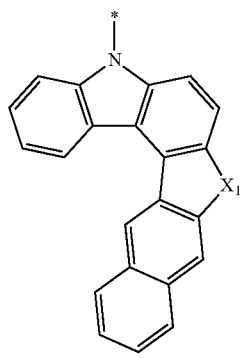
2-52
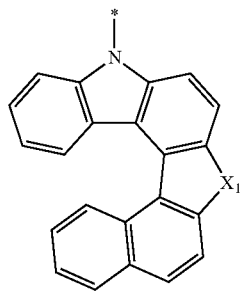
2-53
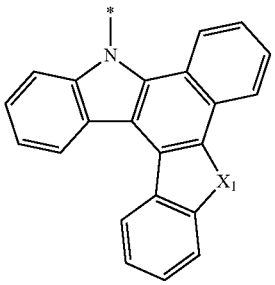

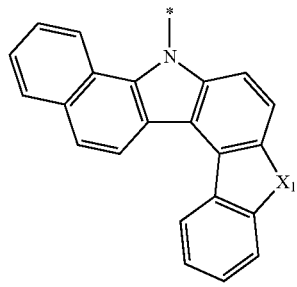
2-54
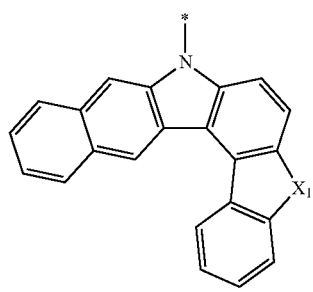
2-55
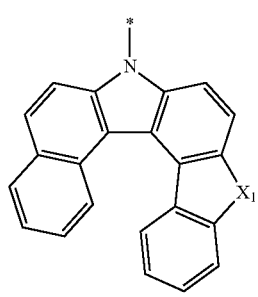
2-56
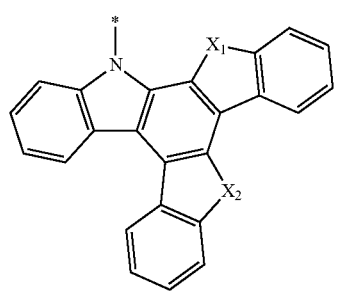
2-57
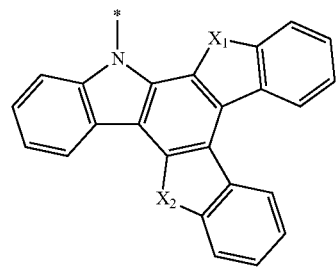
2-58
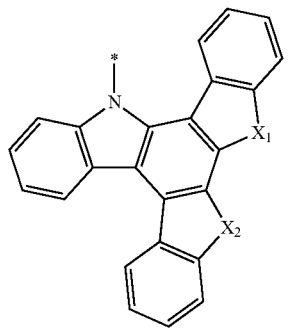
2-59
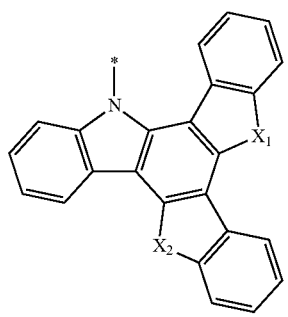
2-60
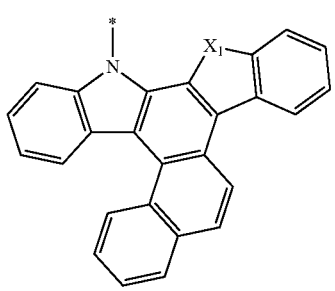
2-61
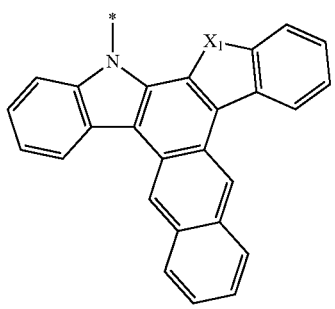
2-62
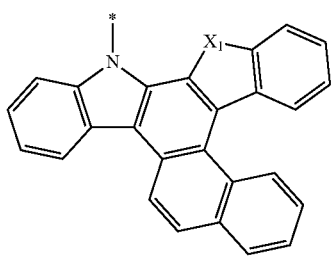
2-63

251
-continued
2-64
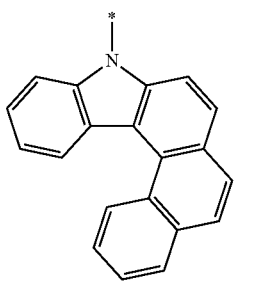
2-65
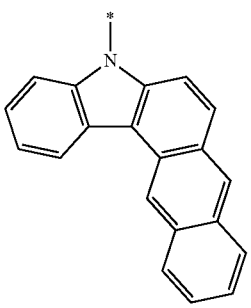
2-66
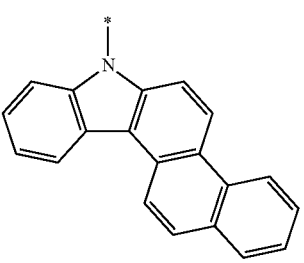
2-67
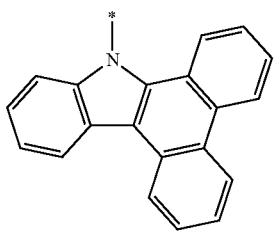
2-68
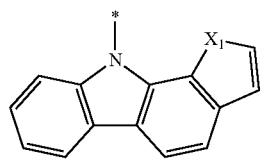
2-69
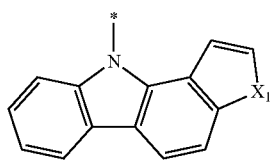
2-70
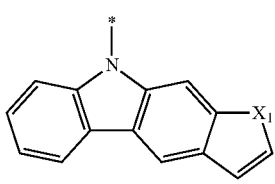
252
-continued
2-71
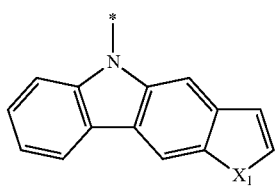
2-72
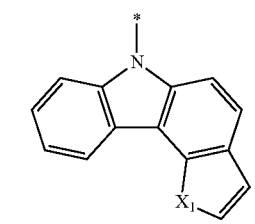
2-73
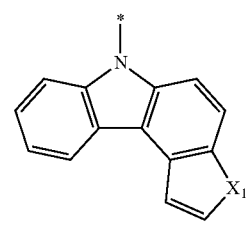
2-74
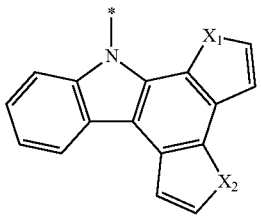
2-75
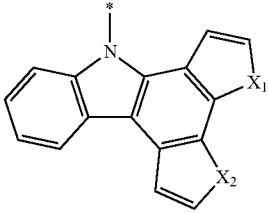
2-76
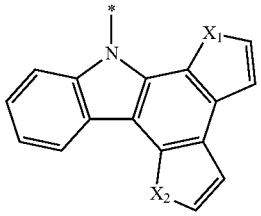
2-77
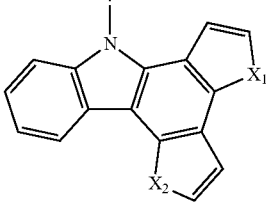

253
-continued
2-78
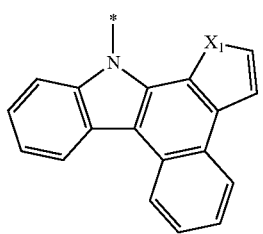
2-79
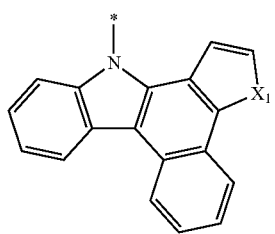
2-80
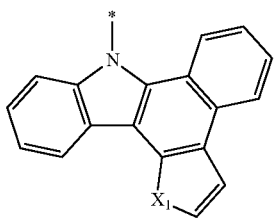
2-81
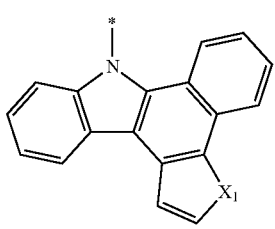
2-82
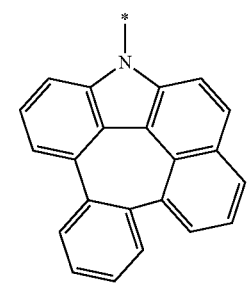
2-83
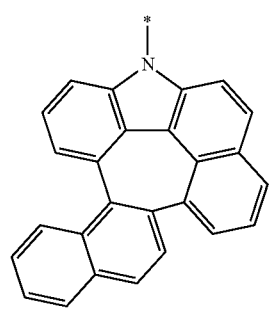
254
-continued
2-84
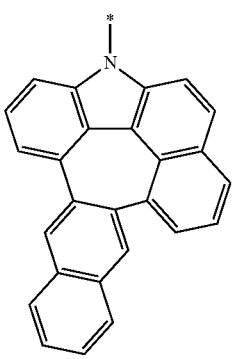
2-85
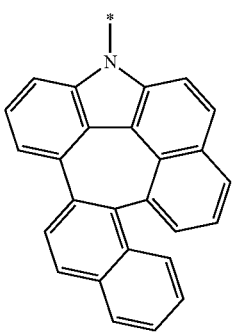
2-86
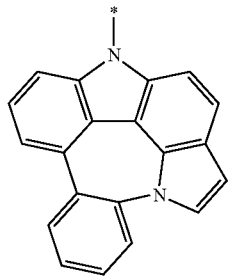
2-87
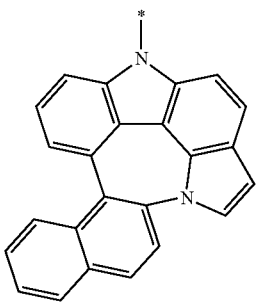
2-88
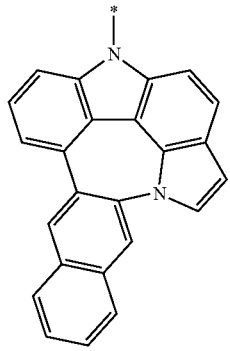

2-89
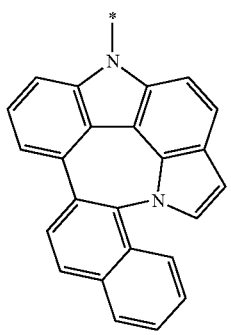
2-90
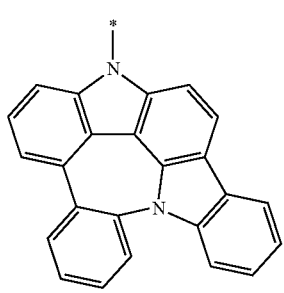
2-91
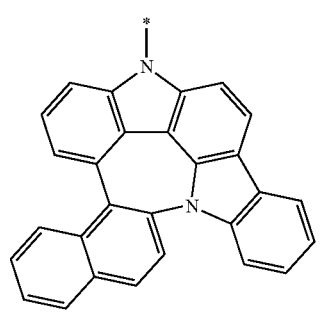
2-92
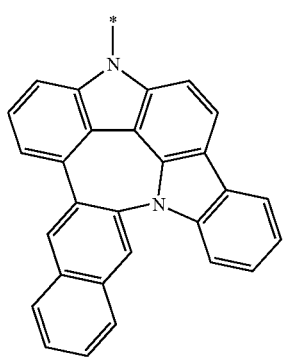
2-93
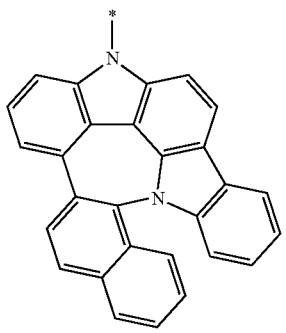
wherein, in Formulae 2-1 to 2-93,
$X_1$ is O, S, $N(R_{31})$, $C(R_{31})(R_{32})$, or $Si(R_{31})(R_{32})$,
$X_2$ is O, S, $N(R_{33})$, $C(R_{33})(R_{34})$, or $Si(R_{33})(R_{34})$,
$R_{31}$ to $R_{34}$ are each understood by referring to the description of $R_{30}$ in claim 1, and
\* in Formula 2 indicates a binding site to $Ar_1$ or $Ar_2$.
12. The composition of claim 1, wherein $Ar_2$ in Formula 2 is a group represented by one of Formulae 5-1 to 5-31:
5-1
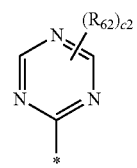
5-2
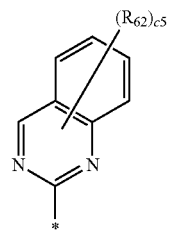
5-3
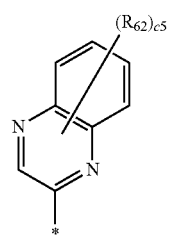
5-4
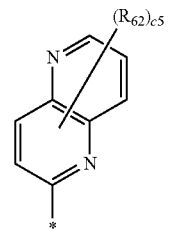

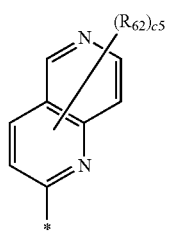
5-5
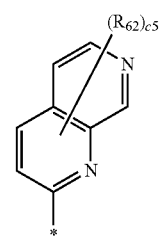
5-6
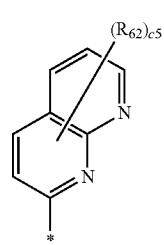
5-7
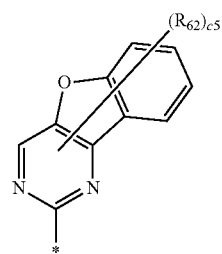
5-8
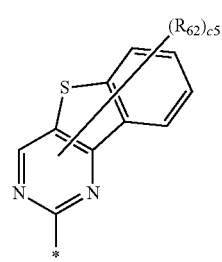
5-9
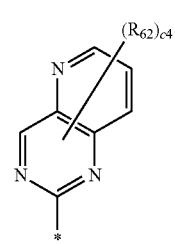
5-10
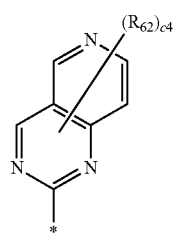
5-11
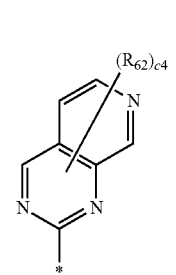
5-12
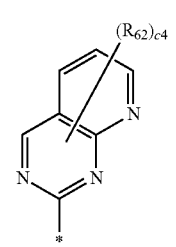
5-13
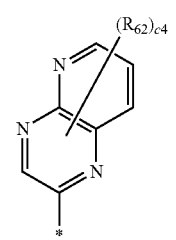
5-14
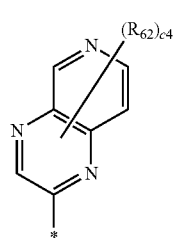
5-15
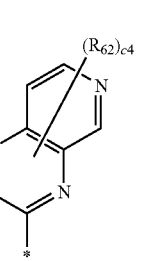
5-16

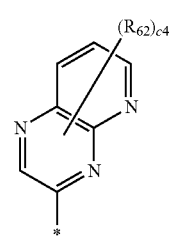
5-17
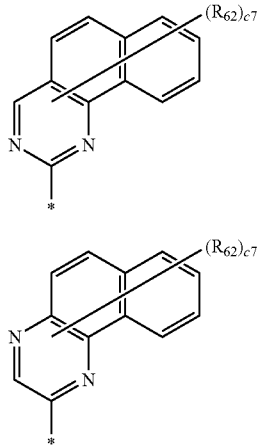
5-18
5-19
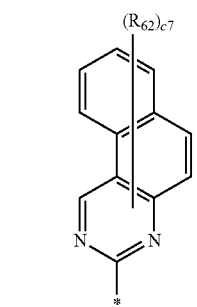
5-20
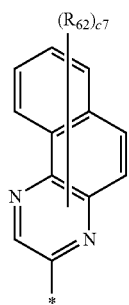
5-21
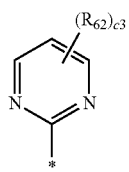
5-22
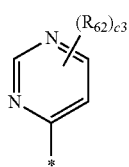
5-23
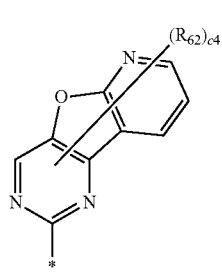
5-24
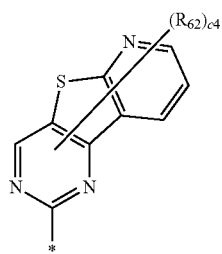
5-25
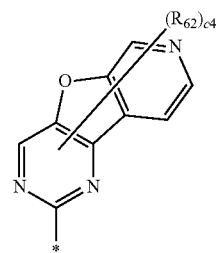
5-26
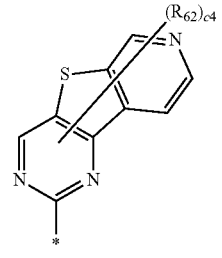
5-27
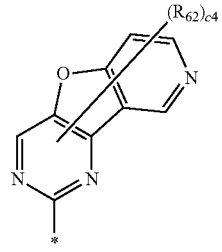
5-28
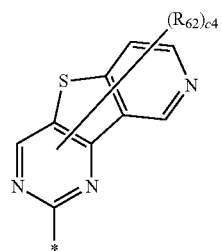
5-29

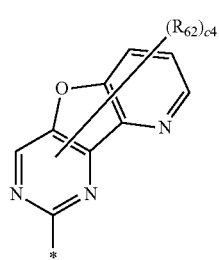
5-30
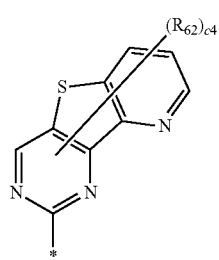
5-31
wherein, in Formulae 5-1 to 5-31,
$R_{62}$ is understood by referring to the description of $R_{62}$ in claim 1,
c2 is an integer from 0 to 2,
c3 is an integer from 0 to 3,
c4 is an integer from 0 to 4,
c5 is an integer from 0 to 5,
c7 is an integer from 0 to 7, and
* indicates a binding site to $Ar_1$ or N in Formula 2.
13. The composition of claim 1, wherein the second compound comprises at least one of Compounds H1 to H90:
H1
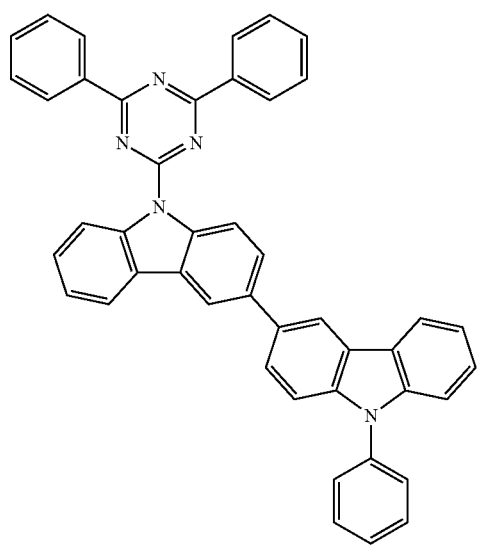
H2
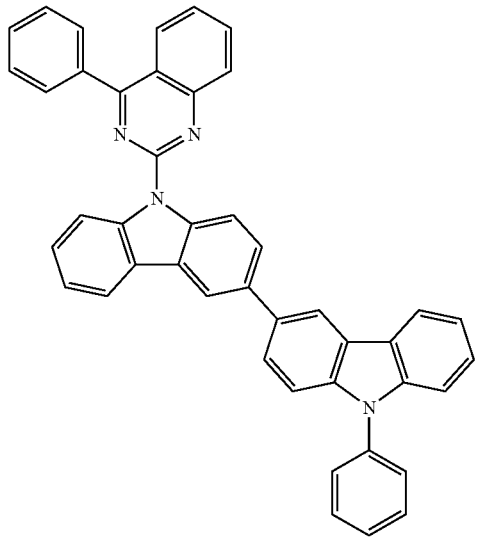
H3
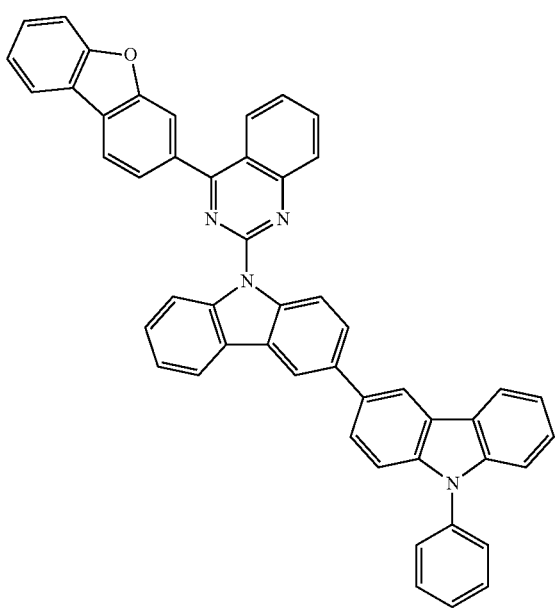

263
-continued
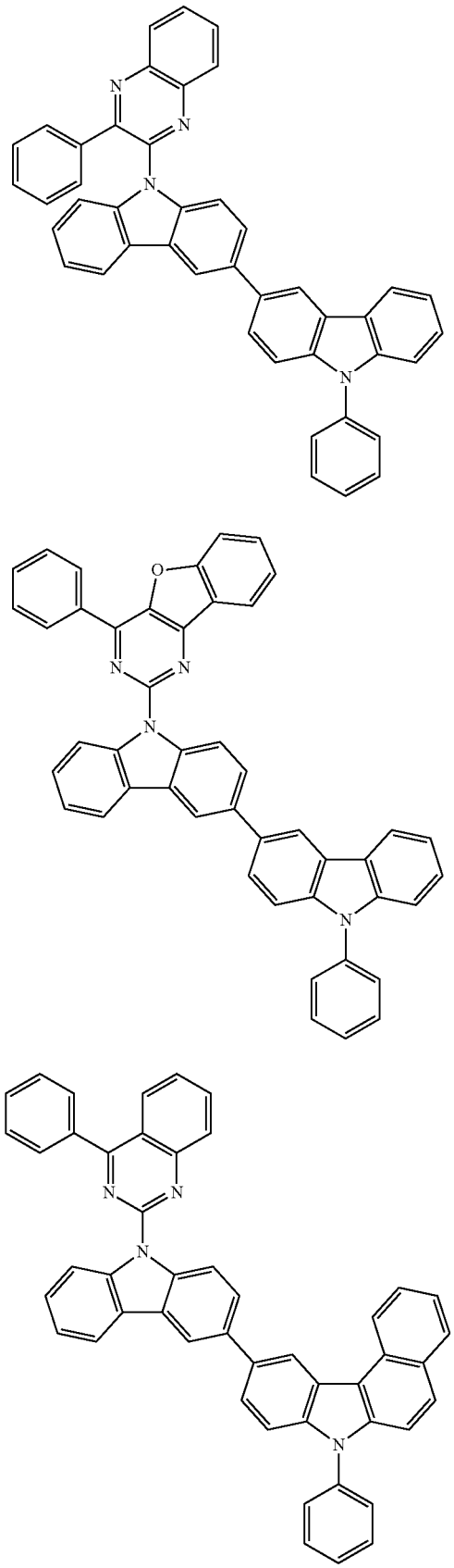
H4
H5
H6
264
-continued
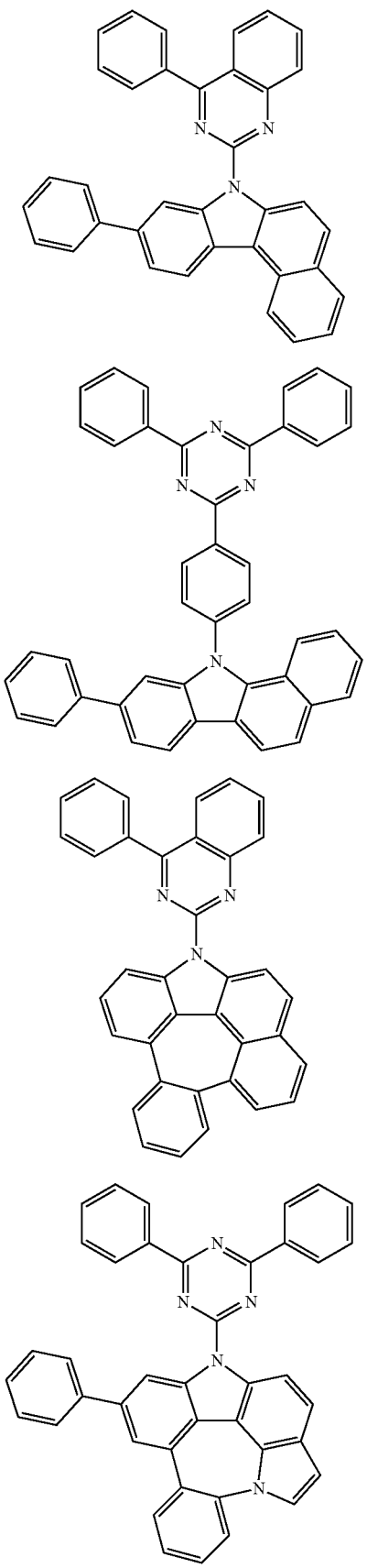
H7
H8
H9
H10

H11
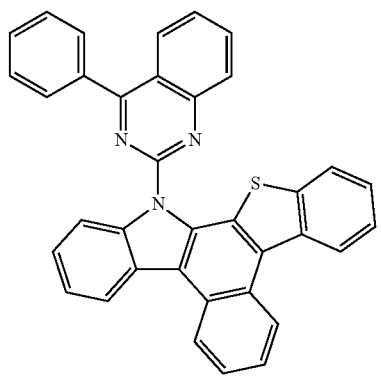
H12
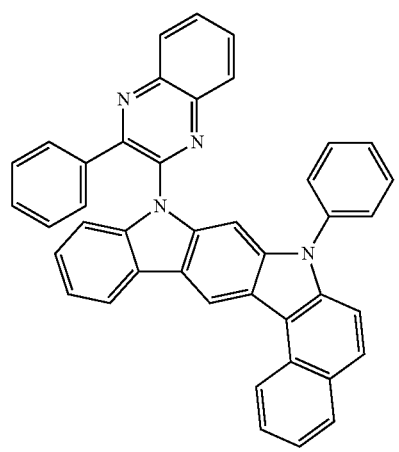
H13
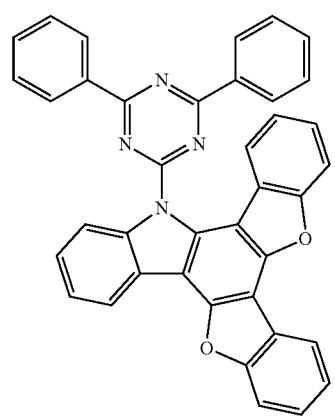
H14
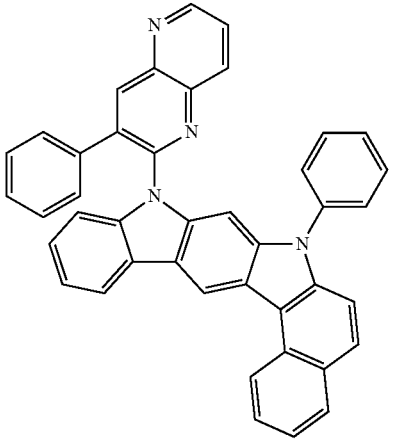
H15
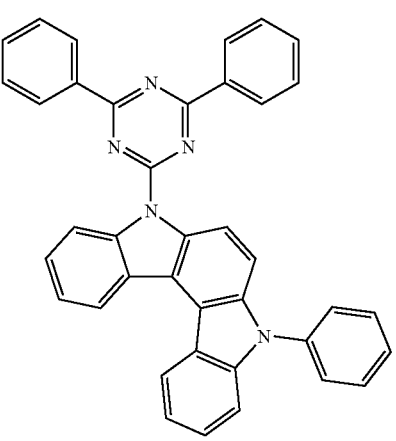
H16
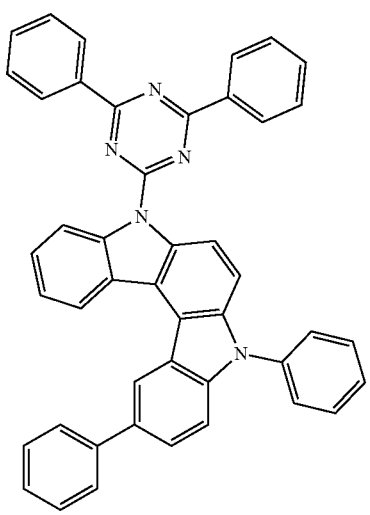

267
-continued
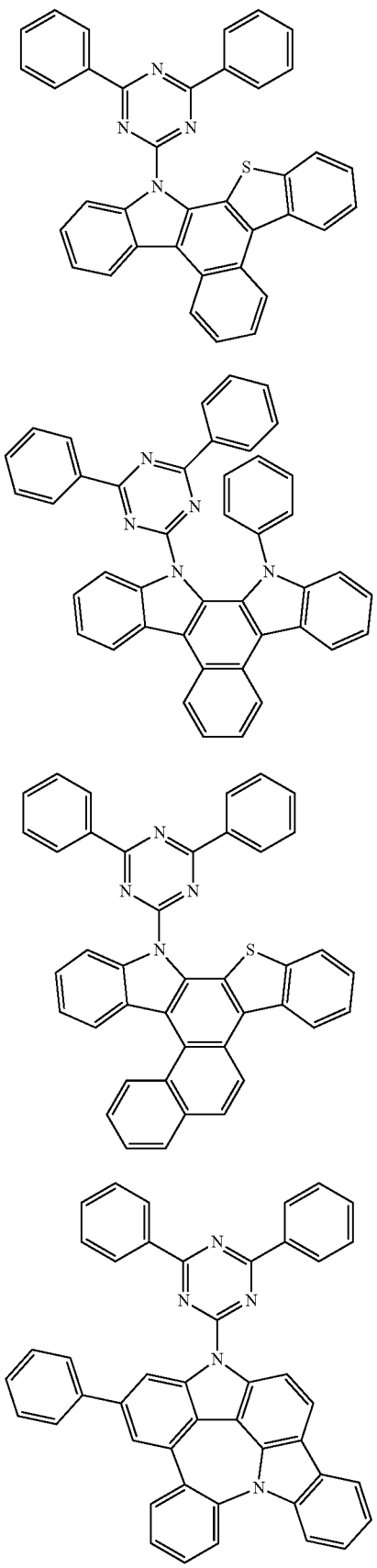
H17
H18
H19
H20
268
-continued
H21
H22

269
-continued
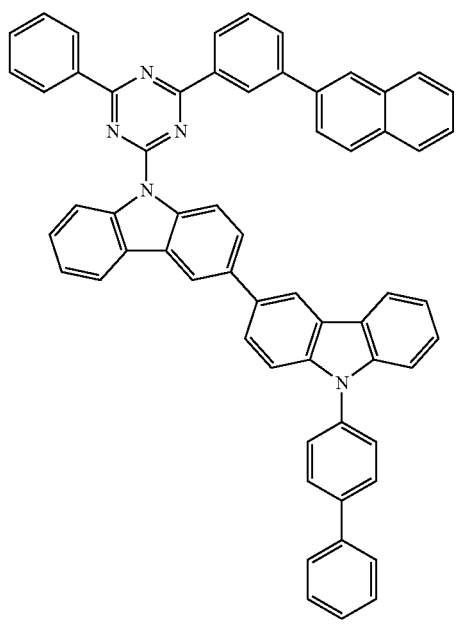
H23
270
-continued
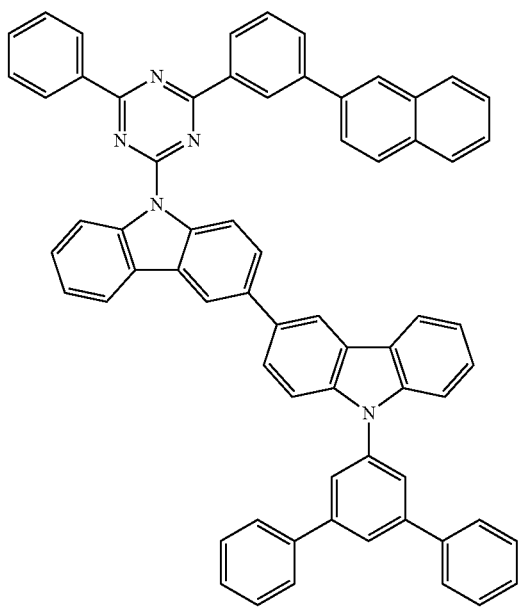
H25
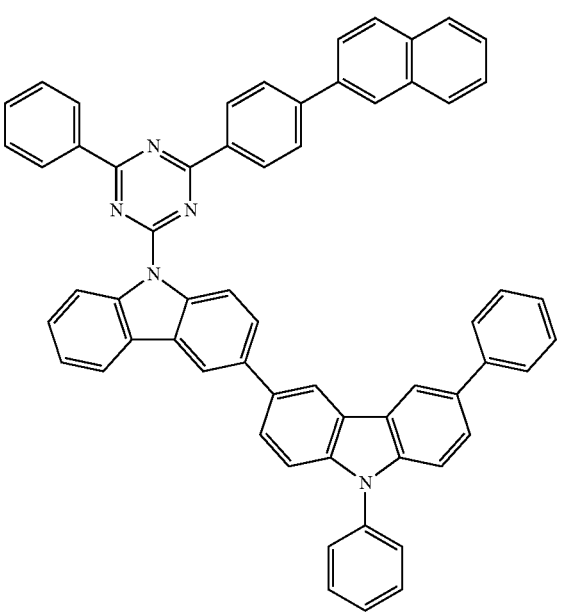
H26

271
-continued
H27
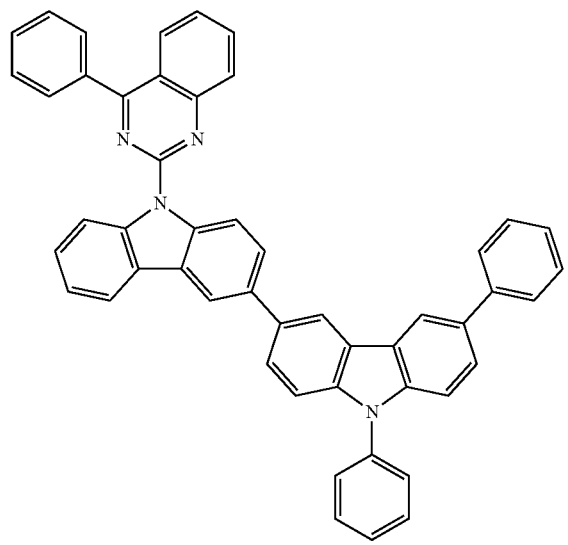
H28
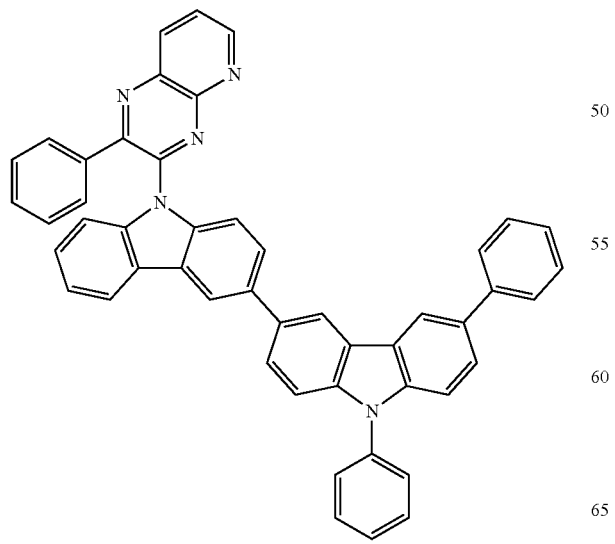
272
-continued
H29
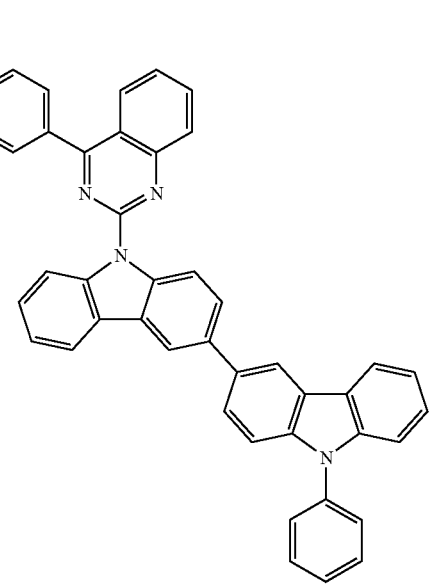
H30
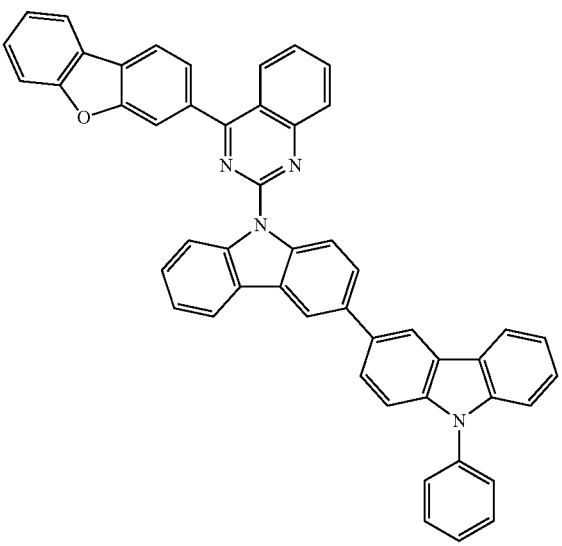

273
-continued
H31
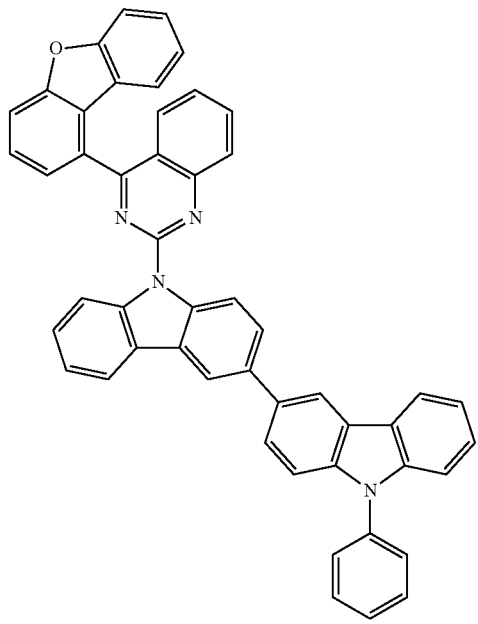
H32
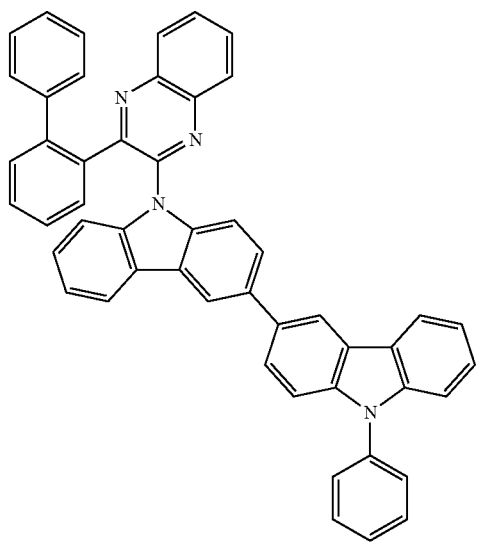
274
-continued
H33
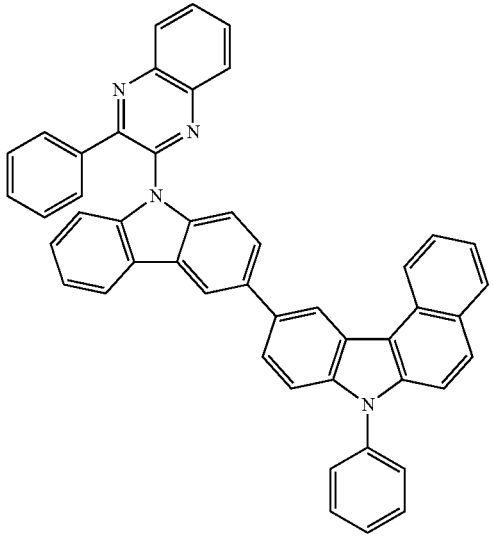
H34
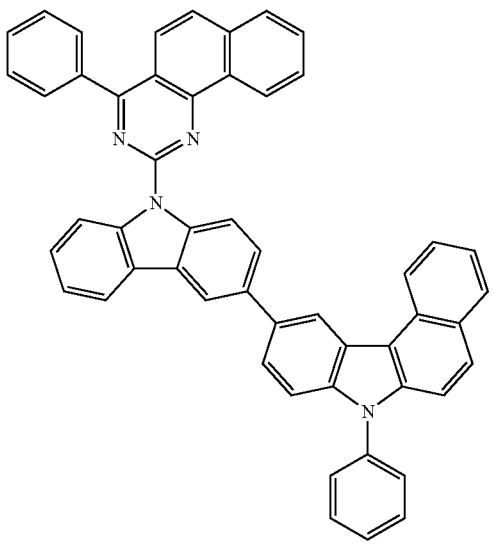
H35
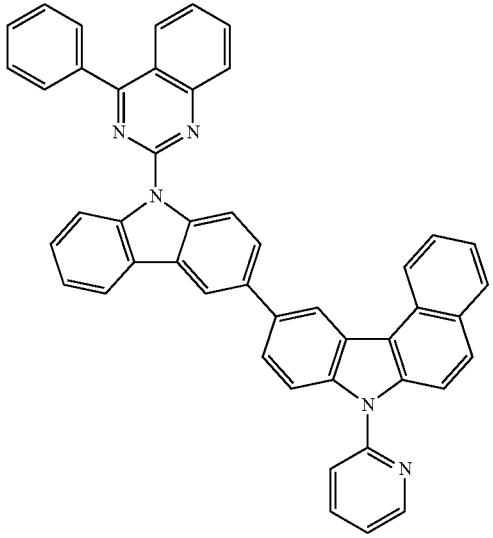

275
-continued
H36
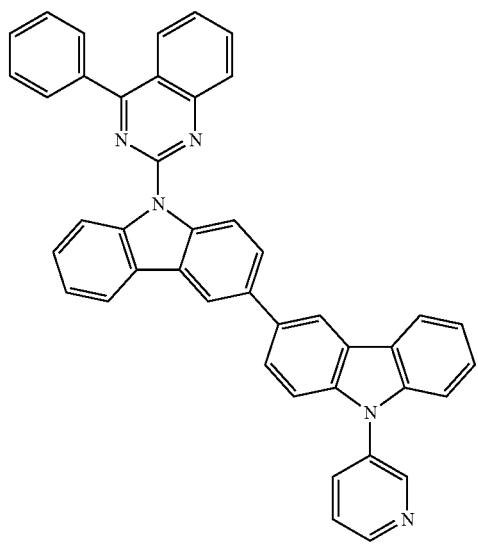
H37
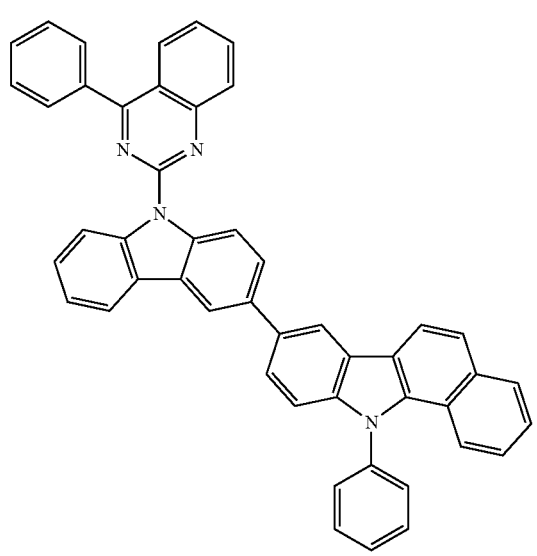
H38
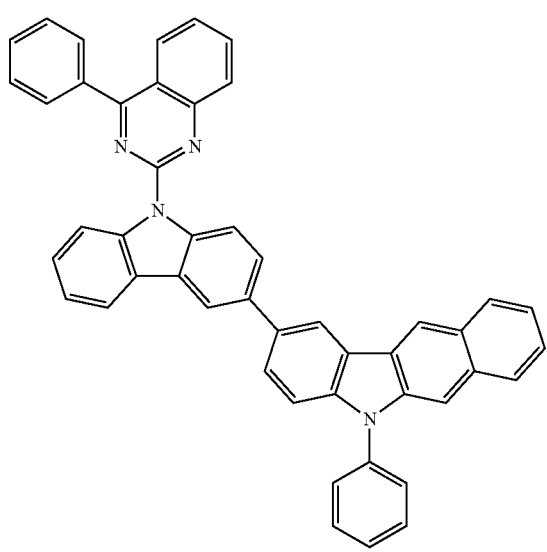
276
-continued
H39
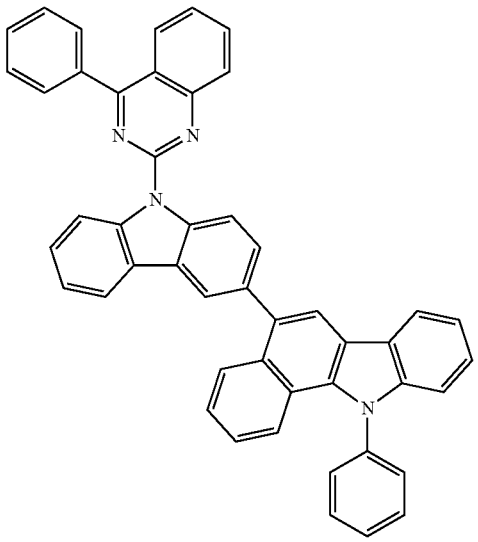
H40
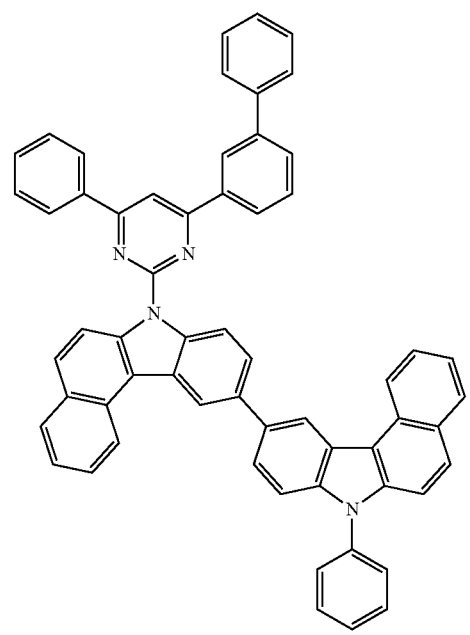
H41
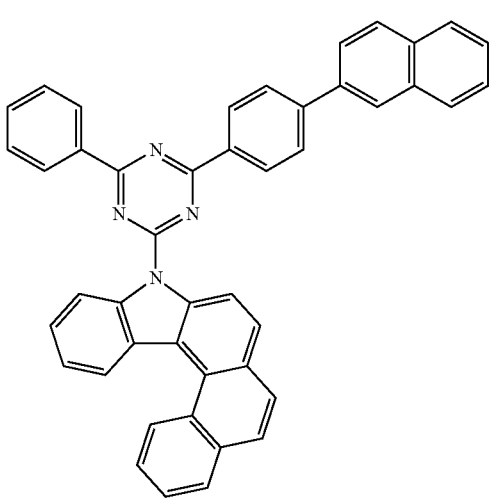

H42
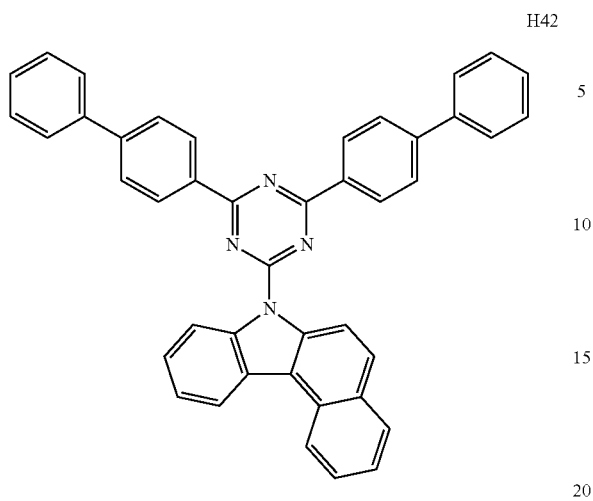
H45
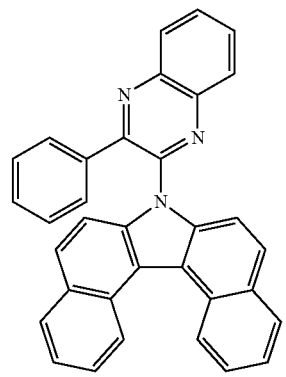
H43
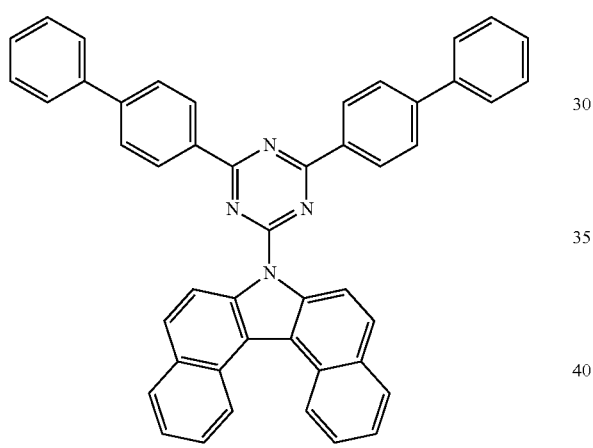
H46
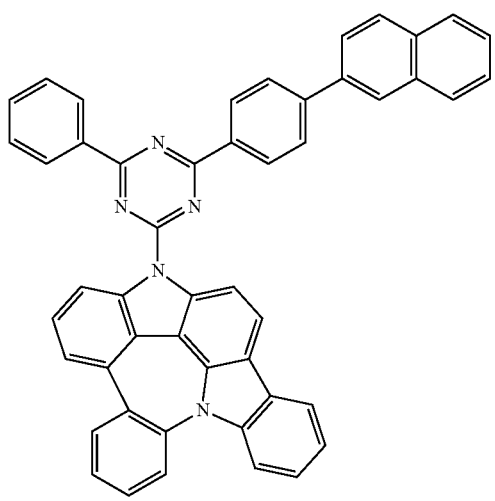
H44
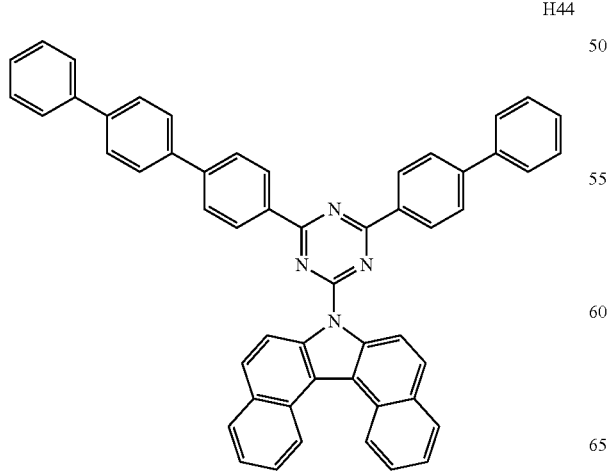
H47
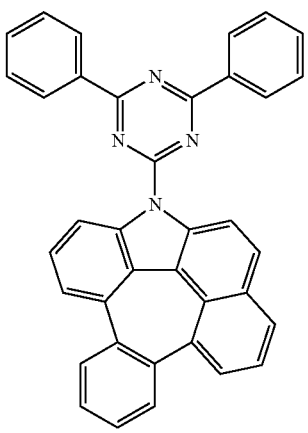

H48
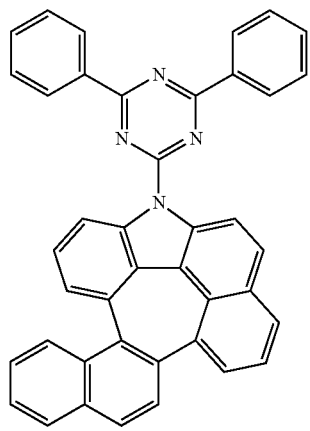
H49
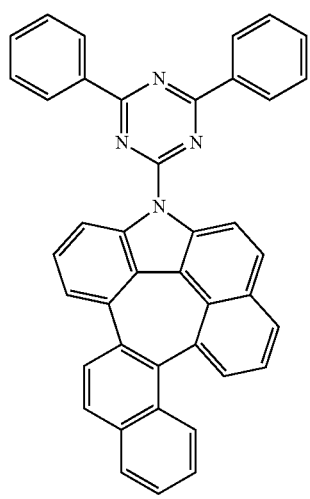
H50
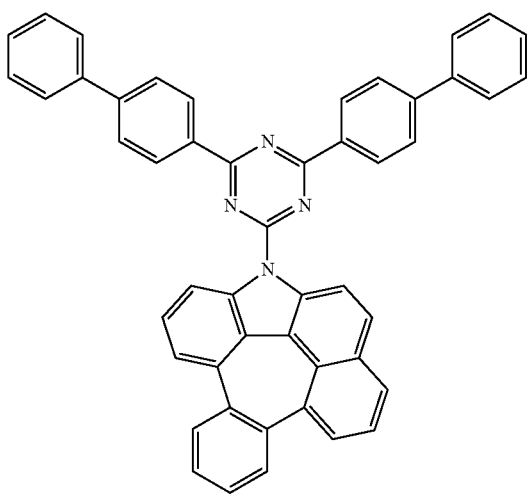
H51
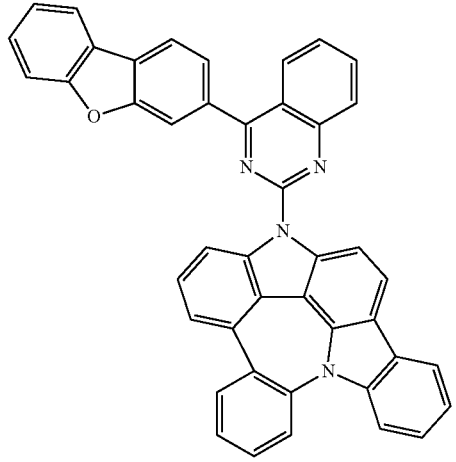
H52
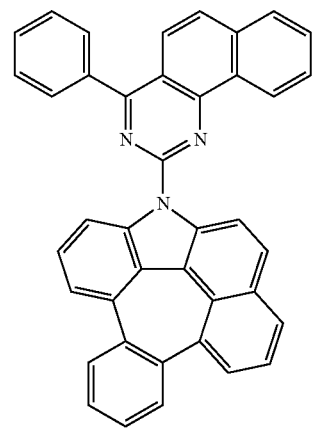
H53
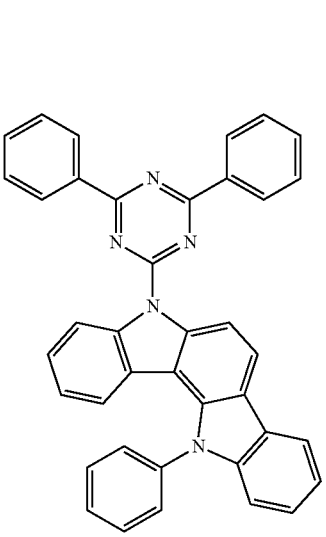

H54
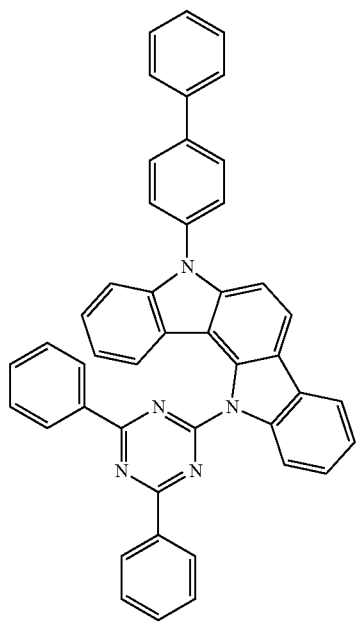
H55
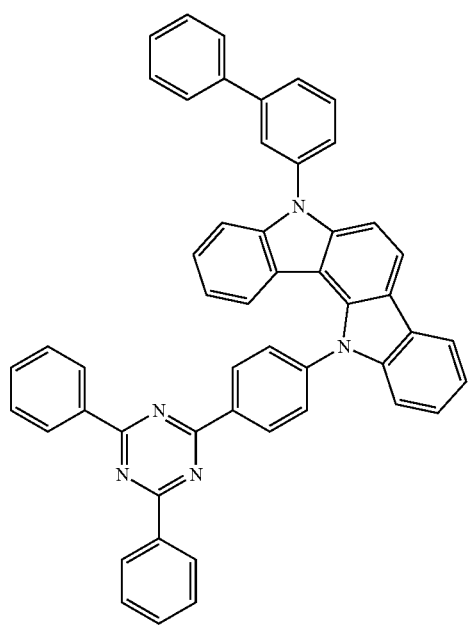
H56
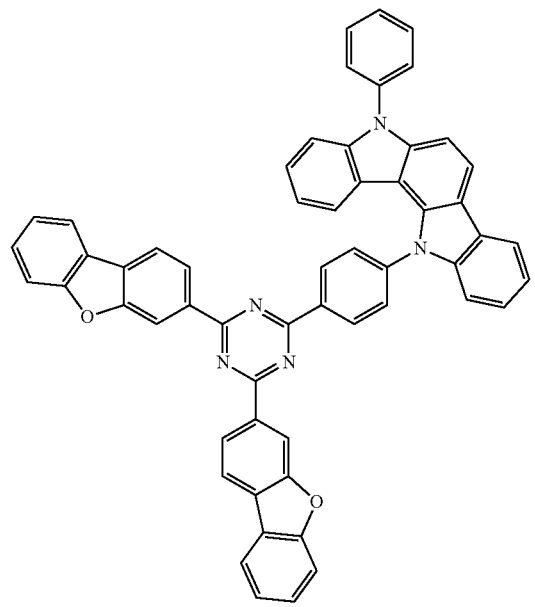
H57
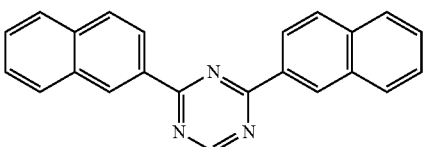
H58
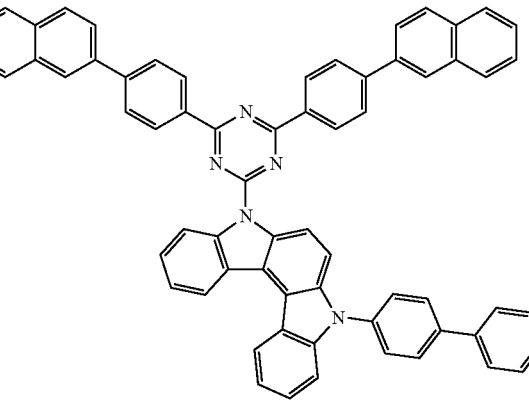

H59
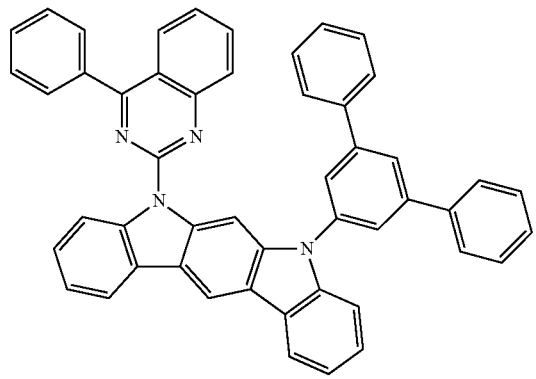
H60
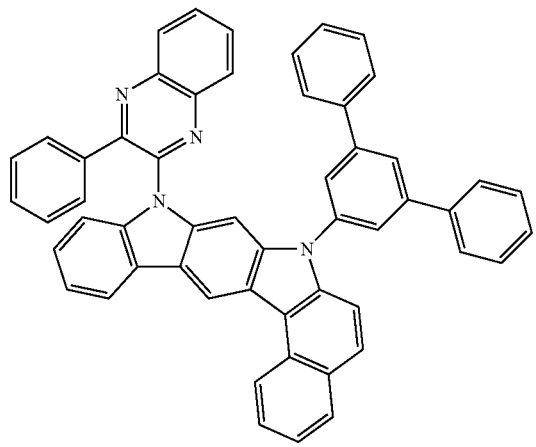
H61
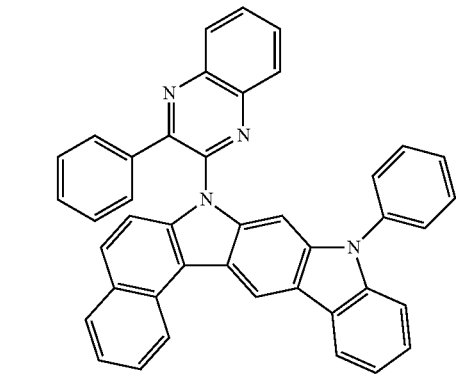
H62
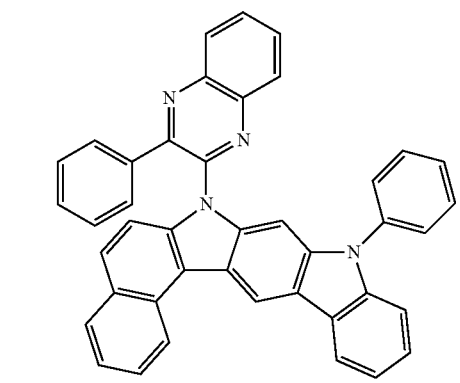
H63
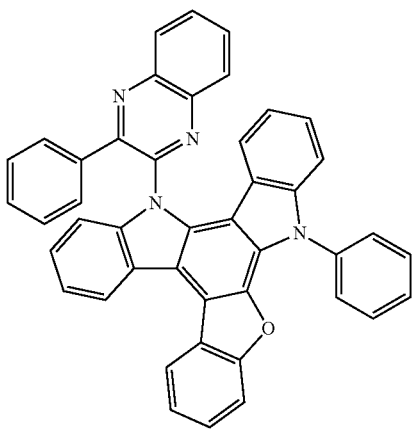
H64
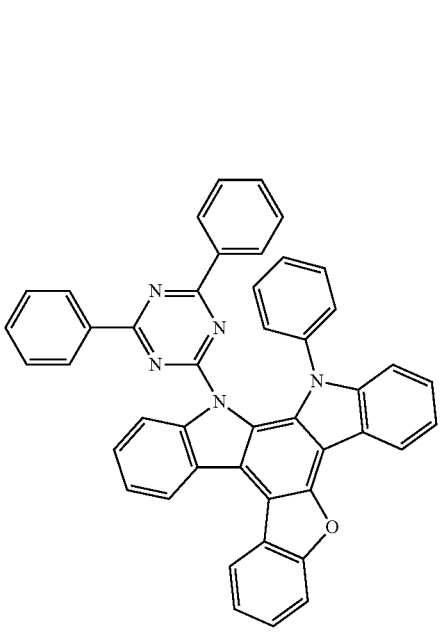
H65
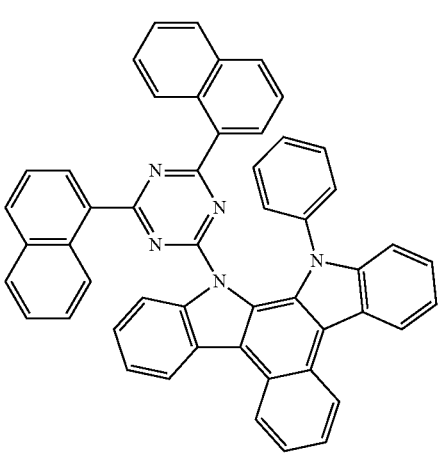

H66
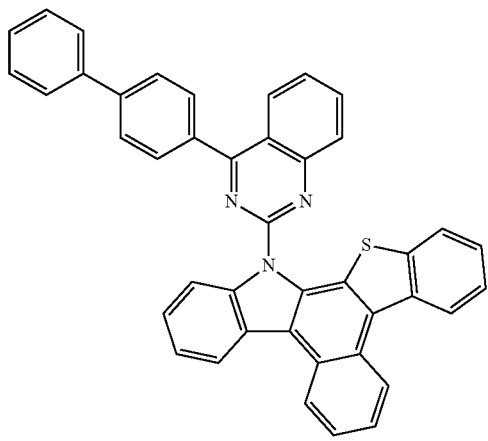
H67
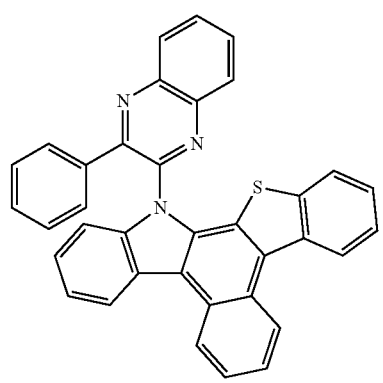
H68
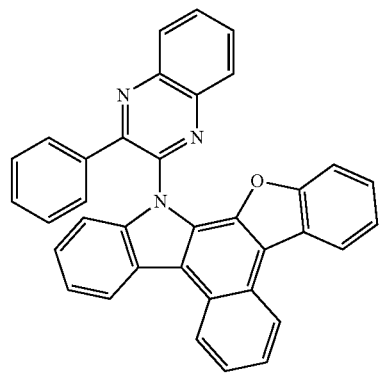
H69
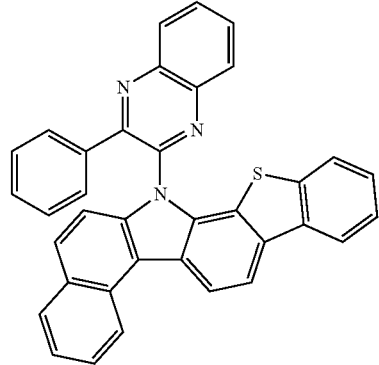
H70
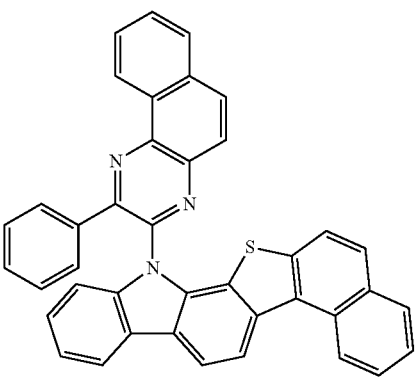
H71
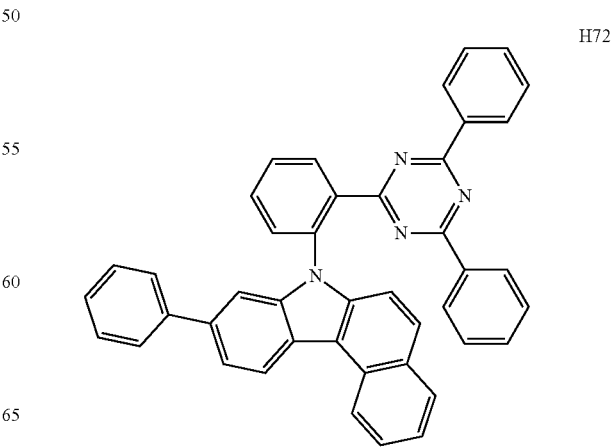
H72

H73
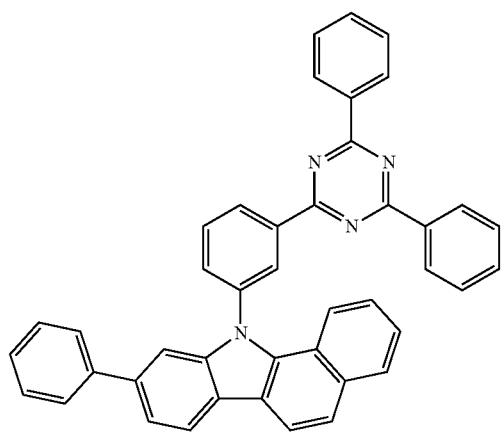
H74
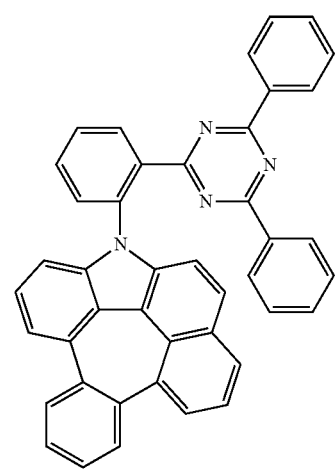
H75
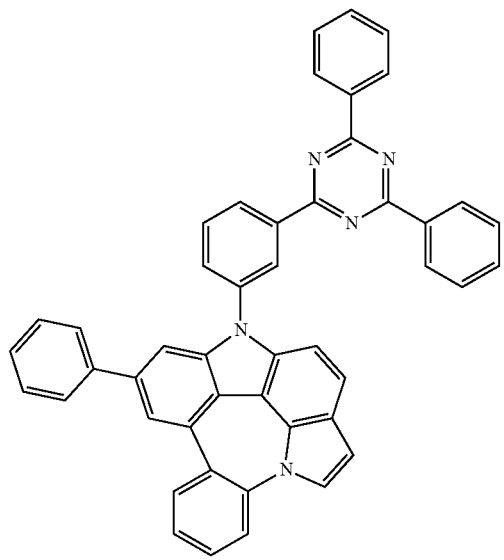
H76
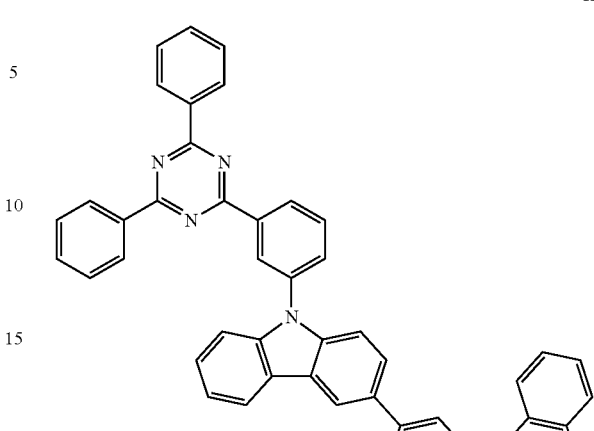
H77
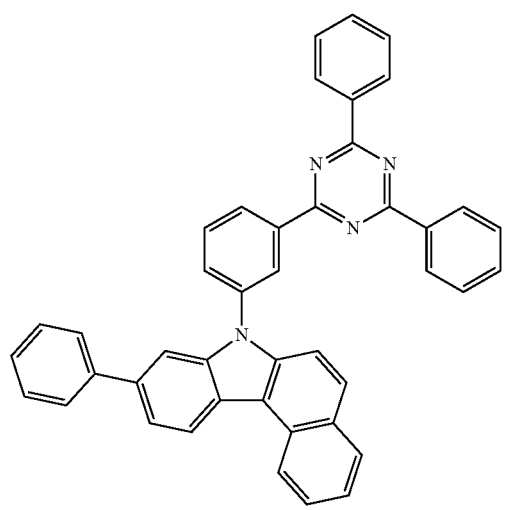
H78
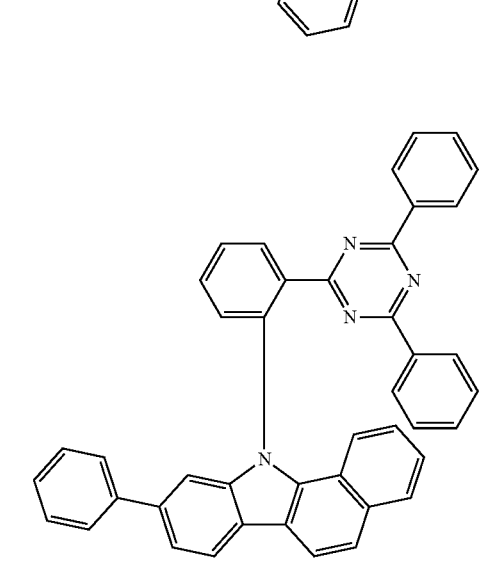

-continued
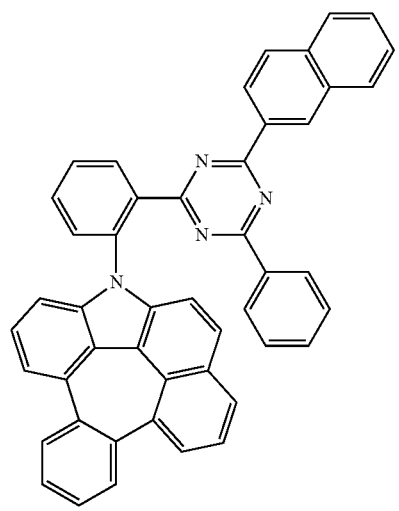
H79
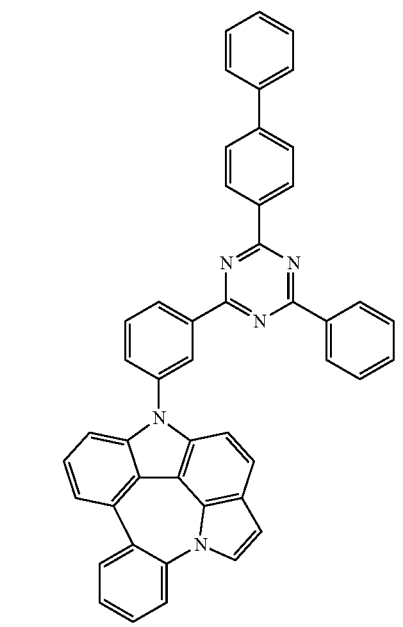
H80
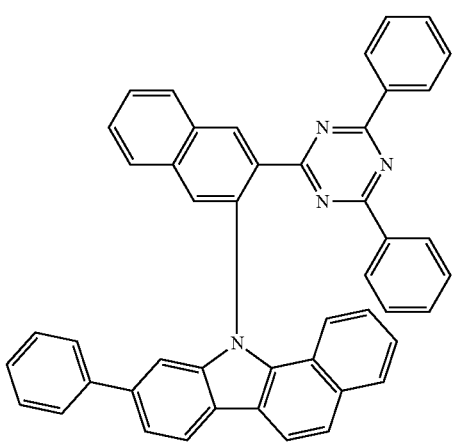
H81
-continued
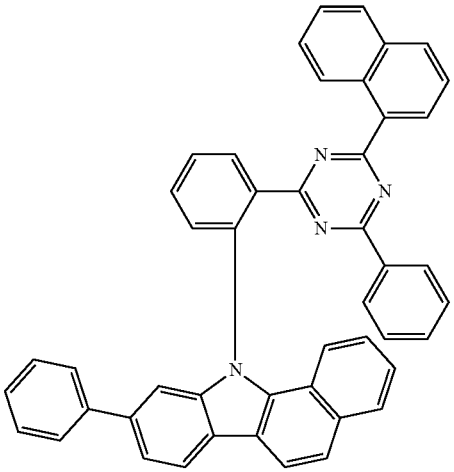
H82
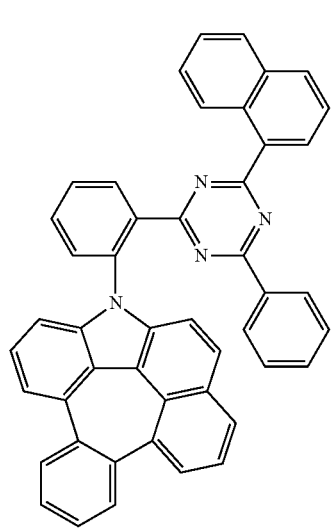
H83
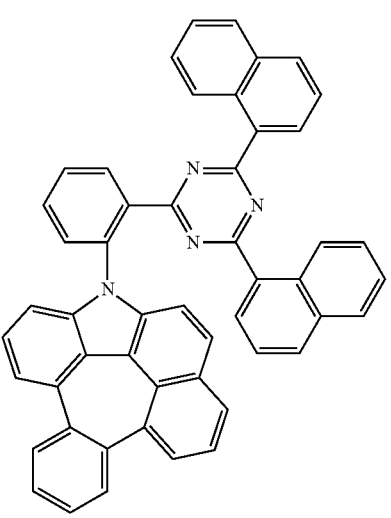
H84

-continued
H85
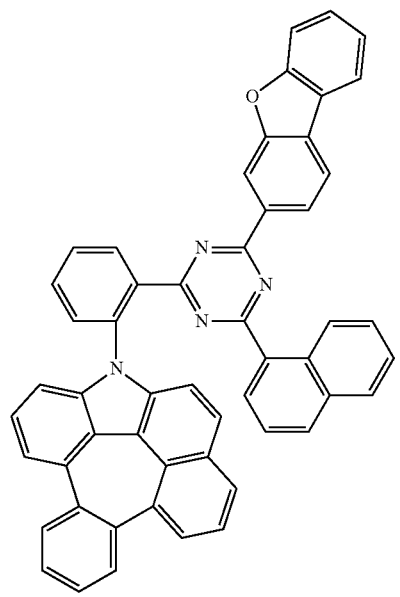
H86
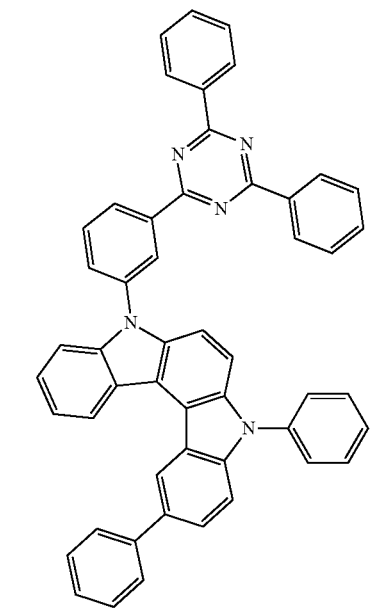
H87
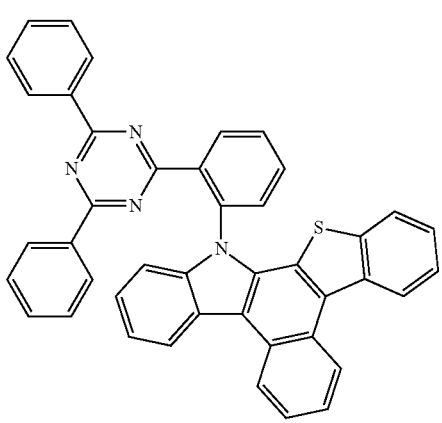
-continued
H88
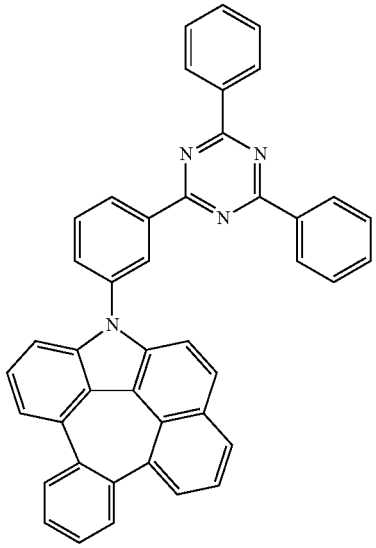
H89
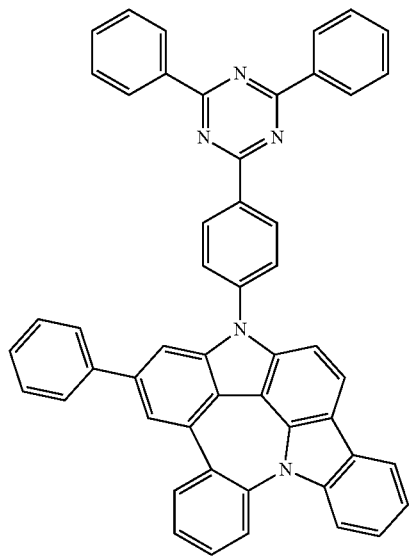
H90
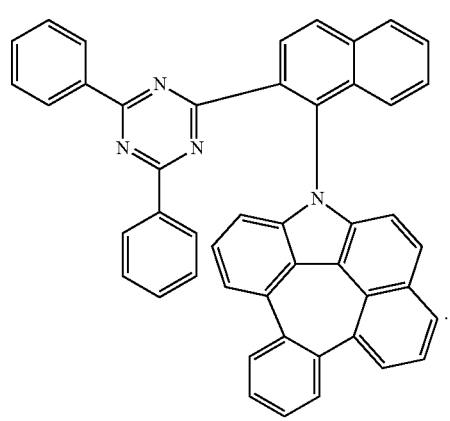

14. An organic light-emitting device comprising:
a first electrode;
a second electrode; and
an organic layer between the first electrode and the second electrode and comprising an emission layer and the composition of claim 1.

15. The organic light-emitting device of claim 14, wherein
the first electrode is an anode,
the second electrode is a cathode, and
the organic layer further comprises a hole transport region between the first electrode and the emission layer and an electron transport region between the emission layer and the second electrode,
the hole transport region comprises a hole injection layer, a hole transport layer, an electron blocking layer, a buffer layer, or a combination thereof, and
the electron transport region comprises a hole blocking layer, an electron transport layer, an electron injection layer, or a combination thereof.

16. The organic light-emitting device of claim 14, wherein the composition is comprised in the emission layer.

17. The organic light-emitting device of claim 14, wherein the emission layer emits red light.

* * * * *